United States Patent
Uehara et al.

(10) Patent No.: US 9,518,150 B2
(45) Date of Patent: Dec. 13, 2016

(54) RESIN COMPOSITION, STRETCHED FILM, CIRCULARLY POLARIZING PLATE, AND IMAGE DISPLAY DEVICE

(71) Applicant: MITSUBISHI CHEMICAL CORPORATION, Chiyoda-ku (JP)

(72) Inventors: Hisatoshi Uehara, Kanagawa (JP); Hiroyuki Hayashi, Kanagawa (JP); Naoko Sumitani, Kanagawa (JP); Haruhiko Kusaka, Tokyo (JP); Shingo Namiki, Fukuoka (JP); Yuuichi Hirami, Fukuoka (JP)

(73) Assignee: MITSUBISHI CHEMICAL CORPORATION, Chiyoda-ku (JP)

( * ) Notice: Subject to any disclaimer, the term of this patent is extended or adjusted under 35 U.S.C. 154(b) by 0 days.

(21) Appl. No.: 14/685,982

(22) Filed: Apr. 14, 2015

(65) Prior Publication Data
US 2015/0247002 A1 Sep. 3, 2015

Related U.S. Application Data

(63) Continuation of application No. PCT/JP2013/078009, filed on Oct. 15, 2013.

(30) Foreign Application Priority Data

Oct. 16, 2012 (JP) ................................. 2012-228946
Jun. 21, 2013 (JP) ................................. 2013-130882

(51) Int. Cl.

| C08G 64/30 | (2006.01) |
|---|---|
| B29C 55/04 | (2006.01) |
| C07C 33/36 | (2006.01) |
| C07C 69/616 | (2006.01) |
| C08J 5/18 | (2006.01) |
| C08G 64/16 | (2006.01) |
| C07C 43/23 | (2006.01) |
| C07C 67/00 | (2006.01) |
| G02B 1/08 | (2006.01) |
| G02B 5/30 | (2006.01) |
| C08G 64/06 | (2006.01) |
| B29K 227/12 | (2006.01) |

(52) U.S. Cl.
CPC ............. *C08G 64/305* (2013.01); *B29C 55/04* (2013.01); *C07C 33/36* (2013.01); *C07C 43/23* (2013.01); *C07C 67/00* (2013.01); *C07C 69/616* (2013.01); *C08G 64/16* (2013.01); *C08G 64/302* (2013.01); *C08J 5/18* (2013.01); *G02B 1/08* (2013.01); *G02B 5/3083* (2013.01); *B29K 2227/12* (2013.01); *B29K 2995/0034* (2013.01); *C07C 2103/18* (2013.01); *C08J 2369/00* (2013.01)

(58) Field of Classification Search
CPC ........ C08G 64/305; C08G 64/302; C08J 5/18; C07C 33/36
USPC .................................................. 528/196, 198
See application file for complete search history.

(56) References Cited

U.S. PATENT DOCUMENTS

| 3,324,084 A | 6/1967 | Horn et al. |
|---|---|---|
| 3,833,617 A | 9/1974 | Webb et al. |
| 7,794,856 B2 * | 9/2010 | Shiobara ............... H01L 51/004 313/504 |
| 2010/0003490 A1 | 1/2010 | Iida et al. |
| 2010/0301271 A1 | 12/2010 | Adlem et al. |
| 2012/0170118 A1 | 7/2012 | Wang et al. |
| 2012/0231255 A1 | 9/2012 | Tanaka et al. |
| 2012/0308796 A1 | 12/2012 | Tanaka et al. |
| 2013/0085254 A1 | 4/2013 | Namiki et al. |

FOREIGN PATENT DOCUMENTS

| CN | 101796164 A | 8/2010 |
|---|---|---|
| JP | 10-101786 | 4/1998 |
| JP | 2006-063230 | 3/2006 |
| JP | 2008-112124 | 5/2008 |
| JP | 2010-261008 | 11/2010 |
| JP | 2012-031369 | 2/2012 |
| JP | 2012-031370 | 2/2012 |
| WO | 2006/041190 A1 | 4/2006 |
| WO | WO 2009/030352 A1 | 3/2009 |
| WO | 2011/149073 A1 | 12/2011 |

OTHER PUBLICATIONS

Partial supplementary European Search Report issued Jun. 15, 2015 in Patent Application No. 13847237.8.
International Search Report issued Jan. 14, 2014 in PCT/JP2013/078009 filed Oct. 15, 2013.
Extended European Search Report issued Oct. 7, 2015 in Patent Application No. 13847237.8.
Combined Office Action and Search Report issued on Nov. 9, 2015 in Chinese Patent Application No. 201380051990.5 with partial English translation and English translation of category of cited documents.
Office Action issued May 3, 2016 in Chinese Patent Application No. 201380051990.5 (with English language translation).
Office Action issued Oct. 12, 2016, in corresponding European Patent Application No. 13847237.8.

* cited by examiner

*Primary Examiner* — Terressa Boykin
(74) *Attorney, Agent, or Firm* — Oblon, McClelland, Maier & Neustadt, L.L.P.

(57) ABSTRACT

The invention relates to a resin composition which comprises a polymer having a divalent oligofluorene as a repeating unit therein, wherein the divalent oligofluorene contains at least two fluorene units optionally having a substituent, and the 9-positioned carbon atoms of the fluorene units bond to each other via a direct bond or via an alkylene group optionally having a substituent, an arylene group optionally having a substituent, or an aralkylene group optionally having a substituent, and a ratio of a retardation measured at a wavelength of 450 nm (Re450) to a retardation measured at a wavelength of 550 nm (Re550) satisfies the following formula (2): Re450/Re550≤1.0.

43 Claims, 1 Drawing Sheet

RESIN COMPOSITION, STRETCHED FILM, CIRCULARLY POLARIZING PLATE, AND IMAGE DISPLAY DEVICE

TECHNICAL FIELD

The present invention relates to a resin composition excellent in optical properties, heat resistance and melt processability, and to a stretched film, a circularly polarizing plate and an image display device produced using the composition.

BACKGROUND ART

Recently, polycarbonate resins and polyester resins derived from dihydroxy compounds having a fluorene ring in the side chain thereof have been reported, and making full use of the fluorene ring-derived characteristics such as optical properties and heat resistance thereof, those resins have been proposed as materials useful for optical applications (for example, see PTL 1). PTL 2 and 3 disclose as follows: When the content of the fluorene ring-having repeating unit in a polycarbonate resin is controlled to fall within a specific range, the stretched film formed of the polycarbonate resin exhibits reversed wavelength dispersion characteristics of such that the retardation of the film is smaller at a shorter wavelength, and therefore, the film has excellent performance as a retardation film. Such a retardation film exhibiting so-called reversed wavelength dispersion characteristics of such that the retardation of the film is smaller at a shorter wavelength can have ideal retardation characteristics at each wavelength in a visible light region, and is therefore useful as a circularly polarizing film for prevention of outer light reflection and viewing angle correction in image display devices.

PTL 4 discloses as follows: When the content of the fluorene ring-having repeating unit in a polyimide resin is controlled to fall within a specific range, the stretched film formed of the polyimide resin exhibits flat wavelength dispersion characteristics of such that the retardation of the film changes little in a broad area from a short wavelength side to a long wavelength side, and therefore, the film has excellent performance as a retardation film. Such a retardation film exhibiting flat wavelength dispersion characteristics is useful for correcting VA (vertical alignment)-mode liquid crystals.

As dihydroxy compounds having a fluorene ring in the side chain thereof, well used are 9,9-bis(4-(2-hydroxyethoxyl)phenyl)fluorene and 9,9-bis(4-hydroxy-3-methylphenyl)fluorene described in PTL 2 and 3. On the other hand, PTL 4 discloses a diamine compound having a fluorene ring in the side chain thereof, and describes a stretched film of a polyimide resin using the compound. PTL 5 discloses a diester compound having two fluorene ring in one molecule, and describes a polyester resin using the compound. PTL 6 discloses a dihydroxy compound and a diester compound having two fluorene rings in one molecule, and describes a stretched film of a polyester resin using the compound.

CITATION LIST

Patent Literature

PTL 1: JP-A 10-101786
PTL 2: WO2006/041190
PTL 3: WO2011/149073
PTL 4: JP-A 2008-112124
PTL 5: U.S. Pat. No. 3,324,084
PTL 6: US Patent Application Publication 2012/0170118

SUMMARY OF INVENTION

Technical Problem

The development in the field of FPD is remarkable, and FPD has become desired to satisfy various characteristics. For example, materials for use for reversed wavelength dispersion films, $1/4\lambda$ plates and flat wavelength dispersion retardation films are desired to have a low photoelastic coefficient and have desired optical properties and are additionally desired to satisfy other various physical properties of sufficient heat resistance and melt processability as well as mechanical strength, etc.

It is known that the stretched film of a polycarbonate resin having a fluorene in PTL 2 and 3 is useful as a retardation film exhibiting reversed wavelength dispersion characteristics and as a circularly polarizing plate for prevention of external light reflection in image display devices. However, the present inventors' investigations have revealed that, in order that the resin using 9,9-bis[4-hydroxy-3-methylphenyl]fluorene in PTL 2 or the resin using 9,9-bis[4-(2-hydroxyethoxyl)phenyl]fluorene in PTL 3 could express the desired reversed wavelength dispersion characteristics of retardation, the proportion of the fluorene ring-having repeating units must increase, and therefore the latitude in molecular planning in copolymerization is lowered and further it is difficult for the resins to satisfy both various physical properties such as heat resistance, melt processability, mechanical strength and the like and optical properties. In addition, for the purpose of correcting color leakage in image display devices, it is desired to control the reversed wavelength dispersion characteristics of the film in accordance with the properties of the devices, and for this, the film is desired to have an extremely small retardation ratio, while maintaining various characteristics thereof, and to be able to exhibit strong reversed wavelength dispersion characteristics of retardation. However, the dihydroxy compounds having a fluorene ring in the side chain thereof, described in the above-mentioned PTL 2 and PTL 3, expresses weakly the reversed wavelength dispersion characteristics thereof, and in case where a retardation film is formed of the resin using the compound, the film could hardly exhibit strong reversed wavelength dispersion characteristics while maintaining the other necessary physical properties thereof. Consequently, for further improving the optical properties and other physical properties such as mechanical resistance and the like of resins, it is desired to use, as the starting material, a novel compound excellent in the balance between optical properties and other physical properties such as mechanical strength, etc. The polyester described in PTL 5 is not used as a film, and the optical properties thereof are unclear. PTL 6 says that the polyester described therein has a negative birefringence in the stretching direction, or shows negative refractive index anisotropy. A retardation film must have positive refractive index anisotropy in the stretching direction, and the above-mentioned polyester stretched film does not satisfy this requirement. In addition, the wavelength dependency of the retardation of the film is unclear.

On the other hand, a material for use for a flat wavelength dispersion retardation film is required to have excellent optical properties of flat wavelength dispersion of such that the wavelength dispersion of retardation is weak, and is further required to have a low photoelastic coefficient. The stretched film of a fluorene skeleton-having polyimide film in PTL 4 is known to be useful for correcting VA-mode liquid crystals. However, the photoelastic coefficient of the film, that is important for retardation film, is unclear.

An optical material of flat wavelength dispersion with zero birefringence, or that is, a broadband zero-birefringence material is desired in broad applications for polarizer-protective films in liquid-crystal display devices, optical lenses, etc.

The first object of the present invention is to provide a resin composition which, when formed into a film, exhibits excellent optical properties, and which satisfies various physical properties such as heat resistance, melt processability, mechanical strength and the like as using a structural unit capable of efficiently expressing desired optical properties even when the proportion thereof in the resin is low, therefore increasing the latitude in resin planning, and to provide an oligofluorene diester monomer for use in such a resin composition, as well as a production method for such an oligofluorene diester monomer. Further, the second object of the present invention is to provide a diol monomer for use in a resin composition having excellent optical properties of a low photoelastic coefficient and a small wavelength dispersion of retardation.

Solution to Problem

The present inventors have made assiduous investigations for solving the above-mentioned problems and, as a result, have found that, of a resin composition which contains a polymer having a specific divalent oligofluorene as the repeating unit therein and which has specific optical properties, the physical properties can be readily controlled, and the film formed of the resin composition exhibits excellent optical properties and excellent mechanical properties, therefore attaining the first object, and have reached the present invention.

Further, the present inventors have made assiduous investigations for solving the above-mentioned problems and, as a result, have found that a specific oligofluorene-diol has, in a resin composition containing it, excellent optical properties of a low photoelastic coefficient and a small wavelength dispersion of retardation, therefor attaining the second object, and have reached the present invention.

Specifically, the gist of the present invention includes the following:

[1] A resin composition which comprises a polymer having a divalent oligofluorene as a repeating unit therein, wherein the divalent oligofluorene contains at least two fluorene units optionally having a substituent, and the 9-positioned carbon atoms of the fluorene units bond to each other via a direct bond or via an alkylene group optionally having a substituent, an arylene group optionally having a substituent, or an aralkylene group optionally having a substituent, and wherein a ratio of a retardation measured at a wavelength of 450 nm (Re450) to a retardation measured at a wavelength of 550 nm (Re550) satisfies the following formula (2):

$$Re450/Re550 \leq 1.0 \quad (2)$$

[2] A resin composition which comprises a polymer having a divalent oligofluorene as a repeating unit therein, wherein the divalent oligofluorene contains at least two fluorene units optionally having a substituent, and the 9-positioned carbon atoms of the fluorene units bond to each other via a direct bond or via an alkylene group optionally having a substituent, an arylene group optionally having a substituent, or an aralkylene group optionally having a substituent, wherein a molar fraction of the divalent oligofluorene to the polymer is 1% or more, and the resin composition has a positive refractive index anisotropy.

[3] The resin composition according to the [1] or [2] above, wherein the polymer is a polycarbonate.

[4] A resin composition which comprises a polycarbonate polymer having a divalent oligofluorene as a repeating unit therein, wherein the divalent oligofluorene contains at least two fluorene units optionally having a substituent, and the 9-positioned carbon atoms of the fluorene units bond to each other via a direct bond or via an alkylene group optionally having a substituent, an arylene group optionally having a substituent, or an aralkylene group optionally having a substituent.

[5] The resin composition according to any one of the [2] to [4] above, wherein a ratio of a retardation measured at a wavelength of 450 nm (Re450) to a retardation measured at a wavelength of 550 nm (Re550) satisfies the following formula (2):

$$Re450/Re550 \leq 1.0 \quad (2)$$

[6] The resin composition according to any one of the [1] to [5] above, wherein the divalent oligofluorene is represented by the following general formula (1):

[Chem. 1]

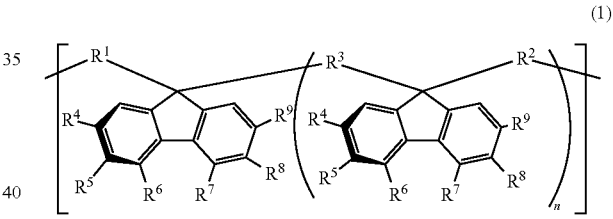

(1)

(In the formula, $R^1$ and $R^2$ each independently represent a direct bond, an optionally-substituted alkylene group having from 1 to 10 carbon atoms, an optionally-substituted arylene group having from 4 to 10 carbon atoms, or an optionally-substituted aralkylene group having from 6 to 10 carbon atoms, or a group formed by bonding at least two groups selected from the group consisting of an optionally-substituted alkylene group having from 1 to 10 carbon atoms, an optionally-substituted arylene group having from 4 to 10 carbon atoms and an optionally-substituted aralkylene group having from 6 to 10 carbon atoms, via an oxygen atom, an optionally-substituted sulfur atom, an optionally-substituted nitrogen atom or a carbonyl group, $R^3$ represents a direct bond, an optionally-substituted alkylene group having from 1 to 10 carbon atoms, an optionally-substituted arylene group having from 4 to 10 carbon atoms, or an optionally-substituted aralkylene group having from 6 to 10 carbon atoms, $R^4$ to $R^9$ each independently represent a hydrogen atom, an optionally-substituted alkyl group having from 1 to 10 carbon atoms, an optionally-substituted aryl group having from 4 to 10 carbon atoms, an optionally-substituted acyl group having from 1 to 10 carbon atoms, an optionally-substituted alkoxy group having from 1 to 10 carbon atoms, an optionally-substituted aryloxy group having from 1 to 10 carbon atoms, an optionally-substituted amino group, a substituent-having sulfur atom, a halogen atom, a nitro group, or a Gubstitucnt having cyano group, and at least two adjacent groups of $R^4$ to $R^9$ may bond to each other to form a ring, n indicates an integer value of from 1 to 5.)

[7] The resin composition according to any one of the [1] to [6] above, which further has a divalent organic group represented by the following general formula (3) as a repeating unit therein:

[Chem. 2]

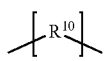

(3)

(In the formula, $R^{10}$ represents an optionally-substituted alkylene group having from 2 to 20 carbon atoms, an optionally-substituted arylene group having from 4 to 20 carbon atoms, an optionally-substituted aralkylene group having from 6 to 20 carbon atoms, an optionally-substituted alkylene-ether group having from 2 to 100 carbon atoms, an optionally-substituted organic group having an alicyclic structure of from 4 to 20 carbon atoms, or an optionally-substituted organic group having heterocyclic structure of from 4 to 20 carbon atoms.)

[8] The resin composition according to the [7] above, wherein the divalent organic group represented by the general formula (3) is at least one of the following formulae (4) to (9):

[Chem. 3]

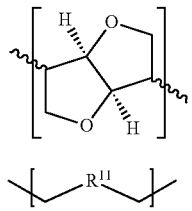

(4)

(5)

(In the formula (5), $R^{11}$ represents an optionally-substituted linear alkylene group having from 0 to 18 carbon atoms),

[Chem. 4]

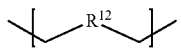

(6)

[Chem. 8]

(In the formula (6), $R^{12}$ represents an optionally-substituted cycloalkylene group having from 4 to 20 carbon atoms),

[Chem. 5]

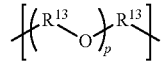

(7)

(In the formula (7), $R^{13}$ represents an optionally-substituted alkylene group having from 2 to 10 carbon atoms, and p indicates an integer of from 1 to 40),

[Chem. 6]

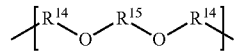

(8)

(In the formula (8), $R^{14}$ represents an optionally-substituted alkylene group having from 2 to 10 carbon atoms, and $R^{15}$ represents an optionally-substituted arylene group having from 12 to 30 carbon atoms.)

[Chem. 7]

(9)

(In the formula (9), $R^{16}$ represents an optionally-substituted group having an acetal ring of from 2 to 20 carbon atoms.)

[9] The resin composition according to any one of the [1] to [8] above, wherein the glass transition temperature is 90° C. or higher and 170° C. or lower.

[10] The resin composition according to any one of the [1] to [9] above, wherein a melt viscosity at a measurement temperature of 240° C. and at a shear rate of 91.2 sec$^{-1}$ is 500 Pa·s or more and 5000 Pa·s or less.

[11] The resin composition according to any one of the [1] to [10] above, wherein the photoelastic coefficient is 45×10$^{-12}$ Pa$^{-1}$ or less.

[12] The resin composition according to any one of the [1] to [11] above, wherein a molar fraction of the divalent oligofluorene to the polymer is 1% or more and less than 50%.

[13] The resin composition according to the [3] or [4] above, wherein the polymer is produced through melt polycondensation of a dihydroxy compound represented by the following general formula (10a) and diester carbonate represented by the following general formula (11):

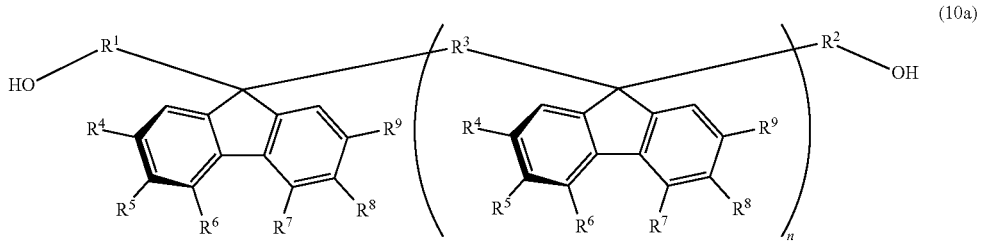

(10a)

(In the formula, $R^1$ and $R^2$ each independently represent a direct bond, an optionally-substituted alkylene group having from 1 to 10 carbon atoms, an optionally-substituted arylene group having from 4 to 10 carbon atoms, or an optionally-substituted aralkylene group having from 6 to 10 carbon atoms, or a group formed by bonding at least two groups selected from the group consisting of an optionally-substituted alkylene group having from 1 to 10 carbon atoms, an optionally-substituted arylene group having from 4 to 10 carbon atoms and an optionally-substituted aralkylene group having from 6 to 10 carbon atoms, via an oxygen atom, an optionally-substituted sulfur atom, an optionally-substituted nitrogen atom or a carbonyl group, $R^3$ represents a direct bond, an optionally-substituted alkylene group having from 1 to 10 carbon atoms, an optionally-substituted arylene group having from 4 to 10 carbon atoms, or an optionally-substituted aralkylene group having from 6 to 10 carbon atoms,

[Chem. 10]

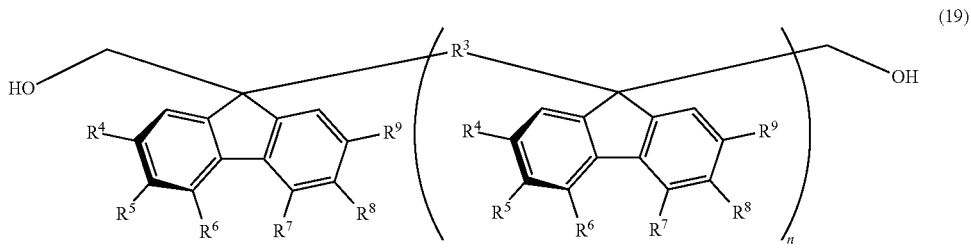

(19)

$R^4$ to $R^9$ each independently represent a hydrogen atom, or a substituent selected from the group consisting of an optionally-substituted alkyl group having from 1 to 10 carbon atoms, an optionally-substituted aryl group having from 4 to 10 carbon atoms, an optionally-substituted acyl group having from 1 to 10 carbon atoms, an optionally-substituted alkoxy group having from 1 to 10 carbon atoms, an optionally-substituted aryloxy group having from 1 to 10 carbon atoms, an optionally-substituted amino group, a substituent-having sulfur atom, a halogen atom, a nitro group, and a cyano group, and at least two adjacent groups of $R^4$ to $R^9$ may bond to each other to form a ring, n indicates an integer value of from 1 to 5.),

[Chem. 9]

(11)

(In the formula, $A^1$ and $A^2$ each represent a substituted or unsubstituted aliphatic hydrocarbon group having from 1 to 18 carbon atoms, or a substituted or unsubstituted aromatic hydrocarbon group, and $A^1$ and $A^2$ may be the same or different.)

[14] The resin composition according to the [13] above, wherein the total content ratio of Na, K, Cs and Fe is 3 ppm by mass or less.

[15] The resin composition according to the [13] or [14] above, wherein the content ratio of the monohydroxy compound formed from the diester carbonate represented by the general formula (11) is 1500 ppm by mass or less.

[16] The resin composition according to any one of the [13] to [15] above, wherein $R^1$ and $R^2$ in the general formula (10a) are a methylene group.

[17] A shaped article obtained by shaping the resin composition of any one of the [1] to [16] above.

[18] An optical member comprising the resin composition of any one of the [1] to [16] above.

[19] A film comprising the resin composition of any one of the [1] to [16] above.

[20] A stretched film produced by stretching the film of the [19] above in at least one direction.

[21] A ¼λ plate comprising the stretched film of the [20] above.

[22] A circularly polarizing plate comprising the ¼λ plate of the [21] above.

[23] A image display device comprising the circularly polarizing plate of the [22] above.

[24] An oligofluorene-diol represented by the following general formula (19):

(In the formula, $R^3$ represents an optionally-substituted alkylene group having from 1 to 10 carbon atoms, an optionally-substituted arylene group having from 4 to 10 carbon atoms, or an optionally-substituted aralkylene group having from 6 to 10 carbon atoms, $R^4$ to $R^9$ each independently represent a hydrogen atom, an optionally-substituted alkyl group having from 1 to 10 carbon atoms, an optionally-substituted aryl group having from 4 to 10 carbon atoms, an optionally-substituted acyl group having from 1 to 10 carbon atoms, an optionally-substituted alkoxy group having from 1 to 10 carbon atoms, an optionally-substituted aryloxy group having from 1 to 10 carbon atoms, an optionally-substituted amino group, a substituent-having sulfur atom, a halogen atom, a nitro group, or a cyano group, and at least two adjacent groups of $R^4$ to $R^9$ may bond to each other to form a ring, n indicates an integer value of from 1 to 5.)

[25] The oligofluorene-diol according to the [24] above, wherein the chlorine content ratio is 100 ppm by mass or less in terms of Cl mass.

[26] The oligofluorene-diol according to the [24] or [25] above, wherein the content ratio of the metal of Group 1 and Group 2 of the Long Periodic Table is 500 ppm by mass or less.

[27] The oligofluorene-diol according to any one of the [24] to [26] above, wherein a 5% weight reduction temperature in thermogravimetry is 250° C. or higher.

[28] The oligofluorene-diol according to any one of the [24] to [27] above, wherein in the general formula (19), $R^3$ is a methylene group, an ethylene group, an n-propylene group, an n-butylene group or a 2,2-dimethylpropylene group, $R^4$ to $R^9$ are a hydrogen atom, and n is 1 or 2.

[29] A method for producing an oligofluorene diester represented by the following general formula (VII-1), which comprises reacting an oligofluorene compound represented by the following general formula (II) with an unsaturated carboxylate ester represented by the following general formula (VI-1) in the presence of a base:

[Chem. 11]

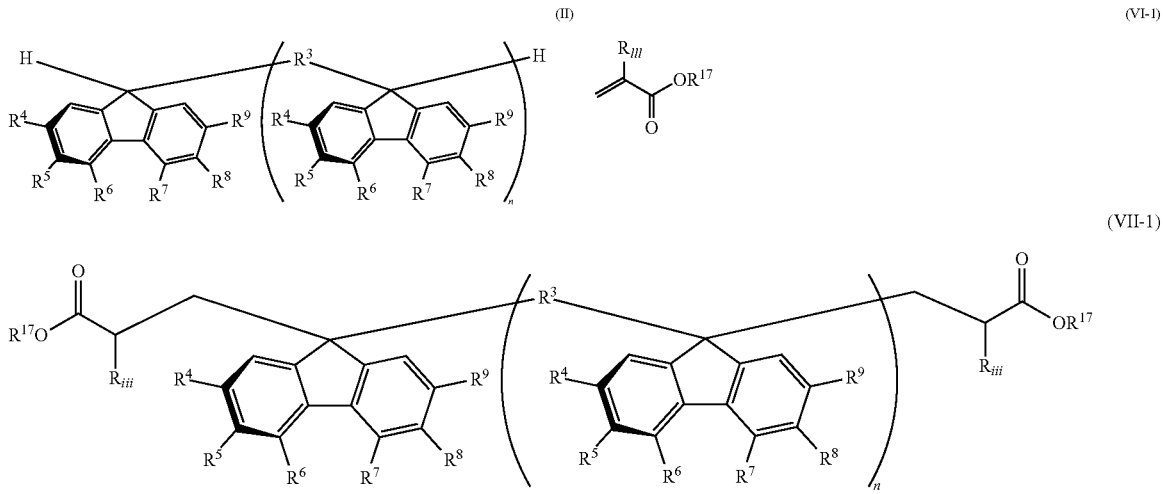

(In the formulae, $R^3$ represents a direct bond, an optionally-substituted alkylene group having from 1 to 10 carbon atoms, an optionally-substituted arylene group having from 4 to 10 carbon atoms, or an optionally-substituted aralkylene group having from 6 to 10 carbon atoms, $R^4$ to $R^9$ each independently represent a hydrogen atom, an optionally-substituted alkyl group having from 1 to 10 carbon atoms, an optionally-substituted aryl group having from 4 to 10 carbon atoms, an optionally-substituted acyl group having from 1 to 10 carbon atoms, an optionally-substituted alkoxy group having from 1 to 10 carbon atoms, an optionally-substituted aryloxy group having from 1 to 10 carbon atoms, an optionally-substituted amino group, a substituent-having sulfur atom, a halogen atom, a nitro group, or a cyano group, and at least two adjacent groups of $R^4$ to $R^9$ may bond to each other to form a ring, $R_{iii}$ represents a hydrogen atom, an optionally-substituted alkyl group having from 1 to 10 carbon atoms, an optionally-substituted aryl group having from 4 to 10 carbon atoms, or an optionally-substituted aralkyl group having from 6 to 10 carbon atoms, $R^{17}$ represents an organic substituent having from 1 to 10 carbon atoms, n indicates an integer value of from 1 to 5.)

[30] An oligofluorene diaryl ester represented by the following general formula (10d):

(In the formula, $R^1$ and $R^2$ each independently represent a direct bond, an optionally-substituted alkylene group having from 1 to 10 carbon atoms, an optionally-substituted arylene group having from 4 to 10 carbon atoms, or an optionally-substituted aralkylene group having from 6 to 10 carbon atoms, or a group formed by bonding at least two groups selected from the group consisting of an optionally-substituted alkylene group having from 1 to 10 carbon atoms, an optionally-substituted arylene group having from 4 to 10 carbon atoms and an optionally-substituted aralkylene group having from 6 to 10 carbon atoms, via an oxygen atom, an optionally-substituted sulfur atom, an optionally-substituted nitrogen atom or a carbonyl group, $R^3$ represents an optionally-substituted alkylene group having from 1 to 10 carbon atoms, an optionally-substituted arylene group having from 4 to 10 carbon atoms, or an optionally-substituted aralkylene group having from 6 to 10 carbon atoms, $R^4$ to $R^9$ each independently represent a hydrogen atom, an optionally-substituted alkyl group having from 1 to 10 carbon atoms, an optionally-substituted aryl group having from 4 to 10 carbon atoms, an optionally-substituted acyl group having from 1 to 10 carbon atoms, an optionally-substituted alkoxy group having from 1 to 10 carbon atoms, an optionally-substituted aryloxy group having from 1 to 10 carbon atoms, an optionally-substituted amino group, a substituent-having sulfur atom, a halogen atom, a nitro group, or a cyano group, and at least two adjacent groups of $R^4$ to $R^9$ may bond to each other to form a ring,

[Chem. 14]

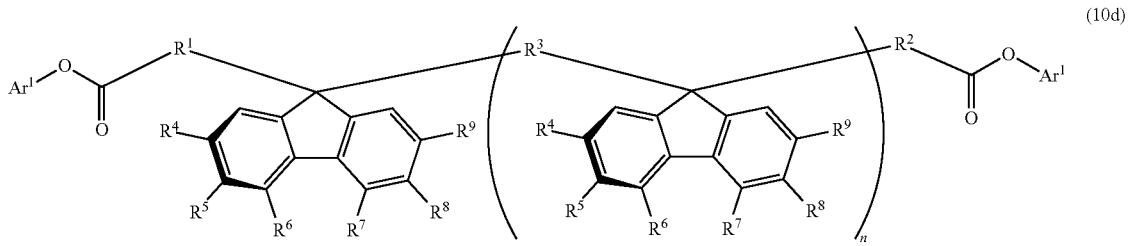

Ar¹ represents an optionally-substituted aryl group having from 4 to 10 carbon atoms, n indicates an integer value of from 1 to 5.)

[31] The oligofluorene diaryl ester according to the [30] above, wherein a 5% weight reduction temperature in thermogravimetry is 250° C. or higher.

[32] The oligofluorene diaryl ester according to the [30] or [31] above, wherein in the general formula (10d), $R^3$ is a methylene group, an ethylene group, an n-propylene group, an n-butylene group or a 2,2-dimethylpropylene group, $R^4$ to $R^9$ are a hydrogen atom, $Ar^1$ is a phenyl group, and n is an integer value of 1 or 2.

[33] A method for producing the oligofluorene diaryl ester of any one of the [30] to [32] above, which comprises reacting an oligofluorene dialkyl ester represented by the following general formula (10f) with an diaryl carbonate represented by the following general formula (11a) in the presence of an interesterification catalyst:

[Chem. 15]

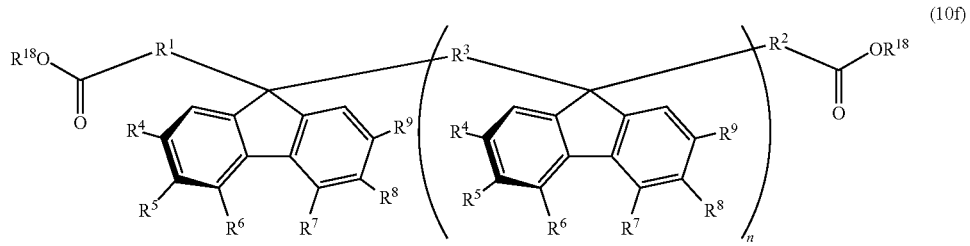

(10f)

[Chem. 16]

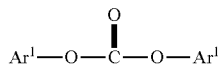

(11a)

(In the formula, $Ar^1$ represents an optionally-substituted aryl group having from 4 to 10 carbon atoms.)

Advantageous Effects of Invention

When formed into a film, the resin composition of the present invention exhibits excellent optical properties. Using a repeating unit capable of efficiently expressing desired optical properties even when the proportion thereof in the resin is low, the resin composition of the present invention increases the latitude in resin planning and satisfies various physical properties such as heat resistance, melt processability, mechanical strength and others, and consequently, the resin composition is useful for optical applications, especially for retardation films. In addition, the present invention provides an oligofluorene diester monomer favorably used for the resin composition, and provides a production method for the monomer. Further, the oligofluorene-diol of the present invention has, when incorporated in a resin composition, excellent optical properties of a low photoelastic coefficient and a small wavelength dispersion of retardation, and is therefore useful as a material for optical applications, especially for retardation films.

BRIEF DESCRIPTION OF DRAWINGS

FIG. 1A shows a structural formula of the compound, FIG. 1B shows a space-filling model of the trans conformation of the compound, and FIG. 1C shows a space-filling model of the gauche conformation of the compound.

FIG. 2A shows a structural formula of the compound, FIG. 2B shows a space-filling model of the trans conformation of the compound, and FIG. 2C shows a space-filling model of the gauche conformation of the compound.

DESCRIPTION OF EMBODIMENTS

Figure 1A:
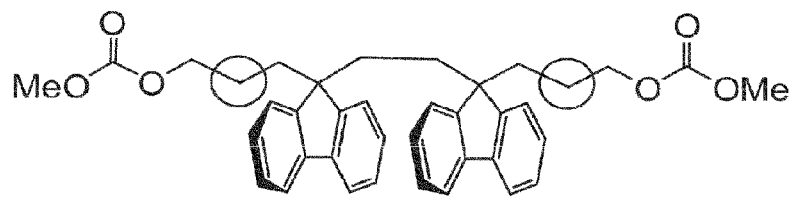
FIGS. 1A to 1C show the compound 7B modified with methyl carbonate at the terminal group thereof.

Embodiments of the present invention are described in detail hereinunder. However, the description of the constituent features given below is for some examples (typical examples) of the embodiments of the present invention, and (In the formula, $R^1$ and $R^2$ each independently represent a direct bond, an optionally-substituted alkylene group having from 1 to 10 carbon atoms, an optionally-substituted arylene group having from 4 to 10 carbon atoms, or an optionally-substituted aralkylene group having from 6 to 10 carbon atoms, or a group formed by bonding at least two groups selected from the group consisting of an optionally-substituted alkylene group having from 1 to 10 carbon atoms, an optionally-substituted arylene group having from 4 to 10 carbon atoms and an optionally-substituted aralkylene group having from 6 to 10 carbon atoms, via an oxygen atom, an optionally-substituted sulfur atom, an optionally-substituted nitrogen atom or a carbonyl group, $R^3$ represents a direct bond, an optionally-substituted alkylene group having from 1 to 10 carbon atoms, an optionally-substituted arylene group having from 4 to 10 carbon atoms, or an optionally-substituted aralkylene group having from 6 to 10 carbon atoms, $R^4$ to $R^9$ each independently represent a hydrogen atom, an optionally-substituted alkyl group having from 1 to 10 carbon atoms, an optionally-substituted aryl group having from 4 to 10 carbon atoms, an optionally-substituted acyl group having from 1 to 10 carbon atoms, an optionally-substituted alkoxy group having from 1 to 10 carbon atoms, an optionally-substituted aryloxy group having from 1 to 10 carbon atoms, an optionally-substituted amino group, a substituent-having sulfur atom, a halogen atom, a nitro group, or a cyano group, and at least two adjacent groups of $R^4$ to $R^9$ may bond to each other to form a ring, $R^{18}$ represents a hydrogen atom, or an optionally-substituted alkyl group having from 1 to 10 carbon atoms, n indicates an integer value of from 1 to 5.)

not overstepping the scope and the spirit thereof, the present invention is not restricted to the following contents. In the present invention, "weight" has the same meaning as "mass". The polycarbonate resin composition of the present invention includes not only a polymer having a carbonate structure but also any other polymer as well as various compounds formed during production of the polymer, and the composition further includes those prepared by adding various additives to the polymer.

The repeating unit in the present invention means a partial structure sandwiched between any linking groups in a polymer. The unit includes a partial structure of the terminal moiety of a polymer, in which one end is a linking group and the other is a polymerization reactive group. In the present invention, the structural unit has the same meaning as the repeating unit.

In the present invention, "optionally having a substituent" has the same meaning as "optionally-substituted".

The resin composition of the present invention is a resin composition that contains a polymer having a divalent oligofluorene as a repeating unit therein.

To that effect, the resin composition of the present invention may contain any other polymer to be mentioned below, in addition to the polymer having a divalent oligofluorene as a repeating unit. The resin composition of the present invention may comprise a polymer having a divalent oligofluorene as a repeating unit.

<1. Oligofluorene>

The polymer contained in the resin composition of the present invention has a divalent oligofluorene as a repeating unit therein.

The divalent oligofluorene contains at least two fluorene units optionally having a substituent, in which the 9-positioned carbon atoms of the fluorene units bond to each other via a direct bond, or the 9-positioned carbon atoms of the fluorene units bond to each other via an alkylene group optionally having a substituent, an arylene group optionally having a substituent, or an aralkylene group optionally having a substituent.

The carbon number of the alkylene group is not specifically defined. From the viewpoint of increasing the fluorene ratio to be mentioned below, the carbon number is generally 1 or more and is generally 10 or less, preferably 5 or less, more preferably 3 or less.

The carbon number of the arylene group is not specifically defined. From the viewpoint of increasing the fluorene ratio to be mentioned below, the carbon number is generally 4 or more and is generally 10 or less, preferably 8 or less, more preferably 6 or less.

The carbon number of the aralkylene group is not specifically defined. From the viewpoint of increasing the fluorene ratio to be mentioned below, the carbon number is generally 6 or more and is generally 10 or less, preferably 9 or less, more preferably 8 or less.

The substituent that the fluorene unit may have includes a halogen atom (e.g., fluorine atom, chlorine atom, bromine atom, iodine atom); an alkyl group having from 1 to 10 carbon atoms (e.g., methyl group, ethyl group, isopropyl group, etc.); an alkoxy group having from 1 to 10 carbon atoms (e.g., methoxy group, ethoxy group, etc.); an acyl group having from 1 to 10 carbon atoms (e.g., acetyl group, benzoyl group, etc.); an acylamino group having from 1 to 10 carbon atoms (e.g., acetamide group, benzoylamide group, etc.); a nitro group; a cyano group; an aryl group (e.g., phenyl group, naphthyl group, etc.) having from 6 to 10 carbon atoms and optionally having from 1 to 3 substituents selected from a halogen atom (e.g., fluorine atom, chlorine atom, bromine atom, iodine atom), an alkyl group having from 1 to 10 carbon atoms (e.g., methyl group, ethyl group, isopropyl group, etc.), an alkoxy group having from 1 to 10 carbon atoms (e.g., methoxy group, ethoxy group, etc.), an acyl group having from 1 to 10 carbon atoms (e.g., acetyl group, benzoyl group, etc.), an acylamino group having from 1 to 10 carbon atoms (e.g., acetamide group, benzoylamide group, etc.), a nitro group, a cyano group and others, etc. Not specifically defined, the number of the substituents is preferably from 1 to 3. When the unit has 2 or more substituents, the type of the substituents may be the same or different. From the viewpoint of industrial inexpensive production, the unit is unsubstituted.

Of two or more fluorene units of the divalent oligofluorene, the 9-positioned carbon atom of the fluorene unit positioned at both terminals may be a divalent group (or that is, corresponding to the case of the general formula (1) to be mentioned below where $R^1$ and $R^2$ are direct bonds), while on the other hand, the 9-positioned carbon atom of the fluorene unit positioned at both terminals may have substituents $\alpha^1$ and $\alpha^2$ bonding to each terminal, and the substituents $\alpha^1$ and $\alpha^2$ each may be a divalent group. In the latter case, $\alpha^1$ and $\alpha^2$ may be the same or different.

In particular, in the case where the 9-positioned carbon atom of the fluorene unit positioned at both terminals is a divalent group, or in the case where the 9-positioned carbon atom of the fluorene unit positioned at both terminals each have a substituent $\alpha^1$ or $\alpha^2$ bonding thereto, and at least one of $\alpha^1$ and $\alpha^2$ have 2 or more carbon atoms, the fluorene ring (fluorene unit) is oriented nearly vertical to the main chain, and in those cases, therefore, even when the proportion of the divalent oligofluorene in the resin composition is small, the composition tends to readily express reversed wavelength dispersion characteristics of retardation. In the latter case, from the same viewpoint, it is desirable that both $\alpha^1$ and $\alpha^2$ have 2 or more carbon atoms. On the other hand, in the case where $\alpha^1$ and $\alpha^2$ bonding to the 9-positioned carbon atoms of the fluorene units at both terminals each are a divalent group, and both $\alpha^1$ and $\alpha^2$ have one carbon atom (that is, the two each are an optionally-substituted methylene group), the fluorene ring (fluorene unit) is not oriented nearly vertical to the main chain and is oriented as greatly tilted from the main chain. Therefore, in these cases, even when the proportion of the divalent oligofluorene in the resin composition is changed in a broad range, the composition tends to readily exhibit flat wavelength dispersion characteristics of retardation having a small retardation difference in a broad region.

As $\alpha^1$ and $\alpha^2$ each having 1 carbon atom, there is mentioned an unsubstituted methylene group or a methylene group having a substituent. From the viewpoint of increasing the fluorene ratio in the repeating unit of the divalent oligofluorene, preferred is an unsubstituted methylene group. The optional substituent includes a methyl group, an ethyl group, a fluorine atom, a chlorine atom, a methoxy group. From the viewpoint of increasing the fluorene ratio, preferred is a methyl group. In the methylene group having a substituent, both the two hydrogen atoms that the methylene group has may be substituted with a substituent, or any one may be substituted. From the viewpoint of increasing the fluorene ratio, it is desirable that any one is substituent with a substituent of a methyl group.

To that effect, the resin composition of the present invention contains a polymer having a repeating unit of 2 or more fluorene units of which the 9-positioned carbon atoms are linked to each other via a specific carbon-carbon bond therebetween, and therefore can more effectively get the fluorene ring-derived optical properties.

As the divalent oligofluorene, concretely, preferred is use of any one represented by the following general formula (1):

[Chem. 15]

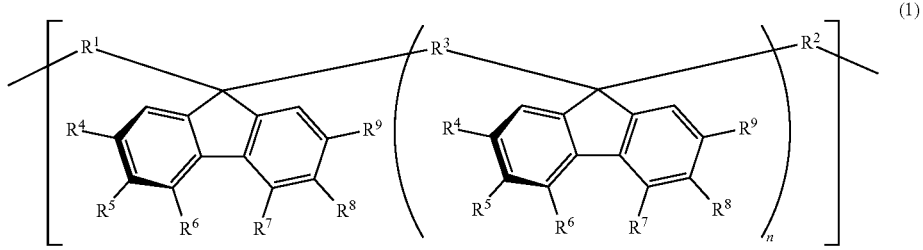

(1)

(In the formula, $R^1$ and $R^2$ each independently represent a direct bond, an optionally-substituted alkylene group having from 1 to 10 carbon atoms, an optionally-substituted arylene group having from 4 to 10 carbon atoms, or an optionally-substituted aralkylene group having from 6 to 10 carbon atoms, or a group formed by bonding at least two groups selected from the group consisting of an optionally-substituted alkylene group having from 1 to 10 carbon atoms, an optionally-substituted arylene group having from 4 to 10 carbon atoms and an optionally-substituted aralkylene group having from 6 to 10 carbon atoms, via an oxygen atom, an optionally-substituted sulfur atom, an optionally-substituted nitrogen atom or a carbonyl group, $R^3$ represents a direct bond, an optionally-substituted alkylene group having from 1 to 10 carbon atoms, an optionally-substituted arylene group having from 4 to 10 carbon atoms, or an optionally-substituted aralkylene group having from 6 to 10 carbon atoms, $R^4$ to $R^9$ each independently represent a hydrogen atom, an optionally-substituted alkyl group having from 1 to 10 carbon atoms, an optionally-substituted aryl group having from 4 to 10 carbon atoms, an optionally-substituted acyl group having from 1 to 10 carbon atoms, an optionally-substituted alkoxy group having from 1 to 10 carbon atoms, an optionally-substituted aryloxy group having from 1 to 10 carbon atoms, an optionally-substituted amino group, a substituent-having sulfur atom, a halogen atom, a nitro group, or a cyano group.

n indicates an integer value of from 1 to 5.)

$R^1$ and $R^2$ have the same meanings as described below.

$R^1$ and $R^2$ are each independently any one selected from the following groups (a) to (e).

(a) a direct bond,
(b) an optionally-substituted alkylene group having from 1 to 10 carbon atoms,
(c) an optionally-substituted arylene group having from 4 to 10 carbon atoms,
(d) an optionally-substituted aralkylene group having from 6 to 10 carbon atoms,
(e) a group formed by bonding at least two groups selected from the group consisting of an optionally-substituted alkylene group having from 1 to 10 carbon atoms, an optionally-substituted arylene group having from 4 to 10 carbon atoms, or an optionally-substituted aralkylene group having from 6 to 10 carbon atoms, via an oxygen atom, an optionally-substituted sulfur atom, an optionally-substituted nitrogen atom or a carbonyl group.

<1-1. Examples of Substituents>

In $R^1$ to $R^3$, specific structures of "optionally-substituted alkylene group having from 1 to 10 carbon atoms" are as follows, to which, however, the invention is not limited: A linear alkylene group such as a methylene group, an ethylene group, an n-propylene group, an n-butylene group, an n-pentylene group, an n-hexylene group, etc.; a branched chain-containing alkylene group such as a methylmethylene group, a dimethylmethylene group, an ethylmethylene group, a propylmethylene group, a butylmethylene group, a (1-methylethyl)methylene group, a 1-methylethylene group, a 2-methylethylene group, a 1-ethylethylene group, a 2-ethylethylene group, a 1-methylpropylene group, a 2-methylpropylene group, a 1,1-dimethylethylene group, a 2,2-dimethylpropylene group, a 3-methylpropylene group, etc. (in $R^1$ and $R^2$, the substituent position is numbered from the carbon on the fluorene ring side); an alicyclic alkylene group having the chemical bond of a linear or branched alkylene group at any two positions of an alicyclic structure shown in the following group [C]:

[Chem. 16]

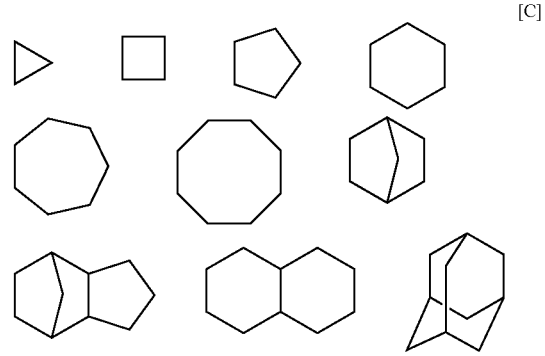

[C]

(the substituting position of the two bonds in each cyclic structure shown in the above group [C] is any arbitrary one, and two bonds may be on one and the same carbon); a heterocyclic alkylene group having the chemical bond of a linear or branched alkylene group at any two positions of a heterocyclic structure shown in the following group [D]:

[Chem. 17]

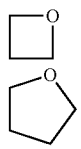

[D]

-continued

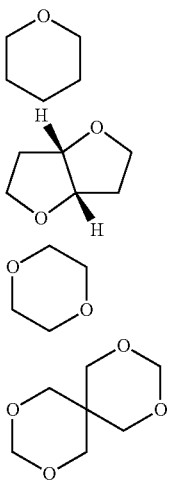

(the substituting position of the two bonds in each cyclic structure shown in the above group [D] is any arbitrary one, and two bonds may be on one and the same carbon).

Specific structures of the chemical bond of the linear or branched alkylene group where the alicyclic structure shown in the above-mentioned group [C] or the heterocyclic structure shown in the above-mentioned group [D] has at any two arbitrary positions include the following, to which, however, the present invention is not limited: The specific structures include a linear alkylene group such as a methylene group, an ethylene group, an n-propylene group, an n-butylene group, an n-pentylene group, an n-hexylene group, etc.; a branched chain-containing alkylene group such as a 1-methylethylene group, a 2-methylethylene group, a 1-ethylethylene group, a 2-ethylethylene group, a 1-methylpropylene group, a 2-methylpropylene group, a 1,1-dimethylethylene group, a 2,2-dimethylpropylene group, a 3-methylpropylene group, etc. (Here, the substituent position is numbered from the carbon bonding to the cyclic structure.)

The carbon number of the optionally-substituted alkylene group having from 1 to 10 carbon atoms is preferably 6 or less, more preferably 3 or less.

In particular, from the viewpoint of expressing reversed wavelength dispersion characteristics of retardation and in case where $R^1$ and/or $R^2$ each are an optionally-substituted alkylene group, the carbon number thereof is preferably 2 or more. On the other hand, from the viewpoint of expressing flat wavelength dispersion characteristics and in where $R^1$ and/or $R^2$ each are an optionally-substituted alkylene group, the carbon number thereof is preferably 1.

Further, in the case of expressing reversed wavelength dispersion characteristics of retardation and when $R^1$ and/or $R^2$ each are an optionally-substituted alkylene group, the carbon number thereof is preferably 5 or less, more preferably 4 or less, even more preferably 3 or less, still more preferably 2 or less, from the viewpoint of facilitating fixation of the orientation of the fluorene ring relative to the main chain and of efficiently attaining the reversed wavelength dispersion characteristics. On the other hand, from the viewpoint of imparting flexibility to the resin composition, the carbon number is preferably 2 or more, more preferably 3 or more, even more preferably 4 or more.

From the viewpoint of increasing the fluorene ratio and in case where $R^3$ is an optionally-substituted alkylene group, the carbon number thereof is preferably 4 or less, more preferably 2 or less.

The substituent that the alkylene group may have includes a halogen atom (e.g., fluorine atom, chlorine atom, bromine atom, iodine atom); an alkoxy group having from 1 to 10 carbon atoms (e.g., methoxy group, ethoxy group, etc.), an acyl group having from 1 to 10 carbon atoms (e.g., acetyl group, benzoyl group, etc.); an acylamino group having from 1 to 10 carbon atoms (e.g., acetamide group, benzoylamide group, etc.); a nitro group; a cyano group; an aryl group (e.g., phenyl group, naphthyl group, etc.) having from 6 to 10 carbon atoms and optionally having from 1 to 3 substituents selected from a halogen atom (e.g., fluorine atom, chlorine atom, bromine atom, iodine atom), an alkyl group having from 1 to 10 carbon atoms (e.g., methyl group, ethyl group, isopropyl group, etc.), an alkoxy group having from 1 to 10 carbon atoms (e.g., methoxy group, ethoxy group, etc.), an acyl group having from 1 to 10 carbon atoms (e.g., acetyl group, benzoyl group, etc.), an acylamino group having from 1 to 10 carbon atoms (e.g., acetamide group, benzoylamide group, etc.), a nitro group, a cyano group and others, etc. Not specifically defined, the number of the substituents is preferably from 1 to 3. When the alkylene group has 2 or more substituents, the type of the substituents may be the same or different. From the viewpoint of industrial inexpensive production, the alkylene group is unsubstituted.

Specific examples of the optionally-substituted alkylene group include an alkyl group-substituted alkylene group such as a cyclobutylmethylene group, a cyclopentylmethylene group, a cyclohexylmethylene group, a 1-cyclohexylpropylene group, etc.; an aryl group-substituted alkylene group such as a phenylmethylene group, a 1-phenylethylene group, a 1-phenylpropylene group, etc.; a halogen atom-substituted alkylene group such as a 1,1,2,2-tetrafluoroethylene group, a trichloromethylmethylene group, a trifluoromethylmethylene group, etc.; an alkoxy group-substituted alkylene group such as a 2-methoxymethyl-2-methylpropylene group, etc. (In $R^1$ and $R^2$, the substituent position is numbered from the carbon on the fluorene ring side.)

In $R^1$ to $R^3$, specific structures of "optionally-substituted arylene group having from 4 to 10 carbon atoms" include the following, to which, however, the invention is not limited: There are mentioned a phenylene group such as a 1,2-phenylene group, a 1,3-phenylene group, a 1,4-phenylene group, etc.; a naphthylene group such as a 1,5-naphthylene group, a 2,6-naphthylene group, etc.; a heteroarylene group such as a 2,5-pyridylene group, a 2,4-thienylene group, a 2,4-furylene group, etc.

The carbon number of the optionally-substituted arylene group having from 4 to 10 carbon atoms is preferably 8 or less, more preferably 6 or less.

From the viewpoint of increasing the fluorene ratio and in case where $R^3$ is an optionally-substituted arylene group, the carbon number thereof is preferably 8 or less, more preferably 6 or less.

The substituent that the arylene group may have includes a halogen atom (e.g., fluorine atom, chlorine atom, bromine atom, iodine atom); an alkyl group having from 1 to 10 carbon atoms (e.g., methyl group, ethyl group, isopropyl group, etc.), an alkoxy group having from 1 to 10 carbon atoms (e.g., methoxy group, ethoxy group, etc.), an acyl group having from 1 to 10 carbon atoms (e.g., acetyl group, benzoyl group, etc.); an acylamino group having from 1 to 10 carbon atoms (e.g., acetamide group, benzoylamide group, etc.); a nitro group; a cyano group, etc. Not specifically defined, the number of the substituents is preferably from 1 to 3. When the arylene group has 2 or more substituents, the type of the substituents may be the same or different. From the viewpoint of industrial inexpensive production, the arylene group is unsubstituted.

Specific examples of the optionally-substituted arylene group include a 2-methyl-1,4-phenylene group, a 3-methyl-1,4-phenylene group, a 3,5-dimethyl-1,4-phenylene group, a 3-methoxy-1,4-phenylene group, a 3-trifluoromethyl-1,4-phenylene group, a 2,5-dimethoxy-1,4-phenylene group, a 2,3,5,6-tetrafluoro-1,4-phenylene group, a 2,3,5,6-tetrachloro-1,4-phenylene group, a 3-nitro-1,4-phenylene group, a 3-cyano-1,4-phenylene group, etc.

In $R^1$ to $R^3$, specific structures of "optionally-substituted aralkylene group having from 6 to 10 carbon atoms" include the following, to which, however, the invention is not limited: Aralkylene groups shown in the following group [E]:

[Chem. 18]

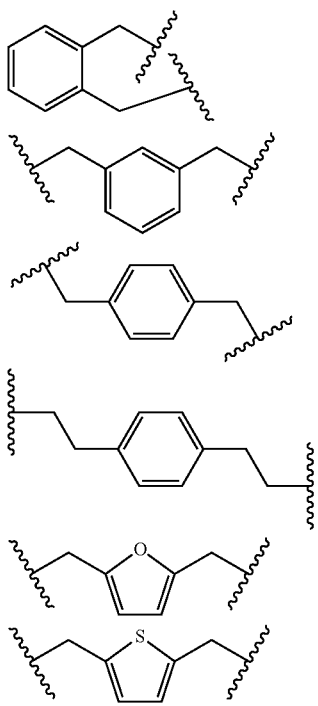

[E]

The carbon number of the optionally-substituted aralkylene group having from 6 to 10 carbon atoms is preferably 8 or less.

From the viewpoint of increasing the fluorene ratio and in case where $R^3$ is an optionally-substituted aralkylene group, the carbon number thereof is preferably 8 or less. The substituent that the aralkylene group may have includes a halogen atom (e.g., fluorine atom, chlorine atom, bromine atom, iodine atom); an alkyl group having from 1 to 10 carbon atoms (e.g., methyl group, ethyl group, isopropyl group, etc.); an alkoxy group having from 1 to 10 carbon atoms (e.g., methoxy group, ethoxy group, etc.), an acyl group having from 1 to 10 carbon atoms (e.g., acetyl group, benzoyl group, etc.); an acylamino group having from 1 to 10 carbon atoms (e.g., acetamide group, benzoylamide group, etc.); a nitro group; a cyano group; an aryl group (e.g., phenyl group, naphthyl group, etc.) having from 6 to 10 carbon atoms and optionally having from 1 to 3 substituents selected from a halogen atom (e.g., fluorine atom, chlorine atom, bromine atom, iodine atom), an alkyl group having from 1 to 10 carbon atoms (e.g., methyl group, ethyl group, isopropyl group, etc.), an alkoxy group having from 1 to 10 carbon atoms (e.g., methoxy group, ethoxy group, etc.), an acyl group having from 1 to 10 carbon atoms (e.g., acetyl group, benzoyl group, etc.), an acylamino group having from 1 to 10 carbon atoms (e.g., acetamide group, benzoylamide group, etc.), a nitro group, a cyano group and others, etc. Not specifically defined, the number of the substituents is preferably from 1 to 3. When the aralkylene group has 2 or more substituents, the type of the substituents may be the same or different. From the viewpoint of industrial inexpensive production, the aralkylene group is unsubstituted.

Specific examples of the optionally-substituted aralkylene group include a 2-methyl-1,4-xylylene group, a 2,5-dimethyl-1,4-xylylene group, a 2-methoxy-1,4-xylylene group, a 2,5-dimethoxy-1,4-xylylene group, a 2,3,5,6-tetrafluoro-1,4-xylylene group, an α,α-dimethyl-1,4-xylylene group, an α,α,α',α'-tetramethyl-1,4-xylylene group, etc.

In $R^1$ and $R^2$, specific structures of "group formed by bonding at least two groups selected from the group consisting of an optionally-substituted alkylene group having from 1 to 10 carbon atoms, an optionally-substituted arylene group having from 4 to 10 carbon atoms, or an optionally-substituted aralkylene group having from 6 to 10 carbon atoms, via an oxygen atom, an optionally-substituted sulfur atom, an optionally-substituted nitrogen atom or a carbonyl group" are as follows, to which, however, the invention is not limited. Divalent groups shown by the following group [F]:

[Chem. 19]

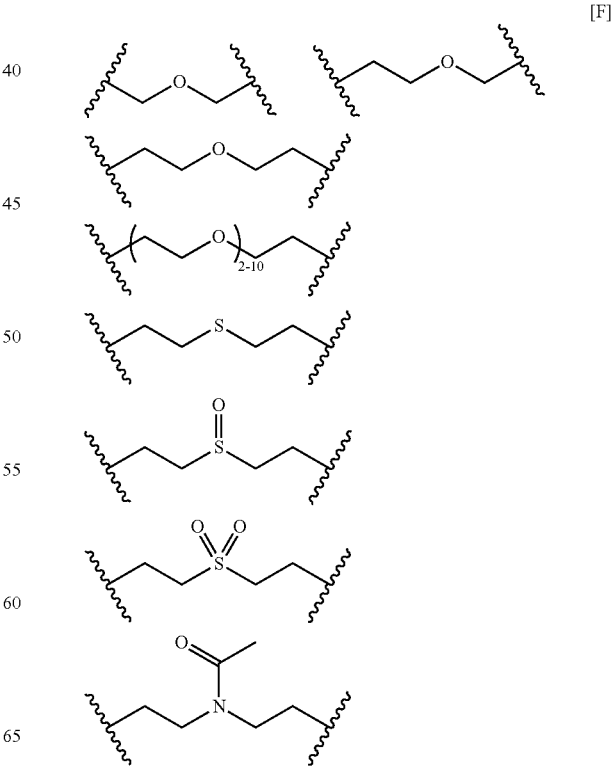

[F]

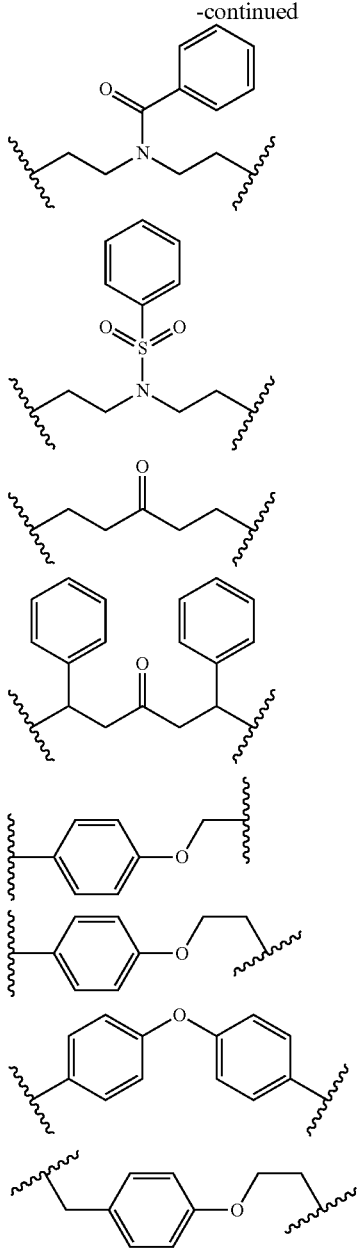

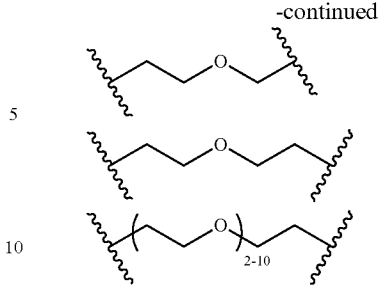

From the viewpoint of increasing the fluorene ratio and in case where $R^3$ is a group formed by bonding the above-mentioned groups, it is desirable that the carbon number of the group is 2 or more and is 6 or less, more preferably 4 or less.

Of those for $R^1$ and $R^2$, preferred is a direct bond, an optionally-substituted alkylene group having from 1 to 10 carbon atoms, an optionally-substituted arylene group having from 4 to 10 carbon atoms, or a group formed by bonding at least two groups selected from the group consisting of an optionally-substituted alkylene group having from 1 to 10 carbon atoms, an optionally-substituted arylene group having from 4 to 10 carbon atoms and an optionally-substituted aralkylene group having from 6 to 10 carbon atoms, via an oxygen atom, an optionally-substituted sulfur atom or a carbonyl group; more preferred is a direct bond, a linear alkylene group, an alkylene group containing a branched chain, an alicyclic alkylene group having a bond of a linear or branched alkylene group at any two sites of an alicyclic structure such as that shown in the above-mentioned group [C], a phenylene group, or a group formed by bonding at least two groups selected from the group consisting of an optionally-substituted alkylene group having from 1 to 10 carbon atoms, an optionally-substituted arylene group having from 4 to 10 carbon atoms and an optionally-substituted aralkylene group having from 6 to 10 carbon atoms, via an oxygen atom; even more preferred is a direct bond, a methylene group, an ethylene group, an n-propylene group, an n-butylene group, a methylmethylene group, a 1-methylethylene group, a 2-methylethylene group, a 2,2-dimethylpropylene group, a 2-methoxymethyl-2-methylpropylene group or an alicyclic alkylene group shown by the following group [H]:

[Chem. 21]

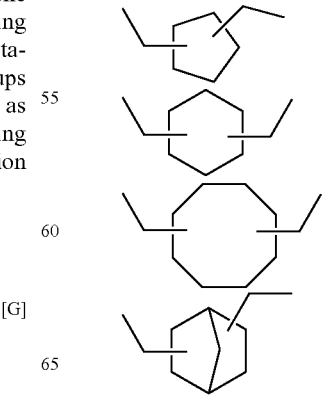

[H]

Of those, preferred are groups formed by bonding at least two groups selected from an alkylene group, an arylene group or an aralkylene group, as capable of imparting flexibility while maintaining the transparency and the stability of the resin composition. More preferred are groups formed by bonding alkylene groups via an oxygen atom, as shown in the following group [G], as capable of elevating the glass transition temperature of the resin composition while imparting flexibility.

[Chem. 20]

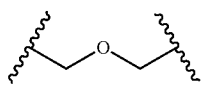

[G]

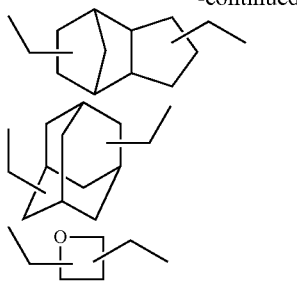

(the substituting position of the two bonds in the cyclic structure shown in the above group [H] is any arbitrary one, and two bonds may bond to one and the same carbon), as having no aromatic ring and therefore capable of attaining a low photoelastic coefficient desired for optical films; still more preferred is a direct bond, a methylene group, an ethylene group, an n-propylene group, an n-butylene group, a methylmethylene group, a 1-methylethylene group, a 2-methylethylene group, or a 2,2-dimethylpropylene group; and further more preferred is a methylene group, an ethylene group or an n-propylene group. When the chain length is long, the glass transition temperature may tend to be low, and therefore, preferred here is a group having a short chain, for example a group having 2 or less carbon atoms. Further, since the molecular structure can be small and therefore the concentration of the fluorene ring (fluorene ratio) in the repeating unit can be increased in the case, the desired optical properties can be efficiently expressed. Most preferred is a methylene group, since the resin composition can have flat wavelength dispersion characteristics of weak wavelength dispersion of retardation even when the oligofluorene component is contained in any desired mass relative to the total mass of the resin composition, and further another advantage of the case is that the oligofluorene can be produced in a short process and inexpensively on an industrial scale.

On the other hand, also preferred is an arylene group having from 4 to 10 carbon atoms, or a group formed by bonding at least two groups selected from an optionally-substituted alkylene group having from 1 to 10 carbon atoms and an arylene group having from 4 to 10 carbon atoms via an oxygen atom, as capable of increasing the glass transition temperature of the resin composition for the purpose of improving the mechanical strength and the high-temperature reliability of the film to be produced; and more preferred is a 1,4-phenylene group, a 1,5-naphthylene group, a 2,6-naphthylene group, or a divalent group shown by the following group [F2]:

[Chem. 22]

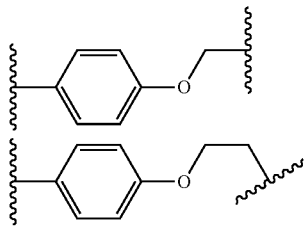

[F2]

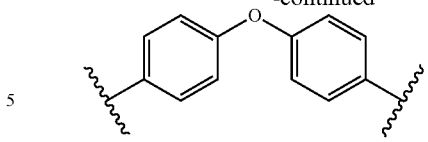

When the resin composition is applied to a retardation film having reversed wavelength dispersion characteristics of retardation, it is important to suitably select $R^1$ and $R^2$. For example, a group having 1 carbon atom such as typically a methylene group tends to unexpectedly provide low-level reversed wavelength dispersion characteristics of retardation, and therefore it is desirable that $R^1$ and $R^2$ are both direct bonds, or at least any one of them is a group having 2 or more carbon atoms.

More preferred is a direct bond, an optionally-substituted alkylene group having from 2 to 10 carbon atoms, an optionally substituted arylene group having from 4 to 10 carbon atoms, or a group formed by bonding at least two groups selected from an optionally substituted alkylene group having from 1 to 10 carbon atoms, an optionally-substituted arylene group having from 4 to 10 carbon atoms and optionally-substituted aralkylene group having from 6 to 10 carbon atoms, via an oxygen atom, an optionally-substituted sulfur atom, an optionally-substituted nitrogen atom or a carbonyl group.

Even more preferred is a direct bond, a linear alkylene group, an alkylene group containing a branched chain, an alicyclic alkylene group having a bond of a linear or branched alkylene group at any two sites of an alicyclic structure such as that shown in the above-mentioned group [C], a phenylene group, or a group formed by bonding at least two groups selected from the group consisting of an optionally-substituted alkylene group having from 1 to 10 carbon atoms, an optionally-substituted arylene group having from 4 to 10 carbon atoms and an optionally-substituted aralkylene group having from 6 to 10 carbon atoms, via an oxygen atom.

Still more preferred is a direct bond, an ethylene group, an n-propylene group, an n-butylene group, a methylmethylene group, a 1-methylethylene group, a 2-methylethylene group, a 2,2-dimethylpropylene group, a 2-methoxymethyl-2-methylpropylene group or an alicyclic alkylene group shown by the above-mentioned group [H], as having no aromatic ring and therefore capable of attaining a low photoelastic coefficient desired for optical films, or as capable of increasing the glass transition temperature of the resin composition, preferred is a 1,4-phenylene group, or a group formed by bonding at least two groups selected from an optionally-substituted alkylene group having from 1 to 10 carbon atoms and an optionally-substituted arylene group having from 4 to 10 carbon atoms, via an oxygen atom.

Especially preferred is a direct bond, an ethylene group, an n-propylene group, an n-butylene group, a methylmethylene group, a 1-methylethylene group, a 2-methylethylene group, or a 2,2-dimethylpropylene group.

Most preferred is an ethylene group or an n-propylene group. When the chain length is long, then the glass transition temperature of the resin composition tends to be low, and therefore preferred is a group having a short chain, for example, a group having 3 or less carbon atoms. Further, since the molecular structure can be small and therefore the concentration of the fluorene ring (fluorene ratio) in the repeating unit can be increased in the case, the desired optical properties can be efficiently expressed.

Also preferably, $R^1$ and $R^2$ are the same, as facilitating compound production.

Of those mentioned above for $R^3$, preferred is an optionally-substituted alkylene group having from 1 to 10 carbon atoms, or an optionally-substituted arylene group having from 4 to 10 carbon atoms, and more preferred is a linear alkylene group, an alkylene group containing a branched chain, an alicyclic alkylene group having a bond of a linear or branched alkylene group at any two sites of an alicyclic structure such as that shown in the above-mentioned group [C], or a phenylene group. Even more preferred is a methylene group, an ethylene group, an n-propylene group, an n-butylene group, a methylmethylene group, a dimethylmethylene group, an ethylmethylene group, a propylmethylene group, a butylmethylene group, a (1-methylethyl)methylene group, a 2,2-dimethylpropylene group, a phenylmethylene group, a trichloromethylmethylene group, a trifluoromethylmethylene group, an alicyclic alkylene group shown by the above-mentioned group [H] or a heterocyclic alkylene group, as having no aromatic ring and therefore capable of attaining a low photoelastic coefficient desired for optical films, or as capable of increasing the glass transition temperature of the resin composition, preferred is a 1,4-phenylene group, and more preferred is a methylene group, a methylmethylene group, an ethylene group, an n-propylene group, or a 2,2-dimethylpropylene group. A long-chain group tends to lower the glass transition temperature of the resin composition.

Specific structures of "optionally-substituted alkyl group having from 1 to 10 carbon atoms" in $R^4$ to $R^9$ include the following, to which, however, the invention is not limited: A linear alkyl group such as a methyl group, an ethyl group, an n-propyl group, an n-butyl group, an n-pentyl group, n-hexyl, n-decyl, etc.; a branched chain-containing alkyl group such as an isopropyl group, a 2-methylpropyl group, a 2,2-dimethylpropyl group, a 2-ethylhexyl group, etc.; a cyclic alkyl group such as a cyclopropyl group, a cyclopentyl group, a cyclohexyl group, a cyclooctyl group, etc.

The carbon number of the optionally-substituted alkyl group having from 1 to 10 carbon atoms is preferably 4 or less, more preferably 2 or less. Falling within the range, the fluorene rings hardly cause steric hindrance, and the oligofluorene tends to have fluorene ring-derived desired optical properties.

The substituent that the alkyl group may have includes a halogen atom (e.g., fluorine atom, chlorine atom, bromine atom, iodine atom); an alkoxy group having from 1 to 10 carbon atoms (e.g., methoxy group, ethoxy group, etc.), an acyl group having from 1 to 10 carbon atoms (e.g., acetyl group, benzoyl group, etc.); an acylamino group having from 1 to 10 carbon atoms (e.g., acetamide group, benzoylamide group, etc.); a nitro group; a cyano group; an aryl group (e.g., phenyl group, naphthyl group, etc.) having from 6 to 10 carbon atoms and optionally having from 1 to 3 substituents selected from a halogen atom (e.g., fluorine atom, chlorine atom, bromine atom, iodine atom), an alkyl group having from 1 to 10 carbon atoms (e.g., methyl group, ethyl group, isopropyl group, etc.), an alkoxy group having from 1 to 10 carbon atoms (e.g., methoxy group, ethoxy group, etc.), an acyl group having from 1 to 10 carbon atoms (e.g., acetyl group, benzoyl group, etc.), an acylamino group having from 1 to 10 carbon atoms (e.g., acetamide group, benzoylamide group, etc.), a nitro group, a cyano group and others, etc. Not specifically defined, the number of the substituents is preferably from 1 to 3. When the alkyl group has 2 or more substituents, the type of the substituents may be the same or different. From the viewpoint of industrial inexpensive production, the alkyl group is unsubstituted.

Specific examples of the optionally-substituted alkyl group include a trifluoromethyl group, a benzyl group, a 4-methoxybenzyl group, a methoxymethyl group, etc.

Specific structures of "optionally-substituted aryl group having from 4 to 10 carbon atoms" in $R^4$ to $R^9$ include the following, to which, however, the invention is not limited: An aryl group such as a phenyl group, a 1-naphthyl group, a 2-naphthyl group, etc.; a heteroaryl group such as a 2-pyridyl group, a 2-thienyl group, a 2-furyl group, etc.

The carbon number of the optionally-substituted aryl group having from 4 to 10 carbon atoms is preferably 8 or less, more preferably 7 or less. Falling within the range, the fluorene rings hardly cause steric hindrance, and the oligofluorene tends to have fluorene ring-derived desired optical properties.

The substituent that the aryl group may have includes a halogen atom (e.g., fluorine atom, chlorine atom, bromine atom, iodine atom); an alkyl group having from 1 to 10 carbon atoms (e.g., methyl group, ethyl group, isopropyl group, etc.); an alkoxy group having from 1 to 10 carbon atoms (e.g., methoxy group, ethoxy group, etc.), an acyl group having from 1 to 10 carbon atoms (e.g., acetyl group, benzoyl group, etc.); an acylamino group having from 1 to 10 carbon atoms (e.g., acetamide group, benzoylamide group, etc.); a nitro group; a cyano group, etc. Not specifically defined, the number of the substituents is preferably from 1 to 3. When the aryl group has 2 or more substituents, the type of the substituents may be the same or different. From the viewpoint of industrial inexpensive production, the aryl group is unsubstituted.

Specific examples of the optionally-substituted aryl group include a 2-methylphenyl group, a 4-methylphenyl group, a 3,5-dimethylphenyl group, a 4-benzoylphenyl group, a 4-methoxyphenyl group, a 4-nitrophenyl group, a 4-cyanophenyl group, a 3-trifluoromethylphenyl group, a 3,4-dimethoxyphenyl group, a 3,4-methylenedioxyphenyl group, a 2,3,4,5,6-pentafluorophenyl group, a 4-methylfuryl group, etc.

Specific structures of "optionally-substituted acyl group having from 1 to 10 carbon atoms" in $R^4$ to $R^9$ include the following, to which, however, the invention is not limited: An aliphatic acyl group such as a formyl group, an acetyl group, a propionyl group, a 2-methylpropionyl group, a 2,2-dimethylpropionyl group, a 2-ethylhexanoyl group, etc.; an aromatic acyl group such as a benzoyl group, a 1-naphthylcarbonyl group, a 2-naphthylcarbonyl group, a 2-furylcarbonyl group, etc.

The carbon number of the optionally-substituted acyl group having from 1 to 10 carbon atoms is preferably 4 or less, more preferably 2 or less. Falling within the range, the fluorene rings hardly cause steric hindrance, and the oligofluorene tends to have fluorene ring-derived desired optical properties.

The substituent that the acyl group may have includes a halogen atom (e.g., fluorine atom, chlorine atom, bromine atom, iodine atom); an alkyl group having from 1 to 10 carbon atoms (e.g., methyl group, ethyl group, isopropyl group, etc.); an alkoxy group having from 1 to 10 carbon atoms (e.g., methoxy group, ethoxy group, etc.), an acylamino group having from 1 to 10 carbon atoms (e.g., acetamide group, benzoylamide group, etc.); a nitro group; a cyano group; an aryl group (e.g., phenyl group, naphthyl group, etc.) having from 6 to 10 carbon atoms and optionally having from 1 to 3 substituents selected from a halogen atom (e.g., fluorine atom, chlorine atom, bromine atom, iodine atom), an alkyl group having from 1 to 10 carbon atoms (e.g., methyl group, ethyl group, isopropyl group, etc.), an alkoxy group having from 1 to 10 carbon atoms (e.g., methoxy group, ethoxy group, etc.), an acyl group having from 1 to 10 carbon atoms (e.g., acetyl group, benzoyl group, etc.), an acylamino group having from 1 to 10 carbon atoms (e.g., acetamide group, benzoylamide group, etc.), a nitro group, a cyano group and others, etc. Not specifically defined, the number of the substituents is preferably from 1 to 3. When the acyl group has 2 or more substituents, the type of the substituents may be the same or different. From the viewpoint of industrial inexpensive production, the acyl group is unsubstituted.

Specific examples of the optionally-substituted acyl group include a chloroacetyl group, a trifluoroacetyl group, a methoxyacetyl group, a phenoxyacetyl group, a 4-methoxybenzoyl group, a 4-nitrobenzoyl group, a 4-cyanobenzoyl group, a 4-trifluoromethylbenzoyl group, etc.

Specific structures of "optionally-substituted alkoxy group or aryloxy group having from 1 to 10 carbon atoms" in $R^4$ to $R^9$ include the following, to which, however, the invention is not limited: An alkoxy group such as a methoxy group, an ethoxy group, an isopropoxy group, a t-butoxy group, a trifluoromethoxy group, a phenoxy group, etc.; an acyloxy group such as an acetoxy group, a benzoyloxy group, etc.

The carbon number of the optionally-substituted alkoxy group or aryloxy group having from 1 to 10 carbon atoms is preferably 4 or less, more preferably 2 or less. Falling within the range, the fluorene rings hardly cause steric hindrance, and the oligofluorene tends to have fluorene ring-derived desired optical properties.

Specific structures of "optionally-substituted amino group" in $R^4$ to $R^9$ include the following, to which, however, the invention is not limited: An amino group; an aliphatic amino group such as an N-methylamino group, an N,N-dimethylamino group, an N-ethylamino group, an N,N-diethylamino group, a N,N-methylethylamino group, an N-propylamino group, an N,N-dipropylamino group, an N-isopropylamino group, an N,N-diisopropylamino group, etc.; an aromatic amino group such as an N-phenylamino group, an N,N-diphenylamino group, etc.; an acylamino group such as a formamide group, an acetamide group, a decanoylamide group, a benzoylamide group, a chloroacetamide group, etc.; an alkoxycarbonylamino group such as a benzyloxycarbonylamino group, a tert-butyloxycarbonylamino group, etc.

Of those, preferred is an N,N-dimethylamino group, an N-ethylamino group or an N,N-diethylamino group, as not having a proton having a high degree of acidity, having a small molecular weight and capable of increasing the fluorene ratio, and more preferred is an N,N-dimethylamino group.

Specific structures of "sulfur atom optionally having a substituent" in $R^4$ to $R^9$ include the following, to which, however, the invention is not limited: A sulfo group; an alkylsulfonyl group such as a methylsulfonyl group, an ethylsulfonyl group, a propylsulfonyl group, an isopropylsulfonyl group, etc.; an arylsulfonyl group such as a phenylsulfonyl group, a p-tolylsulfonyl group, etc.; an alkylsulfinyl group such as a methylsulfinyl group, an ethylsulfinyl group, a propylsulfinyl group, an isopropylsulfinyl group, etc.; an arylsulfinyl group such as a phenylsulfinyl group, a p-tolylsulfonyl group, etc.; an alkylthio group such as a methylthio group, an ethylthio group, etc.; an arylthio group such as a phenylthio group, a p-tolylthio group, etc.; an alkoxysulfonyl group such as a methoxysulfonyl group, an ethoxysulfonyl group, etc.; an aryloxysulfonyl group such as a phenoxysulfonyl group, etc.; an aminosulfonyl group; an alkylsulfonyl group such as an N-methylaminosulfonyl group, an N-ethylaminosulfonyl group, an N-tert-butylaminosulfonyl group, an N,N-dimethylaminosulfonyl group, an N,N-diethylaminosulfonyl group, etc.; an arylaminosulfonyl group such as an N-phenylaminosulfonyl group, an N,N-diphenylaminosulfonyl group, etc. The sulfo group may form a salt with lithium, sodium, potassium, magnesium, ammonium or the like.

Of those, preferred is a methylsulfinyl group, an ethylsulfinyl group or a phenylsulfinyl group, as not having a proton having a high degree of acidity, having a small molecular weight and capable of increasing the fluorene ratio, and more preferred is a methylsulfinyl group.

"Halogen atom" in $R^4$ to $R^9$ includes a fluorine atom, chlorine atom, a bromine atom, an iodine atom.

Of those, preferred is a fluorine atom, a chlorine atom or a bromine atom as introduction of the atom is relatively easy and as the atom is an electron-attracting substituent and tends to increase the reactivity of the 9-position of fluorene. More preferred is a chlorine atom or a bromine atom.

Neighboring $R^4$ to $R^9$ may bond to each other to form a ring. Specific examples of the case include substituted fluorene structures shown in the following group [I]:

[Chem. 23]

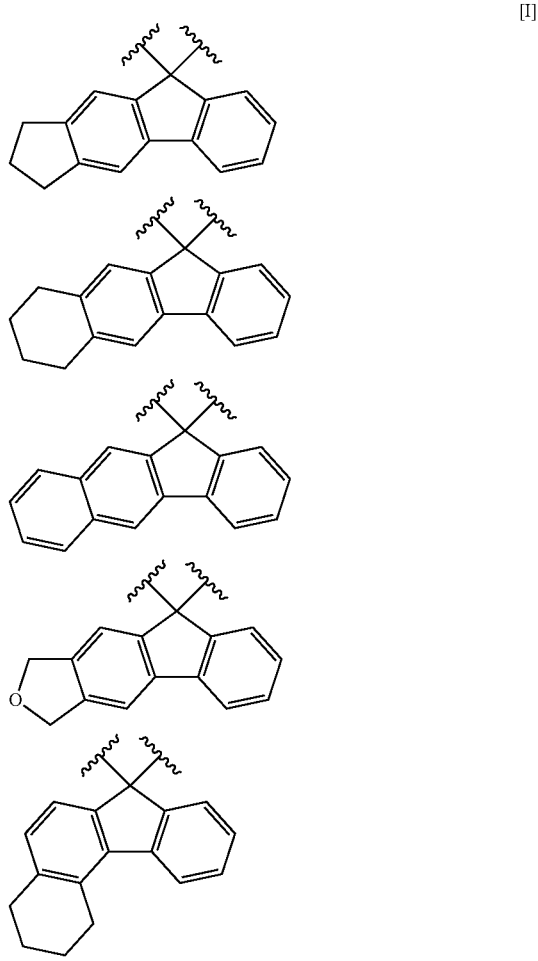

[I]

-continued

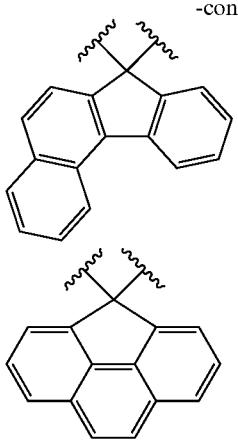

Having the above-mentioned specific atom or substituent in $R^4$ to $R^9$, the steric hindrance between the main chain and the fluorene ring and between the fluorene rings in the oligofluorene can be reduced, and therefore the oligofluorene tends to have fluorene ring-derived desired optical properties.

Preferably, those $R^4$ to $R^9$ are all hydrogen atoms, or $R^4$ and/or $R^9$ each are any one selected from a halogen atom, an acyl group, a nitro group, a cyano group and a sulfo group, and $R^5$ to $R^8$ are all hydrogen atoms. In the case where all are hydrogen atoms, the oligofluorene can be derived from an industrially inexpensive fluorene. In the case where $R^4$ and/or $R^9$ each are any one selected from a halogen atom, an acyl group, a nitro group, a cyano group and a sulfo group, and $R^5$ to $R^8$ are all hydrogen atoms, the reactivity at the 9-position of fluorene increases, and therefore various induction reactions tend to be applicable to fluorene. More preferably, all are hydrogen atoms, or $R^4$ and/or $R^9$ each are any one selected from a fluorine atom, a chlorine atom, a bromine atom and a nitro group, and $R^5$ to $R^8$ are all hydrogen atoms, and even more preferably, all are hydrogen atoms. In these embodiments, the fluorene ratio can be increased, steric hindrance between fluorene rings hardly occurs, and the oligofluorene tends to have fluorene ring-derived desired optical properties.

In the general formula (1), n indicates an integer value of from 1 to 5, but from the viewpoint of easy production of the compound, n is preferably 4 or less, more preferably 3 or less.

As described above, the divalent oligofluorene contains at least two fluorene units, and the 9-positioned carbon atoms of the fluorene units bond to each other via a direct bond or via an alkylene group optionally having a substituent, an arylene group optionally having a substituent, or an aralkylene group optionally having a substituent. More concretely, the 9-positioned carbon atoms of the two or more fluorene units may bond to each other via the group of $R^3$ in the general formula (1) mentioned above. To the substituent that the alkylene group may have, the substituent that the arylene group may have and the substituent that the aralkylene group may have, those exemplified hereinabove as the substituent in $R^3$ in the general formula (1) are applicable. To the substituents $\alpha^1$ and/or $\alpha^2$, $R^1$ and/or $R^2$ in the general formula (1) are applicable.

<1-2. Concrete Structures>

As concrete structures of the divalent oligofluorene represented by the general formula (1), there are mentioned the structures shown in the following group [J]:

[Cem. 24]

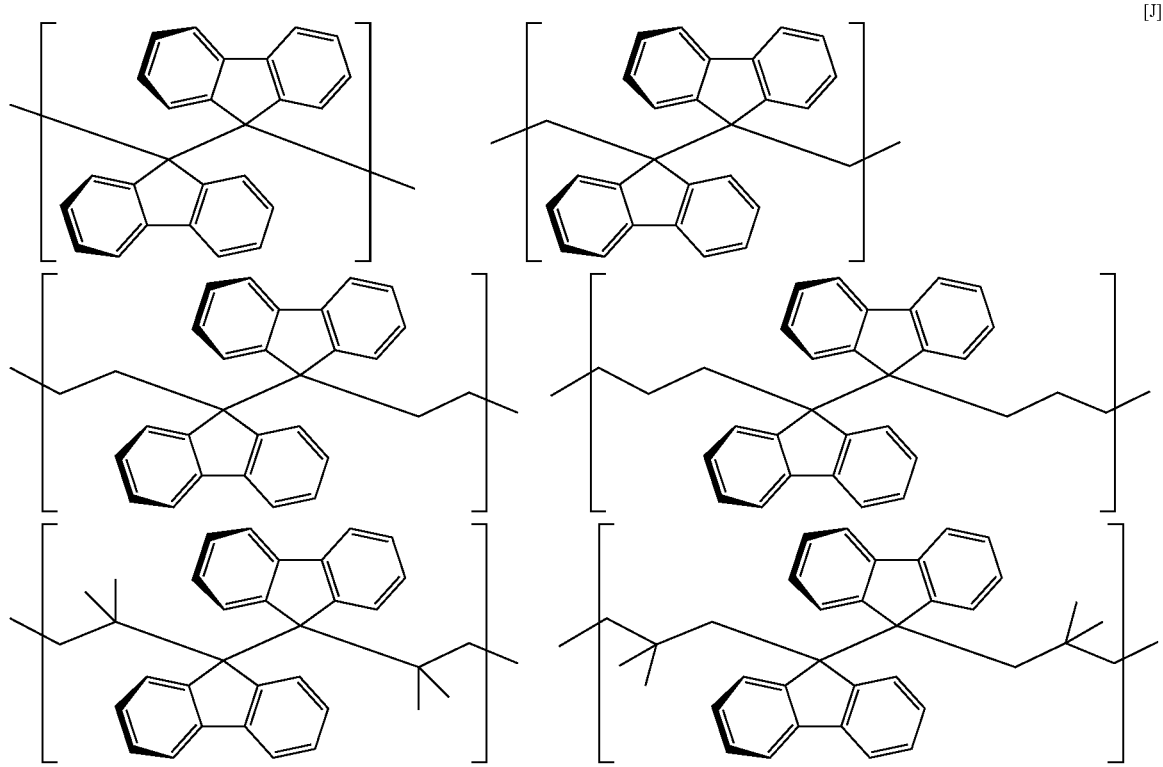

[J]

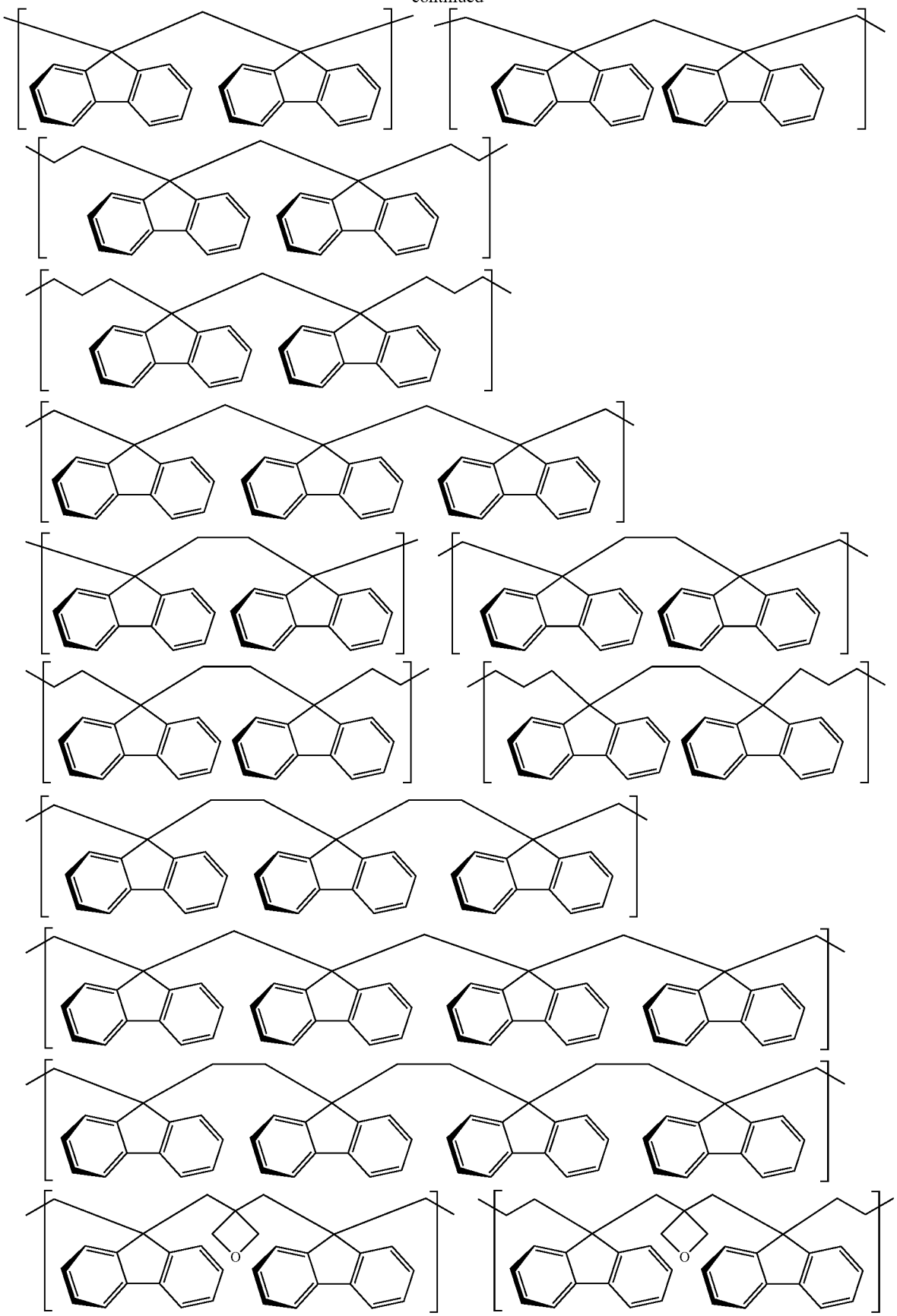

-continued
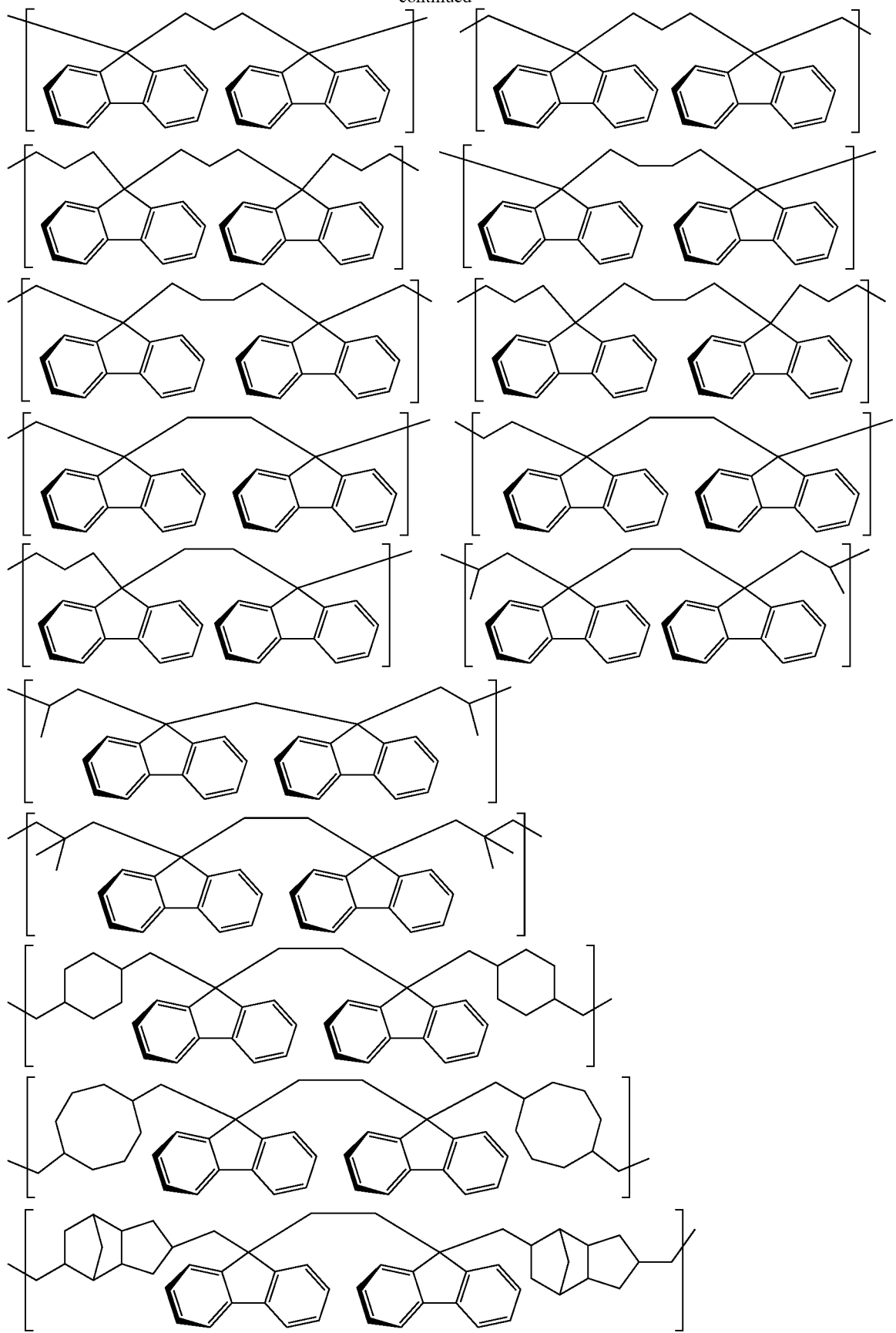

-continued
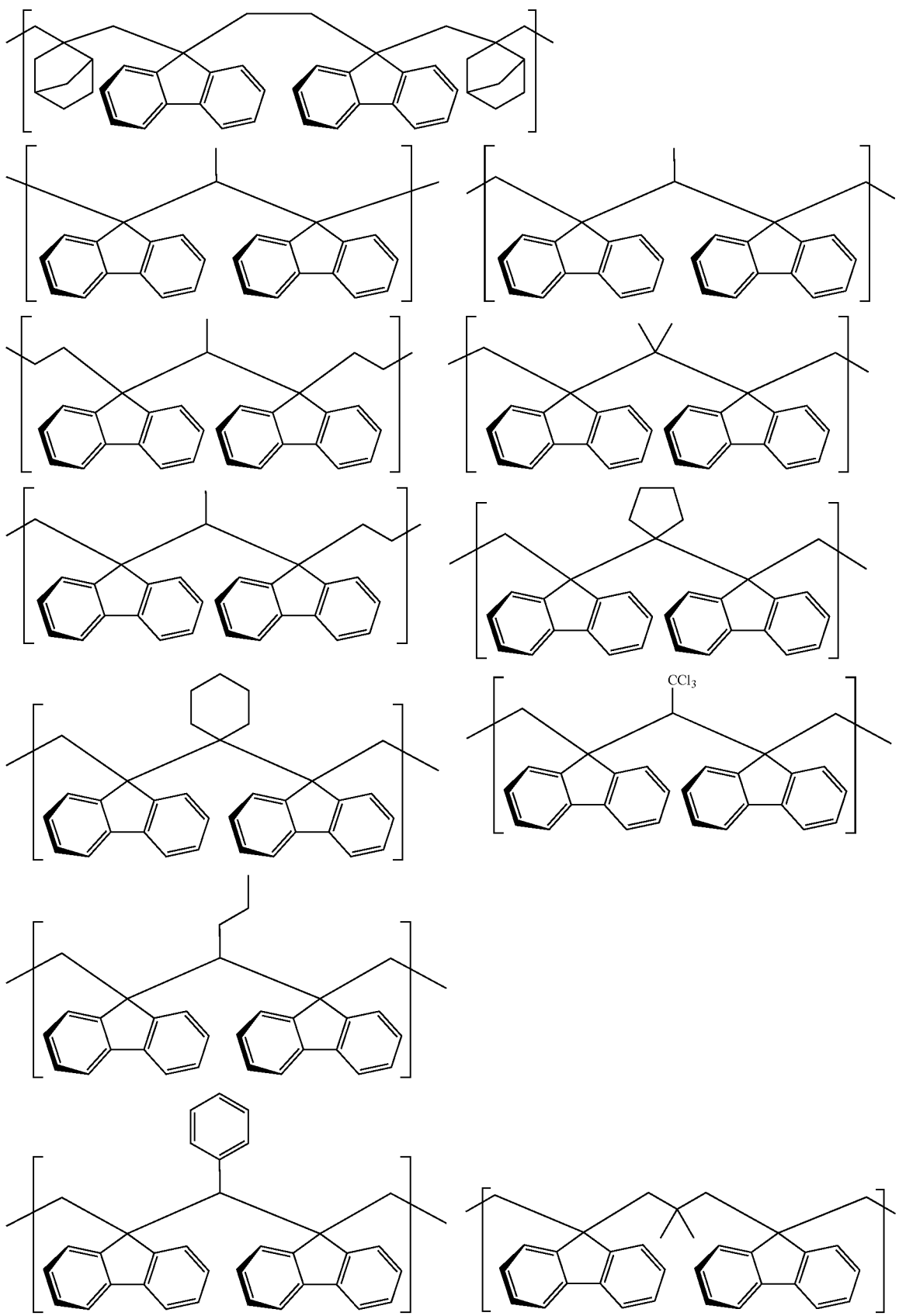

-continued
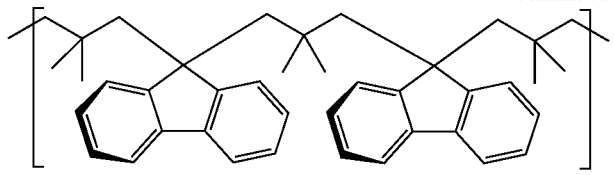
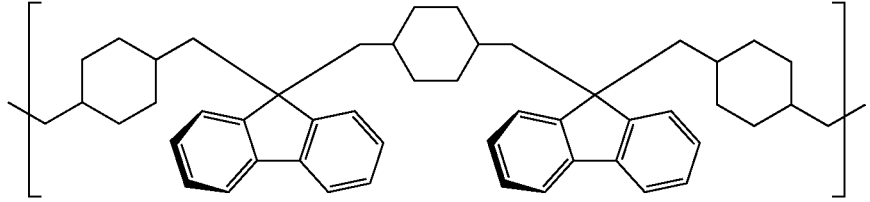
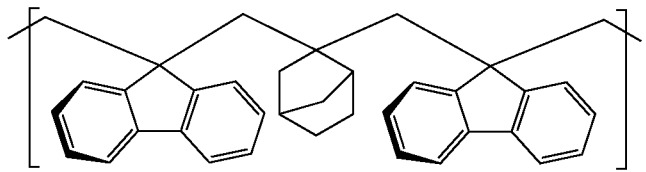
[Chem. 25]
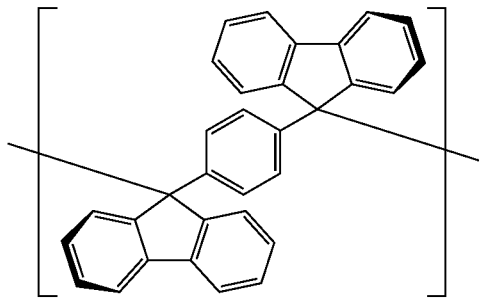
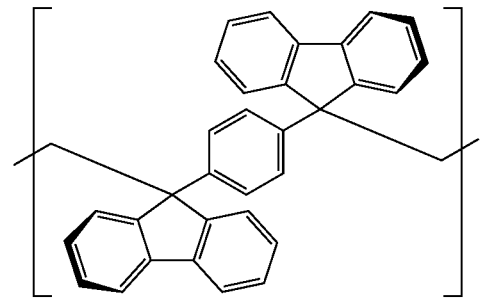
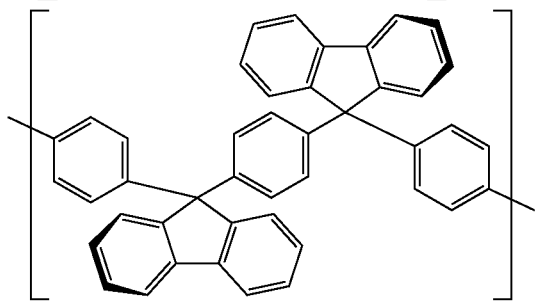
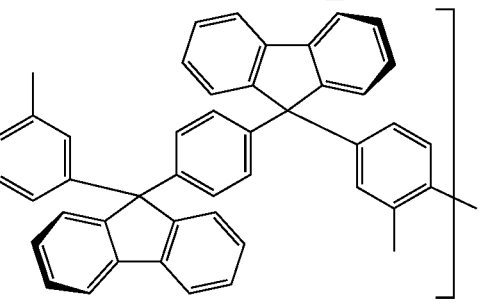
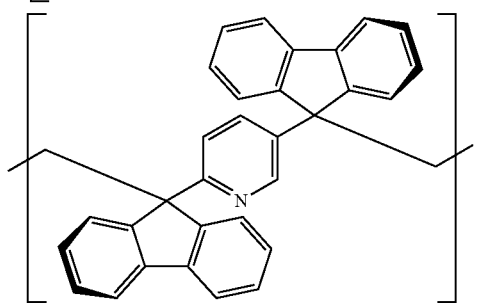
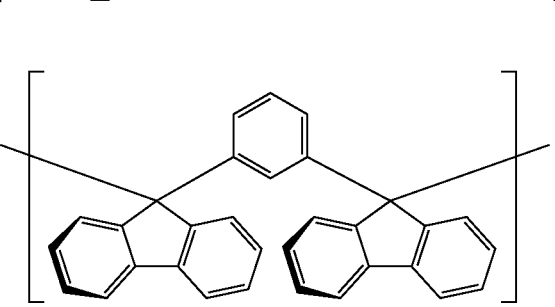
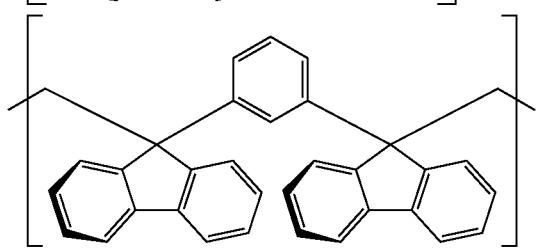
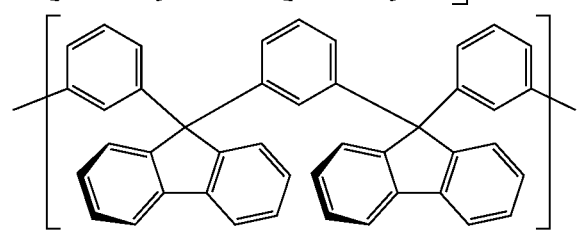

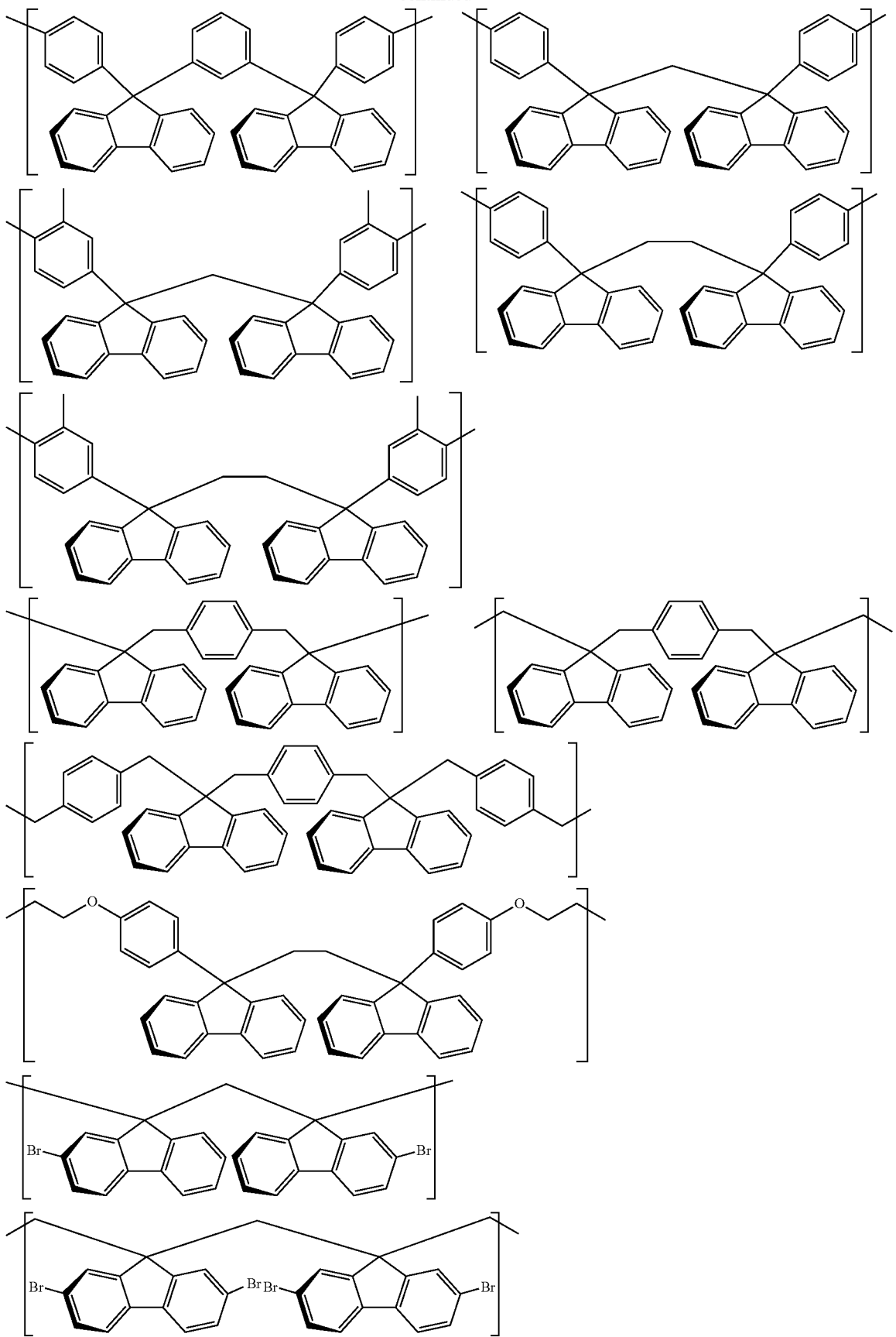

-continued
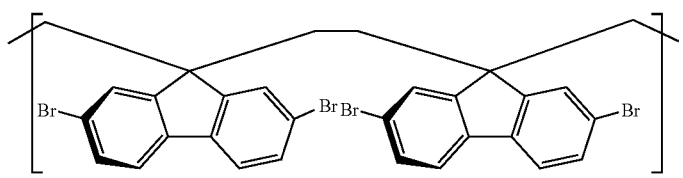
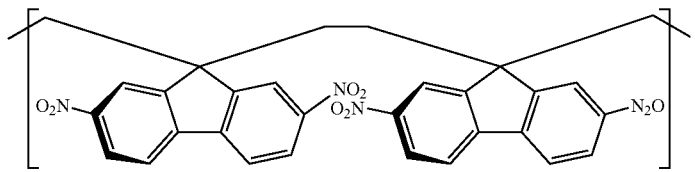
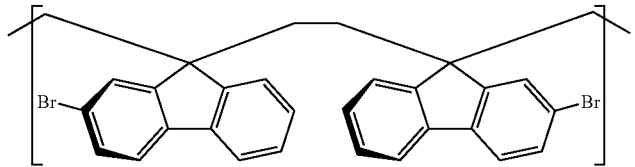
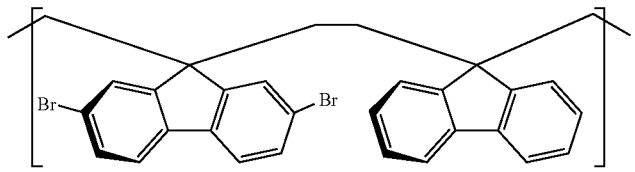
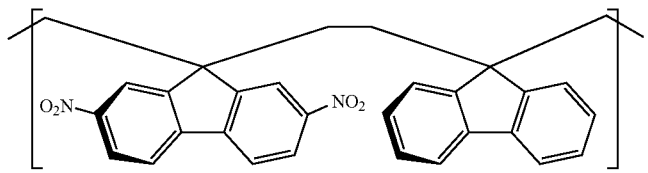
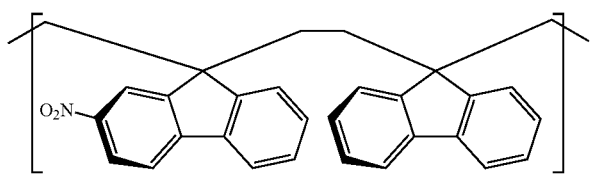
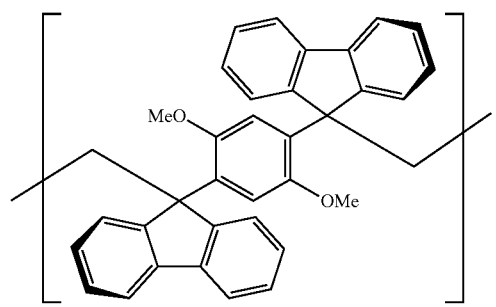
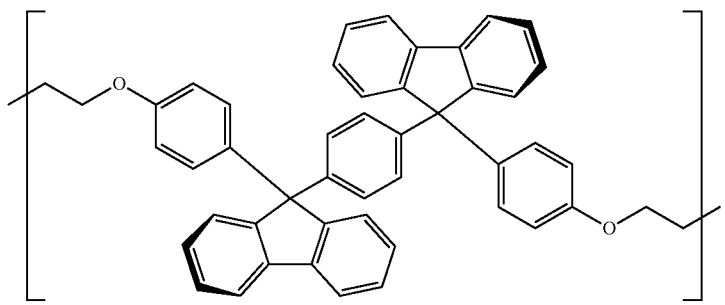
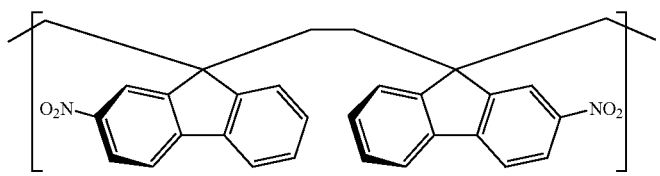

-continued
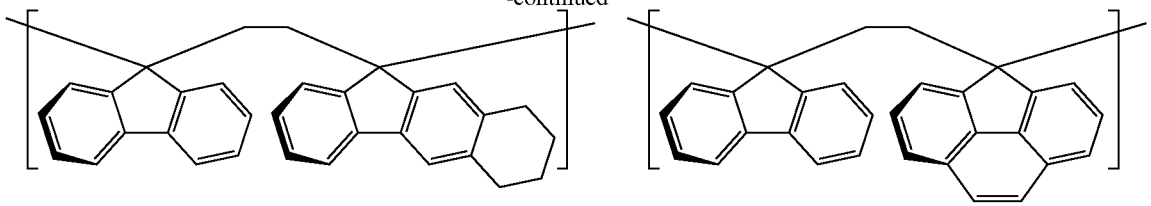
Of those, preferred divalent oligofluorenes are the structures shown in the following group [K]:
[Chem. 26]
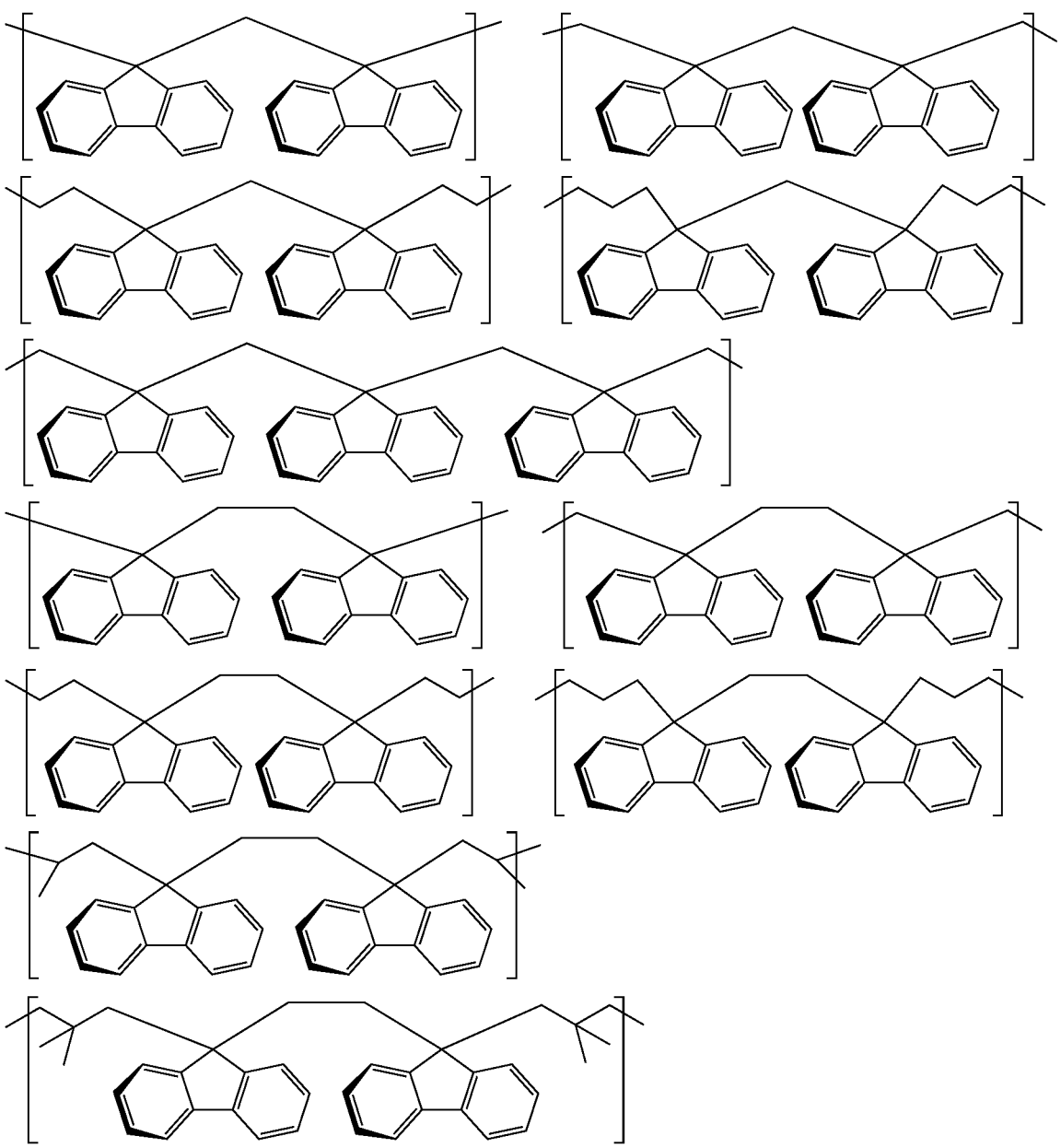
[K]

-continued
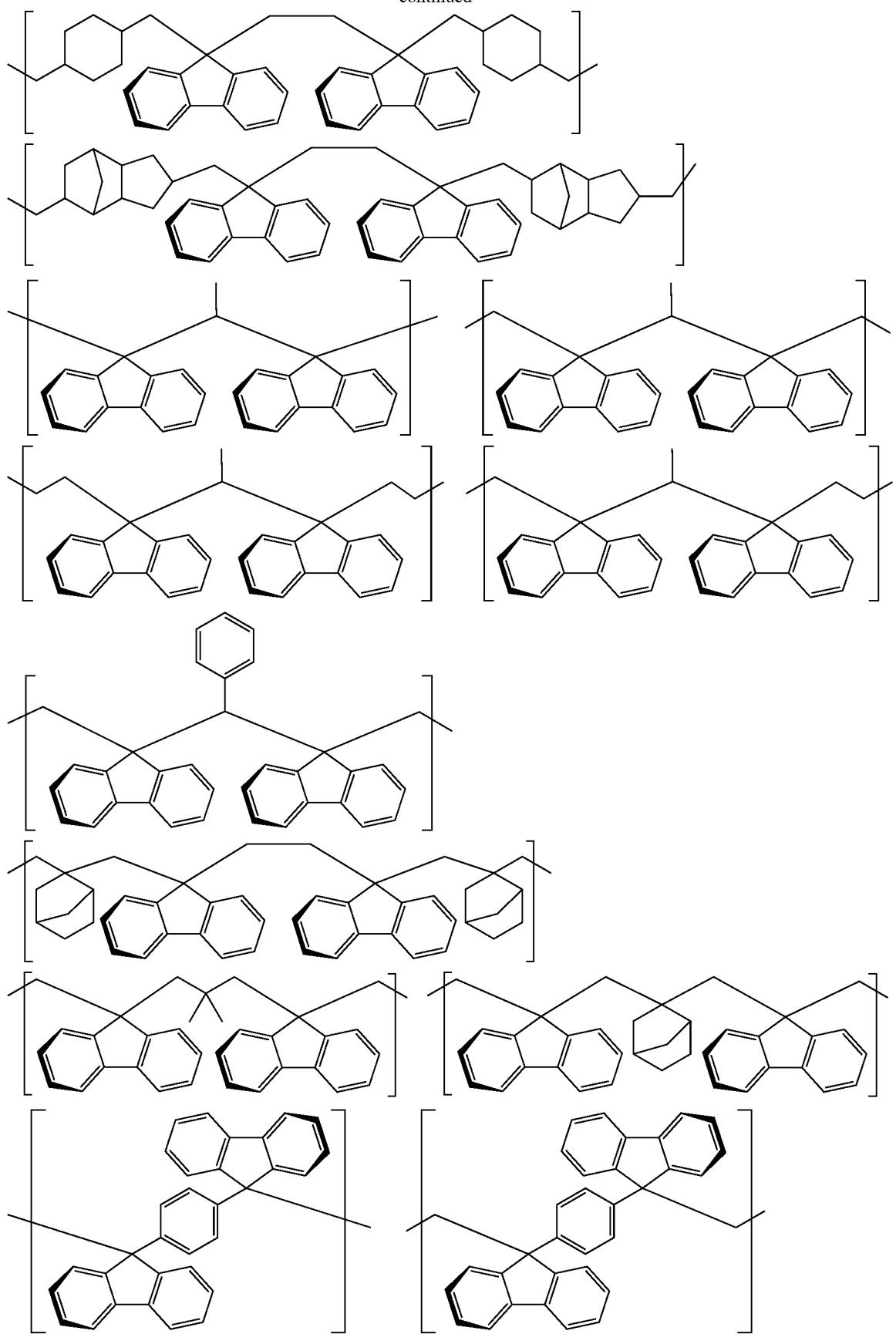

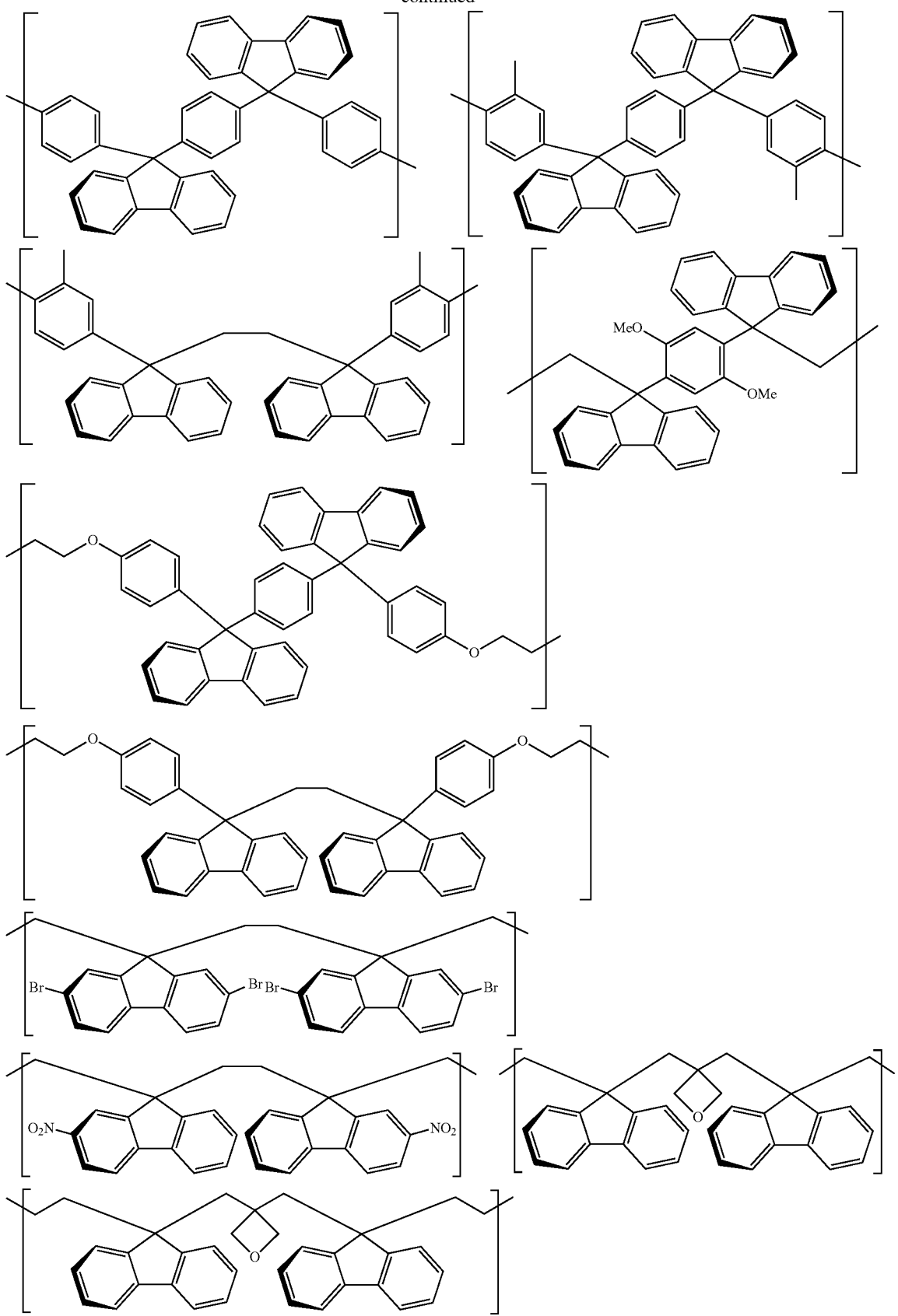

Of those, the divalent oligofluorene shown below contains two unsubstituted fluorene units, in which the 9-positioned carbon atoms of the fluorenes bond directly to each other, and the 9-positioned carbon atom of each fluorene unit is divalent.

[Chem. 27]

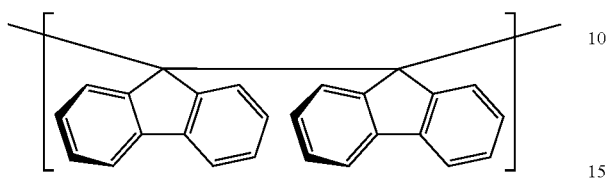

Of the above, the divalent oligofluorene shown below contains three unsubstituted fluorene units, in which the 9-positioned carbon atoms of the three fluorene units bond linearly to each other via a methylene group, and the methylene group bonding to the 9-positioned carbon of the fluorene unit positioned at both ends is a divalent group.

[Chem. 28]

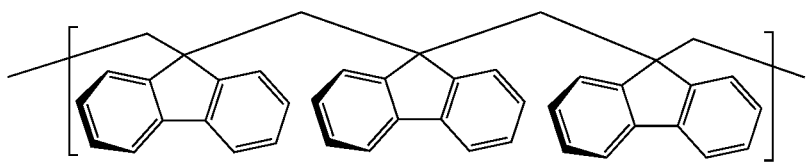

<2. Polymer>

The polymer contained in the resin composition of the present invention is one having a divalent oligofluorene as the repeating unit therein. For example, there is mentioned a polymer in which the divalent oligofluorenes bond to each other via an arbitrary linking group. The polymer may be a copolymer having any other repeating unit than the divalent oligofluorene.

<2-1. Linking Group>

Specific structures of the linking group used in the polymer includes the following, to which, however, the invention is not limited: Linking group shown by the following group [A]:

[Chem. 29]

[A]

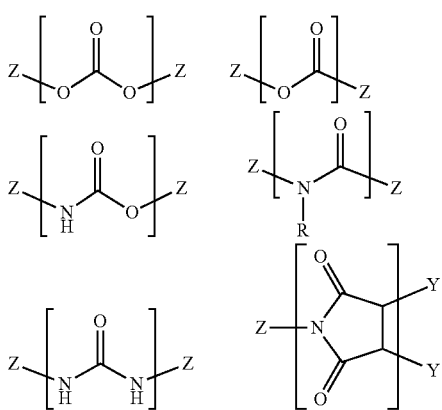

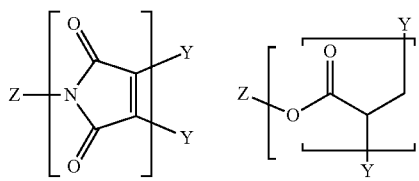

-continued

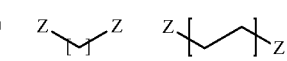

-continued

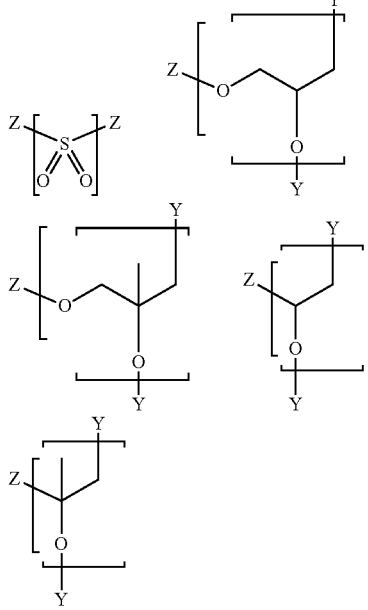

(In each linking group shown by the above-mentioned group [A], Z represents a site at which the repeating units bond to each other, Y represents a bonding site bonding to any other linking group, or a site at which an arbitrary structural unit that bonds the linking groups to each other bonds to the linking group.) A plurality of these linking groups may be used as combined. In case where the linking group is asymmetric, the linking group may bond to the repeating unit in any direction. Of those, preferred are the linking group shown by the following group [B], as constituting polyesters, polycarbonates or polyester carbonates excellent in the balance between heat resistance, melt processability and mechanical strength.

[Chem. 30]

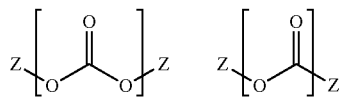

[B]

(In each linking group shown by the above group [B], Z represents a linking site at which the repeating unit bonds to the group.)

One alone or two or more different types of linking groups may be used either singly or as combined.

As the polymer in which the repeating units are bond to each other via a linking group, concretely, there are mentioned polymers containing polyolefin, polyester, polycarbonate, polyamide, polyimide, polyurethane, epoxy resin, polyacrylate, polymethacrylate or polysulfone, and polymers comprising two or more of these. Preferred are polymers containing polyolefin, polyester, polycarbonate, epoxy resin or polyacrylate, which generally have high transparency; more preferred are polymers containing polyester or polycarbonate, which are excellent in the balance between heat resistance, melt processability and mechanical strength; and even more preferred are polymers containing polycarbonate that are generally excellent in heat resistance and chemical resistance.

In the polymer using different types of linking groups as combined therein, the combination of the linking groups is not specifically defined. For example, there are mentioned a polymer using, as the linking groups, a carbonate structure and an ester structure as combined therein, a polymer using, as the linking groups, a carbonate structure and an urethane structure as combined therein, a polymer using, as the linking groups, an ester structure and an amide as combined therein, etc. Preferred is a polymer using, as the linking groups, a carbonate structure and an ester structure as combined therein. Here, specific examples of the case using different types of linking groups include polyester carbonates, carbonate bond-having polyurethanes, polyester amides, polyester imides, etc. Of those, preferred are polyester carbonates as excellent in the balance between heat resistance, melt processability and mechanical strength. In this description, a polymer having a carbonate bond is referred to as polycarbonate, and this includes not only a polymer having a carbonate bond alone as the linking group therein but also a polyester carbonate (polymer having both an ester bond and a carbonate bond), a polyurethane having a carbonate bond, etc. Here, the proportion of the carbonate bond in the polymer that includes polycarbonate may be any arbitrary value, but for the purpose of imparting excellent characteristics such as heat resistance and chemical resistance attributable to carbonate bond, it is desirable that the proportion of the carbonate bond is not less than a predetermined level. The molar fraction of the carbonate bond to all the linking groups is preferably 30% or more, more preferably 50% or more, even more preferably 60% or more, especially preferably 70% or more, and is generally 100% or less.

<2-2. Copolymer>

The polymer having a divalent oligofluorene as the repeating unit therein may be a copolymer further containing any other optional divalent organic group as the repeating unit therein. In this case, the repeating units are preferably bonded to each other via the above-mentioned linking group. In the copolymer, the optional divalent organic group that may be combined with the divalent oligofluorene is preferably a divalent organic group represented by the following general formula (3), from the viewpoint of controlling in the range of optical properties and physical properties needed for the resin composition. In this case, the optional divalent organic group may be further combined with any other divalent organic group than the divalent organic group represented by the general formula (3).

[Chem. 31]

(3)

(In the formula, $R^{10}$ represents an optionally-substituted alkylene group having from 2 to 20 carbon atoms, an optionally-substituted arylene group having from 4 to 20 carbon atoms, an optionally-substituted alkylene ether group having from 2 to 100 carbon atoms, an optionally-substituted organic group having an alicyclic structure having from 4 to 20 carbon atoms, or an optionally-substituted organic group having a heterocyclic structure having from 4 to 20 carbon atoms.)

In case where the polymer contains the divalent organic group represented by the general formula (3), the polymer can have a function of imparting positive refractive index anisotropy to the resin composition, and can control the physical properties of the resin composition in any desired manner, for example, controlling the optical properties such as the wavelength dispersion characteristics of retardation and the photoelastic coefficient of the resin composition to fall within a preferred range and controlling other various physical properties such as the mechanical strength, the heat resistance and the melt processability of the resin composition also to fall within a preferred range.

It is known that a resin composition not having an aromatic ring vertically oriented relative to the main chain of the resin, or even though having such an aromatic ring, a resin composition in which the proportion of the aromatic ring of the type is small as a whole may generally exhibit positive refractive index anisotropy. Of the repeating unit of the divalent organic group represented by the general formula (3), any others than those having an aromatic ring in the side chain all have a structure exhibiting positive refractive index anisotropy, and therefore, it is considered that the resin composition containing the divalent organic group represented by the general formula (3) in an amount of 50 mol % or more could exhibit positive refractive index anisotropy.

<2-3. Examples of Organic Group>

As described above, $R^{10}$ in the general formula (3) represents an optionally-substituted alkylene group having from 2 to 20 carbon atoms, an optionally-substituted arylene group having from 4 to 20 carbon atoms, an optionally-substituted alkylene ether group having from 2 to 100 carbon atoms, an optionally-substituted organic group having an alicyclic structure and having from 4 to 20 carbon atoms, or an optionally-substituted organic group having a heterocyclic structure and having from 4 to 20 carbon atoms.

Specific structures of "optionally-substituted alkylene group having from 2 to 20 carbon atoms" includes the following, to which, however, the invention is not limited: A linear alkylene group such as an ethylene group, an n-propylene group, an n-butylene group, an n-pentylene group, an n-hexylene group, etc.; a branched chain-containing alkylene group such as a 1-methylethylene group, a 2-methylethylene group, a 1-ethylethylene group, a 2-ethylethylene group, a 1-methylpropylene group, a 2-methylpropylene group, a 2,2-dimethylpropylene group, a 3-methylpropylene group, etc. The carbon number is preferably 2 or more and 12 or less, more preferably 6 or less. Of those, more preferred is a linear alkylene group represented by the following general formula (5), having suitable hydrophobicity and flexibility and capable of imparting a low photoelastic coefficient.

[Chem. 32]

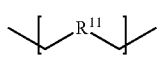

(5)

(In the formula, $R^{11}$ represents an optionally-substituted, linear alkylene group having from 0 to 18 carbon atoms.)

Specific structures of "optionally-substituted, linear alkylene group having from 0 to 18 carbon atoms" includes the following, to which, however, the present invention is not limited: An ethylene group, an n-propylene group, an n-butylene group, an n-pentylene group, an n-hexylene group, etc. The carbon number of the group is preferably 2 or more and 10 or less, and more preferably 4 or less.

Specific structures of "optionally-substituted arylene group having from 4 to 20 carbon atoms" include the following, to which, however, the present invention is not limited; A phenylene group such as a 1,2-phenylene group, a 1,3-phenylene group, a 1,4-phenylene group, etc.; a naphthylene group such as a 1,5-naphthylene group, a 2,6-naphthylene group, etc.; a heteroarylene group such as a 2,5-pyridylene group, a 2,4-thienylene group, a 2,4-furylene group, etc. The carbon number of the group is preferably 4 or more and 8 or less, more preferably 6 or less. Of those, more preferred is a 1,2-phenylene group, a 1,3-phenylene group or a 1,4-phenylene group, from the viewpoint of industrial availability and inexpensiveness.

The substituent that "optionally-substituted alkylene group having from 2 to 20 carbon atoms, "optionally-substituted linear alkylene group having from 2 to 20 carbon atoms" and "optionally-substituted arylene group having from 4 to 20 carbon atoms" may have includes a halogen atom (e.g., fluorine atom, chlorine atom, bromine atom, iodine atom); an alkyl group having from 1 to 10 carbon atoms (e.g., methyl group, ethyl group, isopropyl group, etc.); an alkoxy group having from 1 to 10 carbon atoms (e.g., methoxy group, ethoxy group, etc.), an acyl group having from 1 to 10 carbon atoms (e.g., acetyl group, benzoyl group, etc.), an acylamino group having from 1 to 10 carbon atoms (e.g., acetamide group, benzoylamide group, etc.); a nitro group; a cyano group; an aryl group (e.g., phenyl group, naphthyl group, etc.) having from 6 to 10 carbon atoms and optionally having from 1 to 3 substituents selected from a halogen atom (e.g., fluorine atom, chlorine atom, bromine atom, iodine atom), an alkyl group having from 1 to 10 carbon atoms (e.g., methyl group, ethyl group, isopropyl group, etc.), an alkoxy group having from 1 to 10 carbon atoms (e.g., methoxy group, ethoxy group, etc.), an acyl group having from 1 to 10 carbon atoms (e.g., acetyl group, benzoyl group, etc.), an acylamino group having from 1 to 10 carbon atoms (e.g., acetamide group, benzoylamide group, etc.), a nitro group, a cyano group and others, etc. Not specifically defined, the number of the substituents is preferably from 1 to 3. When the group has 2 or more substituents, the type of the substituents may be the same or different. From the viewpoint of industrial inexpensive production, the group is unsubstituted.

Specific examples of the alkylene group having a substituent include a phenylethylene group, a 1-phenylpropylene group, a 1-cyclohexylpropylene group, a 1,1,2,2-tetrafluoroethylene group, etc.

Specific examples of the arylene group having a substituent include a substituted arylene group such as a 2-methyl-1,4-phenylene group, a 5-methyl-1,3-phenylene group, a 2,5-dimethyl-1,4-phenylene group, a 2-methoxy-1,4-phenylene group, a 2-trifluoromethyl-1,4-phenylene group, a 2,5-dimethoxy-1,4-phenylene group, a 2,3,5,6-tetrafluoro-1,4-phenylene group, etc.

Specific structures of "optionally-substituted aralkylene group having from 6 to 20 carbon atoms" include the following, to which, however, the present invention is not limited, an aralkylene group shown by the following group [M].

[Chem. 33]

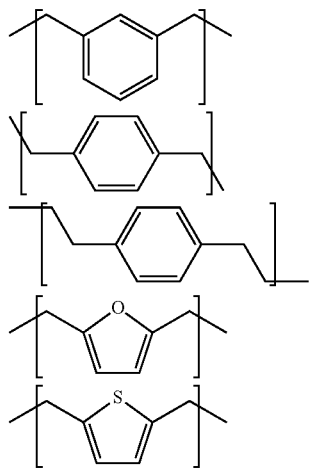

[M]

The carbon number of the group is preferably 6 or more and 10 or less, more preferably 8 or less. Of those, more preferred is an o-xylylene group, an m-xylylene group or a p-xylylene group from the viewpoint of industrial availability and inexpensiveness.

The substituent that "optionally-substituted aralkylene group having from 6 to 20 carbon atoms" may have includes a halogen atom (e.g., fluorine atom, chlorine atom, bromine atom, iodine atom); an alkyl group having from 1 to 10 carbon atoms (e.g., methyl group, ethyl group, isopropyl group, etc.); an alkoxy group having from 1 to 10 carbon atoms (e.g., methoxy group, ethoxy group, etc.), an acyl group having from 1 to 10 carbon atoms (e.g., acetyl group, benzoyl group, etc.), an acylamino group having from 1 to 10 carbon atoms (e.g., acetamide group, benzoylamide group, etc.); a nitro group; a cyano group; an aryl group (e.g., phenyl group, naphthyl group, etc.) having from 6 to 10 carbon atoms and optionally having from 1 to 3 substituents selected from a halogen atom (e.g., fluorine atom, chlorine atom, bromine atom, iodine atom), an alkyl group having from 1 to 10 carbon atoms (e.g., methyl group, ethyl group, isopropyl group, etc.), an alkoxy group having from 1 to 10 carbon atoms (e.g., methoxy group, ethoxy group, etc.), an acyl group having from 1 to 10 carbon atoms (e.g., acetyl group, benzoyl group, etc.), an acylamino group having from 1 to 10 carbon atoms (e.g., acetamide group, benzoylamide group, etc.), a nitro group, a cyano group and others, etc. Not specifically defined, the number of the substituents is preferably from 1 to 3. When the group has 2 or more substituents, the type of the substituents may be the same or different. From the viewpoint of industrial inexpensive production, the group is unsubstituted.

"Optionally-substituted alkylene ether group having from 2 to 100 carbon atoms" is a divalent group having one or more alkylene groups and etheric oxygen atoms. The carbon number of the group is preferably 4 or more, more preferably 6 or more and is preferably 60 or less, more preferably 50 or less, even more preferably 40 or less, still more preferably 30 or less. More concretely, there are mentioned a group represented by the following general formula (7):

[Chem. 34]

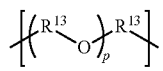
(7)

(wherein $R^{13}$ represents an optionally-substituted alkylene group having from 2 to 10 carbon atoms, and p indicates an integer of from 1 to 40), and a group represented by the following general formula (8):

[Chem. 35]

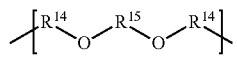
(8)

(wherein $R^{14}$ represents an optionally-substituted alkylene group having from 2 to 10 carbon atoms, $R^{15}$ represents an optionally-substituted arylene group having from 12 to 30 carbon atoms).

In the formula (7) and the formula (8), $R^{13}$ and $R^{14}$ each represent an optionally-substituted alkylene group having from 2 to 10 carbon atoms. Not limited thereto, specific structures of the group include a linear alkylene group such as an ethylene group, an n-propylene group, an n-butylene group, an n-pentylene group, an n-hexylene group, etc.; a branched chain-containing alkylene group such as a 1-methylethylene group, a 2-methylethylene group, a 1-ethylethylene group, a 2-ethylethylene group, a 1-methylpropylene group, a 2-methylpropylene group, a 2,2-dimethylpropylene group, a 3-methylpropylene group, etc. (Here, the substituent position is numbered from the carbon on the terminal side.)

The carbon number of the group is preferably 2 or more and 8 or less, more preferably 4 or less.

The substituent that "optionally-substituted alkylene ether group having from 2 to 100 carbon atoms" and "optionally-substituted alkylene group having from 2 to 10 carbon atoms" may have includes a halogen atom (e.g., fluorine atom, chlorine atom, bromine atom, iodine atom); an alkyl group having from 1 to 10 carbon atoms (e.g., methyl group, ethyl group, isopropyl group, etc.); an alkoxy group having from 1 to 10 carbon atoms (e.g., methoxy group, ethoxy group, etc.), an acyl group having from 1 to 10 carbon atoms (e.g., acetyl group, benzoyl group, etc.), an acylamino group having from 1 to 10 carbon atoms (e.g., acetamide group, benzoylamide group, etc.); a nitro group; a cyano group; an aryl group (e.g., phenyl group, naphthyl group, etc.) having from 6 to 10 carbon atoms and optionally having from 1 to 3 substituents selected from a halogen atom (e.g., fluorine atom, chlorine atom, bromine atom, iodine atom), an alkyl group having from 1 to 10 carbon atoms (e.g., methyl group, ethyl group, isopropyl group, etc.), an alkoxy group having from 1 to 10 carbon atoms (e.g., methoxy group, ethoxy group, etc.), an acyl group having from 1 to 10 carbon atoms (e.g., acetyl group, benzoyl group, etc.), an acylamino group having from 1 to 10 carbon atoms (e.g., acetamide group, benzoylamide group, etc.), a nitro group, a cyano group and others, etc. Not specifically defined, the number of the substituents is preferably from 1 to 3. When the group has 2 or more substituents, the type of the substituents may be the same or different. From the viewpoint of industrial inexpensive production, the group is unsubstituted.

Specific examples of the alkylene group having a substituent include a phenylethylene group, a 1-phenylpropylene group, a 1-cyclohexyl propylene group, a 1,1,2,2-tetrafluoroethylene group, etc.

Of these $R^{13}$ and $R^{14}$, preferred is a linear alkylene group having no asymmetric point and therefore facilitating quality control of monomer. More preferred is an ethylene group as capable of being introduced industrially inexpensively and capable of imparting flexibility and water absorbability.

In the formula (7), p is an integer of from 1 to 40, and is preferably 1 or more, more preferably 2 or more and is preferably 30 or less, more preferably 20 or less.

In the formula (8), $R^{15}$ represents an optionally-substituted arylene group having from 12 to 30 carbon atoms. Specific structures of the group include the following, to which, however, the present invention is not limited. From the viewpoint of the ability thereof to elevate the glass transition temperature of the resin composition, preferred is an arylene group shown by the following group [N]:

[Chem. 36]

[N]

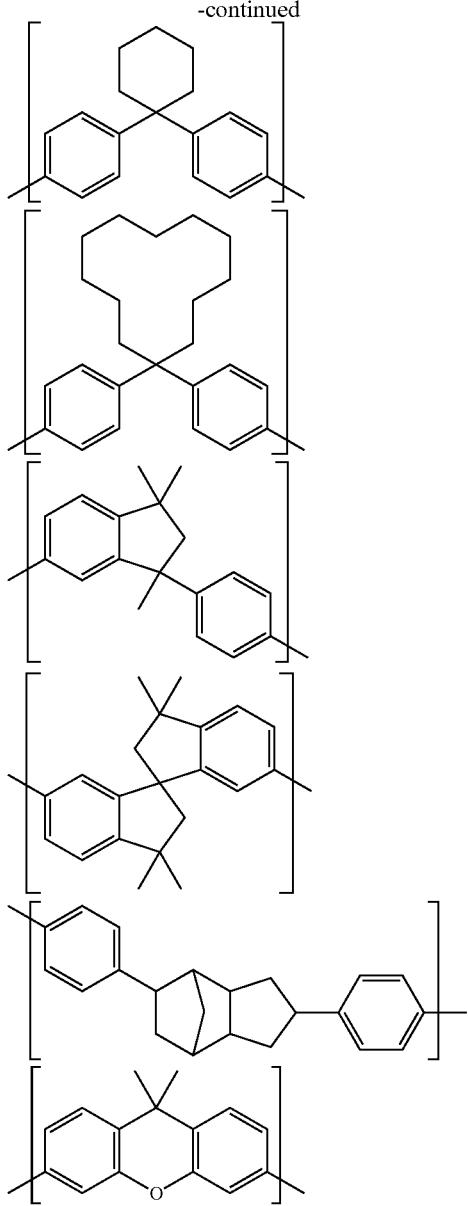

The substituent that "optionally-substituted arylene group having from 6 to 20 carbon atoms" may have includes a halogen atom (e.g., fluorine atom, chlorine atom, bromine atom, iodine atom); an alkyl group having from 1 to 10 carbon atoms (e.g., methyl group, ethyl group, isopropyl group, etc.); an alkoxy group having from 1 to 10 carbon atoms (e.g., methoxy group, ethoxy group, etc.), an acyl group having from 1 to 10 carbon atoms (e.g., acetyl group, benzoyl group, etc.), an acylamino group having from 1 to 10 carbon atoms (e.g., acetamide group, benzoylamide group, etc.); a nitro group; a cyano group; an aryl group (e.g., phenyl group, naphthyl group, etc.) having from 6 to 10 carbon atoms and optionally having from 1 to 3 substituents selected from a halogen atom (e.g., fluorine atom, chlorine atom, bromine atom, iodine atom), an alkyl group having from 1 to 10 carbon atoms (e.g., methyl group, ethyl group, isopropyl group, etc.), an alkoxy group having from 1 to 10 carbon atoms (e.g., methoxy group, ethoxy group, etc.), an acyl group having from 1 to 10 carbon atoms (e.g., acetyl group, benzoyl group, etc.), an acylamino group having from 1 to 10 carbon atoms (e.g., acetamide group, benzoylamide group, etc.), a nitro group, a cyano group and others, etc. Not specifically defined, the number of the substituents is preferably from 1 to 3. When the group has 2 or more substituents, the type of the substituents may be the same or different. From the viewpoint of industrial inexpensive production, the group is unsubstituted.

Not limited thereto, specific structures of the formula (7) include the following, an alkylene ether group shown by the following group [O]:

[Chem. 37]

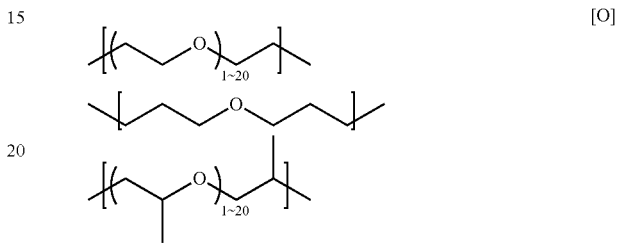

(In the above group [O], the structure capable of having diastereomers may be in any form of diastereomers, or may also be a mixture of diastereomers.)

Also not limited thereto, specific structures of the formula (8) include the following, an alkylene ether group shown by the following group [P]:

[Chem. 38]

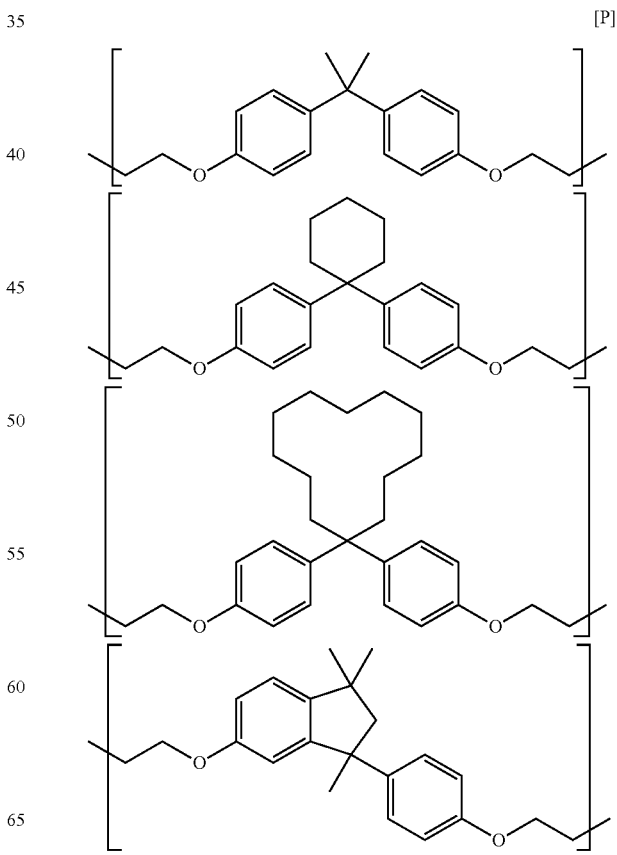

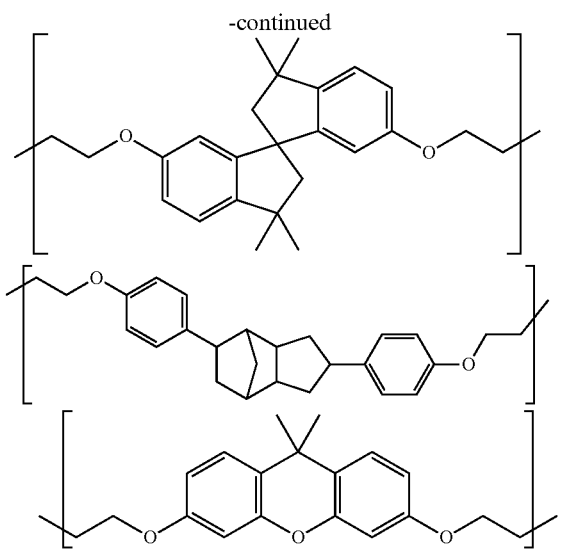

(In the above group [P], the structure capable of having diastereomers may be in any form of diastereomers, or may also be a mixture of diastereomers.)

Specific structures of "optionally-substituted organic group having an alicyclic structure having from 4 to 20 carbon atoms or optionally-substituted organic group having a heterocyclic structure having from 4 to 20 carbon atoms" include the following, to which, however, the present invention is not limited. From the viewpoint of the ability thereof to elevate the glass transition temperature and to lower the photoelasticity coefficient of the resin composition, preferred is an organic group having a bond of a linear or branched alkylene group at any two sites of an alicyclic structure or a heterocyclic structure such as that shown in the above-mentioned group [Q]:

[Chem. 39]

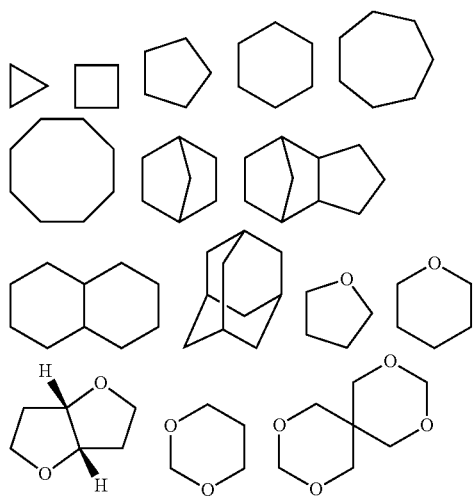

[Q]

(The substituting position of the two bonds in the cyclic structure shown in the above group [Q] is any arbitrary one, and two bonds may bond to one and the same carbon.) Here, the bond is a direct bond, or a linear or branched alkylene group having from 1 to 5 carbon atoms, and the two bonds may differ in the length thereof. A direct bond or a methylene group is a preferred bond, which hardly lowers the glass transition temperature of the resin composition.

The substituent that "optionally-substituted organic group having an alicyclic structure and having from 4 to 20 carbon atoms or optionally-substituted organic group having a heterocyclic structure and having from 4 to 20 carbon atoms" may have includes a halogen atom (e.g., fluorine atom, chlorine atom, bromine atom, iodine atom); an alkyl group having from 1 to 10 carbon atoms (e.g., methyl group, ethyl group, isopropyl group, etc.); an alkoxy group having from 1 to 10 carbon atoms (e.g., methoxy group, ethoxy group, etc.), an acyl group having from 1 to 10 carbon atoms (e.g., acetyl group, benzoyl group, etc.), an acylamino group having from 1 to 10 carbon atoms (e.g., acetamide group, benzoylamide group, etc.); a nitro group; a cyano group; an aryl group (e.g., phenyl group, naphthyl group, etc.) having from 6 to 10 carbon atoms and optionally having from 1 to 3 substituents selected from a halogen atom (e.g., fluorine atom, chlorine atom, bromine atom, iodine atom), an alkyl group having from 1 to 10 carbon atoms (e.g., methyl group, ethyl group, isopropyl group, etc.), an alkoxy group having from 1 to 10 carbon atoms (e.g., methoxy group, ethoxy group, etc.), an acyl group having from 1 to 10 carbon atoms (e.g., acetyl group, benzoyl group, etc.), an acylamino group having from 1 to 10 carbon atoms (e.g., acetamide group, benzoylamide group, etc.), a nitro group, a cyano group and others, etc. Not specifically defined, the number of the substituents is preferably from 1 to 3. When the group has 2 or more substituents, the type of the substituents may be the same or different. From the viewpoint of industrial inexpensive production, the group is unsubstituted.

Not limited thereto, preferred specific structures of "optionally-substituted organic group having an alicyclic structure having from 4 to 20 carbon atoms or optionally-substituted organic group having a heterocyclic structure having from 4 to 20 carbon atoms" include the following, as capable of imparting high transparency and glass transition temperature, water absorbability, birefringence and low photoelastic coefficient: A group represented by the following general formula (4):

[Chem. 40]

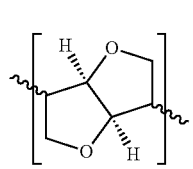

(4)

A group represented by the following general formula (6):

[Chem. 41]

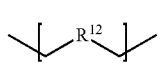

(6)

(In the formula, $R^{12}$ represents an optionally-substituted cycloalkylene group having from 4 to 20 carbon atoms.) A group represented by the following general formula (9):

[Chem. 42]

(9)

(In the formula $R^{16}$ represents an optionally-substituted group having an acetal ring having from 2 to 20 carbon atoms.)

In the formula (6), $R^{12}$ represents an optionally-substituted cycloalkylene group having from 4 to 20 carbon atoms. Not limited thereto, specific structures of the group include the following, as capable of increasing the glass transition temperature and capable of lowering the photoelastic coefficient: A cycloalkylene group shown by the following group [R]:

[Chem. 43]

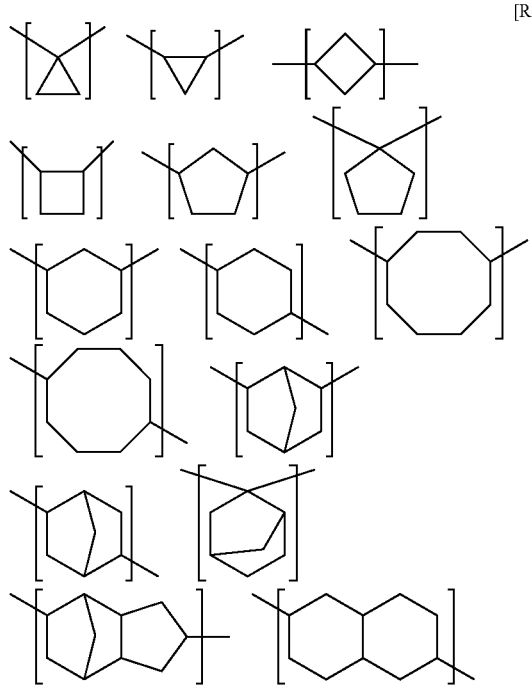

[R]

(In the above group [R], the structure capable of having diastereomers may be in any form of diastereomers, or may also be a mixture of diastereomers.)

The substituent that "optionally-substituted cycloalkylene group having from 4 to 20 carbon atoms" may have includes a halogen atom (e.g., fluorine atom, chlorine atom, bromine atom, iodine atom); an alkyl group having from 1 to 10 carbon atoms (e.g., methyl group, ethyl group, isopropyl group, etc.); an alkoxy group having from 1 to 10 carbon atoms (e.g., methoxy group, ethoxy group, etc.), an acyl group having from 1 to 10 carbon atoms (e.g., acetyl group, benzoyl group, etc.), an acylamino group having from 1 to 10 carbon atoms (e.g., acetamide group, benzoylamide group, etc.); a nitro group; a cyano group; an aryl group (e.g., phenyl group, naphthyl group, etc.) having from 6 to 10 carbon atoms and optionally having from 1 to 3 substituents selected from a halogen atom (e.g., fluorine atom, chlorine atom, bromine atom, iodine atom), an alkyl group having from 1 to 10 carbon atoms (e.g., methyl group, ethyl group, isopropyl group, etc.), an alkoxy group having from 1 to 10 carbon atoms (e.g., methoxy group, ethoxy group, etc.), an acyl group having from 1 to 10 carbon atoms (e.g., acetyl group, benzoyl group, etc.), an acylamino group having from 1 to 10 carbon atoms (e.g., acetamide group, benzoylamide group, etc.), a nitro group, a cyano group and others, etc. Not specifically defined, the number of the substituents is preferably from 1 to 3. When the group has 2 or more substituents, the type of the substituents may be the same or different. From the viewpoint of industrial inexpensive production, the group is unsubstituted.

Not limited thereto, specific structures of the formula (6) include the following, an organic group having an alicyclic structure shown by the following group [S]:

[Chem. 44]

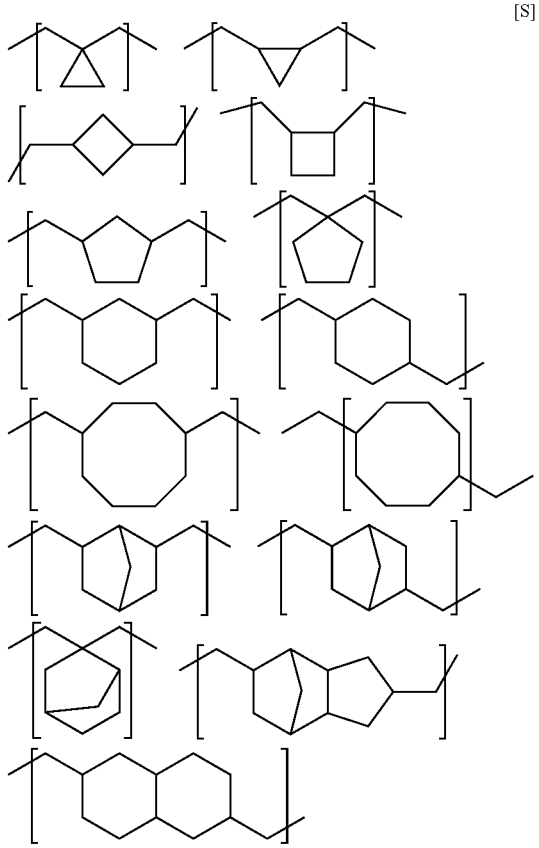

[S]

(In the above group [S], the structure capable of having diastereomers may be in any form of diastereomers, or may also be a mixture of diastereomers.) Of those, preferred is an organic group having an alicyclic structure shown by the following group [S-2], from the viewpoint of industrial availability and inexpensiveness:

[Chem. 45]

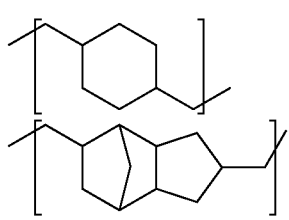

[S-2]

In the formula (9), $R^{16}$ represents an optionally-substituted group having an acetal ring having from 2 to 20 carbon atoms. Not limited thereto, specific structures of the group include the following as capable of increasing the glass transition temperature and the birefringence and capable of lowering the photoelastic coefficient: Preferred is a group having an acetal ring shown by the following group [T]:

[Chem. 46]

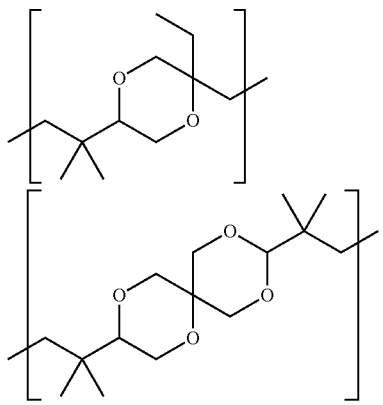

[T]

(In the above group [T], the structure capable of having diastereomers may be in any form of diastereomers, or may also be a mixture of diastereomers.)

The substituent that "optionally-substituted acetal ring having from 2 to 20 carbon atoms" may have includes a halogen atom (e.g., fluorine atom, chlorine atom, bromine atom, iodine atom); an alkyl group having from 1 to 10 carbon atoms (e.g., methyl group, ethyl group, isopropyl group, etc.); an alkoxy group having from 1 to 10 carbon atoms (e.g., methoxy group, ethoxy group, etc.), an acyl group having from 1 to 10 carbon atoms (e.g., acetyl group, benzoyl group, etc.), an acylamino group having from 1 to 10 carbon atoms (e.g., acetamide group, benzoylamide group, etc.); a nitro group; a cyano group; an aryl group (e.g., phenyl group, naphthyl group, etc.) having from 6 to 10 carbon atoms and optionally having from 1 to 3 substituents selected from a halogen atom (e.g., fluorine atom, chlorine atom, bromine atom, iodine atom), an alkyl group having from 1 to 10 carbon atoms (e.g., methyl group, ethyl group, isopropyl group, etc.), an alkoxy group having from 1 to 10 carbon atoms (e.g., methoxy group, ethoxy group, etc.), an acyl group having from 1 to 10 carbon atoms (e.g., acetyl group, benzoyl group, etc.), an acylamino group having from 1 to 10 carbon atoms (e.g., acetamide group, benzoylamide group, etc.), a nitro group, a cyano group and others, etc. Not specifically defined, the number of the substituents is preferably from 1 to 3. When the group has 2 or more substituents, the type of the substituents may be the same or different. From the viewpoint of industrial inexpensive production, the group is unsubstituted.

Of the divalent organic group represented by the general formula (3), preferred is an optionally-substituted alkylene group, an optionally-substituted alkylene ether group, an optionally-substituted organic group having an alicyclic structure, or an optionally-substituted organic group having a heterocyclic structure, as having no aromatic ring or containing many partial structures except aromatic ring in the main chain, and therefore capable of attaining a low photoelastic coefficient desired for optical films. More preferred is at least one selected from the following general formula (4) capable of imparting high transparency and glass transition temperature, water absorbability, birefringence and low photoelastic coefficient:

[Chem. 47]

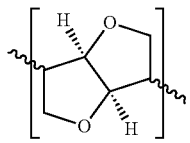

(4)

or the following general formula (5) capable of imparting suitable hydrophobicity and flexibility and low photoelastic coefficient:

[Chem. 48]

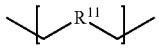

(5)

(wherein $R^{11}$ represents an optionally-substituted linear alkylene group having from 0 to 18 carbon atoms), or the following general formula (6) capable of imparting high transparency and glass transition temperature and suitable flexibility:

[Chem. 49]

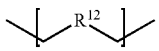

(6)

(wherein $R^{12}$ represents an optionally-substituted cycloalkylene group having from 4 to 20 carbon atoms), or the following general formula (7) capable of imparting flexibility and water absorbability and low photoelastic coefficient:

[Chem. 50]

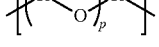

(7)

(wherein $R^{13}$ represents an optionally-substituted alkylene group having from 2 to 10 carbon atoms, and p indicates an integer of from 1 to 40), or the following general formula (8) capable of imparting high transparency and glass transition temperature:

[Chem. 51]

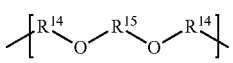

(8)

(wherein $R^{14}$ represents an optionally-substituted alkylene group having from 2 to 10 carbon atoms, $R^{15}$ represents an optionally-substituted arylene group having from 12 to 30 carbon atoms), or the following general formula (9) capable of imparting high transparency and glass transition temperature, and birefringence:

[Chem. 52]

(9)

(wherein $R^{16}$ represents an optionally-substituted group having an acetal ring having from 2 to 20 carbon atoms). More preferred is the group represented by the above-mentioned general formula (4), as capable of imparting high transparency and glass transition temperature, water absorbability and low photoelastic coefficient, and as capable of imparting excellent physical properties suitable for retardation films.

One alone or two or more types of the divalent organic groups represented by the general formula (3) may be used here either singly or as combined. From the viewpoint of quality control of reducing the fluctuation of optical properties and mechanical properties of each batch, preferred is single use of one alone of the group. On the other hand, from the viewpoint of satisfying both good optical properties and mechanical properties, preferred is combined use of two or more types of the groups, and in general, at most 4 types, more preferably at most 3 types of the groups are combined.

In case where two or more types of the divalent organic groups represented by the general formula (3) are combined and used here, the combination is not specifically defined. For example, for the purpose of imparting high transparency and glass transition temperature and birefringence, preferred is the organic group represented by the general formula (4) or the organic group represented by the general formula (9). For the purpose of imparting flexibility, preferred is the organic group represented by the general formula (5) or the organic group represented by the general formula (7). On the other hand, for the purpose of imparting high transparency and glass transition temperature and suitable flexibility, preferred is the organic group represented by the general formula (6). Of those, in accordance with the combination of the desired objects, combinations of the organic groups corresponding to the desired objects may be selected. Concretely, preferred is a combination of an ISB-derived repeating unit corresponding to the organic group represented by the general formula (4) and a CHDM-derived repeating unit corresponding to the organic group represented by the general formula (6); or a combination of an SPG-derived repeating unit corresponding to the organic group represented by the general formula (9) and a CHDM-derived repeating unit corresponding to the organic group represented by the general formula (6).

<2-4. Copolymerization Composition>

As in the above, in a case where a copolymer that contains at least two of a divalent oligofluorene and a divalent organic group represented by the general formula (3) as the repeating unit therein is used, the divalent oligofluorene and the divalent organic group represented by the general formula (3) may be contained in the copolymer in any desired mass ratio falling within a range capable of expressing the optical properties to be mentioned below.

A preferred content ratio of the divalent oligofluorene is preferably 5% by mass or more relative to the total mass of the copolymer, for the purpose of expressing reversed wavelength dispersion characteristics of retardation and for maintaining melt workability and mechanical strength, more preferably 10% by mass or more, even more preferably 15% by mass or more, and is preferably 90% by mass or less, more preferably 80% by mass or less, even more preferably 70% by mass or less, still more preferably 60% by mass or less. From the same viewpoint, a preferred molar fraction of the divalent oligofluorene is preferably 1% or more relative to all the repeating units contained in the copolymer, more preferably 2% or more, even more preferably 3% or more, still preferably 4% or more, most preferably 5% or more, and is preferably 50% or less, more preferably less than 50%, even more preferably 40% or less, still more preferably 35% or less, especially preferably 30% or less, most preferably 20% or less. Also from the same viewpoint, a preferred content ratio of the divalent organic group represented by the general formula (3) is preferably 10% by mass or more relative to the total mass of the copolymer, more preferably 20% by mass or more, even more preferably 30% by mass or more, still more preferably 40% by mass or more, and is preferably 95% by mass or less, more preferably 90% by mass or less, even more preferably 88% by mass or less, still more preferably 85% by mass or less, most preferably 80% by mass or less. Also from the same viewpoint, a preferred molar fraction of the divalent organic group represented by the general formula (3) is 10% or more relative to all the repeating units contained in the copolymer, more preferably 20% or more, even more preferably 30% or more, still more preferably 40% or more, and is preferably 98% or less, more preferably 95% or less, even more preferably 92% or less, still more preferably 90% or less, further more preferably 85% or less, most preferably 80% or less.

On the other hand, in a case of using a divalent oligofluorene in which $R^1$ and $R^2$ each are an optionally-substituted methylene group, the divalent oligofluorene may be contained in the copolymer in any desired mass ratio relative to the total mass of the copolymer to express flat wavelength dispersion of weak wavelength dispersion characteristics of retardation. On the other hand, increasing the content ratio can lower the retardation and the birefringence while maintaining the flat wavelength dispersion characteristics of retardation as such, and therefore, the resin composition of the type can be used as a broadband zero birefringence material that would hardly express retardation and birefringence in the entire wavelength region. A preferred content ratio in the case is preferably 30% by mass or more relative to the total mass of the copolymer, more preferably 40% by mass or more, even more preferably 50% by mass or more, still more preferably 60% by mass or more, and is preferably 95% by mass or less, more preferably 90% by mass or less, even more preferably 85% by mass or less, still more preferably 80% by mass or less. From the same viewpoint, a preferred molar fraction of the divalent oligofluorene is preferably 10% or more relative to all the repeating units contained in the copolymer, more preferably 15% or more, even more preferably 20% or more, still more preferably 25% or more, and is preferably 80% or less, more preferably 75% or less, even more preferably 70% or less, still more preferably 65% or less. Also from the same viewpoint, a preferred content ratio of the divalent organic group represented by the general formula (3) is preferably 5% by mass or more relative to the total mass of the copolymer, more preferably 10% by mass or more, even more preferably 15% by mass or more, still more preferably 20% by mass or more, and is preferably 70% by mass or less, more preferably 60% by mass or less, even more preferably 50% by mass or less, still more preferably 40% by mass or less. Also from the same viewpoint, a preferred molar fraction of the divalent organic group represented by the general formula (3) is preferably 20% or more relative to all the repeating units contained in the copolymer, more preferably 25% or more, even more preferably 30% or more, still more preferably 35% or more, and is preferably 90% or less, more preferably 85% or less, even more preferably 80% or less, still more preferably 75% or less.

<3. Resin Composition>

The resin composition of the present invention contains a polymer having a divalent oligofluorene as the repeating unit therein. The resin composition of the present invention may additionally contain any other component than the polymer.

<3-1. Polymer Blend>

The resin composition of the present invention may contain any other polymer component, expecting expression of any other effect caused by polymer blending. In other words, the resin composition may contain any other polymer optionally coexisting along with polymer having a divalent oligofluorene as the repeating unit therein.

Here, "coexistence" means that two or more polymers exist in the resin composition, and though not specifically defined in point of the method of incorporation of the polymers, there are mentioned a method of mixing two or more polymers in the form of a solution thereof or in the form of a melt thereof, and a method of promoting polymerization in a solution or a melt containing one or more polymers.

For example, a polymer having the divalent organic group represented by the general formula (3) as a repeating unit therein may be blended in, or a polymer having any other repeating unit may be blended in. The polymer having the divalent organic group represented by the general formula (3) as a repeating unit may further contain any other divalent organic group than that of the general formula (3) as a repeating unit therein, or may contain two or more different types of the divalent organic groups represented by the general formula (3) as relating units therein. Here, as the divalent organic group represented by the general formula (3), usable are those exemplified hereinabove for the copolymer.

In particular, from the viewpoint of favorable use for retardation films, it is desirable that a blend or a copolymer of a polymer or an oligomer having positive refractive index anisotropy is made to coexist in the resin composition. More preferably, a thermoplastic resin is made to coexist therein as capable of bettering optical performance and enabling melt casting or solution casting film formation. As those capable of being made to coexist in the composition, concretely mentioned are a polycondensate polymer, an olefinic polymer, or an addition-polymerization polymer. Preferred is a polycondensate polymer. The polycondensate polymer includes polyester, polyamide, polyester carbonate, polyamide, polyimide, etc., and above all, preferred is polyester or polycarbonate.

More concretely, there are mentioned olefinic polymers such as polyethylene, polypropylene, etc.; polycarbonates having a structural unit derived from bisphenol A, bisphenol Z, isosorbitol, etc.; polyesters such as polyethylene terephthalate, polybutylene terephthalate, polynaphthalene dicarboxylate, polycyclohexanedimethylenecyclohexane dicarboxylate, polycyclohexanedimethylene terephthalate, etc. Of those, two or more polymers may be used here as combined.

The optional polymer that may be contained in the resin composition of the present invention may be contained in the resin composition in any desired ratio falling within a range capable of expressing the necessary optical properties and physical properties. Preferably, the content of the optional polymer is 5% by mass or more relative to the total mass of the resin composition, more preferably 10% by mass or more, even more preferably 20% by mass or more, and is preferably 90% by mass or less, more preferably 80% by mass or less, even more preferably 60% by mass or less. When the content ratio is too small, then the resultant resin composition could hardly exhibit desired physical properties to be caused by the polymer blending, but on the other hand, when too large, then the ratio of the divalent oligofluorene in the composition may relatively lower and the composition could hardly exhibit the necessary physical properties.

In particular, in a case where a polymer having a divalent oligofluorene as a relating unit therein and a polymer having the divalent organic group represented by the general formula (3) as a repeating unit are made to coexist in the resin composition, then the blend ratio of the two is not specifically defined so far as it falls within the ratio capable of expressing the optical properties to be mentioned below.

A preferred content ratio of the divalent oligofluorene is preferably 5% by mass or more relative to the total mass of the resin composition, for the purpose of expressing reversed wavelength dispersion characteristics of retardation and maintaining melt processability and mechanical strength, more preferably 10% by mass or more, even more preferably 12% by mass or more, still more preferably 15% by mass or less, most preferably 20% by mass or more, and is also preferably 90% by mass or less, more preferably 80% by mass or less, even more preferably 70% by mass or less, still more preferably 60% by mass or less, most preferably 55% by mass or less. From the same viewpoint, a preferred molar fraction of the divalent oligofluorene is preferably 1% or more relative to all the repeating units contained in the resin composition, more preferably 2% or more, even more preferably 3% or more, still more preferably 4% or more, most preferably 5% or more, and is preferably 50% or less, more preferably less than 50%, even more preferably 40% or less, still more preferably 35% or less, especially more preferably 30% or less, most preferably 20% or less. Also from the same viewpoint, a preferred content ratio of the divalent organic group represented by the general formula (3) is preferably 10% by mass or more relative to the total mass of the resin composition, more preferably 20% by mass or more, even more preferably 30% by mass or more, still more preferably 40% by mass or more, and is preferably 95% by mass or less, more preferably 90% by mass or less, even more preferably 88% by mass or less, still more preferably 85% by mass or less, most preferably 80% by mass or less. Also from the same viewpoint, a preferred molar fraction of the divalent organic group represented by the general formula (3) is preferably 10% or more relative to all the repeating units contained in the resin composition, more preferably 20% or more, even more preferably 30% or more, still more preferably 40% or more, and is preferably 98% or less, more preferably 95% or less, even more preferably 92% or less, still more preferably 90% or less, further more preferably 85% or less, most preferably 80% or less.

Also from the same viewpoint, a preferred content ratio of the divalent oligofluorene is preferably 5% by mass or more relative to the mass of the polymer having the divalent oligofluorene as a repeating unit therein, more preferably 10% by mass or more, even more preferably 12% by mass or more, still more preferably 15% by mass or more, most preferably 20% by mass or more, and is preferably 90% by mass or less, more preferably 80% by mass or less, even more preferably 70% by mass or less, still more preferably 60% by mass or less, most preferably 55% by mass or less. Also from the same viewpoint, a preferred molar fraction of divalent oligofluorene is preferably 1% or more relative to the polymer containing the divalent oligofluorene as a repeating unit therein, more preferably 2% or more, even more preferably 3% or more, still more preferably 4% or more, most preferably 5% or more, and is preferably 50% or less, more preferably less than 50%, even more preferably 40% or less, still more preferably 35% or less, further more preferably 30% or less, most preferably 20% or less. Also from the same viewpoint, a preferred content ratio of the divalent organic group represented by the general formula (3) is preferably 10% by mass or more relative to the mass of the polymer having the divalent oligofluorene as a repeating unit therein, more preferably 20% by mass or more, even more preferably 30% by mass or more, still more preferably 40% by mass or more, and is preferably 95% by mass or less, more preferably 90% by mass or less, even more preferably 88% by mass or less, still more preferably 85% by mass or less, most preferably 80% by mass or less. Also from the same viewpoint, a preferred molar fraction of the divalent organic group represented by the general formula (3) is preferably 10% or more relative to the polymer having the divalent oligofluorene as a repeating unit therein, more preferably 20% or more, even more preferably 30% or more, still more preferably 40% or more, and is preferably 98% or less, more preferably 95% or less, even more preferably 92% or less, still more preferably 90% or less, further more preferably 85% or less, most preferably 80% or less.

On the other hand, in a case of using a divalent oligofluorene in which $R^1$ and $R^2$ each are an optionally-substituted methylene group, the divalent oligofluorene may be contained in the resin composition in any desired mass ratio relative to the total mass of the resin composition to express flat wavelength dispersion of weak wavelength dispersion characteristics of retardation. In particular, increasing the content ratio can lower the retardation and the birefringence while maintaining the flat wavelength dispersion characteristics of retardation as such, and therefore, the resin composition of the type can be used as a broadband zero birefringence material that would hardly express retardation and birefringence in the entire wavelength region. A preferred content ratio in the case is preferably 30% by mass or more relative to the total mass of the resin composition, more preferably 40% by mass or more, even more preferably 50% by mass or more, still more preferably 60% by mass or more, and is preferably 95% by mass or less, more preferably 90% by mass or less, even more preferably 85% by mass or less, still more preferably 80% by mass or less. From the same viewpoint, a preferred molar fraction of the divalent oligofluorene is preferably 10% or more relative to all the repeating units contained in the resin composition, more preferably 15% or more, even more preferably 20% or more, still more preferably 25% or more, and is preferably 80% or less, more preferably 75% or less, even more preferably 70% or less, still more preferably 65% or less. Also from the same viewpoint, a preferred content ratio of the divalent organic group represented by the general formula (3) is preferably 5% by mass or more relative to the total mass of the resin composition, more preferably 10% by mass or more, even more preferably 15% by mass or more, still more preferably 20% by mass or more, and is preferably 70% by mass or less, more preferably 60% by mass or less, even more preferably 50% by mass or less, still more preferably 40% by mass or less. Also from the same viewpoint, a preferred molar fraction of the divalent organic group represented by the general formula (3) is preferably 20% or more relative to all the repeating units contained in the resin composition, more preferably 25% or more, even more preferably 30% or more, still more preferably 35% or more, and is preferably 90% or less, more preferably 85% or less, even more preferably 80% or less, still more preferably 75% or less.

Also from the same viewpoint, a preferred content ratio of the divalent oligofluorene is preferably 30% by mass or more relative to the mass of the polymer having the divalent oligofluorene as a repeating unit therein, more preferably 40% by mass or more, even more preferably 50% by mass or more, still more preferably 60% by mass or more, and is preferably 95% by mass or less, more preferably 90% by mass or less, even more preferably 85% by mass or less, still more preferably 80% by mass or less. From the same viewpoint, a preferred molar fraction of the divalent oligofluorene is preferably 10% or more relative to the mass of the polymer having the divalent oligofluorene as a repeating unit therein, more preferably 15% or more, even more preferably 20% or more, still more preferably 25% or more, and is preferably 80% or less, more preferably 75% or less, even more preferably 70% or less, still more preferably 65% or less. Also from the same viewpoint, a preferred content ratio of the divalent organic group represented by the general formula (3) is preferably 5% by mass or more relative to the mass of the polymer having the divalent oligofluorene as a repeating unit therein, more preferably 10% by mass or more, even more preferably 15% by mass or more, still more preferably 20% by mass or more, and is preferably 70% by mass or less, more preferably 60% by mass or less, even more preferably 50% by mass or less, still more preferably 40% by mass or less. Also from the same viewpoint, a preferred molar fraction of the divalent organic group represented by the general formula (3) is preferably 20% or more relative to the mass of the polymer having the divalent oligofluorene as a repeating unit therein, more preferably 25% or more, even more preferably 30% or more, still more preferably 35% or more, and is preferably 90% or less, more preferably 85% or less, even more preferably 80% or less, still more preferably 75% or less.

In case where the resin composition of the present invention is formed into a film, it is desirable that the film is optically transparent, and therefore, the polymer to be blended therein is preferably one of which the refractive index is close to that of the polymer having a divalent oligofluorene as a repeating unit to be in the composition, or a combination of polymers having miscibility with each other is preferably selected.

<3. Formulation of Resin Composition>

From the viewpoint of expressing reversed wavelength dispersion characteristics of retardation and keeping melt processability and mechanical strength, a preferred content ratio of the divalent oligofluorene in the resin composition is preferably 5% by mass or more relative to the total mass of the resin composition, more preferably 10% by mass or more, even more preferably 12% by mass or more, still more preferably 15% by mass or less, most preferably 20% by mass or more, and is preferably 90% by mass or less, more preferably 80% by mass or less, even more preferably 70% by mass or less, still more preferably 60% by mass or less. From the same viewpoint, a preferred molar fraction of the divalent oligofluorene is preferably 1% or more relative to all the repeating units contained in the resin composition, more preferably 2% or more, even more preferably 3% or more, still more preferably 4% or more, most preferably 5% or more, and is preferably 50% or less, more preferably less than 50%, even more preferably 40% or less, still more preferably 35% or less, especially more preferably 30% or less, most preferably 20% or less. Also from the same viewpoint, a preferred content ratio of the divalent organic group represented by the general formula (3) is preferably 10% by mass or more relative to the total mass of the resin composition, more preferably 20% by mass or more, even more preferably 30% by mass or more, still more preferably 40% by mass or more, and is preferably 95% by mass or less, more preferably 90% by mass or less, even more preferably 88% by mass or less, still more preferably 85% by mass or less, most preferably 80% by mass or less. Also from the same viewpoint, a preferred molar fraction of the divalent organic group represented by the general formula (3) is preferably 10% or more relative to all the repeating units contained in the resin composition, more preferably 20% or more, even more preferably 30% or more, still more preferably 40% or more, and is preferably 98% or less, more preferably 95% or less, even more preferably 92% or less, still more preferably 90% or less, further more preferably 85% or less, most preferably 80% or less.

On the other hand, in a case of using a divalent oligofluorene in which $R^1$ and $R^2$ each are an optionally-substituted methylene group, the divalent oligofluorene may be contained in the resin composition in any desired mass ratio relative to the total mass of the resin composition to express flat wavelength dispersion of weak wavelength dispersion characteristics of retardation. In particular, increasing the content ratio can lower the retardation and the birefringence while maintaining the flat wavelength dispersion characteristics of retardation as such, and therefore, the resin composition of the type can be used as a broadband zero birefringence material that would hardly express retardation and birefringence in the entire wavelength region. A preferred content ratio in the case is preferably 30% by mass or more relative to the total mass of the resin composition, more preferably 40% by mass or more, even more preferably 50% by mass or more, still more preferably 60% by mass or more, and is preferably 95% by mass or less, more preferably 90% by mass or less, even more preferably 85% by mass or less, still more preferably 80% by mass or less. From the same viewpoint, a preferred molar fraction of the divalent oligofluorene is preferably 10% or more relative to all the repeating units contained in the resin composition, more preferably 15% or more, even more preferably 20% or more, still more preferably 25% or more, and is preferably 80% or less, more preferably 75% or less, even more preferably 70% or less, still more preferably 65% or less. Also from the same viewpoint, a preferred content ratio of the divalent organic group represented by the general formula (3) is preferably 5% by mass or more relative to the total mass of the resin composition, more preferably 10% by mass or more, even more preferably 15% by mass or more, still more preferably 20% by mass or more, and is preferably 70% by mass or less, more preferably 60% by mass or less, even more preferably 50% by mass or less, still more preferably 40% by mass or less. Also from the same viewpoint, a preferred molar fraction of the divalent organic group represented by the general formula (3) is preferably 20% or more relative to all the repeating units contained in the resin composition, more preferably 25% or more, even more preferably 30% or more, still more preferably 35% or more, and is preferably 90% or less, more preferably 85% or less, even more preferably 80% or less, still more preferably 75% or less.

The resin composition of the present invention may contain two or more types of the divalent organic groups represented by the general formula (3). For example, in a case where an ISB-derived repeating unit and a CHDM-derived repeating unit are combined and used here, the content ratio of the two is not specifically defined. From the viewpoint of high glass transition temperature and birefringence, and water absorption, the molar fraction of the ISB-derived repeating unit relative to the resin composition is preferably 30 mol % or more, more preferably 40 mol % or more, even more preferably 50 mol % or more and is preferably 95 mol % or less, more preferably 90 mol % or less, even more preferably 85 mol % or less.

In a case where an ISB-derived repeating unit and a CHDM-derived repeating unit are combined and used here, the content ratio of the two is not specifically defined. From the viewpoint of flexibility, the molar fraction of the CHDM-derived repeating unit relative to the resin composition is preferably 5 mol % or more, more preferably 10 mol % or more, even more preferably 15 mol % or more and is preferably 50 mol % or less, more preferably 40 mol % or less, even more preferably 30 mol % or less.

In a case where an SPG-derived repeating unit and a CHDM-derived repeating unit are combined and used here, the content ratio of the two is not specifically defined. From the viewpoint of high glass transition temperature and birefringence, and water absorption, the molar fraction of the SPG-derived repeating unit relative to the resin composition is preferably 30 mol % or more, more preferably 40 mol % or more, even more preferably 50 mol % or more and is preferably 95 mol % or less, more preferably 90 mol % or less, even more preferably 85 mol % or less.

In a case where an SPG-derived repeating unit and a CHDM-derived repeating unit are combined and used here, the content ratio of the two is not specifically defined. From the viewpoint of flexibility, the molar fraction of the CHDM-derived repeating unit relative to the resin composition is preferably 5 mol % or more, more preferably 10 mol % or more, even more preferably 15 mol % or more and is preferably 50 mol % or less, more preferably 40 mol % or less, even more preferably 30 mol % or less.

<3-3. Refractive Index Anisotropy>

Having any of positive or negative refractive index anisotropy, the resin composition of the present invention exhibits reversed wavelength dispersion characteristics of retardation so far as it satisfies the condition for use thereof as reversed wavelength dispersion films described in the section of <3-4. Retardation Ratio> given hereinunder. Here, for obtaining reversed wavelength dispersion films having negative refractive index anisotropy, it is necessary to use, as combined, a structural unit having positive refractive index anisotropy and having large wavelength dispersion characteristics of retardation of such that the wavelength dispersion is larger at a shorter wavelength, and a structural unit having large negative refractive index anisotropy and having small wavelength dispersion characteristics of retardation. However, the latter material is generally unknown, and it is generally difficult to obtain a reversed wavelength dispersion film having negative refractive index anisotropy. Consequently, in case where the resin composition of the present invention is used for an optical material having desired optical properties of reversed wavelength dispersion characteristics of retardation or flat wavelength dispersion characteristics of retardation, it is desirable that the resin composition has positive refractive index anisotropy.

In the present invention, "resin composition having positive refractive index anisotropy" means a resin composition which, when formed into a stretched film, exhibits positive refractive index anisotropy under the measurement condition mentioned below. "Negative refractive index anisotropy" is defined also in the same manner.

In the present invention, the refractivity of the resin composition is determined according to the method mentioned below. First, the resin composition is pressed with a hot pressing machine to form a film. The film is cut into a predetermined size, and monoaxially stretched on the free end thereof to give a stretched film. Using a retardation meter (Oji Scientific Instruments' KOBRA-WPR), the retardation of the stretched film is measured. In case where the film has a positive retardation relative to the stretching direction, the resin composition expresses positive refractive index anisotropy, but when the film has a negative retardation, then the resin composition expresses negative refractive index anisotropy. The detailed measurement condition is described hereinunder.

In general, it is known that a polymer mainly containing a repeating unit having a fluorene ring bonding to the main chain thereof at the 9-positioned carbon atom tends to express negative refractive index anisotropy. In the present invention, the method of realizing "resin composition having positive refractive index anisotropy" is not specifically defined. For example, usable is any or the method A, the method B or the method C to be mentioned below, or usable is a combination of any of those methods.

Method A:

A method of using, as a polymer, a copolymer containing a divalent oligofluorene and a divalent organic group represented by the general formula (3) as repeating units therein.

Method B:

A method of using, as combined, both a polymer having a divalent oligofluorene as a repeating unit therein and a polymer having a divalent organic group represented by the general formula (3) as a repeating unit therein.

Method C:

A method of suitably selecting $R^1$ to $R^3$ so that the polymer having a divalent oligofluorene as a repeating unit therein could have positive refractive index anisotropy.

Of those, from the viewpoint of the transparency and the uniformity of the resultant resin composition, preferred is use of the method A or use of a combination of the method A and any other method. In the method A, it is desirable that the divalent organic group represented by the general formula (3) has a structure expressing positive refractive index anisotropy.

In these methods, one type alone of the divalent organic group represented by the general formula (3) may be used singly, or different types of the divalent organic groups falling within the range of the general formula (3) may be used as combined. Also one alone or two or more different types of divalent oligofluorenes may be used either singly or as combined.

<3-3-1. Method A>

The method A for realizing "resin composition having positive refractive index anisotropy" is a method of using, as a polymer, a copolymer containing at least two or more types of a divalent oligofluorene and a divalent organic group represented by the general formula (3) as repeating units therein.

In the method A, as the divalent oligofluorene, preferably employed are those exemplified in the above-mentioned section <1. Oligofluorene>. Further, as the organic group represented by the general formula (3), preferably employed are the organic groups exemplified in the above-mentioned section <2-3. Examples of Organic Group>.

In the method A, the resin composition of the present invention is good to contain, as a polymer, a copolymer containing at least two or more of a divalent oligofluorene and a divalent organic group represented by the general formula (3) as repeating units therein, and may further contain any other optional polymer than the copolymer. Further, the copolymer may contain any other repeating unit than the divalent oligofluorene and the general formula (3) (excepting the above-mentioned linking group).

<3-2-2. Method B>

The method B for realizing "resin composition having positive refractive index anisotropy" is a method of using, as combined, both a polymer having a divalent oligofluorene as a repeating unit therein and a polymer having a divalent organic group represented by the general formula (3) as a repeating unit therein.

In the method B, as the divalent oligofluorene represented by the general formula (1), preferably employed are those exemplified in the above-mentioned section <1. Oligofluorene>. Further, as the organic group represented by the general formula (3), preferably employed are the organic groups exemplified in the above-mentioned section <2-3. Examples of Organic Group>.

The polymer having a divalent oligofluorene as a repeating unit therein may be one having, as a repeating unit therein, any other divalent organic group than a divalent oligofluorene (excepting the above-mentioned linking group), while on the other hand, the polymer having a divalent organic group represented by the general formula (3) as a repeating unit therein may be one having, as a repeating unit therein, any other divalent organic group than the general formula (3) (excepting the above-mentioned linking group).

In the above-mentioned method B, the resin composition of the present invention can be obtained, for example, by blending a polymer having a divalent oligofluorene as a repeating unit therein and a polymer having a divalent organic group represented by the general formula (3) as a repeating unit therein. Further, any other optional polymer and/or compound may be blended, except for the polymer having a divalent oligofluorene as a repeating unit therein and the polymer having a divalent organic group represented by the general formula (3) as a repeating unit therein.

<3-3-3. Method C>

The method C for realizing "resin composition having positive refractive index anisotropy" is a method of suitably selecting $R^1$ to $R^3$ so that the polymer having a divalent oligofluorene as a repeating unit therein could have positive refractive index anisotropy.

$R^1$ to $R^3$ with which the polymer having a divalent oligofluorene as a repeating unit therein could have positive refractive index anisotropy are not specifically defined so far as they are so selected that the polymer having them could have positive refractive index anisotropy. Concretely, $R^1$ and $R^2$ each are independently an optionally-substituted arylene group having from 4 to 10 carbon atoms, an optionally-substituted aralkylene group having from 6 to 10 carbon atoms, or a group formed by bonding at least two groups selected from an optionally substituted alkylene group having from 1 to 10 carbon atoms, an optionally-substituted arylene group having from 4 to 10 carbon atoms and an optionally-substituted aralkylene group having from 6 to 10 carbon atoms, via an oxygen atom, an optionally-substituted sulfur atom, an optionally-substituted nitrogen atom or a carbonyl group; and $R^3$ is an optionally-substituted arylene group having from 4 to 10 carbon atoms, or an optionally-substituted aralkylene group having from 6 to 10 carbon atoms. It is expected that introducing an aromatic ring into the main chain of the polymer could cancel the negative refractive index anisotropy that the fluorene ring orthogonal to the main chain has and could impart positive refractive index anisotropy to the resultant polymer. Consequently, the number of the aromatic rings that $R^1$ to $R^3$ have is preferably 2 or more as the total thereof that $R^1$ to $R^3$ have, more preferably 3 or more, even more preferably 4 or more.

In the method C where the divalent oligofluorene is one represented by the general formula (1), $R^4$ to $R^9$ each are preferably any one selected from those exemplified hereinabove in the above-mentioned section <1. Oligofluorene>. The polymer having a divalent oligofluorene as a repeating unit therein may contain any other divalent organic group than the divalent oligofluorene (excepting the above-mentioned linking group).

On the other hand, when the above-mentioned method C is employed, the divalent oligofluorene in the resin composition of the present invention has positive refractive index anisotropy by itself, and therefore the resin composition may be enough to contain a polymer that contains a divalent oligofluorene having specific $R^1$ to $R^3$ as a repeating unit therein, and the resin composition may further contain any other optional polymer and/or compound than the polymer having a divalent oligofluorene as a repeating unit therein.

In the method C, the divalent oligofluorene may be contained in any desired mass ratio in the resin composition, falling within a range capable of expressing the optical properties to be mentioned below. A preferred content ratio of the divalent oligofluorene represented by the general formula (1) is preferably 5% by mass or more relative to the total mass of the resin composition, for the purpose of expressing reversed wavelength dispersion characteristics of retardation and for keeping melt processability and mechanical strength, preferably 10% by mass or more, more preferably 12% by mass or more, even more preferably 15% by mass or more, most preferably 20% by mass or more, and is preferably 90% by mass or less, more preferably 80% by mass or less, even more preferably 70% by mass or less, still more preferably 60% by mass or less. From the same viewpoint, a preferred molar fraction of the divalent oligofluorene is preferably 1% or more relative to all the repeating units contained in the resin composition, more preferably 2% or more, even more preferably 3% or more, still more preferably 4% or more, most preferably 5% or more, and is preferably 50% or less, more preferably less than 50%, even more preferably 40% or less, still more preferably 30% or less, most preferably 20% or less.

Also from the same viewpoint, a preferred content ratio of the divalent oligofluorene is preferably 5% by mass or more relative to the mass of the polymer having the oligofluorene as a repeating unit therein, more preferably 10% by mass or more, even more preferably 12% by mass or more, still more preferably 15% by mass or more, most preferably 20% by mass or more, and is preferably 90% by mass or less, more preferably 80% by mass or less, even more preferably 70% by mass or less, still more preferably 60% by mass or less. Also from the same viewpoint, a preferred molar fraction of the divalent oligofluorene is preferably 1% or more relative to the polymer having the divalent oligofluorene as a repeating unit therein, more preferably 2% or more, even more preferably 3% or more, still more preferably 4% or more, most preferably 5% or more, and is preferably 50% or less, more preferably less than 50%, even more preferably 40% or less, still more preferably 35% or less, further more preferably 30% or less, most preferably 20% or less.

On the other hand, in a case of using a divalent oligofluorene in which $R^1$ and $R^2$ each are an optionally-substituted methylene group, the divalent oligofluorene may be contained in the resin composition in any desired mass ratio relative to the total mass of the resin composition to express flat dispersion of weak wavelength dispersion characteristics of retardation. In particular, increasing the content ratio can lower the retardation while maintaining the flat wavelength dispersion retardation characteristics of retardation as such, and therefore, the resin composition of the type can be used as a broadband zero birefringence material that would hardly express retardation in the entire wavelength region. A preferred content ratio in the case is preferably 30% by mass or more relative to the total mass of the resin composition, more preferably 40% by mass or more, even more preferably 50% by mass or more, still more preferably 60% by mass or more, and is preferably 95% by mass or less, more preferably 90% by mass or less, even more preferably 85% by mass or less, still more preferably 80% by mass or less. From the same viewpoint, a preferred molar fraction of the divalent oligofluorene is preferably 10% or more relative to all the repeating units contained in the resin composition, more preferably 15% or more, even more preferably 20% or more, still more preferably 25% or more, and is preferably 80% or less, more preferably 75% or less, even more preferably 70% or less, still more preferably 65% or less.

Also from the same viewpoint, a preferred content ratio of the divalent oligofluorene is preferably 30% by mass or more relative to the mass of the polymer that contains the divalent oligofluorene as a repeating unit therein, more preferably 40% by mass or more, even more preferably 50% by mass or more, still more preferably 60% by mass or more, and is preferably 95% by mass or less, more preferably 90% by mass or less, even more preferably 85% by mass or less, still more preferably 80% by mass or less. Also from the same viewpoint, a preferred molar fraction of the divalent oligofluorene is preferably 10% or more relative to the polymer containing the divalent oligofluorene as a repeating unit therein, more preferably 15% or more, even more preferably 20% or more, still more preferably 25% or more, and is preferably 80% or less, more preferably 75% or less, even more preferably 70% or less, still more preferably 65% or less.

<3-4. Retardation Ratio>

Assuming use thereof for retardation films, the resin composition of the present invention is preferably such that the ratio of the retardation thereof measured at a wavelength of 450 nm (Re450) to the retardation measured at a wavelength of 550 nm (Re550), or that is, the retardation ratio of the resin composition satisfies the following formula (2):

$$Re450/Re550 \leq 1.0 \qquad (2)$$

Here, "the retardation ratio of the resin composition of the present invention satisfying the above formula (2)" means that the ratio of the retardation of the stretched film formed of the resin composition, as measured at a wavelength of 450 nm (Re450), to the retardation thereof measured at a wavelength of 550 nm (Re550) satisfies the above-mentioned formula (2).

In particular, in case where use of the resin composition of the present invention for a retardation film having reversed wavelength dispersion characteristics of retardation is taken into consideration, or that is, in case where the resin composition is intended to be used as a retardation film having reversed wavelength dispersion characteristics of retardation, it is desirable that the retardation ratio satisfies the following formula (2'):

$$0.5 \geq Re450/Re550 < 1.0 \qquad (2')$$

From the viewpoint of favorable use thereof for retardation films, the resin composition of the present invention preferably contains a polymer having the above-mentioned divalent oligofluorene as a repeating unit therein, of which the ratio of the retardation measured at a wavelength of 450 nm (Re450) to the retardation measured at a wavelength of 550 nm (Re550) satisfies the above-mentioned formula (2). In particular, when the resin composition of the present invention contains a polymer having the divalent oligofluorene as a repeating unit therein and satisfies the above-mentioned formula (2), then the composition tends to exhibit sufficient reversed wavelength dispersion characteristics of retardation even though the content ratio of the divalent oligofluorene therein is small.

The retardation ratio may be determined according to the method mentioned below. The resin composition is pressed with a hot pressing machine to form a film. The film is cut into a predetermined size, and monoaxially stretched on the free end thereof to give a stretched film. Using a retardation meter (Oji Scientific Instruments' KOBRA-WPR), the retardation at a wavelength of 450 nm of the stretched film (Re450) and the retardation thereof at a wavelength of 550 nm (Re550) are measured. In case where the retardation ratio (Re450/Re550) relative to the stretching direction satisfies the above-mentioned formula (2), the resin composition exhibits wavelength dispersion characteristics of retardation useful as retardation films. In case where the retardation ratio (Re450/Re550) satisfies the above formula (2'), the resin composition exhibits reversed wavelength dispersion characteristics of retardation useful as reversed wavelength dispersion films. The detailed measurement condition is described below.

Assuming use of the resin composition of the present invention for retardation films having reversed wavelength dispersion characteristics of retardation, it is desirable that the upper limit of the retardation ratio (Re450/Re550) of the resin composition 1.0 or less, more preferably less than 1.0, even more preferably 0.95 or less, still more preferably 0.93 or less, especially more preferably 0.91 or less. The lower limit of the retardation ratio (Re450/Re550) is preferably 0 or more, more preferably 0.50 or more, even more preferably more than 0.50, still more preferably 0.70 or more, further more preferably 0.75 or more, especially more preferably 0.80 or more.

When the retardation ratio (Re450/Re550) falls within the above range, then the composition can express higher retardation at a longer wavelength, and can attain ideal retardation characteristics at each wavelength in a visible light region. For example, when a retardation film formed of the resin composition having such wavelength dispersion characteristics of retardation is used as a ¼λ plate that changes the phase of the polarizing light oscillating at right angles to each other by ¼ wavelength (90°), and when the film is stuck to a polarizing plate, then a circularly polarizing plate or the like can be produced, and it is possible to realize a circularly polarizing plate and an image display device excellent in black display and having an external light antireflection function at any and every wavelength. On the other hand, when the retardation ratio (Re450/Re550) falls outside the above-mentioned range, then wavelength-dependent color loss would increase and there may occur color problems in circularly polarizing plates and image display devices.

Assuming use thereof for reversed wavelength dispersion retardation films, the resin composition of the present invention is preferably such that the ratio of the retardation thereof measured at a wavelength of 630 nm (Re630) to the retardation measured at a wavelength of 550 nm (Re550), or that is, the (retardation ratio)' of the resin composition satisfies the following formula (25):

$$1.0 \leq Re630/Re550 \quad (25)$$

Here, "the (retardation ratio)' of the resin composition of the present invention satisfying the above formula (25)" means that the ratio of the retardation of the stretched film formed of the resin composition, as measured at a wavelength of 630 nm (Re630), to the retardation thereof measured at a wavelength of 550 nm (Re550) satisfies the above-mentioned formula (25).

The (retardation ratio)' may be determined according to the method mentioned below. The resin composition is pressed with a hot pressing machine to form a film. The film is cut into a predetermined size, and monoaxially stretched on the free end thereof to give a stretched film. Using a retardation meter (Oji Scientific Instruments' KOBRA-WPR), the retardation at a wavelength of 630 nm of the stretched film (Re630) and the retardation thereof at a wavelength of 550 nm (Re550) are measured. In case where the (retardation ratio)' (Re630/Re550) relative to the stretching direction satisfies the above-mentioned formula (25), the resin composition exhibits wavelength dispersion characteristics of retardation useful as retardation films.

Assuming use of the resin composition of the present invention for retardation films having reversed wavelength dispersion characteristics of retardation, it is desirable that the upper limit of the (retardation ratio)' (Re630/Re550) of the resin composition is 1.25 or less, more preferably 1.20 or less, even more preferably 1.15 or less. The lower limit of the retardation ratio (Re630/Re550) is preferably 1.00 or more, more preferably 1.01 or more, even more preferably 1.02 or more, still more preferably 1.03 or more.

When the (retardation ratio)' (Re630/Re550) falls within the above range, then the composition can express higher retardation at a longer wavelength, and can attain ideal retardation characteristics at each wavelength in a visible light region. For example, when a retardation film formed of the resin composition having such wavelength dispersion characteristics of retardation is used as a ¼λ plate and when the film is stuck to a polarizing plate, then a circularly polarizing plate or the like can be produced, and it is possible to realize a circularly polarizing plate and an image display device excellent in black display and having an external light antireflection function at any and every wavelength. On the other hand, when the (retardation ratio)' (Re630/Re550) falls outside the above-mentioned range, then wavelength-dependent color loss would increase and there may occur color problems in circularly polarizing plates and image display devices. In particular, from the viewpoint of realizing an external light antireflection function irrespective of wavelength, it is desirable that both the values of the retardation ratio (Re450/Re550) and the (retardation ratio)' (Re630/Re550) are made to fall each within the above-mentioned range.

Any specific method for making the retardation ratio (Re450/Re550) and the (retardation ratio)' (Re630/Re550) each fall within the above-mentioned range is not defined at all, but for example, for that purpose, there may be mentioned a method of using a divalent oligofluorene in which the 9-positioned carbon atom of the fluorene positioned at both terminals is a divalent group, or using a divalent oligofluorene in which $R^1$ and $R^2$ each bonding to the 9-positioned carbon atom of the fluorene positioned at both terminals is a divalent group, in which at least one of $R^1$ and $R^2$ has a carbon number of 2 or more, each in a predetermined amount. In this case, also usable is a divalent oligofluorene in which $R^1$ and $R^2$ having a carbon number of 1 and bonding to the 9-positioned carbon atoms of the fluorene positioned at both terminals each are a divalent group.

Assuming use of the resin composition for retardation films having reversed wavelength dispersion characteristics of retardation and capable of preventing color leakage in image display devices, the retardation ratio (Re450/Re550) may be set to be the optimum one for preventing color leakage in accordance with the type of the devices. When the upper limit of the ratio is less than 1.0, then the lower limit thereof is not specifically defined.

On the other hand, when the resin composition of the present invention is expected to be used as flat wavelength dispersion retardation materials having small wavelength dispersion characteristics of retardation, then the resin composition is desired to satisfy the following formula (23):

$$0.9 < Re450/Re550 < 1.1 \qquad (23)$$

Here, "the retardation ratio of the resin composition of the present invention satisfying the above formula (23)" means that the ratio of the retardation of the stretched film formed of the resin composition, as measured at a wavelength of 450 nm (Re450), to the retardation thereof measured at a wavelength of 550 nm (Re550) satisfies the above-mentioned formula (23).

When the resin composition of the present invention is expected to be used as flat wavelength dispersion retardation materials having small wavelength dispersion characteristics of retardation, then the retardation ratio (Re450/Re550) is preferably 0.93 or more, more preferably 0.95 or more, even more preferably 0.98 or more, and is preferably 1.08 or less, more preferably 1.06 or less, even more preferably 1.05 or less.

When the retardation ratio (Re450/Re550) falls within the above range, then the resin composition of the present invention can form a retardation film capable of preventing color loss in VA-mode liquid-crystal display devices, therefore realizing liquid-crystal display devices free from a problem of wavelength-dependent color loss. Further, when the resin composition satisfies the requirement described in the section of <3-12. Birefringence> to be given below, then the resin composition of the type realizes ideal retardation characteristics at any and every wavelength in a visible light region, therefore providing broadband zero birefringence materials. In addition, when the broadband zero birefringence material of the present invention is stuck to a polarizing plate, then there can be realized polarizing plates and image display devices free from wavelength-dependent color loss.

When the resin composition of the present invention is expected to be used as flat wavelength dispersion retardation materials, then the ratio of the retardation thereof measured at a wavelength of 630 nm (Re630) to the retardation measured at a wavelength of 550 nm (Re550), or that is, the (retardation ratio)' of the resin composition preferably satisfies the following formula (26):

$$0.97 < Re630/Re550 < 1.02 \qquad (26)$$

Here, "the (retardation ratio)' of the resin composition of the present invention satisfying the above formula (26)" means that the ratio of the retardation of the stretched film formed of the resin composition, as measured at a wavelength of 630 nm (Re630), to the retardation thereof measured at a wavelength of 550 nm (Re550) satisfies the above-mentioned formula (26).

Assuming use of the resin composition of the present invention for flat wavelength dispersion retardation materials, it is desirable that the upper limit of the (retardation ratio)' (Re630/Re550) of the resin composition is 1.02 or less, more preferably 1.01 or less, even more preferably 1.00 or less. The lower limit of the retardation ratio (Re630/Re550) is preferably 0.97 or more, more preferably 0.98 or more, even more preferably 0.99 or more.

When the (retardation ratio)' (Re630/Re550) falls within the above range, then the resin composition of the present invention can realize a retardation film capable of preventing color loss in VA-mode liquid-crystal display devices, and can therefore realize liquid-crystal display devices free from wavelength-dependent color loss. Further, when the resin composition satisfies the requirement described in the section of <3-12. Birefringence> to be given below, then the resin composition of the type realizes ideal retardation characteristics at any and every wavelength in a visible light region, therefore providing broadband zero birefringence materials. In addition, when the broadband zero birefringence material of the present invention is stuck to a polarizing plate to provide a polarizer protective film for liquid-crystal display devices, then there can be realized polarizing plates and image display devices free from wavelength-dependent color loss. Further, it is especially preferable that both the retardation ratio (Re450/Re550) and the (retardation ratio)' (Re630/Re550) are made each to fall within the above-mentioned range.

Any specific method for making the retardation ratio (Re450/Re550) and the (retardation ratio)' (Re630/Re550) each fall within the above-mentioned range is not defined at all, but for example, for that purpose, there may be mentioned a method of using a predetermined amount of a divalent oligofluorene in which $R^1$ and $R^2$ each bonding to the 9-positioned carbon atom of the fluorene positioned at both terminals is a divalent group having a carbon number of 1. This case may be further combined with a case where the 9-positioned carbon atom of the fluorene positioned at both terminals is a divalent group, or with a case where $R^1$ and $R^2$ having a carbon number of 2 or more and bonding to the 9-positioned carbon atom of the fluorene positioned at both terminals each are a divalent group.

<3-5. Mass of Fluorene Skeleton>

The mass of the fluorene skeleton relative to the mass of the resin composition of the present invention is preferably 5% or more, more preferably 8% or more, even more preferably 10% or more, and is preferably 70% or less, more preferably 50% or less, even more preferably 30% or less. Falling within the range, the resin composition tends to have the desired optical properties such as reversed wavelength dispersion characteristics of retardation and positive birefringence anisotropy. When the mass is lower than the range, then there is a possibility that the resin composition could not express reversed wavelength dispersion characteristics of retardation or the reversed wavelength dispersion characteristics of the resin composition would be insufficient. On the other hand, when the mass is higher than the range, then there is a possibility that the refractive index anisotropy of the resin composition would be negative or the mechanical strength thereof would lower in such that the resin would be brittle.

On the other hand, in a case of using a divalent oligofluorene in which $R^1$ and $R^2$ each are an optionally-substituted methylene group, the divalent oligofluorene may be contained in the resin composition of the present invention in any desired mass ratio of the fluorene skeleton relative to the mass of the resin composition to express flat dispersion of weak wavelength dispersion characteristics of retardation. In particular, increasing the content ratio can lower the retardation while maintaining the flat wavelength dispersion characteristics of retardation as such, and therefore, the resin composition of the type can be used as a broadband zero birefringence material that would hardly express retardation in the entire wavelength region. A preferred content ratio in the case is preferably 20% by mass or more relative to the total mass of the resin composition, more preferably 25% by mass or more, even more preferably 30% by mass or more, still more preferably 35% by mass or more, and is preferably 90% by mass or less, more preferably 85% by mass or less, even more preferably 80% by mass or less, still more preferably 75% by mass or less.

Here, the fluorene skeleton shows the structure that contains 13 carbon atoms forming the fluorene ring in the general formula (1) and the substituents $R^4$ to $R^9$. However, the fluorene skeleton as referred to herein is not limited to those contained in the polymer that has the divalent oligofluorene represented by the general formula (1) as a repeating unit therein, but includes the entire amount thereof contained in the resin composition.

<3-6. Fluorene Ratio>

On the other hand, the resin composition that contains the polymer having fluorene as a repeating unit therein tends to express the desired optical properties as the aromatic ring-having fluorene ring is oriented relative to the main chain. For example, in a case where the fluorene ring is oriented nearly vertical to the main chain, the resin composition exhibits reversed wavelength dispersion characteristics of retardation, in a case where the fluorene ring is oriented obliquely at 45 degrees or so relative to the main chain, the resin composition could exhibit flat wavelength dispersion characteristics of retardation. Consequently, for efficiently expressing the desired optical properties such as reversed wavelength dispersion characteristics of retardation, flat wavelength dispersion characteristics of retardation or broadband zero birefringence, it is desirable to increase the proportion of the fluorene rings in the repeating unit. In this description, this is referred to as a fluorene ration, and is defined as the following formula (27). Here, the molecular weight of the fluorene ring is the sum total of the atomic weight of 13 carbon atoms, or that is, hydrogen atoms are not contained in the molecular weight. In a case where the ring has a substituent, the substituent is not contained in the molecular weight. The sum total of the molecular weight of the fluorene ring means the total value of the molecular weight of all the fluorene rings contained in the fluorene-containing repeating unit, and for example, in a case containing two fluorene rings, the molecular weight corresponds to two fluorene rings, and in a case containing three fluorene rings, the molecular weight corresponds to three fluorene rings. On the other hand, the molecular weight of the fluorene-containing repeating unit means the molecular weight of the repeating unit itself.

$$\text{Fluorene Ratio (\%)} = \text{(sum total of molecular weight of fluorene ring)/(molecular weight of fluorene-containing repeating unit)} \times 100 \quad (27)$$

In the present invention using a specific divalent oligofluorene, the ratio of the fluorene ring in the repeating unit can be increased, and therefore, even when the content ratio thereof is small, the resin composition tends to express the desired optical properties. From this viewpoint, the fluorene ration is preferably 30% or more, more preferably 40% or more, even more preferably 50% or more, still more preferably 60% or more, and is generally 90% or less.

<3-7. Glass Transition Temperature>

Preferably, the glass transition temperature of the resin composition of the present invention is 90° C. or higher, more preferably 100° C. or higher, even more preferably 110° C. or higher, still more preferably 120° C. or higher, and is preferably 170° C. or lower, more preferably 160° C. or lower, even more preferably 150° C. or lower. When the glass transition temperature is lower than the range, then the optical properties of the resin composition would change from the planned values in operation environments, and there is a possibility that the composition could not satisfy heat resistance necessary for practical use. On the other hand, when the glass transition temperature is higher than the range, then the melt processability of the resin composition would worsen and there is a possibility that shaped articles having a good appearance and a good dimensional accuracy could not be obtained. Further, in such a case, the heat resistance of the composition would be too high, but on the contrary, the mechanical strength thereof would lower, and as a result, the resin composition would be brittle and the processability thereof and also the handleability of the shaped articles thereof would worsen.

<3-8. Melt Viscosity>

The melt viscosity of the resin composition of the present invention, at a measurement temperature of 240° C. and at a shear rate of 91.2 $\text{sec}^{-1}$, is preferably 500 Pa·s or more, more preferably 800 Pa·s or more, even more preferably 1000 Pa·s or more, and is preferably 5000 Pa·s or less, more preferably 4500 Pa·s or less, even more preferably 4000 Pa·s. When the melt viscosity is less than the range, the resin composition could not have mechanical strength at practical level. In addition, there is a possibility that the case would overstep the melt viscosity range suitable for the melt film formation method to be mentioned below. When the melt viscosity is more than the range, the formability of the resin composition would worsen like in the case where the glass transition temperature is too high as mentioned above.

<3-9. Molecular Weight>

The molecular weight of the resin composition of the present invention can be expressed as a reduced viscosity thereof. The reduced viscosity of the resin composition of the present invention is measured as follows, as described in the section of Examples to be given below. Methylene chloride is used as a solvent, and the polymer concentration therein is accurately controlled to be 0.6 g/dL, and using an Ubbelohde viscometer at a temperature of 20.0° C.±0.1° C., the viscosity is measured. Not specifically defined, the reduced viscosity of the resin composition of the present invention is preferably 0.30 dL/g or more, more preferably 0.35 dL/g or more. The upper limit of the reduced viscosity is preferably 1.20 dL/g or less, more preferably 0.60 dL/g or less, even more preferably 0.50 dL/g or less.

<3-10. Metal Content Ratio>

When the resin composition of the present invention contains a large amount of a metal and a metal ion, then the composition may often be discolored or thermally decomposed in polymerization or processing. For example, it is important to remove as much as possible the residual matter of the catalyst used in producing the resin composition, and the metal component that may be in the starting materials of the resin composition as a contaminant therein as well as the metal to be released from the reactor, etc. In particular, the influence of Na, K, Cs and Fe is serious, and therefore it is desirable that, in the polycarbonate resin composition of the present invention, the total content of Na, K, Cs and Fe is at most 3 ppm by mass, more preferably at most 1 ppm by mass, even more preferably at most 0.8 ppm by mass, still more preferably at most 0.5 ppm by mass. The metal content in the resin composition may be determined by collecting the metal from the resin composition through wet-process ashing or the like, and then measuring the amount thereof according to a method of atomic emission, atomic absorption, ICP or the like.

<3-11. Photoelastic Coefficient>

The photoelastic coefficient of the resin composition of the present invention is preferably $45 \times 10^{-12}$ $Pa^{-1}$ or less, more preferably $40 \times 10^{-12}$ $Pa^{-1}$ or less, even more preferably $35 \times 10^{-12}$ $Pa^{-1}$ or less, and is generally $5 \times 10^{-12}$ $Pa^{-1}$ or more. When the photoelastic coefficient is high and when the resin composition is used for large-size shaped articles or the shaped articles of the resin composition are bent or folded, there is a possibility that, in the part thereof given a stress, the birefringence of the material would change to detract from the uniformity of the optical properties thereof.

<3-12. Birefringence>

In case where the resin composition of the present invention is intended to be used as retardation films having reversed wavelength dispersion characteristics of retardation or retardation films having flat wavelength dispersion characteristics of retardation and when the resin composition is formed into such films, it is desirable that the birefringence of the film at 550 nm is 0.001 or more. In case where extremely thin films are planned and formed using the resin composition of the present invention as described below, the birefringence thereof is preferably higher. Accordingly, it is more desirable that the birefringence at 550 nm is 0.002 or more, and is generally 0.005 or less. When the birefringence at 550 nm is less than 0.001, the film thickness would have to be increased much with the result that the amount of the film forming material to be used would increase, and it would be difficult to control the homogeneous of the film from the viewpoint of the thickness, the transparency and the retardation thereof. Consequently, in a case where the birefringence at 550 nm is less than 0.001, there is a possibility that the film would be unsuitable to instruments that are required to have accuracy, thinness and homogeneousness.

The birefringence is a value calculated by dividing the retardation by the thickness of the film. Using a retardation meter (Oji Scientific Instruments' KOBRA-WPR), the retardation of the film is measured, and the film thickness is measured to give the birefringence.

On the other hand, in case where the resin composition of the present invention is intended to be used as a broadband zero birefringence material, it is desirable that the birefringence at 550 nm of the film formed of the composition is 0.0005 or less. As described above, in case where a polarizer protective film having a broadband zero birefringence is planned using the resin composition of the present invention, it is desirable that the birefringence is smaller. Accordingly, the birefringence at 550 nm is more preferably 0.0002 or less, even more preferably 0.0001 or less, and is generally 0.00001 or more. When the birefringence at 550 nm is more than 0.0005, the birefringence is not sufficiently small, and there is a possibility that such thick films would provide color loss.

Especially when used as a protective film for a polarizing plate in liquid-crystal display devices, the optical film expresses extremely excellent characteristics. However, not limited to a protective film for a polarizing plate, the film is usable for any other applications of retardation films, plastic cell substrates, antireflection films, brightness-increasing films, optical disc protective films, diffusion films, etc.

<3-13. Refractive Index>

In case where the resin composition of the present invention is intended to be used as a broadband zero birefringence material such as optical lenses, etc., it is desirable that the refractive index at 589 nm thereof is 1.54 or more. In planning optical lenses using the resin composition of the present invention, the refractive index is preferably higher in order that the lenses could be thin. Accordingly, the refractive index at 589 nm is more preferably 1.56 or more, even more preferably 1.58 or more, and is generally 1.65 or less.

<3-14. Abbe's Number>

In case where the resin composition of the present invention is intended to be used as a broadband zero birefringence material such as optical lenses for imaging application, etc., it is desirable that the Abbe's number thereof is 35 or less. In planning optical lenses for imaging application using the resin composition of the present invention, the Abbe's number is preferably lower. Accordingly, the Abbe's number is more preferably 30 or less, even more preferably 25 or less, and is generally 15 or more.

<3-15. Orientation of Fluorene Ring>

Of the resin composition of the present invention, the intensity ratio of the fluorene orientation-derived absorption at 740 $cm^{-1}$ in the stretching direction to the direction vertical thereto is preferably 1.2 or more, more preferably 1.3 or more, even more preferably 1.4 or more, and is generally 2.0 or less. In case where the resin composition of the present invention is used for films having reversed wavelength dispersion characteristics of retardation, the resultant films tend to readily exhibit reversed wavelength dispersion characteristics of retardation when the intensity ratio of the fluorene orientation-derived absorption of the film at 740 $cm^{-1}$ in the stretching direction to the direction vertical thereto is higher even though the proportion of the fluorene ring-having repeating unit contained in the resin composition is small. The intensity ratio may be determined according to the method mentioned below.

First, a stretched film is formed of the resin composition of the present invention, and analyzed through polarized ATR spectroscopy. In the analysis result, it is confirmed that the intensity ratio of the carbonyl orientation-derived absorption of the film at 1245 $cm^{-1}$ in the stretching direction to the direction vertical thereto (dichroic ratio:intensity in stretching direction/intensity in vertical direction) is 1.2 or more and the main chain is oriented in the stretching direction. Next, the intensity ratio of the fluorene orientation-derived absorption at 740 $cm^{-1}$ in the stretching direction to the direction vertical thereto is calculated.

<3-16. Angle between Main Chain and Fluorene>

The resin composition of the present invention is expected to express reversed wavelength dispersion characteristics of retardation when the specific conformation of the divalent oligofluorene is not a gauche conformation as the stable conformation and when the angle between the trans conformation main chain and the fluorene ring is 50° or more, preferably 60° or more, more preferably 70° or more.

The energy calculation of the specific conformation of the divalent oligofluorene and the calculation of the angle between the fluorene ring of that conformation and the main chain are as mentioned below.

As software, used is US Wavefunction's PC Spartan Pro 1.0.5 (Windows (registered trademark) 32 bit edition) for the AM1 method. For all the input values such as the convergence test value and others that are involved in calculation accuracy, the default values of that software are used.

Here, relating to the divalent oligofluorene, the structure constructed by methyl-carbonating both terminals of the repeating unit is calculated in the case of a polycarbonate resin composition, while the structure constructed by methyl-esterifying both terminals of the repeating unit is calculated in the case of a polyester or polyester carbonate resin composition.

According to the AM1 method, the energy difference between the conformer where the two side chains existing in each monomer have a trans conformation and the conformer where they have two types of gauche conformations is calculated. In addition, regarding the trans conformation and the gauche conformation (stable one of the two gauche conformations), the angle between the main chain and the fluorene ring is calculated.

The angle between the main chain and the fluorene ring is defined as follows. First, the straight line drawn by bonding the carbon atoms of the methyl groups at both terminals is referred to as the main chain direction, and the plane that passes through the 3-, 6- and 9-positioned carbon atoms of fluorene is referred to as the fluorene plane. In this, there may exist unlimited straight lines on the fluorene plane that crosses the main chain direction, but the straight line on the fluorene plane that forms a minimum angle with the main chain direction is specified. That angle is referred to as the angle between the main chain and the fluorene ring.

<4. Oligofluorene Monomer>

The polymer that has the divalent oligofluorene represented by the above-mentioned general formula (1) as a repeating unit therein may be produced, for example, according to a method of polymerization of an oligofluorene monomer represented by the following general formula (20), as mentioned below.

[Chem. 53]

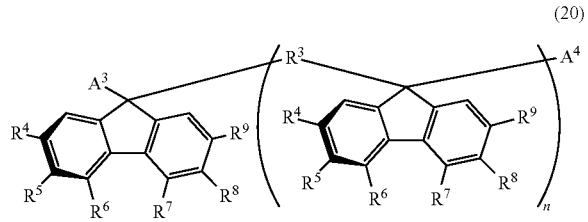

(20)

(In the formula, $R^3$ to $R^9$ and n are the same as those in the above-mentioned general formula (1). $A^3$ and $A^4$ each independently represent a polymerization reactive group.)

<4-1. Polymerization Reactive Group>

In $A^3$ and $A^4$, specific structures of the "polymerization reactive group" are shown below, to which, however, the invention is not limited: A hydroxyl group such as a hydroxymethyl group, a 2-hydroxyethyl group, a 3-hydroxypropyl group, a hydroxybutyl group, a 2,2-dimethyl-3-hydroxypropyl group, a 2-methoxymethyl-2-methylpropyl group, a 4-hydroxyphenyl group, a 4-hydroxy-3-methylphenyl group, a 4-(2-hydroxyethoxyl)phenyl group, a (4-(hydroxymethyl)cyclohexan-1-yl)methyl group, etc.; an ester group such as a methoxycarbonyl, an ethoxycarbonyl group, a phenoxycarbonyl group, an ethoxycarbonylmethyl group, a 2-(ethoxycarbonyl)ethyl group, a 2-(methoxycarbonyl)propyl group, etc.; a hydroxy-ester group such as a 2-hydroxyethoxycarbonyl group, a 2-(2-hydroxyethoxyl)carbonylethyl group, a 2-(2-hydroxyethoxyl)carbonylpropyl group, a 2-(4-hydroxybutoxyl)carbonylethyl group, a 2-[[4-(hydroxymethyl)cyclohexan-1-yl]methoxy]carbonylmethyl group, etc.; a carboxyl group such as a carboxyl group, a carboxymethyl group, a carboxyethyl group, etc.; an amino group such as an aminomethyl group, a 2-aminoethyl group, a 3-aminopropyl group, etc.; an acryl group such as an acryloyloxymethyl group, a methacryloyloxymethyl group, a 2-(acryloyloxy)ethyl group, a 3-(acryloyloxy)propyl group, etc.; an epoxy group such as a 2,3-epoxypropyl group, a 2,3-epoxypropoxymethyl group, a 2-(2,3-epoxypropoxyl)ethyl group, etc.

The oligofluorene monomer represented by the above-mentioned general formula (20) can be used as the starting material for the polymer that has a divalent oligofluorene as a repeating unit therein. Preferably, in this, the polymerization reactive group is only at two sites of $A^3$ and $A^4$, and under the polymerization condition to produce various types of resin compositions, it is desirable that the substituent acting as a polymerization reactive group is not contained in $R^3$ to $R^9$.

$A^3$ and $A^4$ may be the same or different. When the two differ, a combination thereof includes, for example, a combination of a hydroxymethyl group and an ethoxycarbonyl group, a combination of a 2-(2-hydroxyethoxyl)carbonyl group and a carboxyl group, a combination of a 2-(2-hydroxyethoxyl)carbonyl group and a carboxyethyl group, etc.

Of those, preferred is a case where $A^3$ and $A^4$ are the same since the monomer of the type can be produced in a simple process, and more preferred is a case of a hydroxyl group, an ester group or a hydroxy-ester group capable of being used in producing preferred polymers of polyester, polycarbonate or polyester carbonate. A case where $A^3$ and $A^4$ are hydroxyl groups provides a dihydroxy compound having an oligofluorene represented by the following general formula (10a), which is a monomer commonly usable in producing polyesters, polycarbonates and polyester carbonates that are preferred polymers having good optical performance.

[Chem. 54]

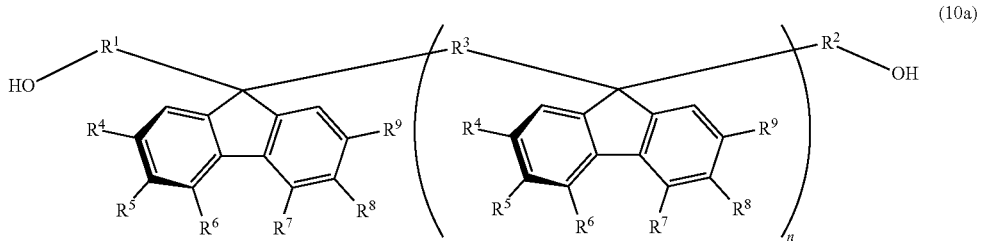

(10a)

(In the formula, $R^1$ to $R^9$ are the same as those in the above-mentioned general formula (1), and n indicates an integer value of from 1 to 5.)

Of the above-mentioned hydroxyl groups, especially preferred is a hydroxymethyl group (in the formula (10a), the —$R^1$—OH group and the —$R^2$—OH in which $R^1$ and $R^2$ are methylene groups), as the group is easy to introduce to give a resin composition having a high glass transition temperature. The hydroxymethyl group can increase the proportion of fluorene in the monomer molecule and, in addition, though having a fluorene skeleton that bonds to the main chain at the 9-position, the negative refractive index anisotropy of the compound is surprisingly small and therefore, in the range in which the mass ratio and/or the molar fraction of the divalent oligofluorene are high in the resin composition, the polymer has positive refractive index anisotropy. Consequently, the polymer tends to provide a resin composition having positive refractive index anisotropy and a high refractive index and having a small photoelastic coefficient. Further, since the wavelength dispersion thereof tends to small, the resin composition of the type is favorable for flat dispersion retardation films. In addition, of the above-mentioned hydroxyl groups, a hydroxypropyl group can exhibit characteristics of retardation films even when the amount thereof added is small, and is therefore especially preferable herein. Specifically, when the refractive index anisotropy of the resin composition is positive and the birefringence thereof at 550 nm is nearly 0, the resin composition can have elevated reversed wavelength dispersion characteristics of retardation, and the structural unit derived from the oligofluorene monomer having a hydroxypropyl group has high-level negative refractive index anisotropy, and accordingly, even when the amount thereof added to the resin composition is small relative to the other structural units having positive refractive index anisotropy, the resultant resin composition can be well controlled to have positive refractive index anisotropy and have birefringence at nearly 0.

A case where $A^3$ and $A^4$ are hydroxyl groups provides a dihydroxy compound having an oligofluorene represented by the following general formula (10b), which is a monomer commonly usable in producing polyesters and polyester carbonates that are preferred polymers having good optical performance.

tyl group, a cyclohexyl group, a cyclooctyl group, etc.; an aryl group such as a phenyl group, a 1-naphthyl group, a 2-naphthyl group, etc.; a heteroaryl group such as a 2-pyridyl group, a 2-thienyl group, a 2-furyl group, etc.; an aralkyl group such as a benzyl group, a 2-phenylethyl group, a p-methoxybenzyl group, etc. Of those, $R^{17}$ is especially preferably a methyl group or an ethyl group, since the monomer of the type can efficiently provide polyesters and polyester carbonates by removing the low-boiling-point alcohol formed in transesterification of the monomer with a dihydroxy compound. On the other hand, a case where $R^{17}$ is an aryl group is also preferred, as facilitating transesterification, and accordingly, putting the above-mentioned diester compound, a dihydroxy compound and a carbonic acid diester all at a time into a reactor gives a preferred polymer, polyester carbonate in one stage. Especially preferred is a phenyl group, since the monomer of the type has a small molecular weight and can be easily evaporated away as phenol after production of polyester carbonate. For the case where $R^{17}$ is an aryl group, preferably used is a diaryl carbonate to be mentioned below as the carbonic acid diester from the viewpoint of the reactivity thereof in polymerization. From the viewpoint of readily removing side products, it is desirable that the aryl group of $R^{17}$ is the same as the aryl group of the diaryl carbonate.

In the oligofluorene monomer represented by the above-mentioned general formula (20) where $A^3$ and $A^4$ each are an ester group, a 2-(methoxycarbonyl)ethyl group, a 2-(ethoxycarbonyl)ethyl group or a 2-(methoxycarbonyl)propyl group of the ester group is especially preferred since the group can be readily introduced into the monomer using industrially-available methyl acrylate, ethyl acrylate or methyl and since the resin composition containing the resultant polymer is highly flexible and can exhibit elevated reversed wavelength dispersion characteristics of retardation even though the amount of the polymer in the composition is small. On the other hand, a phenoxycarbonylalkyl group is also preferred since the ester group can be highly activated to provide easy

[Chem. 55]

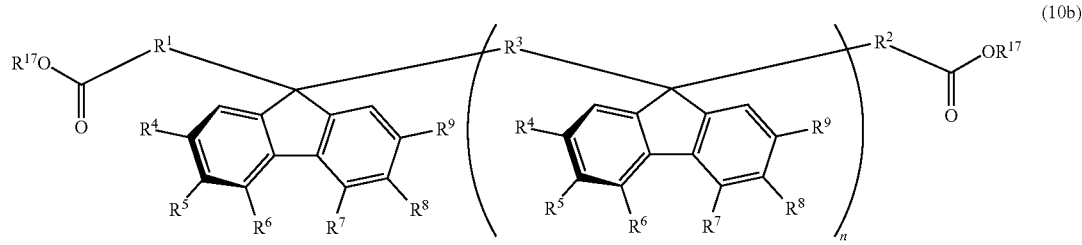

(10b)

(In the formula, $R^1$ to $R^9$ are the same as those in the above-mentioned general formula (1), $R^{17}$ represents an organic substituent having from 1 to 10 carbon atoms, and n indicates an integer value of from 1 to 5. On the right and left sides, $R^{17}$'s may be the same or different.)

In the case where $A^3$ and $A^4$ each are an ester group, specific structures of "organic substituent having from 1 to 10 carbon atoms" for $R^{17}$ include the following, to which, however, the present invention is not limited: There are mentioned a linear alkyl group such as a methyl group, an ethyl group, an n-propyl group, an n-propyl group, an n-butyl group, an n-pentyl group, an n-hexyl group, an n-decyl group, etc.; a branched chain-having alkyl group such as an isopropyl group, a 2-methylpropyl group, a 2,2-dimethylpropyl group, a 2-ethylhexyl group, etc.; a cyclic alkyl group such as a cyclopropyl group, a cyclopenpromotion of interesterification and therefore the above-mentioned diester compound, dihydroxy compound and carbonic diester can be reacted under one and the same condition in one stage to give the preferred polymer, polyester carbonate. In particular, a 2-(phenoxycarbonyl)ethyl group and a 2-(phenoxycarbonyl)propyl group are preferred since an introduction method using phenyl acrylate or phenyl methacrylate or an introduction method using any other acrylates or methacrylates through interesterification is applicable to the case.

A case where $A^3$ and $A^4$ each are a hydroxyester group provides a dihydroxyester compound having an oligofluorene represented by the following general formula (10c), which is a monomer commonly usable in producing polyesters and polyester carbonates that are preferred polymers having good optical performance.

[Chem. 56]

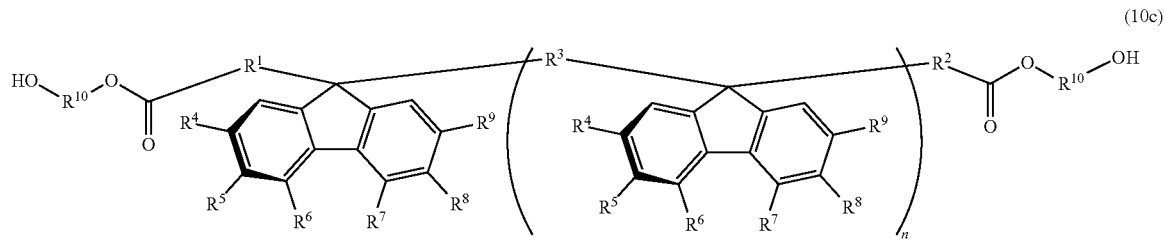

(10c)

(In the formula, $R^1$ to $R^{10}$ are the same as those in the above-mentioned general formulae (1) and (3), and n indicates an integer value of from 1 to 5. On the right and left sides, $R^{10}$'s may be the same or different.) Of the hydroxyether group, a 2-(2-hydroxyethoxyl)carbonylethyl group, a 2-(4-hydroxybutoxyl)carbonylethyl group or a 2-[[(4-(hydroxymethyl)cyclohexan-1-yl]methoxy]carbonylethyl group is preferred since the group can be readily introduced into the monomer through reaction with a corresponding acrylic acid derivative or through interesterification to give a polyester carbonate according to an ordinary polycarbonate production process, and since the resin composition containing the resultant polymer is highly flexible and can exhibit elevated reversed wavelength dispersion characteristics of retardation even though the amount of the polymer in the composition is small.

The dihydroxyester compound having an oligofluorene represented by the general formula (10c) has both the oligofluorene represented by the general formula (1) and the divalent organic group represented by the general formula (3). As $R^{10}$, preferably employed here are those exemplified hereinabove for the divalent organic group $R^{10}$ in the general formula (3) described in the section of <2-3. Examples of Organic Group>.

<4-2. Examples of Oligofluorene Monomer>

Specific examples of the oligofluorene monomer represented by the general formula (20) include structures shown in the following group [L].

[Chem. 57]

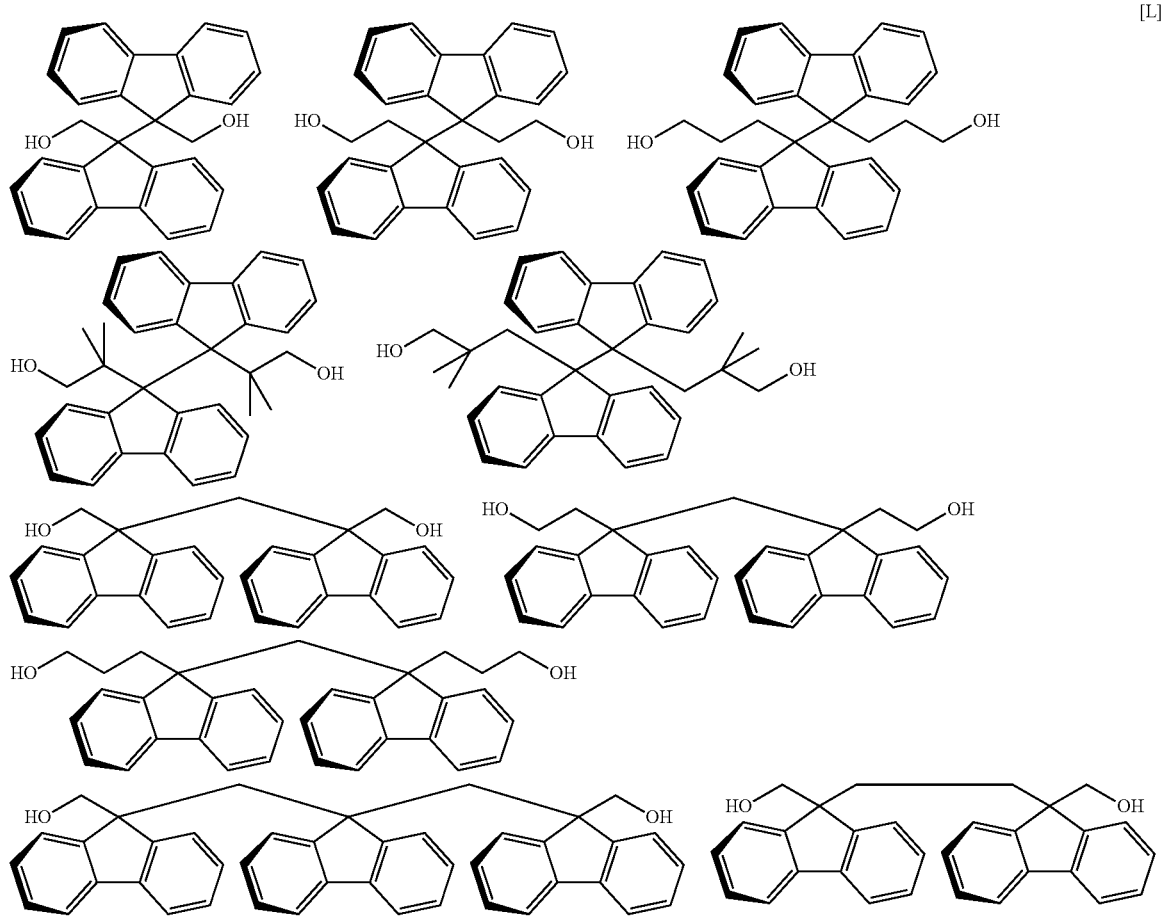

[L]

91            92
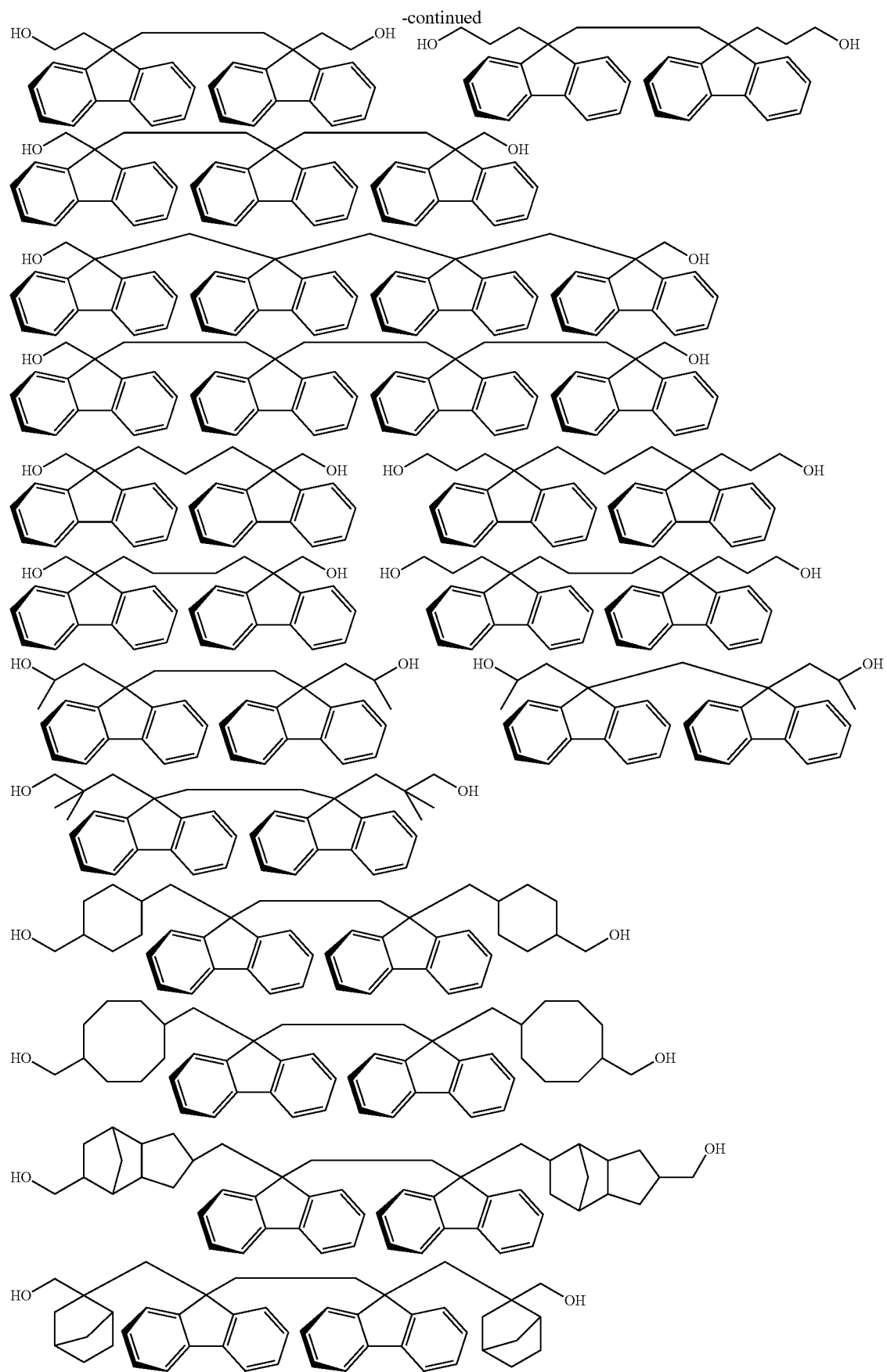
-continued

-continued
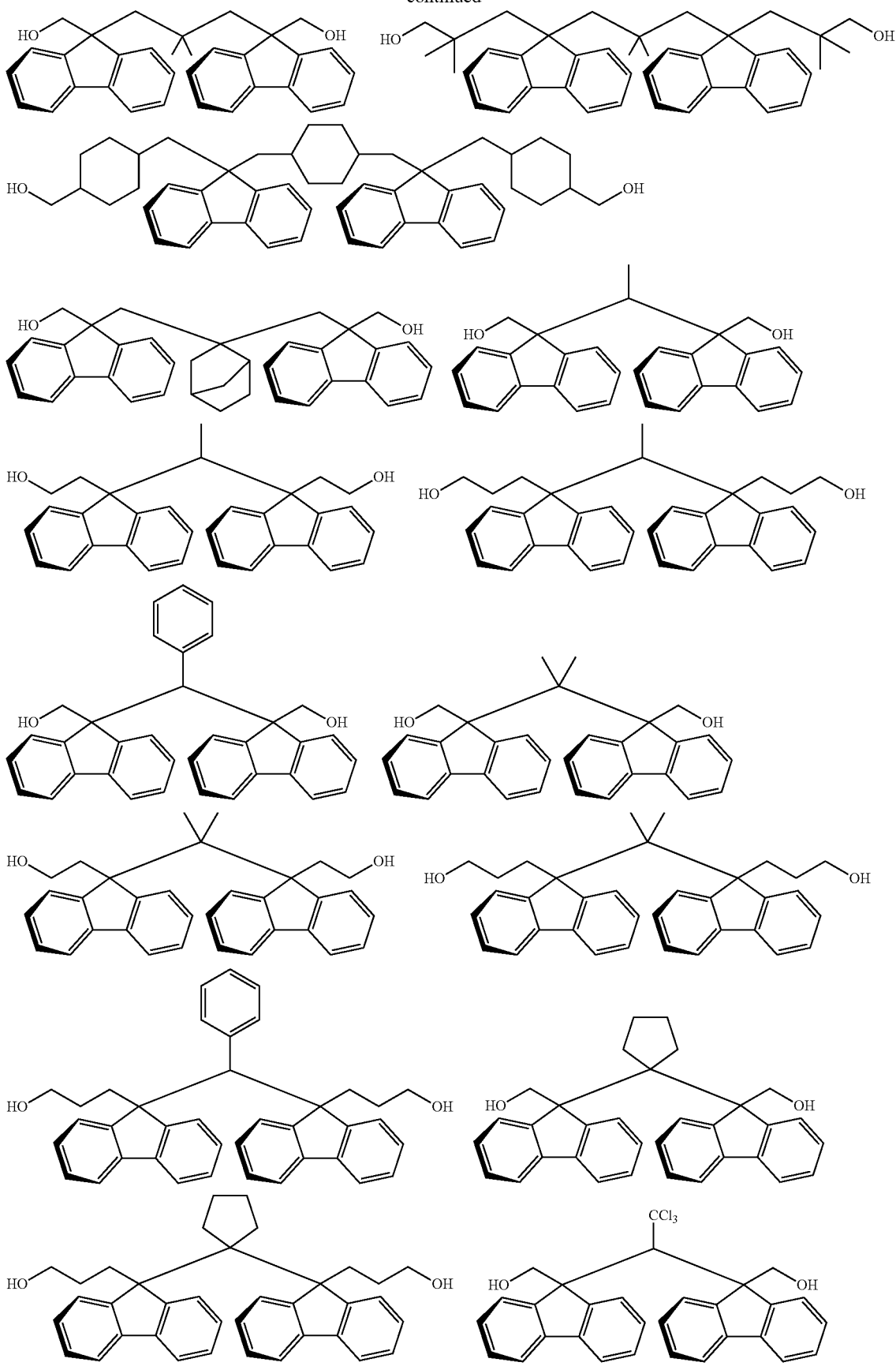

-continued
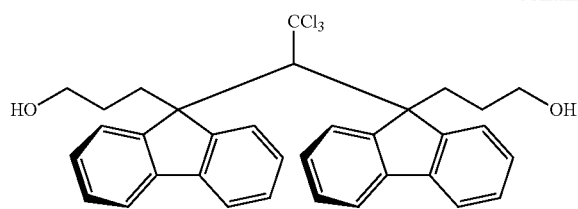
[Chem. 58]
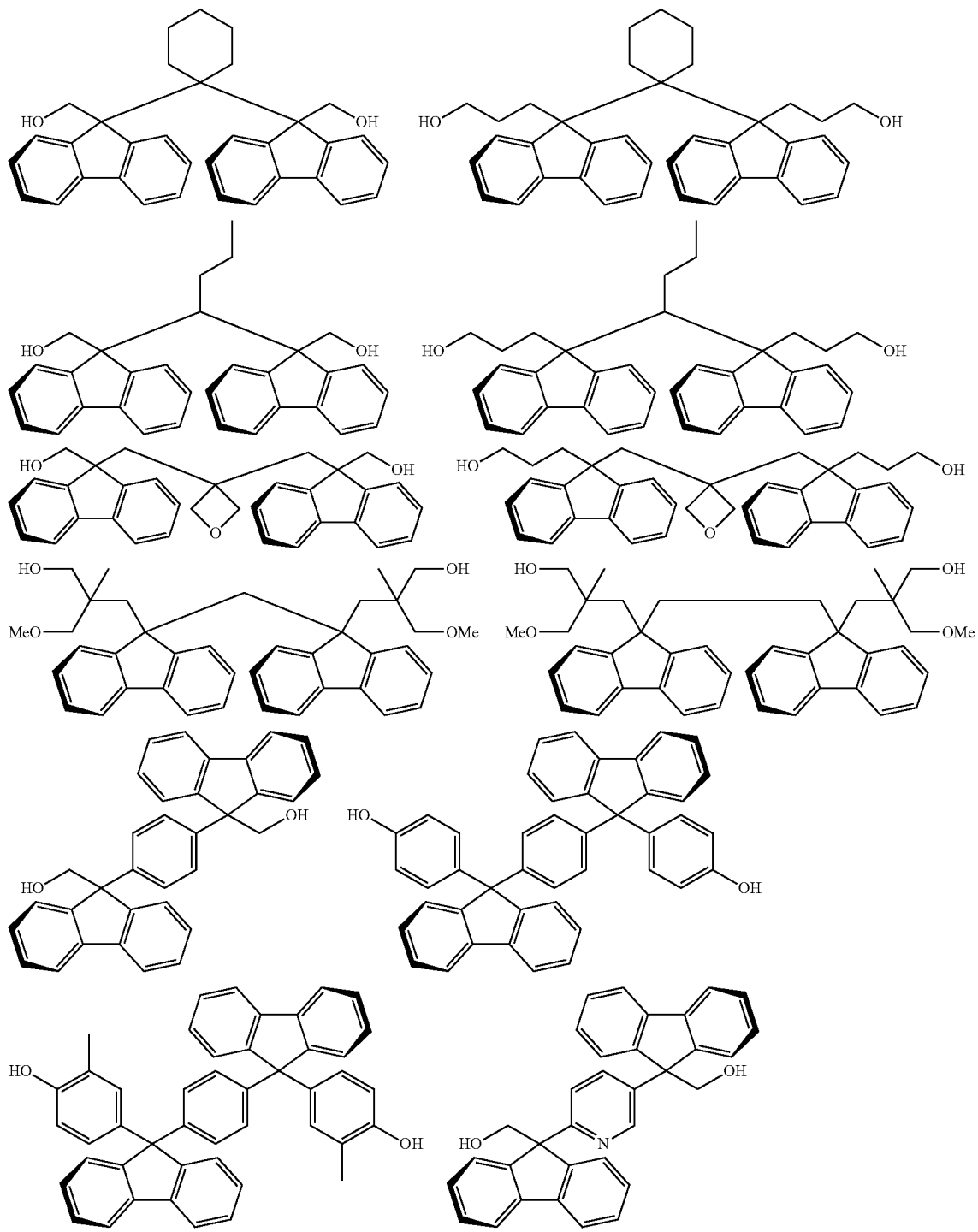

-continued
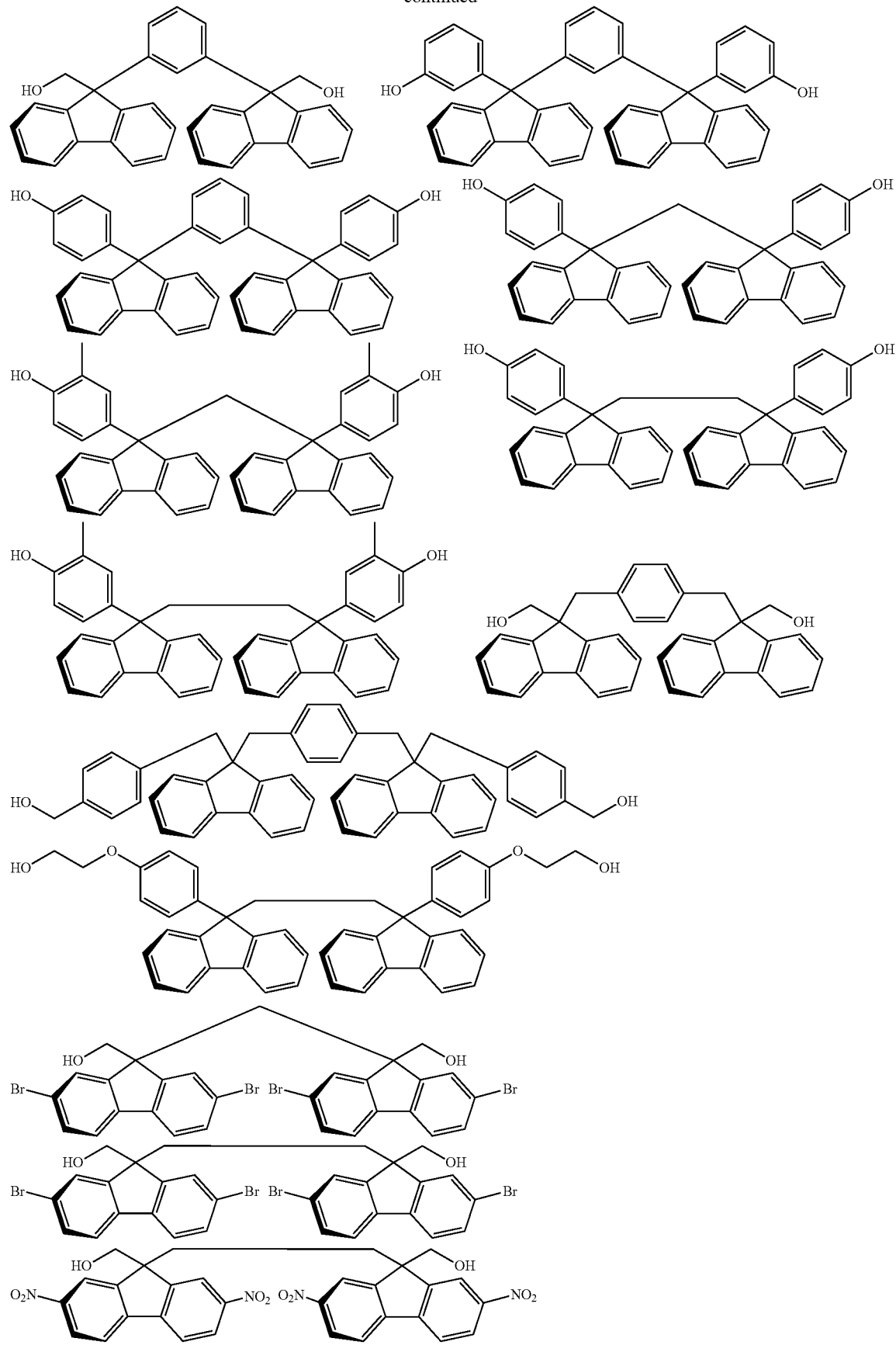

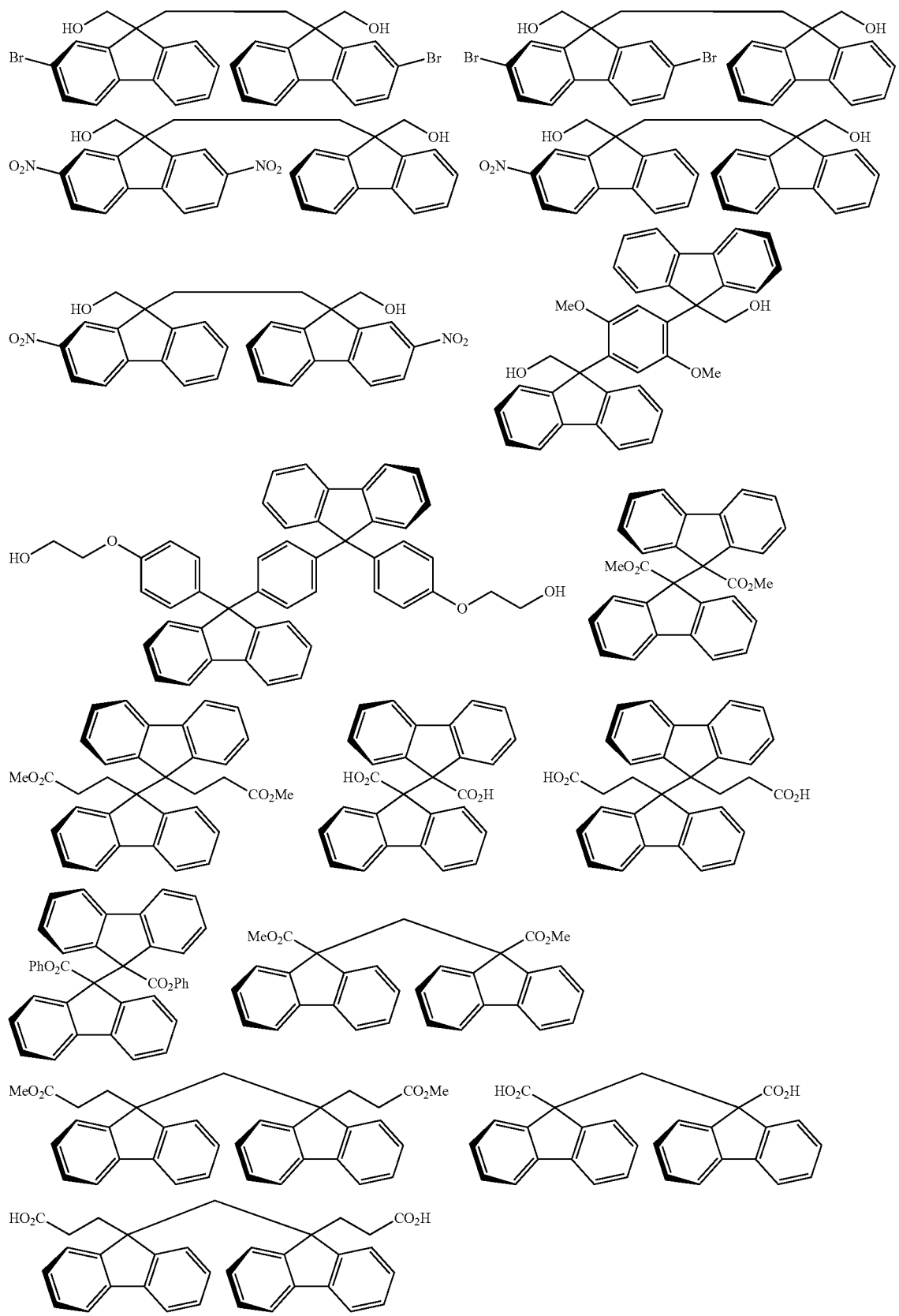

-continued
[Chem. 59]
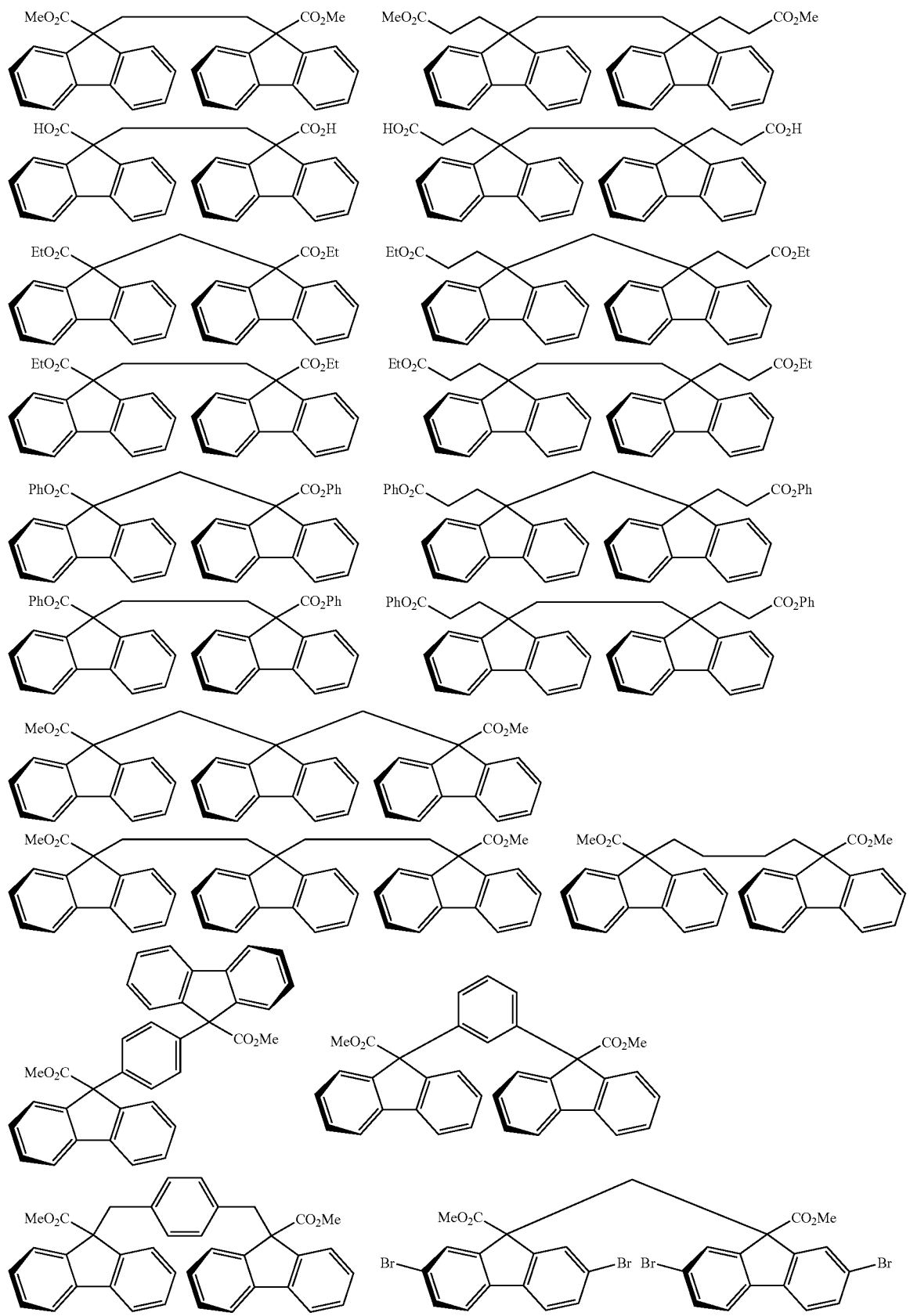

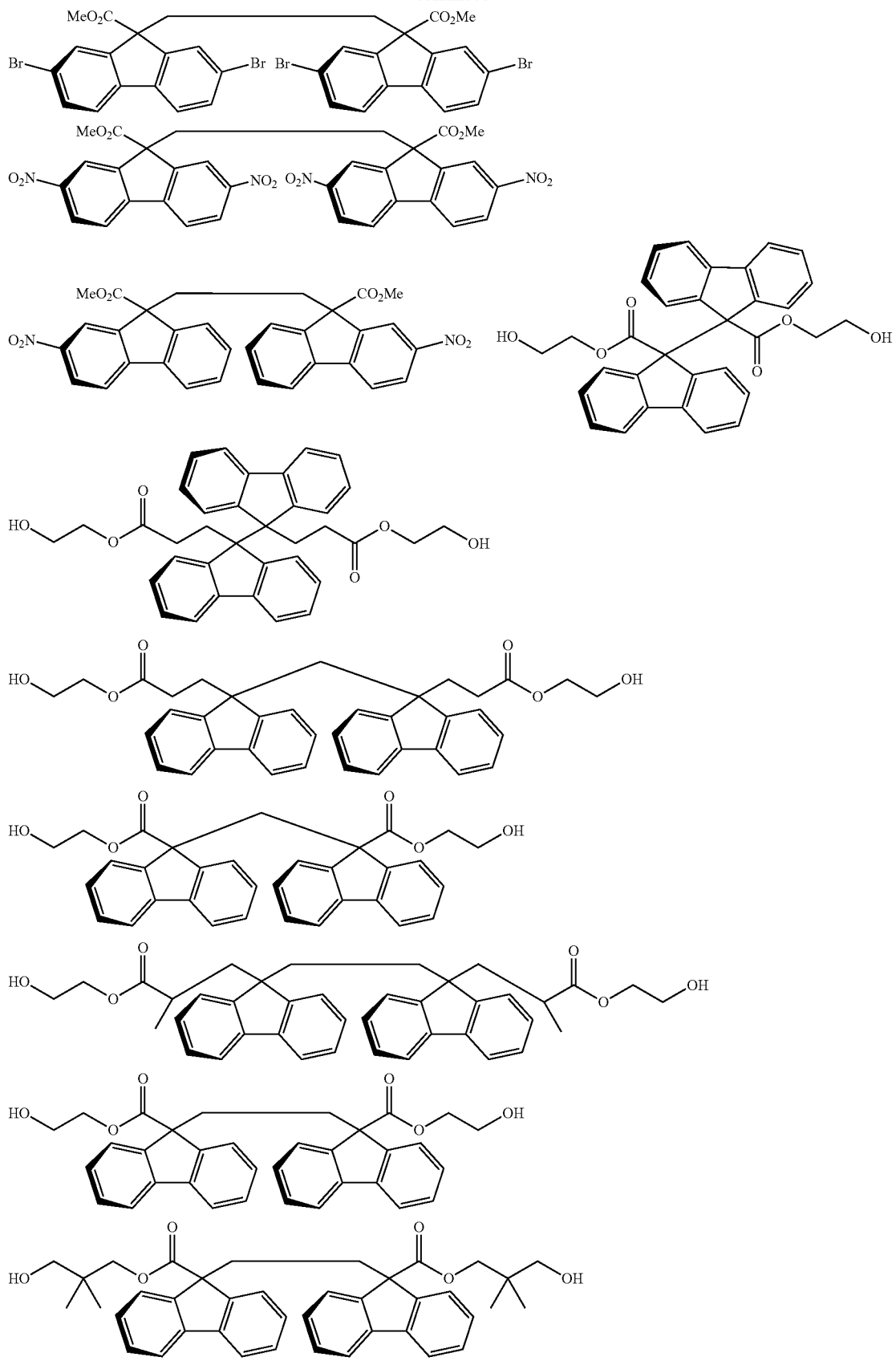

-continued
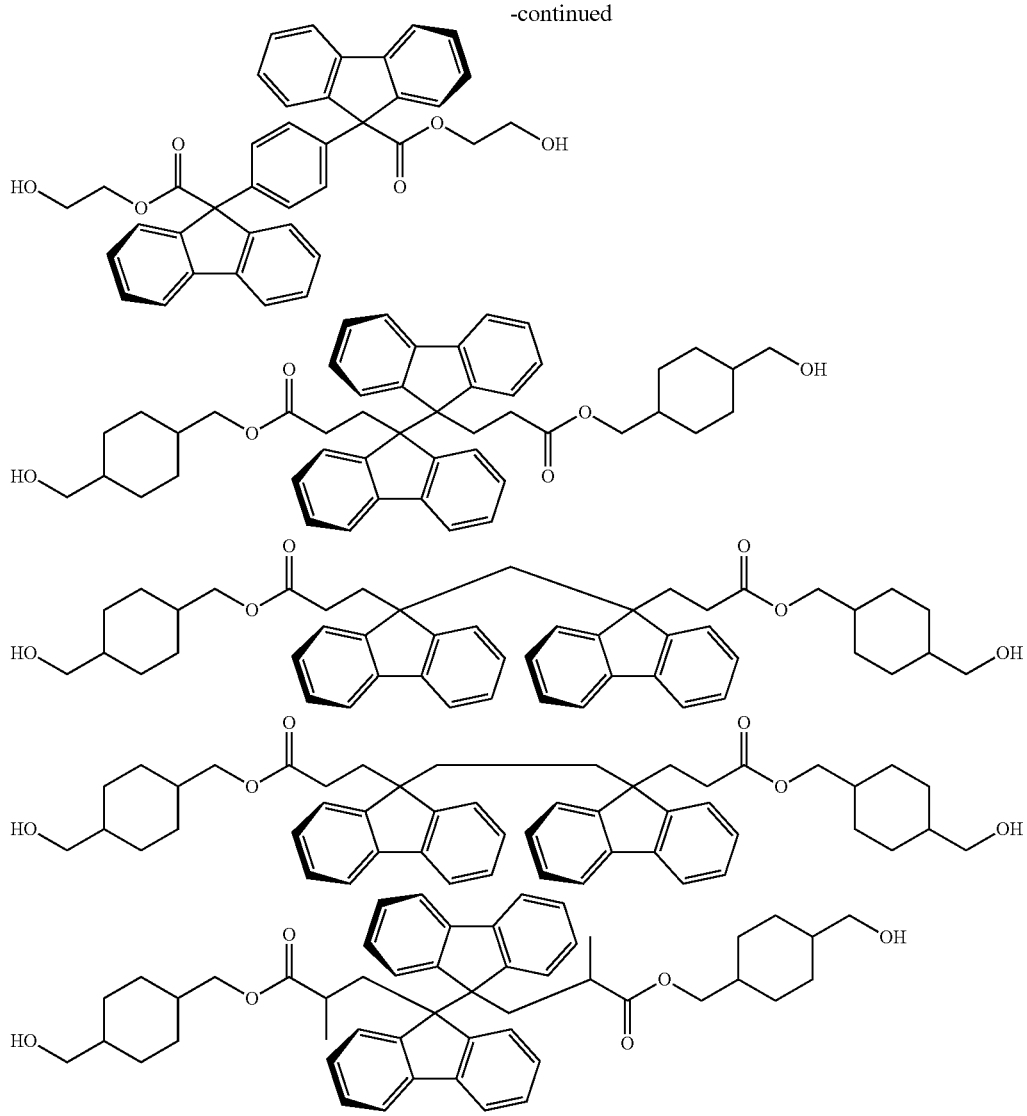
[Chem. 60]
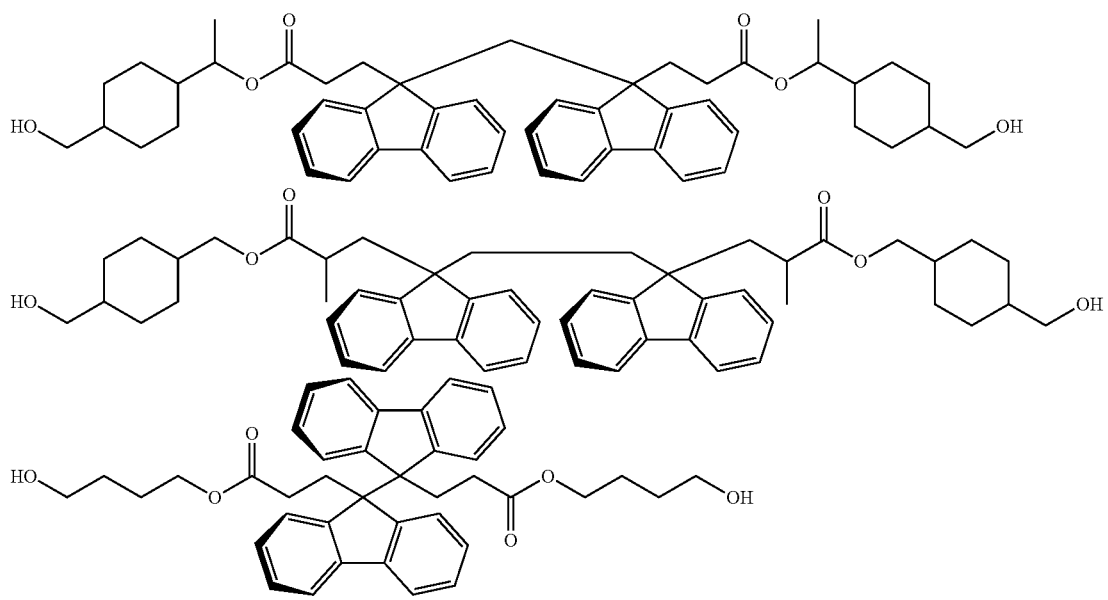

107 108
-continued
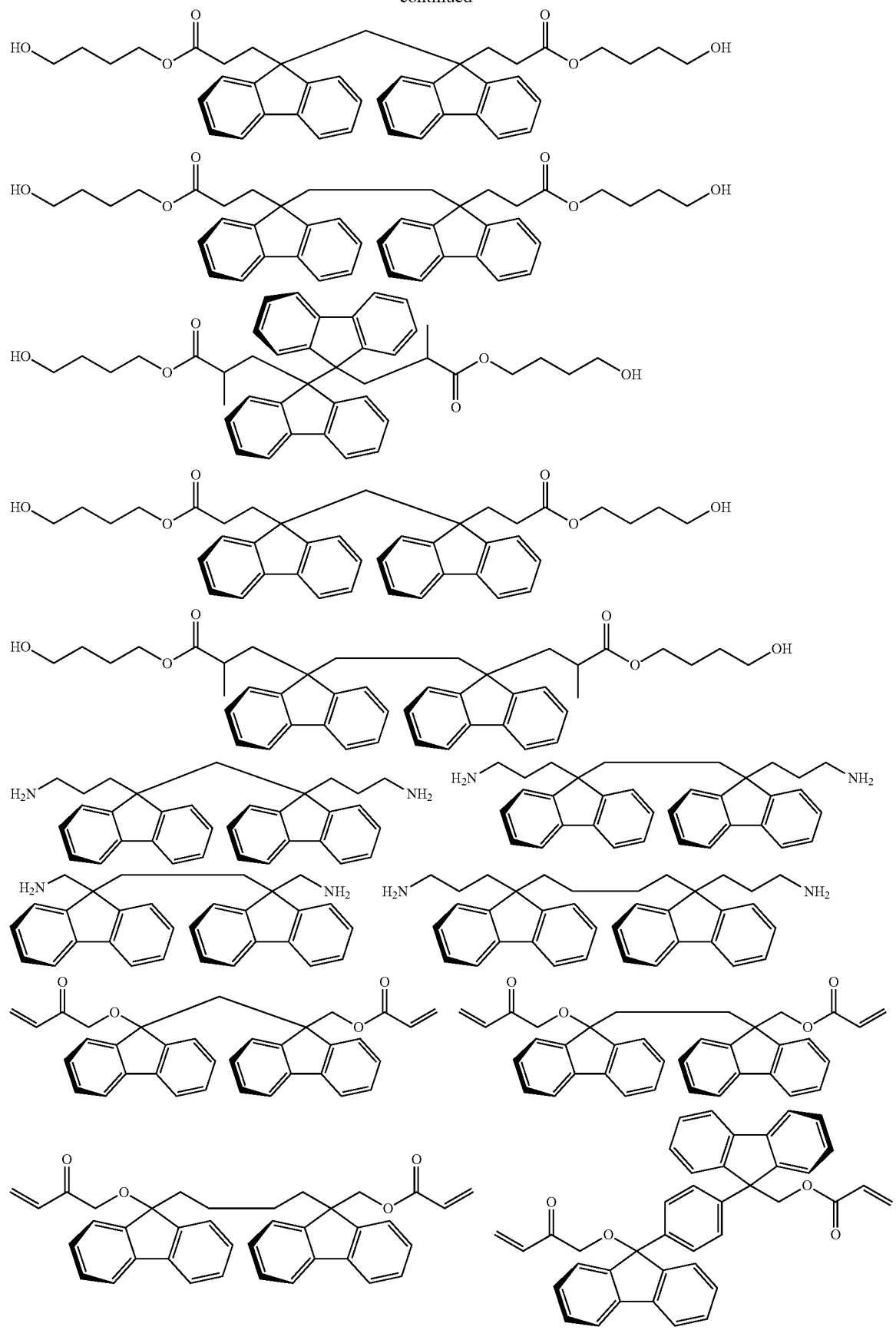

109 110
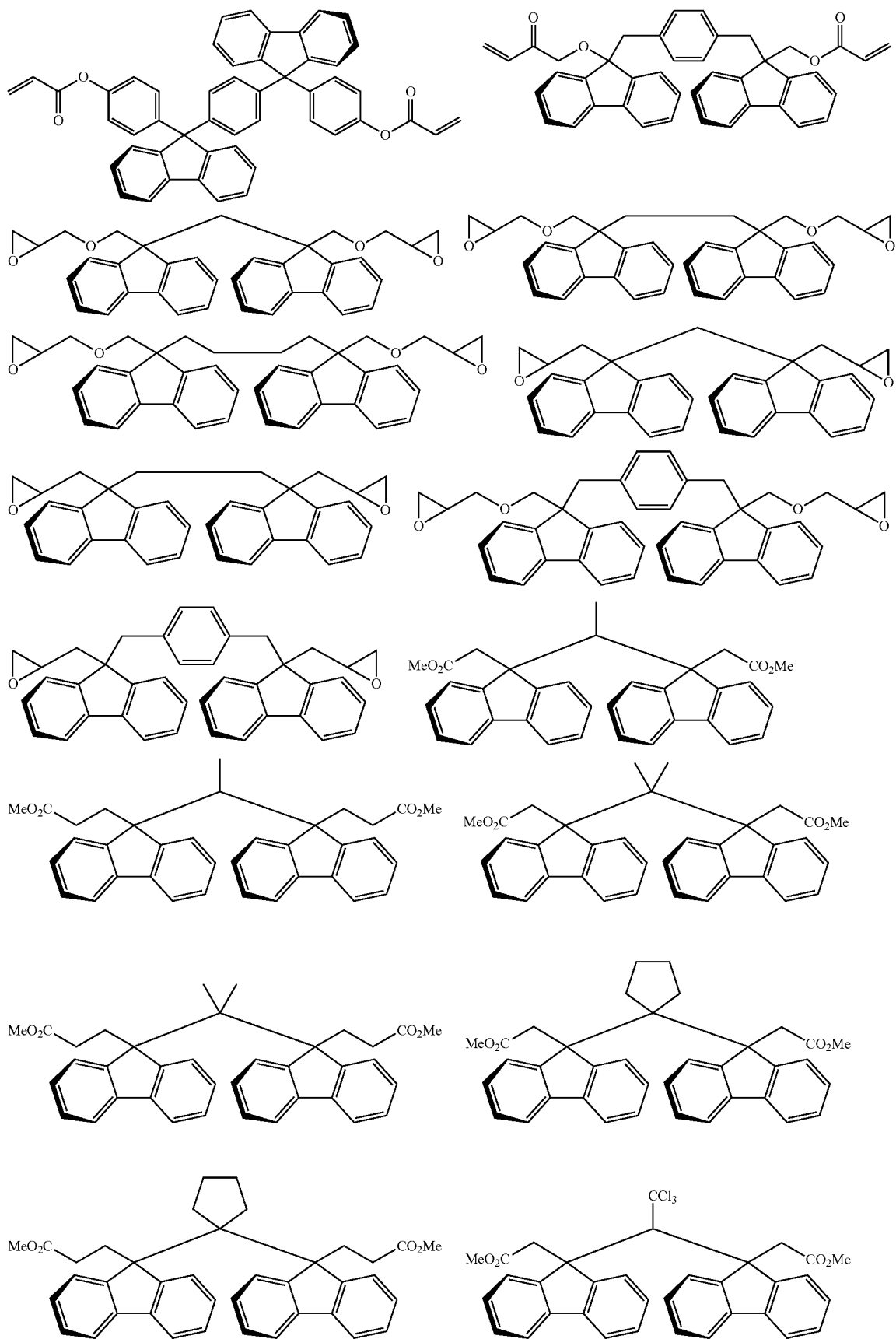

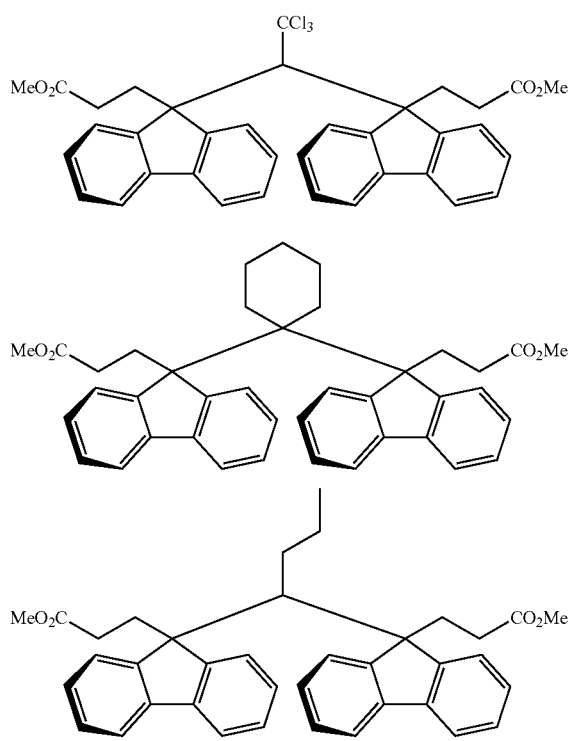
[Chem. 61]
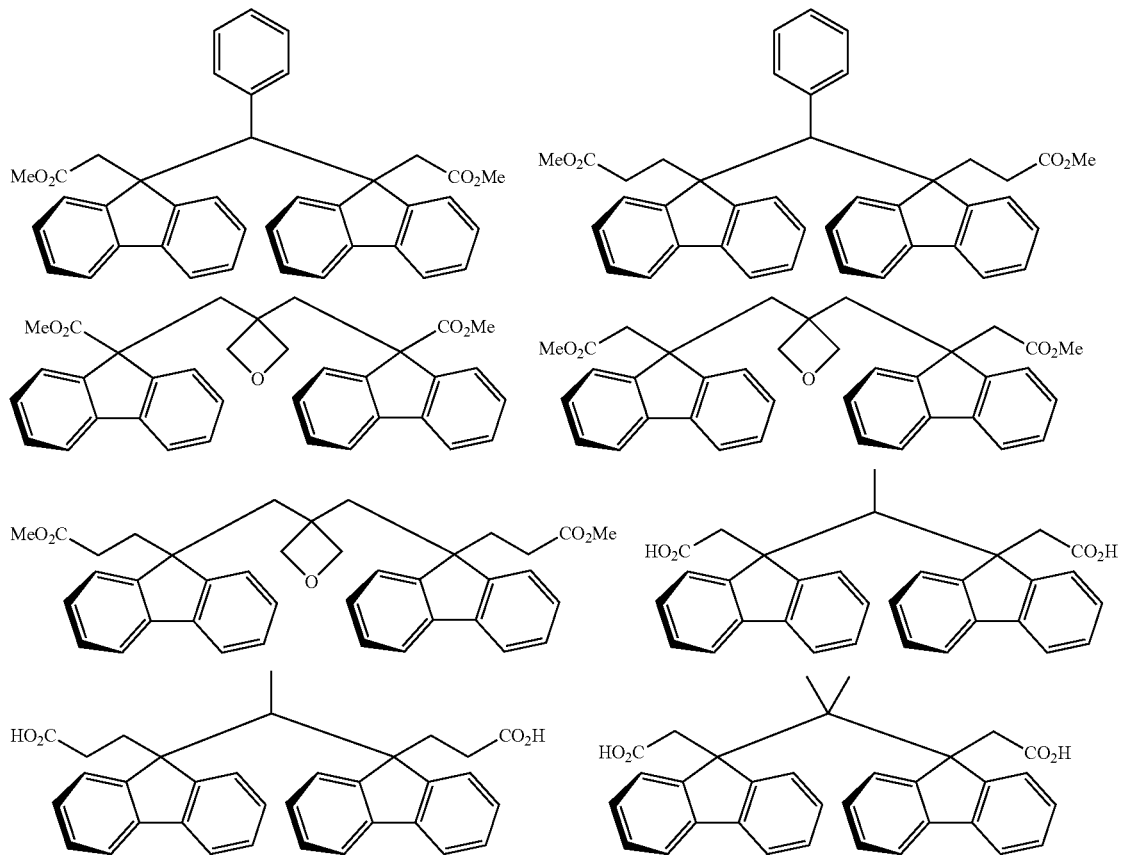

113 114
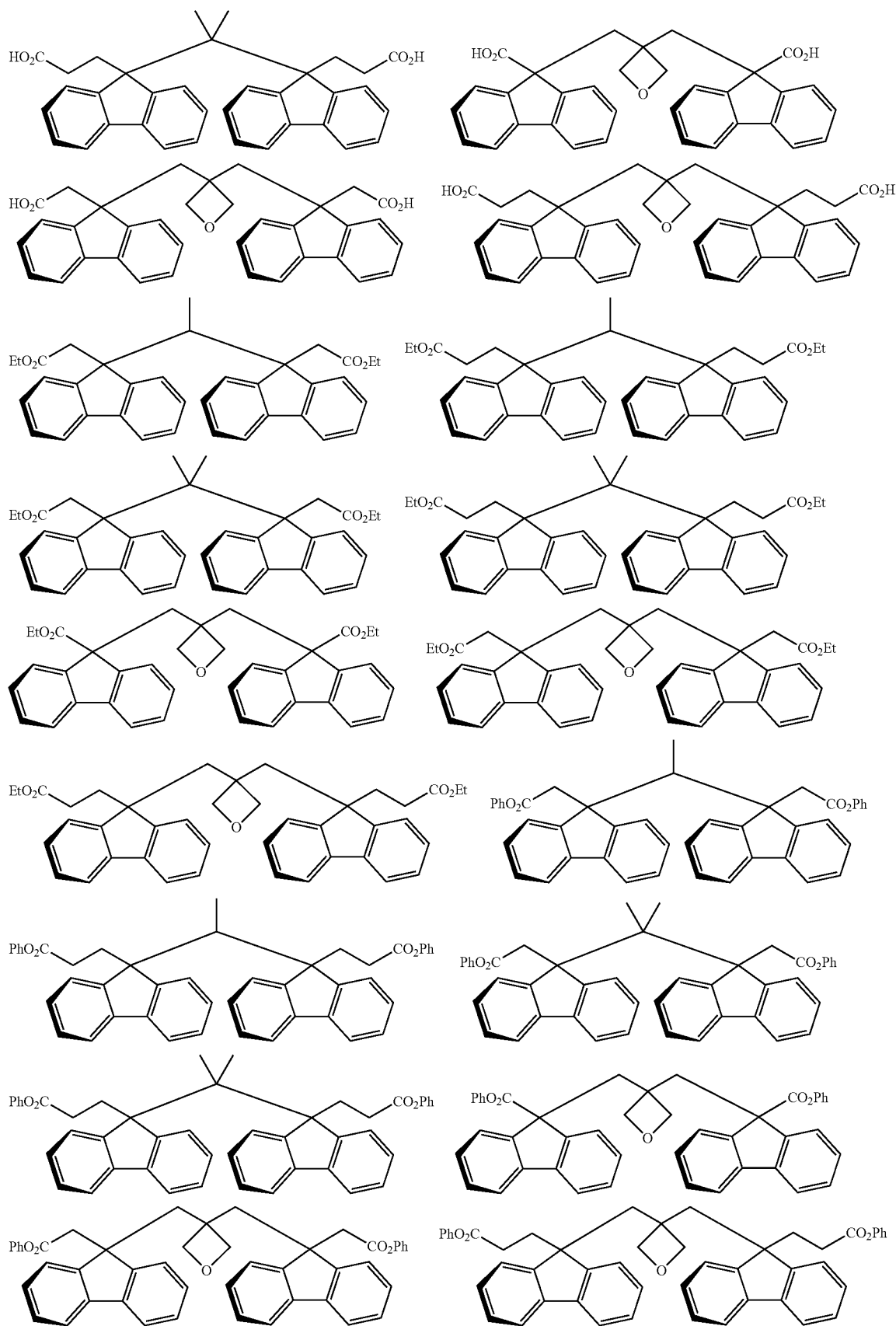
-continued

115
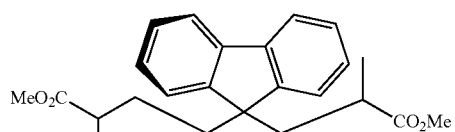
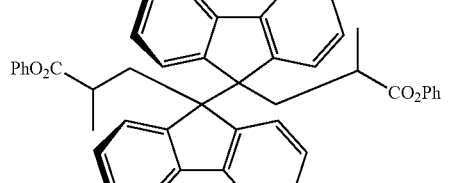
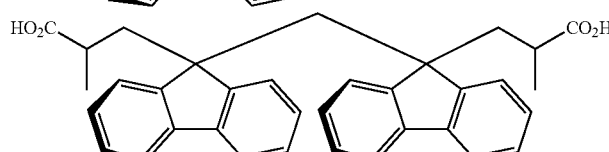
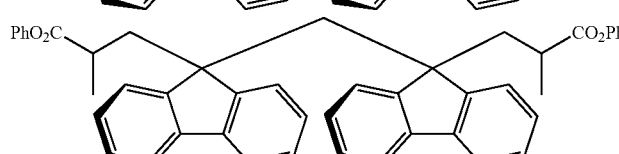
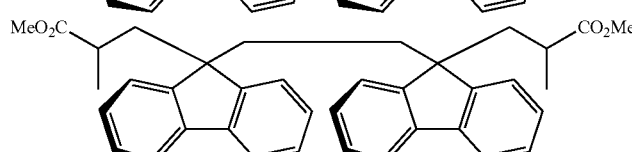
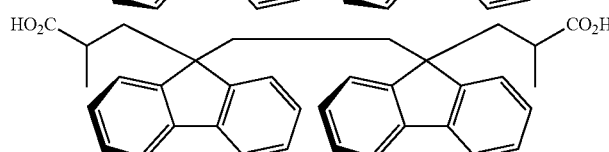
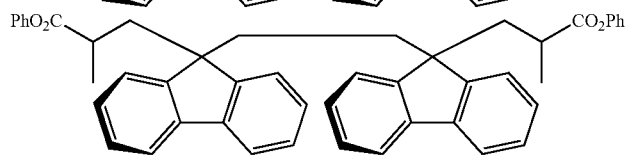
116
-continued
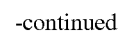
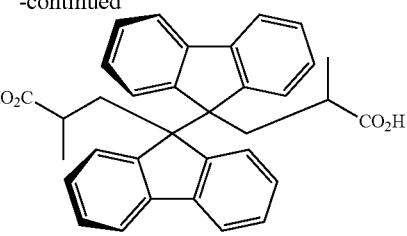
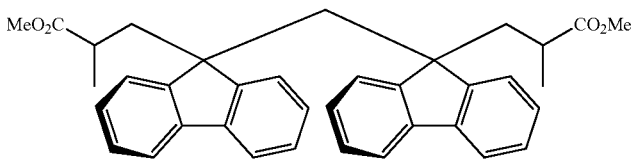
<4-3. Oligofluorene-diol>
Of the oligofluorenes represented by the general formula (10a), especially preferred oligofluorene monomers having a hydroxymethyl group are dihydroxy compounds represented by the following general formula (19) (hereinafter these are referred to as oligofluorene-diols).
[Chem. 62]
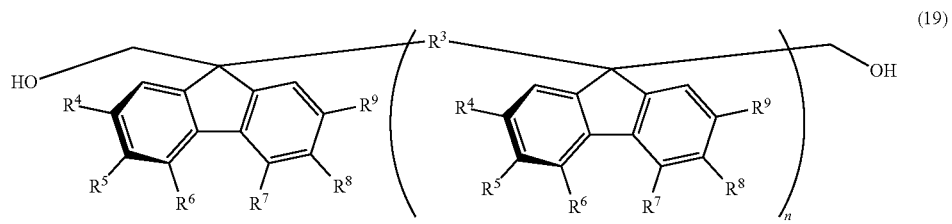
(19)

(In the formula, $R^3$ represents an optionally-substituted alkylene group having from 1 to 10 carbon atoms, an optionally-substituted arylene group having from 4 to 10 carbon atoms, or an optionally-substituted aralkylene group having from 6 to 10 carbon atoms, $R^4$ to $R^9$ each independently represent a hydrogen atom, an optionally-substituted alkyl group having from 1 to 10 carbon atoms, an optionally-substituted aryl group having from 4 to 10 carbon atoms, an optionally-substituted acyl group having from 1 to 10 carbon atoms, an optionally-substituted alkoxy group having from 1 to 10 carbon atoms, an optionally-substituted aryloxy group having from 1 to 10 carbon atoms, an optionally-substituted amino group, a sulfur atom having a substituent, a halogen atom, a nitro group or a cyano group. At least two adjacent groups of $R^4$ to $R^9$ may bond to each other to form a ring. n indicates an integer value of from 1 to 5.)

To $R^3$ to $R^9$ and n, those exemplified hereinabove as preferred examples in the general formula (1) are applicable.

The resin composition prepared using the oligofluorene-diol can simply exhibit flat wavelength dispersion characteristics of retardation, since in the divalent oligofluorene therein, the carbon number of $R^1$ and $R^2$ each bonding to the 9-positioned carbon atom of the fluorene at both terminals can be 1.

Of the above-mentioned general formula (19), preferred are those in which $R^4$ to $R^9$ are all hydrogen atoms, since these can be derived from industrially-inexpensive fluorenes and since, in these, the fluorene ratio can be increased, steric hindrance between fluorene rings hardly occurs, and the oligofluorenes tend to have fluorene ring-derived desired optical properties. More preferred are those in which $R^3$ is an optionally-substituted alkylene group having from 1 to 10 carbon atoms and $R^4$ to $R^9$ are all hydrogen atoms, since the compounds do not contain an aromatic ring in the main chain thereof and are considered to have weak photoelasticity. Even more preferred are those in which $R^3$ is a methylene group, an ethylene group, an n-propylene group, an n-butylene group or a 2,2-dimethylpropylene group, and $R^4$ to $R^9$ are all hydrogen atoms. Still more preferred is bis(9-hydroxymethylfluoren-9-yl)methane or bis(9-hydroxymethylfluoren-9-yl)ethane, in which $R^3$ is a methylene group or an ethylene group, and $R^4$ to $R^9$ are all hydrogen atoms. The compounds in which the substituent $R^3$ has a long chain may lower the glass transition temperature of the resin composition containing the polymer. The resin composition using the hydroxymethyl group-having oligofluorene monomer represented by the general formula (19) has, differing from the resin composition using any other fluorene monomer, surprising characteristics that the composition has positive refractive index anisotropy in almost any and every copolymerization ratio and has nearly flat wavelength dispersion retardation, though the monomer has a fluorene ring bonding to the main chain at the 9-position thereof. This is because the hydroxymethyl group preferentially takes a folding structure and therefore the fluorene ring would not be oriented vertically to the stretching direction but would be oriented obliquely thereto. In addition, changing the copolymerization ratio makes it possible to control the birefringence value, and therefore in the region in which the proportion of the hydroxymethyl group-having oligofluorene monomer is high, the resin composition can be utilized as a broadband zero birefringence material.

Specific examples of the oligofluorene-diol represented by the general formula (19) include bis(9-hydroxymethylfluoren-9-yl)methane, 1,2-bis(9-hydroxymethylfluoren-9-yl)ethane, 1,3-bis(9-hydroxymethylfluoren-9-yl)propane, 1,3-bis(9-hydroxymethylfluoren-9-yl)-2,2-dimethylpropane, 1,4-bis(9-hydroxymethylfluoren-9-yl)butane, 1,4-bis(9-hydroxymethylfluoren-9-yl)benzene, 1,3-bis(9-hydroxymethylfluoren-9-yl)benzene, 1,4-bis[(9-hydroxymethylfluoren-9-yl)methyl]benzene, 9,9-bis[(9-hydroxymethylfluoren-9-yl)methyl]fluorene, 9,9-bis[2-(9-hydroxymethylfluoren-9-yl)ethyl]fluorene, bis[9-[(9-hydroxymethylfluoren-9-yl)methyl]fluoren-9-yl]methane, 1,2-bis[9-[2-(9-hydroxymethylfluoren-9-yl)ethyl]fluoren-9-yl]ethane, etc.

<4-4. Oligofluorene Diaryl Ester>

Of the general formula (10b), especially preferred aryl ester group-having oligofluorene monomers are compounds represented by the following general formula (10d).

Diaryl ester compounds represented by the following:

[Chem. 63]

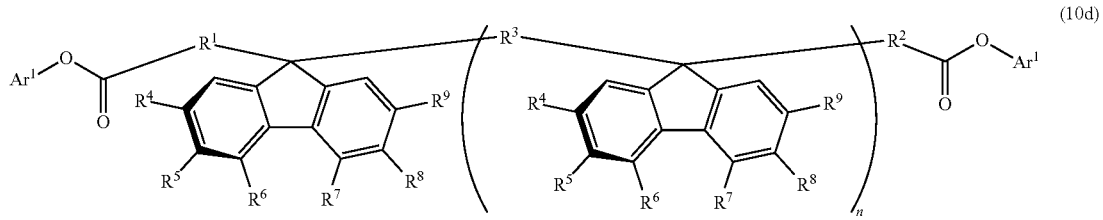

(10d)

In the general formula (10d), $R^1$ and $R^2$ each independently represent a direct bond, an optionally-substituted alkylene group having from 1 to 10 carbon atoms, an optionally-substituted arylene group having from 4 to 10 carbon atoms, or an optionally-substituted aralkylene group having from 6 to 10 carbon atoms, or a group formed by bonding at least two groups selected from an optionally substituted alkylene group having from 1 to 10 carbon atoms, an optionally-substituted arylene group having from 4 to 10 carbon atoms and an optionally-substituted aralkylene group having from 6 to 10 carbon atoms, via an oxygen atom, an optionally-substituted sulfur atom, an optionally-substituted nitrogen atom or a carbonyl group.

$R^3$ represents a direct bond, an optionally-substituted alkylene group having from 1 to 10 carbon atoms, an optionally-substituted arylene group having from 4 to 10 carbon atoms, or an optionally-substituted aralkylene group having from 6 to 10 carbon atoms.

$R^4$ to $R^9$ each independently represent a hydrogen atom, an optionally-substituted alkyl group having from 1 to 10 carbon atoms, an optionally-substituted aryl group having from 4 to 10 carbon atoms, an optionally-substituted acyl group having from 1 to 10 carbon atoms, an optionally-substituted alkoxy group having from 1 to 10 carbon atoms, an optionally-substituted aryloxy group having from 1 to 10 carbon atoms, an optionally-substituted amino group, a sulfur atom having a substituent, a halogen atom, a nitro group or a cyano group. At least two adjacent groups of $R^4$ to $R^9$ may bond to each other to form a ring.

$Ar^1$ represents an optionally-substituted aryl group having from 4 to 10 carbon atoms, and n indicates an integer value of from 1 to 5. On the right and left sides, $Ar^1$'s may be the same or different. (Hereinafter the compounds are referred to as oligofluorene diaryl esters.)

To $R^1$ to $R^9$ and n, those exemplified hereinabove as preferred examples in the general formula (1) are applicable.

$Ar^1$ represents an optionally-substituted aryl group having from 4 to 10 carbon atoms, of which the carbon number is preferably 4 or more, more preferably 6 or more and is 10 or less, preferably 8 or less. Falling within the range, the side products, aryl alcohols in production of polycarbonates or polyester carbonates can be removed through evaporation, and therefore the degree of polymerization of the polycarbonates and polyester carbonates to be produced can be increased. The substituent that the aryl group may have includes a methyl group, an ethyl group, a chlorine atom, a bromine atom, a phenyl group, etc.

Specific examples of $Ar^1$ include a phenyl group, a tolyl group, a chlorophenyl group, a naphthyl group, an m-cresyl group, a biphenyl group, etc. Above all, from the viewpoint that the compounds are industrially inexpensive and have a relatively small molecular weight, the substituent is preferably a phenyl group, a tolyl group, a chlorophenyl group, or an m-cresyl group. More preferred is a phenyl group since the monomer can be evaporated away as phenol through distillation after polymerization.

Of the above-mentioned general formula (10d), preferred are those in which $R^4$ to $R^9$ are all hydrogen atoms, since these can be derived from industrially-inexpensive fluorenes and since, in these, the fluorene ratio can be increased, steric hindrance between fluorene rings hardly occurs, and the oligofluorenes tend to have fluorene ring-derived desired optical properties. More preferred are those in which $R^1$, $R^2$ and $R^3$ each are independently an optionally-substituted alkylene group having from 1 to 10 carbon atoms and $R^4$ to $R^9$ are all hydrogen atoms, since the compounds do not contain an aromatic ring in the main chain thereof and are considered to have a small photoelastic coefficient. Even more preferred are those in which $Ar^1$ is a phenyl group, a tolyl group, a chlorophenyl group, an m-cresyl group, a naphthyl group or a biphenyl group, $R^1$, $R^2$ and $R^3$ are each independently a methylene group, an ethylene group, an n-propylene group, an n-butylene group or a 2,2-dimethyl-propylene group, and $R^4$ to $R^9$ are all hydrogen atoms, since the compounds are industrially inexpensive and have a relatively small molecular weight. Still more preferred is bis[9-(2-phenoxycarbonylethyl)fluoren-9-yl]methane or 1,2-bis[9-(2-phenoxycarbonylethyl)fluoren-9-yl]ethane, in which $Ar^1$ is a phenyl group, $R^1$, $R^2$ and $R^3$ are each a methylene group or an ethylene group, and $R^4$ to $R^9$ are all hydrogen atoms, since the compounds can be evaporated away through distillation as phenol after production of polyesters and polyester carbonates. The compounds in which the substituent $R^3$ has a long chain may lower the glass transition temperature of the resin composition containing the polymer. Of the diaryl ester group-having oligofluorene monomers represented by the general formula (10d), the activity of the ester group is enhanced and the monomers provide easy interesterification. Consequently, the dihydroxy compound and a carbonic diester can be put all at a time into a reactor to give preferred polymers of polyester carbonates in one stage.

Specific examples of the oligofluorene diaryl ester represented by the above-mentioned general formula (10d) include [9-(2-phenoxycarbonylethyl)fluoren-9-yl]methane, 1,2-bis[9-(2-phenoxycarbonylethyl)fluoren-9-yl]ethane, [9-(phenoxycarbonylmethyl)fluoren-9-yl]methane, 1,2-bis[9-(phenoxycarbonylmethyl)fluoren-9-yl]ethane, [9-(2-phenoxycarbonylpropyl)fluoren-9-yl]methane, 1,2-bis[9-(2-phenoxycarbonylpropyl)fluoren-9-yl]ethane, 1,3-bis[9-(2-phenoxycarbonylethyl)fluoren-9-yl]propane, 1,3-bis[9-(2-phenoxycarbonylethyl)fluoren-9-yl]-2,2-dimehtylpropane, 1,4-bis[9-(2-phenoxycarbonylethyl)fluoren-9-yl]butane, 1,4-bis[9-(2-phenoxycarbonylethyl)fluoren-9-yl]benzene, 1,3-bis[9-(2-phenoxycarbonylethyl)fluoren-9-yl]benzene, 1,4-bis[[9-(2-phenoxycarbonylethyl)fluoren-9-yl]methyl]benzene, 9,9-bis[[9-(2-phenoxycarbonylethyl)fluoren-9-yl]methyl]fluorene, 9,9-bis[[9-(2-phenoxycarbonylethyl)fluoren-9-yl]ethyl]fluorene, bis[[[9-(2-phenoxycarbonylethyl)fluoren-9-yl]methyl]fluoren-9-yl]methane, 1,2-bis[[[9-(2-phenoxycarbonylethyl)fluoren-9-yl]ethyl]fluoren-9-yl]ethane, etc.

<4-5. Physical Data of Oligofluorene Monomer>

The chlorine content ratio in the oligofluorene monomer in the present invention is preferably 100 ppm by mass or less in terms of Cl mass. More preferably, the content ratio is 10 ppm by mass or less. When the chlorine component content ratio is large, the monomer may deactivate the catalyst used in polymerization with the result that the polymerization could not go on to give a desired molecular weight or the reaction would be unstable and the productivity would worsen. If so, in addition, the chlorine component may remain in the resultant polymer to worsen the thermal stability of the polymer.

The content ratio of the monohydroxy form in the oligofluorene-diol in the present invention is preferably 10% by mass or less of the entire monomer mass. More preferably, the content ratio is 2% by mass or less. When taken into the resultant polymer formed through polymerization, the monohydroxy form is to be a terminal blocking group, and consequently, when the amount of the monohydroxy form increases, then the polymerization could not go on to give a desired molecular weight or the amount of the low-molecular component such as oligomer and the like remaining in the resultant polymer may increase to worsen the mechanical strength and the heat resistance of the resultant polymer. Another disadvantage in the case is that the low-molecular component may bleed out from the shaped articles formed using the polymer and the quality of the articles would be thereby worsened. Here, the monohydroxy form means a type of oligofluorene-diol in which any one of the terminal hydroxyl groups is in any other form than a polymerization-reactive group.

The content ratio of the oligofluorene monoester form in the oligofluorene diester in the present invention is preferably 10% by mass or less of the entire monomer mass. More preferably, the content ratio is 2% by mass or less. When taken into the resultant polymer formed through polymerization, the oligofluorene monoester form is to be a terminal blocking group, and consequently, when the amount of the oligofluorene monoester form increases, then the polymerization could not go on to give a desired molecular weight or the amount of the low-molecular component such as oligomer and the like remaining in the resultant polymer may increase to worsen the mechanical strength and the heat resistance of the resultant polymer. Another disadvantage in the case is that the low-molecular component may bleed out from the shaped articles formed using the polymer and the quality of the articles would be thereby worsened. Here, the monoester form means a type of oligofluorene diester in which any one of the terminal ester groups is in any other form than a polymerization-reactive group.

There is a possibility that the oligofluorene-diol in the present invention may contain a Group-1 metal of the Long Periodic Table such as sodium, potassium or the like or a Group-2 metal such as calcium or the like, which may be derived from the hydroxymethylation process of reacting with a formaldehyde in the presence of a base, and it is desirable that the metal content ratio is 500 ppm by mass or less, more preferably 200 ppm by mass or less, even more preferably 50 ppm by mass or less, still more preferably 10 ppm by mass or less. When the amount of the metal component is large, then there may be a worry that the polymer would be discolored in polymerization or resin processing. Another disadvantage is that the contained metal component would exhibit a catalytic action or a catalyst deactivating action and the polymerization would be thereby destabilized.

There is a possibility that the oligofluorene diaryl ester in the present invention may contain a transition metal such as titanium, copper, iron or the like, a Group-1 metal of the Long Periodic Table such as sodium, potassium or the like, a Group-2 metal such as magnesium, calcium or the like, a Group-12 metal such as zinc, cadmium or the like, a Group-14 metal such as tin or the like, which may be derived from the interesterification process of reacting with a carbonic diaryl ester in the presence of an interesterification catalyst, and it is desirable that the metal content ratio is 500 ppm by mass or less, more preferably 200 ppm by mass or less, even more preferably 50 ppm by mass or less, still more preferably 10 ppm by mass or less. When the amount of the metal component is large, then there may be a worry that the polymer would be discolored in polymerization or resin processing. Another disadvantage is that the contained metal component would exhibit a catalytic action or a catalyst deactivating action and the polymerization would be thereby destabilized.

Preferably, the color tone of the 10 mass % tetrahydrofuran solution of the oligofluorene monomer in the present invention is 50 or less, more preferably 10 or less. Of the oligofluorene monomer, the absorption end reaches near the region of visible light, and the monomer therefore has a property that when exposed to high temperatures in polymerization or resin processing, it would be discolored. For obtaining a polymer having a good color tone, it is desirable that the oligofluorene monomer to be used for polymerization is colored as little as possible. Color tone is proportional to concentration, and therefore, the color tone of the monomer is measured at a different concentration, and the resultant data may be standardized to give a value of the 10 mass % concentration of the monomer. Here, the color tone (APHA value) of the oligofluorene monomer is measured according to JIS-K0071-1 (1998), as follows: A liquid prepared by diluting a color standard liquid by Kishida Chemical (1000 degrees) and an oligofluorene-diol are separately put into colorimetric tubes each having an inner diameter of 20 mm, and the two are compared with each other.

Preferably, the temperature for the 5% weight loss of the oligofluorene monomer in the present invention in thermogravimetry is 230° C. or higher, more preferably 250° C. or higher, even more preferably 270° C. or higher. Fluorene has an extremely electron-rich structure, and the reactivity of the substituent bonding to the fluorene ring is increased to readily cause thermal decomposition. When an oligofluorene monomer having a low thermal decomposition temperature is used in polymerization, then there may occur thermal decomposition during polymerization and therefore the polymerization could not go on to give a desired molecular weight or the resultant polymer may be discolored.

<5. Method for Introduction of Organic Group>

For introducing the divalent organic group represented by the general formula (3) into the resin composition of the present invention as a repeating unit therein, preferred are the following methods from the viewpoint of the transparency and the uniformity of the resin composition to be produced therein.

1. A method of copolymerizing a dihydroxy compound having an oligofluorene represented by the above-mentioned general formula (10a) and a dihydroxy compound represented by the following formula (21) and having an organic group represented by the above-mentioned general formula (3).

2. A method of two-stage introduction that comprises interestrifying a diester compound having an oligofluorene represented by the above-mentioned general formula (10b) with a dihydroxy compound represented by the following formula (21) and having an organic group represented by the above-mentioned general formula (3), followed by copolymerizing it with a dihydroxy compound represented by the following formula (21) and having an organic group represented by the above-mentioned general formula (3).

3. A method of copolymerizing a diaryl ester compound having an oligofluorene represented by the above-mentioned general formula (10d) and a dihydroxy compound represented by the following formula (21) and having an organic group represented by the above-mentioned general formula (3).

4. A method of copolymerizing a dihydroxy compound having an oligofluorene represented by the formula (10a), a dicarboxylic acid compound represented by the following formula (28) and having an organic group represented by the above-mentioned general formula (3), and a dihydroxy compound represented by the following formula (21) and having an organic group represented by the above-mentioned general formula (3).

HO—R$^{10}$—OH     (21)

HOCOR$^{10}$—COOH     (28)

(In the formulae, R$^{10}$ is the same as that in the above-mentioned general formula (3).)

Here, one alone or two or more different types of the divalent organic groups represented by the general formula (3) may be used either singly or as combined. Combined use of different types of organic groups may be attained by using different types of dihydroxy compounds represented by the general formula (21) and/or using different types of dicarboxylic acids represented by the general formula (28).

<6. Production Method for Polymer>

As described above, polyesters, polycarbonates and polyester carbonates are preferred as the polymers in the present invention. In general, polycarbonates may have a sufficient glass transition temperature and are excellent in hydrolysis resistance as compared with polyesters, and therefore polycarbonates are especially preferred here. On the other hand, in general, polyesters are better than polycarbonates in point of flexibility, and therefore polyesters are especially preferred here. Polyester carbonates are excellent in glass transition temperature and hydrolysis resistance and in the balance thereof and flexibility, and are therefore especially preferred.

Polycarbonates and polyester carbonates may be produced according to the method of <8. Polymerization Method for Polycarbonate>, etc. Polyesters may also be produced according to the same method, and concretely according to the method of <9. Polymerization Method for Polycarbonate>, etc.

<7. Polycarbonate Resin Composition>

In the resin composition of the present invention, preferably, the polymer is a polycarbonate from the viewpoint of the glass transition temperature and the hydrolysis resistance thereof. Hereinafter the resin composition in which the polymer is a polycarbonate may be abbreviated as "polycarbonate resin composition". Above all, it is desirable that the polymer contains a repeating unit structures bonded via a carbonate bond and/or an ester bond shown by the following group [Y], which constitutes a polyester, a polycarbonate or a polyester carbonate excellent in the balance of heat resistance, melt processability and mechanical strength.

[Chem. 64]

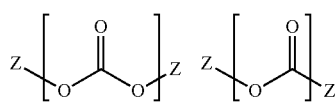

[Y]

(In the linking group shown by the above-mentioned group [Y], Z represents a site at which a divalent oligofluorene, a divalent organic group represented by the general formula (3) and any repeating unit bonds to the formula. When the linking group is asymmetric, the linking group may link to a divalent oligofluorene in any direction.)

The polycarbonate resin composition of the present invention means a resin composition that contains a polycarbonate have the necessary optical properties and physical properties, usable here is a copolymer that comprises a divalent oligofluorene, a divalent organic group represented by the general formula (3) and any repeating unit bonding to each other via at least one linking group shown by the above-mentioned group [Y].

The polycarbonate resin composition of the present invention may additionally contain any other polymer than the polymer having divalent oligofluorenes bonding to each other via a linking group, or may contain a polymer having divalent oligofluorenes bonding to each other via a linking group and a polymer having divalent organic groups represented by the general formula (3) and bonding to each other via a linking group, or may contain a polymer having divalent oligofluorenes bonding to each other via a linking group, a polymer having divalent organic groups represented by the general formula (3) and bonding to each other via a linking group, and a polymer having repeating units bonding to each other via a linking group. For controlling the films formed of the resin composition to have the necessary optical properties and physical properties, the resin composition may comprise a polymer having, as repeating units therein, divalent oligofluorenes bonding to each other via at least one linking group shown by the above-mentioned group [Y], a polymer having, as repeating units therein, divalent organic groups represented by the general formula (3), and a polymer having any repeating unit.

Here, one alone or two or more different types of the divalent organic groups represented by the general formula (3) are usable with singly or as combined.

<7-1. Oligofluorene-Containing Repeating Unit Structure>

Preferably, the polycarbonate resin composition of the present invention contains a polymer having a carbonate bond as the linking group therein and having a repeating unit structure represented by the following general formula (22), as capable of providing a sufficiently high glass transition point and desired optical properties.

[Chem. 65]

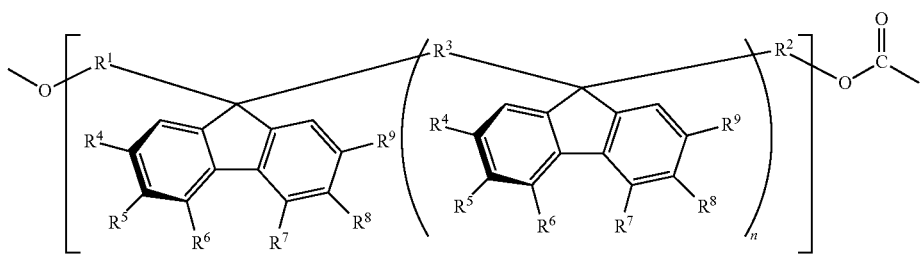

(22)

as the polymer therein, and the polymer therein may be composed of a polycarbonate alone or may contain any other polymer than polycarbonate.

The polycarbonate resin composition of the present invention may contain a polymer in which the divalent oligofluorenes bond to each other via any linking group, or may contain a copolymer in which the divalent oligofluorene bonds to the divalent organic group represented by the general formula (3) via any linking group, or may contain a copolymer in which the divalent oligofluorene, the divalent organic group represented by the general formula (3) and any repeating unit bond to each other via any linking group. For controlling the films formed of the resin composition to (In the formula, $R^1$ and $R^2$ each independently represent a direct bond, an optionally-substituted alkylene group having from 1 to 10 carbon atoms, an optionally-substituted arylene group having from 4 to 10 carbon atoms, or an optionally-substituted aralkylene group having from 6 to 10 carbon atoms, or a group formed by bonding at least two groups selected from the group consisting of an optionally-substituted alkylene group having from 1 to 10 carbon atoms, an optionally-substituted arylene group having from 4 to 10 carbon atoms and an optionally-substituted aralkylene group having from 6 to 10 carbon atoms, via an oxygen atom, an optionally-substituted sulfur atom, an optionally-substituted nitrogen atom or a carbonyl group, $R^3$ represents a direct bond, an optionally-substituted alkylene group having from 1 to 10 carbon atoms, an optionally-substituted arylene group having from 4 to 10 carbon atoms, or an optionally-substituted aralkylene group having from 6 to 10 carbon atoms, $R^4$ to $R^9$ each independently represent a hydrogen atom, an optionally-substituted alkyl group having from 1 to 10 carbon atoms, an optionally-substituted aryl group having from 4 to 10 carbon atoms, an optionally-substituted acyl group having from 1 to 10 carbon atoms, an optionally-substituted alkoxy group having from 1 to 10 carbon atoms, an optionally-substituted aryloxy group having from 1 to 10 carbon atoms, a halogen atom, a nitro group, or a cyano group. At least two adjacent groups of $R^4$ to $R^9$ may bond to each other to form a ring.

n indicates an integer value of from 1 to 5.)

To $R^1$ to $R^9$ and n, those exemplified hereinabove as preferred examples thereof for the general formula (1) are applicable.

Preferably, the polycarbonate resin composition of the present invention contains a polyester carbonate polymer having a repeating unit structure represented by the following general formula (24), in which the polymer has both a carbonate bond and an ester bond as the linking group therein and may be therefore excellent in glass transition temperature and hydrolysis resistance and in the balance thereof and flexibility. Here, the repeating unit structure of the polyester carbonate represented by the following general formula (24) is a repeating unit structure containing an oligofluorene skeleton, and is therefore preferred here since the polymer of the type can readily exhibit reversed wavelength dispersion characteristics of retardation even when the molar fraction and/or the mass ratio of the polymer in the composition may be small.

via a carbonate bond represented by the following general formula (12). The polymer of the type exhibits high hydrolysis resistance.

[Chem. 67]

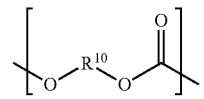

(12)

(In the formula, $R^{10}$ represents an optionally-substituted alkylene group having from 2 to 20 carbon atoms, an optionally-substituted arylene group having from 4 to 20 carbon atoms, an optionally-substituted aralkylene group having from 6 to 20 carbon atoms, an optionally-substituted alkylene ether group having from 2 to 100 carbon atoms, an optionally-substituted organic group having an alicyclic structure having from 4 to 20 carbon atoms, or an optionally-substituted organic group having a heterocyclic structure having from 4 to 20 carbon atoms.)

Of the repeating unit structure represented by the general formula (12), preferred is a repeating unit structure in which $R^{10}$ is an optionally-substituted alkylene group having from 2 to 20 carbon atoms, an optionally-substituted alkylene ether group having from 2 to 100 carbon atoms, an organic group having an optionally-substituted alicyclic structure having from 4 to 20 carbon atoms, or an organic group having an optionally-substituted heterocyclic structure having from 4 to 20 carbon atoms, since the structure of the type does not have an aromatic ring in the main chain thereof or has many other partial structures than aromatic rings in the

[Chem. 66]

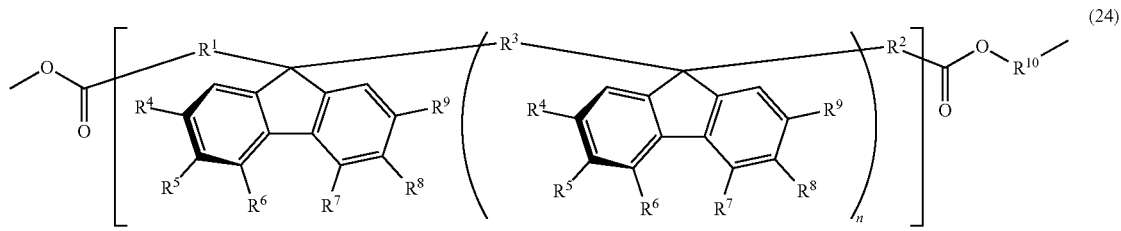

(24)

(In the formula, $R^1$ to $R^{10}$ and n are the same as those in the above-mentioned general formula (22).)

<7-2. Examples of Organic Group-Containing Repeating Unit Structure>

In the polycarbonate resin composition of the present invention, the polymer having a divalent oligofluorene as the repeating unit therein may have a divalent organic group represented by the general formula (3) as the repeating unit therein, for controlling the physical properties and the optical properties of the composition to fall each within a preferred range, and the resin composition may also contain both a polymer having a divalent oligofluorene as the repeating unit therein and a polymer having a divalent organic group represented by the general formula (3) as the repeating unit therein. Here, in the polymer having a divalent organic group represented by the general formula (3) as the repeating unit therein, the repeating unit is preferably in the form of a repeating unit structure bonding to each other main chain thereof and therefore can attain a low photoelastic coefficient necessary for optical films. More preferred is at least one repeating unit structure selected from a repeating unit structure represented by the following general formula (13), which tends to impart high transparency, a suitable glass transition temperature, water absorbability and a low photoelastic coefficient:

[Chem. 68]

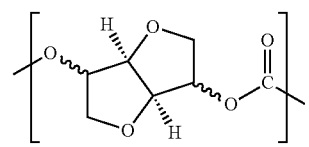

(13)

a repeating unit structure represented by the following general formula (14), which satisfies suitable hydrophobicity and flexibility and which tends to impart a low photoelastic coefficient:

[Chem. 69]

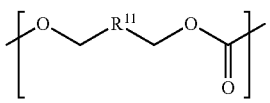
(14)

(wherein $R^{11}$ represents an optionally-substituted, linear alkylene group having from 0 to 18 carbon atoms), a repeating unit structure represented by the following general formula (15), which tends to impart high transparency and a suitable glass transition temperature:

[Chem. 70]

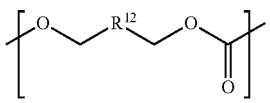
(15)

(wherein $R^{12}$ represents an optionally-substituted cycloalkylene group having from 4 to 20 carbon atoms), a repeating unit structure represented by the following general formula (16), which tends to impart flexibility and water absorbability and to impart a low photoelastic coefficient:

[Chem. 71]

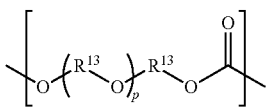
(16)

(wherein $R^{13}$ represents an optionally-substituted alkylene group having from 2 to 10 carbon atoms, and p indicates an integer of from 1 to 40), a repeating unit structure represented by the following general formula (17), which tends to impart high transparency and a suitable glass transition temperature:

[Chem. 72]

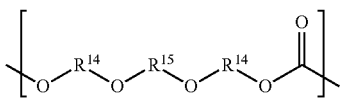
(17)

(wherein $R^{14}$ represents an optionally-substituted alkylene group having from 2 to 10 carbon atoms, and $R^{15}$ represents an optionally-substituted arylene group having from 12 to 30 carbon atoms), and a repeating unit structure represented by the following general formula (18), which tends to impart high transparency and a suitable glass transition temperature:

[Chem. 73]

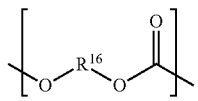
(18)

(wherein $R^{16}$ represents a group having an optionally-substituted acetal ring having from 2 to 20 carbon atoms).

More preferred is a repeating unit structure represented by the above-mentioned general formula (13), which tends to impart high transparency, a suitable glass transition temperature, water absorbability and a low photoelastic coefficient, and which therefore impart excellent physical properties for retardation films.

For $R^{11}$ in the formula (14), employable here are those exemplified hereinabove as preferred examples in the general formula (5). Similarly, for $R^{12}$ in the formula (15), employable are those exemplified hereinabove as preferred examples in the general formula (6), for $R^{13}$ in the formula (16), employable are those exemplified hereinabove as preferred examples in the general formula (7). For $R^{14}$ and $R^{15}$ in the formula (17), employable are those independently exemplified hereinabove as preferred examples in the general formula (8), and for $R^{16}$ in the formula (18), employable are those exemplified hereinabove as preferred examples in the general formula (9).

In the polycarbonate resin composition of the present invention, the divalent oligofluorene and the divalent organic group represented by the general formula (3) may be contained in any desired mass in the polycarbonate resin composition, falling within the range capable of expressing the above-mentioned optical properties.

<8. Polymerization Method for Polycarbonate>

As the production method for the polycarbonate resin composition of the present invention, preferred is one including a method of melt polycondensation of a dihydroxy compound and a carbonic diester represented by the following general formula (11) (melt polymerization method). In an interfacial polymerization method that is known as another general production method for polycarbonates, the usable monomer is limited to an aromatic dihydroxy compound, and therefore, preferred here is use of the melt method capable of applicable to a broader structure including an alcoholic hydroxy group-containing dihydroxy compound. In addition, the interfacial method requires use of toxic phosgene and a chlorine-containing solvent such as methylene chloride, chlorobenzene or the like, and therefore the environmental load to the method tends to high.

[Chem. 74]

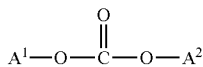
(11)

(In the formula, $A^1$ and $A^2$ each represent a substituted or unsubstituted aliphatic hydrocarbon group having from 1 to 18 carbon atoms, or a substituted or unsubstituted aromatic hydrocarbon group, and $A^1$ and $A^2$ may be the same or different.)

Of the polycarbonate resin composition of the present invention, the production method for the resin composition that contains a polymer having a preferred repeating unit structure represented by the above-mentioned general formula (22) preferably includes a method of melt polycondensation of a dihydroxy compound having an oligofluorene represented by the general formula (10a) and a carbonic diester represented by the general formula (11) (melt polymerization method). In the embodiment, any other dihydroxy compound than the dihydroxy compound having an oligofluorene represented by the general formula (10a) may be additionally used in the method.

Of the polycarbonate resin composition of the present invention, the production method for the resin composition that contains a polymer having a preferred repeating unit structure represented by the above-mentioned general formula (24) includes a two-step method that comprises a former step of interesterification of an oligofluorene diester compound represented by the general formula (10b) with a dihydroxy compound represented by the formula (21) and having an organic group represented by the general formula (3), and a latter step of melt polycondensation of the product formed in the former step with a carbonic diester represented by the general formula (11) (melt polymerization method) (in which in the latter step, a dihydroxy compound of the formula (21) having an organic group represented by the general formula (3) may be used), or a one-step method of melt polycondensation of a diaryl ester compound having an oligofluorene represented by the general formula (10d), a dihydroxy compound represented by the formula (21) and having an organic group represented by the general formula (3), and a carbonic diester represented by the general formula (11) (melt polymerization method).

<8-1. Carbonic Diester, Etc.>

As the carbonic diester to be used in the melt polymerization method, in general, there are mentioned those represented by the general formula (11). The carbonic diesters represented by the formula (11) include diaryl carbonates such as diphenyl carbonate, ditolyl carbonate, bis(chlorophenyl) carbonate, m-cresyl carbonate, dinaphthyl carbonate, bis(biphenyl)carbonate, etc.; dialkyl carbonates such as typically dimethyl carbonate, diethyl carbonate, dibutyl carbonate, dicyclohexyl carbonate, etc. Above all, preferred are diaryl carbonates, and more preferred is diphenyl carbonate. One alone or two or more types of these carbonic diesters may be used here either singly or as combined.

Preferably, the carbonic diester is used in a molar fraction of 0.90 or more relative to all the dihydroxy compounds to be used in the reaction, more preferably 0.96 or more, even more preferably 0.98 or more, and is preferably 1.10 or less, more preferably 1.05 or less, even more preferably 1.03 or less. In a case of introducing a dicarboxylic acid structure, it is desirable that the carbonic diester is used in a molar fraction of 0.90 or more relative to the molar number of the dihydroxy compounds obtained by subtracting the molar number of all the dicarboxylic acids from the molar number of all the dihydroxy compounds, more preferably 0.96 or more, even more preferably 0.98 or more, and is preferably 1.10 or less, more preferably 1.05 or less, even more preferably 1.03 or less. When the molar fraction is less than the lower limit, then the terminal hydroxyl groups in the produced polycarbonate would increase to worsen the thermal stability of the carbonate, or a desired polymer form could not be obtained. When the molar fraction is more than the upper limit, then the rate of interesterification would decreased under the same condition, or it would be difficult to produce a polycarbonate having a desired molecular weight, and in addition, the remaining carbonic diester amount in the produced polycarbonate would increase, and the remaining carbonic diester may evaporate away during film formation or film stretching to thereby cause film defects.

The polycarbonate contained in the polycarbonate resin composition of the present invention is a polymer having a configuration in which the repeating units derived from a dihydroxy compound bond to each other via a carbonate bond. In the present invention, the polycarbonate includes a polyester carbonate in which a part of the carbonate bond is substituted with a dicarboxylic acid structure and, in addition thereto, a carbonate bond-having polyurethane and the like.

<8-2. Polyester Carbonate>

A polyester carbonate can be obtained according to a method in which a part of the carbonic diester to be used for polymerization is substituted with a dicarboxylic acid compound represented by the general formula (28) and/or a dicarboxylic acid compound of an oligofluorene monomer represented by the general formula (20) where the polymerization-reactive groups $A^3$ and $A^4$ are carboxyl groups, or a method where as a part of the dihydroxy compound to be used for polymerization, used are a dihydroxy ester and/or a dihydroxy ester oligomer, etc. The dihydroxy ester and/or the dihydroxy ester oligomer usable here can be produced through reaction of a dicarboxylic acid compound and a dihydroxy compound. The dicarboxylic acid compound represented by the general formula (28) includes aromatic dicarboxylic acids such as terephthalic acid, phthalic acid, isophthalic acid, 4,4'-diphenyldicarboxylic acid, 4,4'-diphenylether-dicarboxylic acid, 4,4'-benzophenone-dicarboxylic acid, 4,4'-diphenoxyethane-dicarboxylic acid, 4,4'-diphenylsulfone-dicarboxylic acid, 2,6-naphthalenedicarboxylic acid, etc.; alicyclic dicarboxylic acids such as 1,2-cyclohexanedicarboxylic acid, 1,3-cyclohexanedicarboxylic acid, 1,4-cyclohexanedicarboxylic acid, etc.; aliphatic dicarboxylic acids such as malonic acid, succinic acid, glutaric acid, adipic acid, pimelic acid, suberic acid, azelaic acid, sebacic acid, etc. From the viewpoint of the heat resistance and the heat stability of the resultant polyester carbonate, preferred are aromatic dicarboxylic acids. Especially in view of the handleability and the availability thereof, preferred are terephthalic acid and isophthalic acid. Among these, more preferred is terephthalic acid. These dicarboxylic acid components may be used as the starting material for the polyester carbonate as they are just dicarboxylic acids, but depending on the production method for the polymer, dicarboxylates such as methyl ester forms, phenyl ester forms or the like, or dicarboxylic acid derivatives such as dicarboxylic acid halides or the like are also usable as the starting material. In case where an oligofluorene monomer represented by the general formula (20) is used as the dicarboxylic acid component, it is not indispensable to use the dihydroxy compound having an oligofluorene represented by the general formula (10a). From the viewpoint of reducing the production cost, it is desirable not to use the dihydroxy compound having an oligofluorene represented by the general formula (10a).

When the polymerization-reactive group $A^3$ and/or $A^4$ in the oligofluorene monomer represented by the general formula (20) for use in polymerization is a hydroxy ester group, or that is, an ester skeleton-having hydroxy group, or when $A^3$ and $A^4$ are a hydroxy group and a carboxyl group, a polyester carbonate may also be produced. Specific examples of the ester skeleton-having hydroxy group include a 2-hydroxyethoxycarbonyl group, a 2-(2-hydroxyethoxy)carbonylethyl group, a 2-(2-hydroxyethoxyl)carbonylpropyl group, etc. Specific examples where $A^3$ and $A^4$ are a hydroxy group and a carboxyl group include a hydroxymethyl group and an ethoxycarbonyl group; a 2-(2-hydroxyethoxyl)carbonyl group and a carboxyl group; a 2-(2-hydroxyethoxyl)carbonylethyl group and a carboxyethyl group; etc.

In the polyester carbonate, the content ratio of the repeating unit structure derived from all dicarboxylic acid compounds is generally 45 mol % or less relative to the total of the repeating structural unit derived from all dihydroxy compounds and the structural unit derived from all carboxylic acid compounds that is referred to as 100 mol %, and the content ratio is preferably 30 mol % or less, more preferably 20 mol % or less, even more preferably 0 mol %. Here, the dicarboxylic acid compound in the content ratio of the dicarboxylic acid compound-derived repeating unit structure includes all the dicarboxylic acid compounds to be used for polymerization, indicating the dicarboxylic acid compound represented by the general formula (28) and the dicarboxylic acid compound of the oligofluorene monomer represented by the general formula (20) where the polymerization-reactive groups $A^3$ and $A^4$ are carboxyl groups. When the content ratio of the dicarboxylic acid compound-derived repeating unit structure is more than the upper limit, then the polymerization performance may lower and the polymerization could not go on to give a desired molecular weight.

<8-3. Polymerization Catalyst>

As the polymerization catalyst (interesterification catalyst) in melt polymerization, for example, used here is a Group-1 and/or Group-2 metal compound of the Long Periodic Table. The interesterification catalyst (hereinafter this may be simply referred to as catalyst or polymerization catalyst) have an extremely significant influence on the reaction speed and on the quality of the polycarbonate resin composition to be obtained through polycondensation.

Not specifically defined, the catalyst to be used may be any one capable of satisfying the transparency, the color tone, the heat resistance, the weather resistance and the mechanical strength of the produced polycarbonate resin composition. For example, there are mentioned metal compounds of Group-1 and/or Group-2 (hereinafter simply expressed as "Group-1", "Group-2") of the Long Periodic Table.

The Group-1 metal compound includes, for example, sodium hydroxide, potassium hydroxide, lithium hydroxide, cesium hydroxide, sodium hydrogencarbonate, potassium hydrogencarbonate, lithium hydrogencarbonate, cesium hydrogencarbonate, sodium carbonate, potassium carbonate, lithium carbonate, cesium carbonate, sodium acetate, potassium acetate, lithium acetate, cesium acetate, sodium stearate, potassium stearate, lithium stearate, cesium stearate, sodium borohydride, potassium borohydride, lithium borohydride, cesium borohydride, sodium borophenylate, potassium borophenylate, lithium borophenylate, cesium borophenylate, sodium benzoate, potassium benzoate, lithium benzoate, cesium benzoate, disodium hydrogenphosphate, dipotassium hydrogenphosphate, dilithium hydrogenphosphate, dicesium hydrogenphosphate, disodium phenylphosphate, dipotassium phenylphosphate, dilithium phenylphosphate, dicesium phenylphosphate, sodium, potassium, lithium and cesium alcoholates and phenolates, disodium salt dipotassium salt, dilithium salt and dicesium salt of bisphenol A, etc. Above all, from the viewpoint of the polymerization activity and the color tone of the resultant polycarbonate resin composition, preferred are lithium compounds.

The Group-2 metal compound includes, for example, calcium hydroxide, barium hydroxide, magnesium hydroxide, strontium hydroxide, calcium hydrogencarbonate, barium hydrogencarbonate, magnesium hydrogencarbonate, strontium hydrogencarbonate, calcium carbonate, barium carbonate, magnesium carbonate, strontium carbonate, calcium carbonate, barium acetate, magnesium acetate, strontium acetate, calcium stearate, barium stearate, magnesium stearate, strontium stearate, etc. Above all, preferred are magnesium compounds, calcium compounds and barium compounds. From the viewpoint of the polymerization activity and the color tone of the resultant polycarbonate resin composition, more preferred are magnesium compounds and/or calcium compounds, and most preferred are calcium compounds.

It is possible to supplementarily use a basic compound such as a basic boron compound, a basic phosphorus compound, a basic ammonium compound, an amine compound or the like, along with the Group-1 and Group-2 metal compound of the Long Periodic Table. However, preferred is use of the Group-1 and/or Group-2 metal compound of the Long Periodic Table alone.

The basic phosphorus compound includes, for example, triethyl phosphine, tri-n-propyl phosphine, triisopropyl phosphine, tri-n-butyl phosphine, triphenyl phosphine, tributyl phosphine, quaternary phosphonium salts, etc.

The basic ammonium compound includes, for example, tetramethylammonium hydroxide, tetraethylammonium hydroxide, tetrapropylammonium hydroxide, tetrabutylammonium hydroxide, trimethylethylammonium hydroxide, trimethylbenzylammonium hydroxide, trimethylphenylammonium hydroxide, triethylmethylammonium hydroxide, triethylbenzylammonium hydroxide, triethylphenylammonium hydroxide, tributylbenzylammonium hydroxide, tributylphenylammonium hydroxide, tetraphenylammonium hydroxide, benzyltriphenylammonium hydroxide, methyltriphenylammonium hydroxide, butyltriphenylammonium hydroxide, etc.

The amine compound includes, for example, 4-aminopyridine, 2-aminopyridine, N,N-dimethyl-4-aminopyridine, 4-diethylaminopyridine, 2-hydroxypyridine, 2-methoxypyridine, 4-methoxypyridine, 2-dimethylaminoimidazole, 2-methoxyimidazole, imidazole, 2-mercaptoimidazole, 2-methylimidazole, aminoquinoline, guanidine, etc.

The amount of the polymerization catalyst to be used is, in a case where a Group-1 or Group-2 metal compound of the Long Periodic Table is used, generally within a range of from 0.1 µmol to 100 µmol as the metal-equivalent amount thereof, preferably within a range of from 0.5 µmol to 50 µmol, more preferably within a range of from 1 µmol to 25 µmol. When the amount of the polymerization catalyst used is too small, then the polymerization activity necessary for producing a polycarbonate having a desired molecular weight could not be obtained; but on the other hand, when the amount of the polymerization catalyst used is too large, then the color tone of the resultant polymer would worsen, side products would form to lower the flowability of the product and to give gels and, as a result, it would be difficult to produce a polycarbonate having an intended quality.

In particular, in a case where a compound containing at least one metal selected from Group-2 metals of the Long Periodic Table and lithium is used, and especially in a case where a magnesium compound and/or a calcium compound is used, the amount of the catalyst is preferably 0.1 µmol or more, as the metal-equivalent amount thereof relative to 1 mol of all the dihydroxy compounds, more preferably 0.3 µmol or more, even more preferably 0.5 µmol or more. The upper limit is preferably 20 µmol or less, more preferably 10 µmol or less, even more preferably 5 µmol or less, especially preferably 3 µmol or less.

When the catalyst amount is too small, then the polymerization speed would be low, and therefore in order to obtain a polycarbonate resin composition having a desired molecular weight, the polymerization temperature would have to be elevated accordingly. Consequently, the color tone of the resultant polycarbonate resin composition would worsen, or unreacted materials would evaporate away during polymerization with the result that the molar ratio of the dihydroxy compound and the carbonic diester would be thereby disordered and a desired molecular weight could not be attained. On the other hand, when the amount of the polymerization catalyst used is too large, then any unfavorable side reaction would occur thereby providing a possibility that the color tone of the resultant polycarbonate resin composition would worsen or the resin being shaped or worked would be discolored.

Of Group-1 metals, sodium, potassium or cesium, when contained much in the polycarbonate resin composition, would have some negative influence on the color tone of the composition. Not only from the catalyst used but also from the starting material and also from the reactor used, these metals may contaminate the resin composition. Irrespective of the source thereof, the total amount of these metal compounds in the polycarbonate resin composition is preferably 1 ppm by weight or less as the metal amount thereof, more preferably 0.5 ppm by weight or less.

For introducing a dicarboxylic acid structure, it is possible to use an interesterification catalyst such as a titanium compound, a tin compound, a germanium compound, an antimony compound, a zirconium compound, a lead compound, an osmium compound or the like, along with or not along with the above-mentioned basic compound. The amount of the interesterification catalyst to be used is generally 10 µmol or more as the metal-equivalent amount thereof relative to 1 mol of all the dihydroxy compounds to be used for reaction, preferably 20 µmol or more, more preferably 50 µmol or more, and is generally 1 mmol or less, preferably 800 µmol or less, more preferably 500 µmol or less.

<8-4. Polymerization Method>

The melt polymerization method for producing the polycarbonate contained in the polycarbonate resin composition of the present invention comprises reacting a dihydroxy compound and a carbonic diester optionally in the presence of a dicarboxylic acid compound as a polymerization catalyst. The polymerization is attained generally in two or more multiple stages. One polymerization reactor may be used in which the condition is changed for two or more stages, or two or more reactors may be used in which the condition is changed for two or more stages. From the viewpoint of the production efficiency, two or more, preferably three or more, more preferably from 3 to 5, even more preferably 4 reactors are used. The polymerization reaction may be a batch mode or a continuous mode or may also be a combination of a batch mode and a continuous mode. From the viewpoint of the production efficiency and the quality stability, preferred is a continuous mode reaction.

In the melt polymerization reaction to obtain the polycarbonate to be contained in the polycarbonate resin composition of the present invention, it is important to control the balance between the temperature and the pressure in the reaction system. When any one of the temperature and the pressure is changed too rapidly, then unreacted monomers would be distilled out of the reaction system so that the molar ratio of the dihydroxy compound and the carbonic diester would change and a desired polymer could not be obtained.

Concretely, in the first-step reaction, the highest internal temperature of the polymerization reactor is generally 130° C. or higher, preferably 140° C. or higher, more preferably 150° C. or higher, and is generally 250° C. or lower, preferably 240° C. or lower, more preferably 230° C. or lower. The pressure is generally 110 kPa or more, preferably 70 kPa or more, more preferably 30 kPa or more, and is generally 5 kPa or less, preferably 3 kPa or less, more preferably 1 kPa or less (absolute pressure). The reaction time is generally 0.1 hours or more, preferably 0.5 hours or more, and is generally 10 hours or less, preferably 3 hours or less. The reaction is continued while the formed carbonic diester-derived monohydroxy compound (when diphenyl carbonate is used as the carbonic diester, the monohydroxy compound is phenol) is taken out of the reaction system through distillation.

In and after the second step, the pressure in the reaction system is gradually lowered from the pressure in the first step, and while the monohydroxy compound being kept formed is removed out of the reaction system, the reaction is further continued finally under a pressure of the reaction system (absolute pressure of 5 kPa or less, preferably 3 kPa or less, at a highest internal temperature of generally 210° C. or higher, preferably 220° C. or higher and generally 270° C. or lower, preferably 260° C. or lower and for generally 0.1 hours or more, preferably 0.5 hours or more, more preferably 1 hour or more and generally 10 hours or less, preferably 6 hours or less, more preferably 3 hours or less.

In particular, for preventing the polycarbonate resin composition of the present invention from being discolored and thermally degraded to obtain a polycarbonate resin composition having a good color tone and good light resistance, it is desirable that the highest internal temperature in all the reaction stages is 270° C. or lower, especially 260° C. or lower.

<8-5. Pelletization>

After produced through polycondensation as mentioned above, the polycarbonate resin composition of the present invention is generally cooled and solidified, and can be pelletized with a rotary cutter or the like. The pelletization method is not defined. For example, employable here is any of a method of extracting a melt resin out of the final polymerization reactor, then cooling and solidifying the strands and pelletizing them, a method of transferring a melt resin from the final polymerization reactor into a single-screw or double-screw extruder, then melt-extruding the resin, cooling and solidifying it and thereafter pelletizing it, a method of extracting a melt resin out of the final polymerization reactor, then cooling and solidifying the strands and once pelletizing them, and thereafter again transferring the resin into a single-screw or double-screw extruder, then melt-extruding the resin, cooling and solidifying it and thereafter pelletizing it. As described below, when a large amount of a side product, carbonic diester-derived monohydroxy compound is contained in the produced polycarbonate, it would change the environment-dependent optical properties of retardation films formed of the polymer, and therefore, it is desirable that the carbonic diester-derived monohydroxy compound is removed from the polycarbonate resin composition of the present invention using an extruder. Above all, preferred is a method where the melt resin is transferred from the final polymerization reactor into a single-vented or multi-vented, single-screw or double-screw extruder, and melt-extruded out of the extruder while the monohydroxy compound is removed by depressurizing through venting, then cooled and solidified and thereafter pelletized.

<8-6. Content of Carbonic Diester-Derived Monohydroxy Compound>

In the melt polymerization method, a side product, monohydroxy compound such as phenol or the like is formed from the carbonic diester in the polymerization reaction, and therefore this may remain in the polycarbonate resin composition of the present invention and may evaporate away during film formation or during film stretching to cause an offensive odor or to cause film defects. In addition, after the polycarbonate resin composition of the present invention is processed into a retardation film, the carbonic diester-derived monohydroxy compound remaining in the film may change the optical properties of the retardation film in environmental changes, and therefore it is desirable that the carbonic diester-derived monohydroxy compound contained in the polycarbonate resin composition of the present invention is 1500 ppm by mass or less. More preferably, the amount is 1000 ppm by mass or less. The lower limit is preferably smaller for solving the above-mentioned problems, but since it is difficult to completely remove the remaining monohydroxy compound from the polymer according to the melt polymerization method and since the removal requires some overwork, the lower limit is generally 1 ppm by mass. For reducing the carbonic diester-derived monohydroxy compound remaining in the polycarbonate resin composition of the present invention, it would be effective to process the polymer for vapor removal using an extruder or to reduce the pressure in the final polymerization stage to 3 kPa or less, preferably 2 kPa or less; however, when the pressure is lowered too much, then the molecular weight would increase rapidly and the reaction control would be difficult. Consequently, it is desirable that the terminal concentration of the polymer to be produced is controlled to be hydroxyl-rich or aryl-rich to thereby bias the terminal group balance in production of the polymer. Above all, from the viewpoint of the thermal stability of the polymer, the hydroxyl terminal concentration is preferably 50 mol/to or less, more preferably 30 mol/ton or less. The hydroxyl terminal concentration can be quantified through $^1$H-NMR, etc. The hydroxyl terminal concentration can be controlled by the molar ratio of the carbonic diester and all the dihydroxy compounds to be introduced into the reactor.

<9. Polymerization Method for Polyester>

According to a method of substituting the carbonic diester to be used for polymerization with the dicarboxylic acid compound represented by the general formula (28) and/or the dicarboxylic acid compound of the oligofluorene monomer represented by the general formula (20) where the polymerization-reactive groups $A^3$ and $A^4$ are carboxyl groups, or according to a method of using, as a part of the dihydroxy compound for polymerization, the dihydroxy acid compound of the oligofluorene monomer represented by the general formula (20) where the polymerization-reactive groups $A^3$ and $A^4$ are hydroxy groups, polyesters can be obtained.

Preferred dicarboxylic acid, polymerization catalyst and polymerization condition are the same as those described in the section of <8. Polymerization Method for Polycarbonate>

<10. Additive>

The resin composition of the present invention or the polycarbonate resin composition of the present invention may contain any additive. Similarly, the polymer contained in the resin composition of the present invention or the polycarbonate resin composition of the present invention may also contain any additive.

<10-1. Heat Stabilizer>

A heat stabilizer may be incorporated in the resin composition of the present invention or the polycarbonate resin composition of the present invention for preventing molecular weight reduction and preventing color tone degradation during shaping. Similarly and for the same reason, a heat stabilizer may also be incorporated in the polymer to be contained in the resin composition of the present invention or the polycarbonate resin composition of the present invention.

The heat stabilizer includes generally-known hindered phenol-type heat stabilizers and/or phosphorus-containing heat stabilizers.

The hindered phenol compound includes, concretely, 2,6-di-tert-butylphenol, 2,4-di-tert-butylphenol, 2-tert-butyl-4-methoxyphenol, 2-tert-butyl-4,6-dimethylphenol, 2,6-di-tert-butyl-4-methylphenol, 2,6-di-tert-butyl-4-ethylphenol, 2,5-di-tert-butylhydroquinone, n-octadecyl-3-(3',5'-di-tert-butyl-4'-hydroxyphenyl)propionate, 2-tert-butyl-6-(3'-tert-butyl-5'-methyl-2'-hydroxybenzyl)-4-methylphenyl acrylate, 2,2'-methylene-bis(4-methyl-6-tert-butylphenol), 2,2'-methylene-6-bis(6-cyclohexyl-4-methylphenol), 2,2'-ethylidene-bis(2,4-di-tert-butylphenol), tetrakis[methylene-3-(3',5'-di-tert-butyl-4'-hydroxyphenyl)propionate]methane, 1,3,5-trimethyl-2,4,6-tris(3,5-di-tert-butyl-4-hydroxybenzyl)benzene, etc. Above all, there are mentioned tetrakis[methylene-3-(3',5'-di-tert-butyl-4'-hydroxyphenyl)propionate]methane, n-octadecyl-3-(3',5'-di-tert-butyl-4'-hydroxyphenyl)propionate, 1,3,5-trimethyl-2,4,6-tris(3,5-di-tert-butyl-4-hydroxybenzyl)benzene.

The phosphorus compound includes phosphorous acid, phosphoric, phosphonous acid, phosphonic acid and their esters, etc. Concretely, there are mentioned triphenyl phosphite, tris(nonylphenyl)phosphite, tris(2,4-di-tert-butylphenyl)phosphite, tridecyl phosphite, trioctyl phosphite, trioctadecyl phosphite, didecylmonophenyl phosphite, dioctylmonophenyl phosphite, diisopropylmonophenyl phosphite, monobutyldiphenyl phosphite, monodecyldiphenyl phosphite, monooctyldiphenyl phosphite, bis(2,6-di-tert-butyl-4-methylphenyl)pentaerythritol diphosphite, 2,2-methylenebis(4,6-di-tert-butylphenyl)octyl phosphite, bis(nonylphenyl)pentaerythritol diphosphite, bis(2,4-di-tert-butylphenyl)pentaerythritol diphosphite, distearylpentaerythritol diphosphite, tributyl phosphate, triethyl phosphate, trimethyl phosphate, triphenyl phosphate, diphenyl-monoorthoxenyl phosphate, dibutyl phosphate, dioctyl phosphate, diisopropyl phosphate, tetrakis(2,4-di-tert-butylphenyl) 4,4'-biphenylenediphosphinate, dimethyl benzenephosphonate, diethyl benzenephosphonate, dipropyl benzenephosphonate, etc. One alone or two or more types of these heat stabilizers may be used here either singly or as combined.

The heat stabilizer of the type may be added to the resin composition during melt polymerization and may be additionally added thereto to be the necessary addition amount thereof. Specifically, it is possible that a suitable amount of a heat stabilizer is added to prepare the resin composition of the present invention or the polycarbonate resin composition of the present invention, and further an additional heat stabilizer is added thereto, and in the mode, while evading haze increase, discoloration and heat resistance degradation, a large amount of the heat stabilizer may be incorporated in the composition to be effective for preventing color tone degradation. In case where a film is formed from the resin composition, for example, using an extruder according to a melt extrusion method or the like, the heat stabilizer may be added to the extruder, or the heat stabilizer may be added to the resin composition or the polycarbonate resin composition previously using an extruder, and then the resultant composition may be shaped into pellets, etc.

The amount of the heat stabilizer to be added is preferably 0.0001 parts by mass or more relative to 100 parts by mass of the resin composition of the present invention or the polycarbonate resin composition of the present invention, more preferably 0.0005 parts by mass or more, even more preferably 0.001 parts by mass or more, and is preferably 1 part by mass or less, more preferably 0.5 parts by mass or less, even more preferably 0.2 parts by mass or less.

<10-2. Antioxidant>

An antioxidant generally known for antioxidation may be incorporated into the resin composition of the present invention or the polycarbonate resin composition of the present invention. As the antioxidant of the type, for example, there are mentioned one or more of pentaerythritol tetrakis(3-mercaptopropionate), pentaerythritol tetrakis(3-laurylthiopropionate), glycerol-3-stearylthiopropionate, triethylene glycol bis[3-(3-tert-butyl-5-methyl-4-hydroxyphenyl)propionate], 1,6-hexanediol bis[3-(3,5-di-tert-butyl-4-hydroxyphenyl)propionate], pentaerythritol tetrakis[3-(3,5-di-tert-butyl-4-hydroxyphenyl)propionate], octadecyl-3-(3,5-di-tert-butyl-4-hydroxyphenyl)propionate, 1,3,5-trimethyl-2,4,6-tris(3,5-di-tert-butyl-4-hydroxybenzypbenzene, N,N-hexamehtylenebis(3,5-di-tert-butyl-4-hydroxy-hydrocinnamide), diethyl 3,5-di-tert-butyl-4-hydroxybenzylphosphonate, tris(3,5-di-tert-butyl-4-hydroxybenzyl) isocyanurate, tetrakis(2,4-di-tert-butylphenyl) 4,4'-biphenylene-diphosphonate, 3,9-bis{1,1-dimethyl-24[3-(3-tert-butyl-4-hydroxy-5-mehtylphenyl)propionyloxy]ethyl}-2,4,8,10-tetroxaspiro(5,5)undecane, etc. The amount of the antioxidant to be added is preferably 0.0001 parts by mass or more relative to 100 parts by mass of the resin composition of the present invention or the polycarbonate resin composition of the present invention, and is preferably 0.5 parts by mass or less.

Further, the resin composition of the present invention or the polycarbonate resin composition of the present invention may contain any ordinary nucleating agent, flame retardant, inorganic filler, impact improver, foaming agent, dye, pigment and others within a range not detracting from the object of the present invention.

The above additives may be mixed in the resin composition of the present invention or the polycarbonate resin composition of the present invention all at a time or in any desired order, using a mixing machine such as a tumbler, a V-shaped blender, a Nauter mixer, a Banbury mixer, a kneading roll, an extruder or the like. Above all, preferred is use of an extruder, especially a double-screw extruder for kneading the composition, from the viewpoint of improving dispersibility.

<11. Use>

The resin composition of the present invention or the polycarbonate resin composition of the present invention has a small photoelastic coefficient and is excellent in heat resistance and shapability, and is further hardly discolored and has high transparency. Consequently, the shaped article of the composition is suitable to optical members such as films, lenses and prisms. For example, the film of the present invention is usable as a retardation film for viewing angle compensation, external light antireflection, color compensation, conversion of linearly-polarized light into circularly-polarized light or the like for various displays (liquid-crystal display devices, organic EL display devices, plasma display devices, FED field emission displays, SED surface-conduction electron-emitter displays). In addition, the lens and the prism of the present invention are usable for optical lenses and optical prisms such as Fresnel lenses, pickup lenses, etc.

<11-1. Film>

The resin composition of the present invention and the polycarbonate resin composition of the present invention are favorably used as a film. The resin composition of the present invention or the polycarbonate resin composition of the present invention may be processed for forming a film.

<11-2. Film Production Method>

A method for forming an unprocessed film using the resin composition of the present invention or the polycarbonate resin composition of the present invention is described. There are mentioned a casting method where the resin composition of the present invention or the polycarbonate resin composition of the present invention is dissolved in a solvent, then cast, and the solvent is removed; and a melt film formation method not using a solvent, concretely, a melt extrusion method using a T-die, an calender molding method, a hot pressing method, a coextrusion method, a co-melting method, a multilayer extrusion method, an inflation forming method, etc. These methods are not specifically defined here. The casting method may have a problem caused by the remaining solvent, and therefore, preferred is a melt film formation method, and more preferred is a melt extrusion method using a T-die since the formed film could be readily stretched in the later step.

In case where an unprocessed film is formed according to a melt film formation method, the forming temperature is preferably 265° C. or lower, more preferably 260° C. or lower, even more preferably 258° C. or lower. When the forming temperature is too high, then the defects in the resultant unprocessed film would increase owing to impurities and bubbles therein, and the unprocessed film would be discolored. However, when the forming temperature is too low, then the viscosity of the resin composition of the present invention or the polycarbonate resin composition of the present invention would be too high and forming of an unprocessed film would be difficult and, in addition, it would be difficult to form an unprocessed film having a uniform thickness. Therefore, the lower limit of the forming temperature is generally 200° C. or higher, preferably 210° C. or higher, more preferably 220° C. or higher. Here, the forming temperature for the unprocessed film is the temperature at the forming according to a melt film formation method, and for this, in general, the temperature of the die port through which a melt resin is extruded out is measured to be the forming temperature.

The thickness of the unprocessed film is not defined. However, when too thick, the film would have thickness unevenness, but when too thin, the film would be broken during stretching. Therefore, the thickness is generally 50 μm or more, preferably 70 μm or more, and is generally 200 μm or less, preferably 120 μm or less. When the unprocessed film has thickness unevenness, then the retardation film formed of the film would thereby have retardation unevenness. Accordingly, the thickness of the film that is used as a retardation film is preferably within a range of a set thickness±3 μm or less, more preferably within a range of a set thickness±2 μm or less, even more preferably within a range of a set thickness±1 μm or less.

<11-3. Physical Properties of Film>

Preferably, the internal haze of the film of the present invention is 3% or less, more preferably 1.5% or less. When the internal haze of the retardation film is larger than the above-mentioned upper limit, then there may occur light scattering, and for example, when the film is laminated with a polarizer, then it would cause depolarization. The lower limit of the internal haze is not specifically defined but is generally 0.2% or more. An adhesive-applied transparent film, of which the haze has been previously measured, is stuck to both surfaces of a film to be analyzed to prepare a sample film from which the influence of external haze thereon is removed, and the sample film is analyzed for measuring the haze thereof. The haze of the adhesive-applied transparent film is subtracted from the haze of the sample film to give the internal haze of the film.

Preferably, the value b* of the film of the present invention is 3 or less. When the value b* of the film is too large, then there may occur a problem of film discoloration. More preferably, the value b* of the film of the present invention is 2 or less, even more preferably 1 or less.

Irrespective of the thickness thereof, the whole light transmittance of the film of the present invention is preferably 80% or more, more preferably 90% or more. When the light transmittance is not lower than the above-mentioned lower limit, then a film with little discoloration can be obtained. When stuck to a polarizing plate, then the film gives a circularly-polarizing plate having a high polarization degree and high transmittance. When used in an image-display device, the film realizes high display quality. The upper limit of the whole light transmittance of the film of the present invention is not specifically defined, but is generally 99% or less.

Preferably, the film of the present invention does not undergo brittle fracture in a folding test to be mentioned below. A film that may undergo brittle fracture would be broken in during film formation or film stretching, and therefore the production yield of the film would be thereby lowered. In order that the film is made not to undergo brittle fracture, it is important that the molecular weight, the melt viscosity and the glass transition temperature of the resin composition of the present invention or the polycarbonate resin composition of the present invention are planned each to fall within the above-mentioned preferred range. In addition, a method is also effective of copolymerizing a component capable of imparting flexibility in the resin composition or the polycarbonate resin composition or mixing such a component in the composition to thereby control the physical properties of the film to be produced.

<11-4. Production Method for Stretched Film>

The unprocessed film thus produced in the manner as above may be stretched in at least one direction to give a stretched film of the present invention. For the stretching method, employable are various stretching methods of free end stretching, fixed end stretching, free end shrinkage, fixed end shrinkage and the like, either singly or as combined simultaneously or successively. The stretching direction is not specifically defined, or that is, the film may be stretched in various directions such as horizontal direction, vertical direction, thickness direction, diagonal direction, etc. Preferred are a horizontal monoaxial stretching method, a vertical/horizontal simultaneous biaxial stretching method, a vertical/horizontal successive biaxial stretching method, etc. As a stretching means, employable here is any suitable stretcher such as a tenter stretcher, a biaxial stretcher, etc.

Depending on the object, the stretching temperature may be suitably selected. Preferably, the stretching temperature is generally (Tg−20° C.) or higher, in which Tg is the glass transition temperature of the unprocessed film (or that is, the glass transition temperature of the resin composition that is the film-forming material for the unprocessed film), preferably (Tg−10° C.) or higher, more preferably (Tg−5° C.) or higher, and is generally (Tg+30° C.) or lower, preferably (Tg+20° C.) or lower, more preferably (Tg+10° C.) or lower. By selecting the condition, the film can readily have a uniform retardation value and is hardly clouded. Concretely, the stretching temperature is generally 90° C. or higher, preferably 100° C. or higher, and is generally 210° C. or lower, preferably 200° C. or lower, more preferably 180° C. or lower.

The draw ratio in stretching may be suitably selected depending on the object, and is preferably 1.1 times or more, based on the unstretched case of 1 time, more preferably 1.5 times or more, even more preferably 1.8 times or more, still more preferably 2 times or more, and is preferably 6 times or less, more preferably 4 times or less, even more preferably 3 times or less, still more preferably 2.5 times or less. When the draw ratio is too large, then the film would be broken during stretching and, in addition, there is a possibility that the optical properties of the film would vary greatly in long-term use under high-temperature condition; but when the draw ratio is too small, then the film could not be given intended optical properties when having a desired thickness.

The drawing speed may also be suitably selected depending on the object, and is generally 50% or more as the strain velocity represented by the following formula, preferably 100% or more, more preferably 200% or more, even more preferably 250% or more, and is generally 2000% or less, preferably 1500% or less, more preferably 1000% or less, even more preferably 500% or less. When the drawing speed is excessively high, then the film would be broken during stretching and there is a possibility that the optical properties of the film would vary greatly in long-term use under high-temperature condition. On the other hand, but when the drawing speed is too low, then the productivity would lower and, in addition, the draw ratio in stretching would have to be excessively increased for obtaining the desired retardation.

Strain Velocity (%/min)=drawing speed (mm/min)/ length of unprocessed film (mm)×100

After stretched, the film may be thermally fixed in a heating furnace, or may be relaxed by controlling the width of the tenter or by controlling the peripheral speed of the roll. The treatment is effective for preventing the optical properties of the stretched film from varying in long-term use under high-temperature condition.

The stretched film of the present invention can be produced by suitably selecting and controlling the processing condition in the stretched step.

<11-5. Physical Properties of Stretched Film>

The stretched film of the present invention is preferably a retardation film, of which the ratio of the retardation measured at a wavelength of 450 nm (Re450) to the retardation measured at a wavelength of 550 nm (Re550) satisfies the following formula (2):

$$Re450/Re550 \leq 1.0 \tag{2}$$

Preferably, the ratio of Re450/Re550 is from 0.50 to 1.00, more preferably from more than 0.5 to less than 1.0, even more preferably from 0.70 to 0.95, still more preferably from 0.75 to 0.93, further more preferably from 0.80 to 0.91. When the value of Re450/Re550 falls within the above range, then the film can express retardation at a longer wavelength and can have ideal retardation characteristics at each wavelength in a visible light region. For example, when the retardation film of the present invention that has such wavelength dependence is, as a ¼λ plate, stuck to a polarizing plate, then a circularly-polarizing plate can be produced, and it is possible to realize a circularly-polarizing plate and an image display device having an external antireflection function at every wavelength and excellent in black expression. On the other hand, when the value of Re450/Re550 falls outside the above range, then wavelength-dependent color loss would increase and there may occur a problem in discoloration of a circularly-polarizing plate and an image display device comprising the film.

The stretched film of the present invention preferably satisfies the physical values described in the section of <3-4. Retardation Ratio>. Similarly, the film preferably satisfies the physical values described in the section of <3-11. Photoelastic Coefficient>. Similarly, the film preferably satisfies the physical values described in the section of <3-12. Birefringence>.

In general, the thickness of the stretched film of the present invention is preferably 150 μm or less, more preferably 100 μm or less, even more preferably 60 μm or less. When the retardation film is too thick, a larger amount of the film-forming material would be needed for producing the film having the same area and the production would be inefficient, and if so, in addition, the thickness of the product using the film would be thick and it would be difficult to control the uniformity of the film. As the case may be, such a thick film could not be applied to instruments that are required to be precision, thin and homogeneous. The lower limit of the thickness of the retardation film of the present invention is preferably 5 μm or more, more preferably 10 μm or more. When too thin, the retardation film would be difficult to handle and would be wrinkled during production, and as the case may be, it would be difficult to stick such a thin film to any other film or sheet such as protective film, etc.

The birefringence of the stretched film of the present invention is preferably 0.001 or more. In order to plan the film to be formed using the resin composition of the present invention mentioned below, so as to be extremely thin, the birefringence of the film is preferably higher. Accordingly, the birefringence is more preferably 0.002 or more. When the birefringence is less than 0.001, then the thickness of the film must be excessively increased, and therefore the amount of the film-forming material to be sued would increase, and it would be difficult to control the homogeneousness of the film from the viewpoint of the thickness, the transparency and the retardation thereof. Consequently, when the birefringence is less than 0.001, the film could not be applied to instruments that are required to be precision, thin and homogeneous.

<11-6. Water Absorption>

Preferably, the saturated water absorption of the film of the present invention is higher than 1.0% by mass. When the saturated water absorption is higher than 1.0% by mass, then the film could readily secure adhesiveness and therefore could be readily adhered to any other film. For example, when the film is stuck to a polarizing plate, the film is hydrophilic and therefore the contact angle to water thereof is low. Accordingly, the adhesive to be sued can be freely planned, and high-level adhesion planning is possible. In case where the saturated water absorption is 1.0% by mass or less, the film would be hydrophobic and the contact angle to water thereof would increase, and if so, the adhesion planning would be difficult. In addition, the film is electrically charged with ease, and therefore, when the film of the type incorporated in a circularly polarizing film and an image display device, there occurs a problem that the film would take in impurities and therefore appearance defects would increase. On the other hand, when the saturated water absorption is higher than 2.0% by mass, then it is unfavorable since the durability of the optical properties of the film in wet environments would worsen. Preferably, the saturated water absorption of the film of the present invention is higher than 1.0% by mass, more preferably 1.1% by mass or more, and is preferably 2.0% by mass or less, more preferably 1.5% by mass or less.

On the other hand, depending on the condition in which the film and the image display device using the film are used, the saturated water absorption may be 1.0% by mass or less.

<11-7. Device Application, Etc.>

The film of the present invention can be used as a retardation film for viewing angle compensation, external light antireflection, color compensation, conversion of linearly-polarized light into circularly-polarized light or the like for various displays (liquid-crystal display devices, organic EL display devices, plasma display devices, FED field emission displays, SED surface-conduction electron-emitter displays).

The resin composition and the polycarbonate resin composition of the present invention have a small photoelastic coefficient, is excellent in heat resistance and formability and has high transparency with little discoloration, and therefore the composition is usable for any other optical films, optical discs, optical prisms, pickup lenses, etc.

The use of the stretched film of the present invention is not specifically defined. Since the film has ideal retardation characteristics at every wavelength in a visible light region, has a small photoelastic coefficient, is excellent in heat resistance and formability, and has high transparency with little discoloration, the film is favorable for a ¼λ plate, a circularly-polarizing plate, an image display device, etc.

For example, when the stretched film of the present invention is controlled to satisfy the condition described in the above-mentioned section <3-4. Retardation Ratio>, then the film can be used as a ¼λ plate. When the ¼λ plate of the present invention thus produced in the manner as above is stuck to a polarizing plate, then a circularly-polarizing plate or the like can be produced, and can be a circularly-polarizing plate having an external light antireflection function at every wavelength and excellent in black expression. Further, when the film of the type is applied to an image display device, it is possible to realize an image display device that is extremely excellent in black reproducibility. The polarizing plate may have any of various known configurations. For example, usable here are those prepared by staining various films through adsorption of a dichroic substance such as iodine, a dichroic dye or the like thereto followed by crosslinking, stretching and drying them to give polarizers, and a protective film may be laminated on the resulting polarizer.

When the stretched film of the present invention is controlled to satisfy the condition described in the section of <3-4. Retardation Ratio>, then a retardation film can be obtained capable of preventing color loss in VA-mode liquid-crystal display devices, and it is possible to realize a liquid-crystal display device free from a trouble of wavelength-dependent color loss. Further, when the film is controlled to satisfy the condition described in the above-mentioned section <1-13. Birefringence>, then the film can have ideal retardation characteristics at a wavelength in a visible light region, and the film can be a broadband zero birefringence material. When the broadband zero birefringence material of the present invention is stuck to a polarizing plate, then it is possible to realize a polarizing plate and an image display device free from free from wavelength-dependent color loss.

<12. Production Method for Oligofluorene Monomer>

The production method for the oligofluorene monomer (20) for use in the present invention is not defined at all. For example, the monomer can be produced according to the production method A, the production method B or the production method C mentioned below.

[Chem. 75]
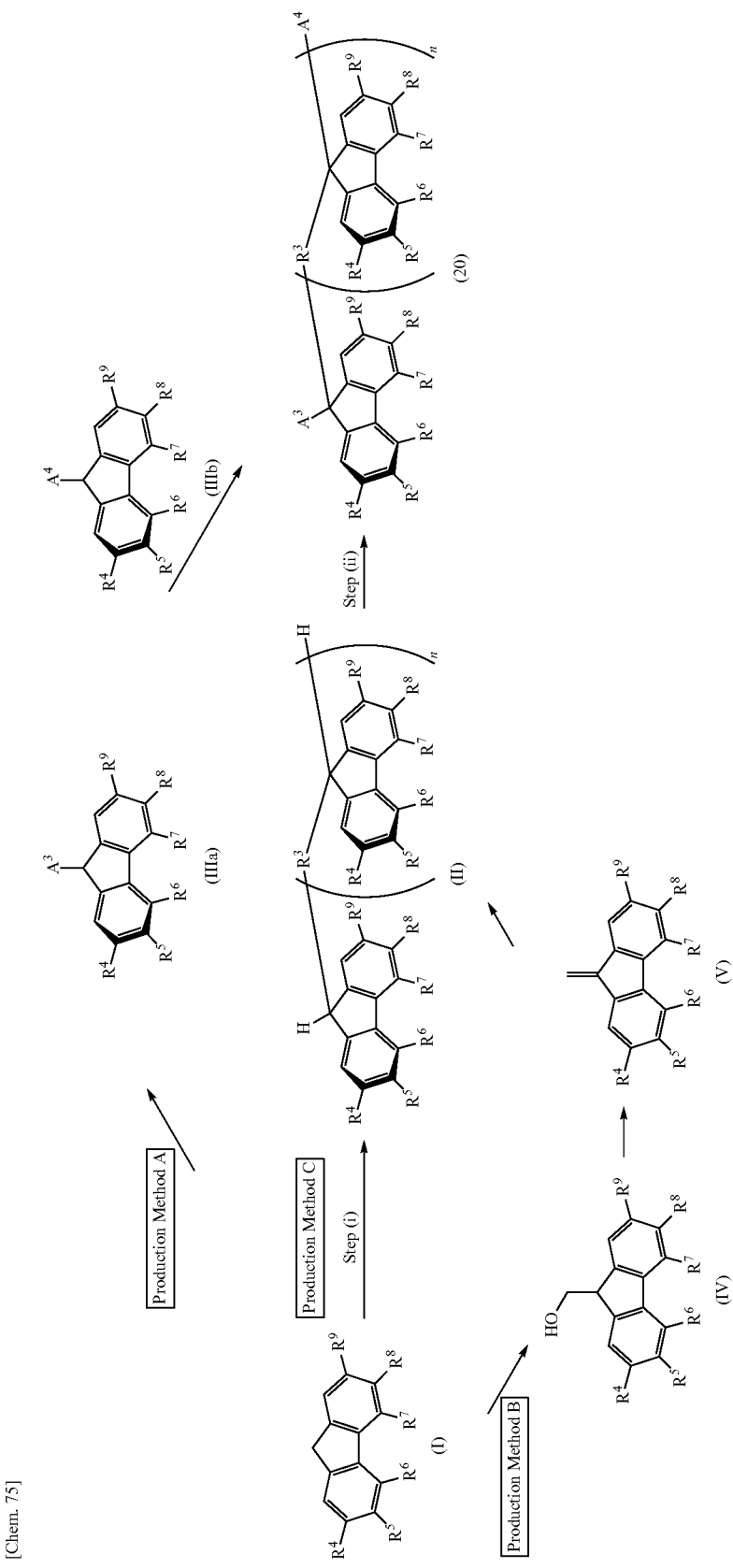

Here, in each structural formula, $R^3$ represents a direct bond, an optionally-substituted alkylene group having from 1 to 10 carbon atoms, an optionally-substituted arylene group having from 4 to 10 carbon atoms, or an optionally-substituted aralkylene group having from 6 to 10 carbon atoms, $R^4$ to $R^9$ each independently represent a hydrogen atom, an optionally-substituted alkyl group having from 1 to 10 carbon atoms, an optionally-substituted aryl group having from 4 to 10 carbon atoms, an optionally-substituted acyl group having from 1 to 10 carbon atoms, an optionally-substituted alkoxy group having from 1 to 10 carbon atoms, an optionally-substituted aryloxy group having from 1 to 10 carbon atoms, an optionally-substituted amino group, a substituent-having sulfur atom, a halogen atom, a nitro group, or a cyano group. At least two adjacent groups of $R^4$ to $R^9$ may bond to each other to form a ring.

$A^3$ and $A^4$ each independently represent a polymerization-reactive group. n indicates an integer value of from 1 to 5.

Here, preferred examples of the substituents of $R^3$ to $R^9$ in each structural formula are the same as those of $R^3$ to $R^9$ in the above-mentioned general formula (1). Preferred values of n in each structure are also the same as those of n in the general formula (1).

<12-1. Production Method A>

The production method A is a method for producing the oligofluorene monomer (20), in which a 9-monosubstituted fluorenes (IIIa) and (IIIb) are produced starting from the fluorene (I), and these monosubstituted forms are cross-linked to give the monomer. Here, the general formulae (IIIa) and (IIIb) may be the same or different. Not starting from the fluorene (I), the 9-monosubstituted fluorenes (IIIa) and/or (IIIb) may be produced.

For example, as a method for producing a 9-fluorene-carboxylate, there are known a method of using fluorene (J. Chem. Soc., 1949, 2623) and a method of using benzilic acid (Can. J. Chem., 1956, 34, 991). Also known is a method of crosslinking a 9-fluorene-carboxylate with an alkylene group (Anal. Chem., 1960, 32, 554). With reference to these, a monosubstituted fluorene is prepared, and then crosslinked to give the oligofluorene monomer (20).

<12-2. Production Method B>

The production method B is a method for producing the oligofluorene compound (IIa) where $R^3$ is a methylene group, in which the starting fluorene (I) is converted into a 9-hydroxymethylfluorene (IV), then dehydrated to give an olefin form (V), and this is reacted with a fluorenyl anion to give the compound. The unsubstituted 9-hydroxymethyl-fluorene is commercially available as a chemical reagent. According to the step (ii) in the Production Method C, a polymerization-reactive group $A^3$ and $A^4$ may be introduced into the resultant oligofluorene compound (IIa) to give the oligofluorene monomer (20).

For example, there is known a method of producing a mixture with an oligofluorene (IIa) through conversion of a 9-hydroxymethylfluorene into a dibenzofulvene followed by anionic polymerization (J. Am. Chem. Soc., 123, 2001, 9182-9183). With reference to these, an oligofluorene (IIa) can be produced.

<12-3. Production Method C>

The production method C is a method for producing the oligofluorene monomer (20), in which the starting fluorene (I) is crosslinked (step (i)) to give an oligofluorene compound (II), and thereafter a polymerization-reactive group such as a hydroxyl group, an ester group, a carboxyl group or the like is introduced into the compound (step (ii)) to give the monomer.

[Chem. 76]

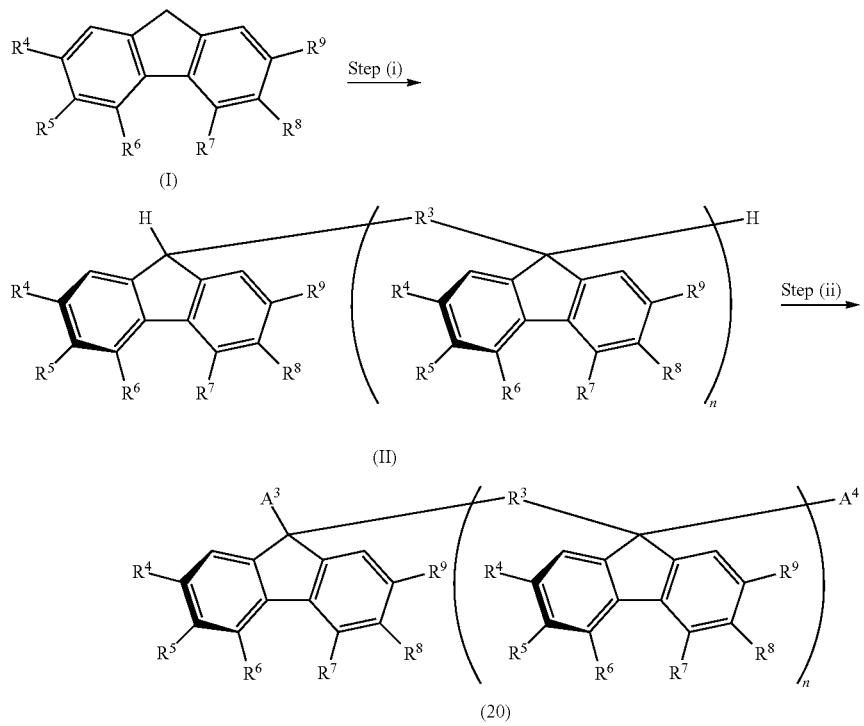

(In the formulae, $R^3$ to $R^9$ and n have the same meanings as those of $R^3$ to $R^9$ and n in the formula (1). $A^3$ and $A^4$ each independently represent a polymerization-reactive group.)

The Production Method C is further described below, as divided into the step (i) for production of an oligofluorene compound (II), and the step (ii) for production of an oligofluorene monomer (20).

<12-4. Step (i): Production Method for Oligofluorene Compound (II)>

[Chem. 77]

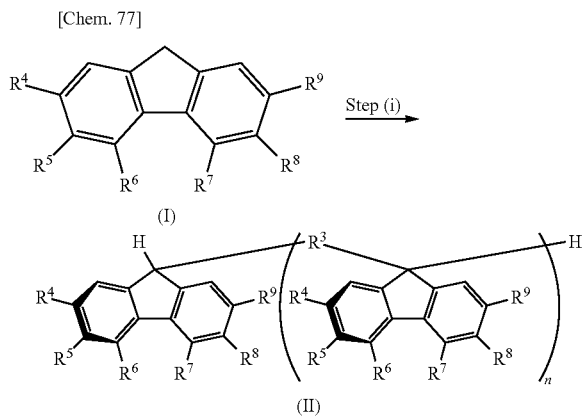

(In the formula, $R^3$ to $R^9$ and n have the same meanings as those of $R^3$ to $R^9$ and n in the formula (1).) The Production Method for the oligofluorene compound (II) in the step (i) is described below, as divided into individual cases depending on $R^3$ and n.

<12-4-1. Production Method for 9,9'-bifluorenyl where $R^3$ is Direct Bond and n=1>

Different methods are known for production of 9,9'-bifluorenyl from fluorenone or 9-bromofluorenone (J. Chem. Res., 2004, 760; Tetrahedron Lett., 2007, 48, 6669). 9,9'-Bifluorenyl is commercially available as a chemical reagent.

<12-4-2. Step (ia): Production Method where $R^3$ is Methylene and n=1 to 5>

An oligofluorene compound having a methylene crosslink represented by the following general formula (IIa) can be produced from a fluorene (I) and a formaldehyde substance in the presence of a base through the reaction shown by the following formula.

[Chem. 78]

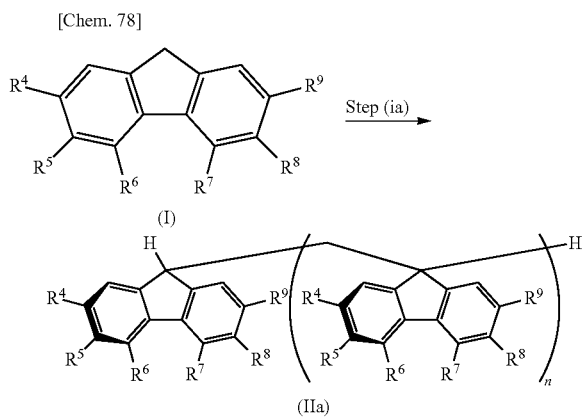

(In the formulae, $R^4$ to $R^9$ and n have the same meanings as those of $R^4$ to $R^9$ and n in the formula (1).)

<12-4-2-1. Formaldehyde Substance>

Not specifically defined, the formaldehyde substance to be used in the step (ia) may be any substance capable of donating formaldehyde to the reaction system, and includes gaseous formaldehyde, aqueous formaldehyde solution, paraformaldehyde formed through polymerization of formaldehyde, trioxane, etc. Of those, especially preferred is use of paraformaldehyde since the substance is industrially inexpensive and powdery and since the substance is easy to handle and can be accurately weighed.

(Definition of Theoretical Amount)

In case where the oligofluorene compound (IIa) having an intended number n is produced, the theoretical amount (molar ratio) of the formaldehyde substance to be used relative to the starting olefin (I) is expressed as n/(n+1).

(Reason why it is Better not to be More than the Theoretical Amount)

In case where an excessive theoretical amount of a formaldehyde substance is used relative to the fluorene (I), an oligofluorene compound (IIa) would be formed in which n is more than the intended value. With increase in the number n, the solubility of the product lowers. Consequently, when an oligofluorene compound (IIa) in which n is more than the intended value exists in the product, then it is known that the purification load would increase. Therefore, in general, the amount of the formaldehyde substance to be used is preferably n/(n+1) times by mol the theoretical amount in accordance with the intended value n.

(Reason why it is Better not to be Greatly Lower than the Theoretical Value)

On the other hand, when the amount of the formaldehyde substance to be used is greatly lower than n/(n+1) of the theoretical amount, then the oligofluorene compound (IIa) where n is lower than the intended value would come to be the main product or the starting fluorene (I) would remain as unreacted, and therefore it is known that the production yield would greatly lower.

Consequently, the optimal amount of the formaldehyde substance to be used is concretely 0.1 times by mol or more relative to the fluorene (I) in case where n=1, preferably 0.3 times by mol or more, more preferably 0.38 times by mol or more, and is generally 0.5 times by mol or less, preferably 0.46 times by mol or less, more preferably 0.42 times by mol or less.

When n=2, the amount is generally 0.5 times by mol or more, preferably 0.55 times by mol or more, more preferably 0.6 times by mol or more, and is generally 0.66 times by mol or less, preferably 0.65 times by mol or less, more preferably 0.63 times by mol or less. To that effect, it is known that the structure of the main product and the ratio of the main product greatly vary depending on the amount of the formaldehyde substance used, and by specifically defining the amount of the formaldehyde substance to be used, it is possible to obtain the oligofluorene compound (IIa) having an intended value n at high yield.

<12-4-2-2. Base>

The base to be used in the step (ia) includes alkali metal hydroxides such as lithium hydroxide, sodium hydroxide, potassium hydroxide, etc.; alkaline earth metal hydroxides such as calcium hydroxide, barium hydroxide, etc.; alkali metal carbonates such as sodium carbonate, sodium hydrogencarbonate, potassium carbonate, etc.; alkaline earth metal carbonates such as magnesium carbonate, calcium carbonate, etc.; alkali metal phosphates such as sodium phosphate, sodium hydrogenphosphate, potassium phosphate, etc.; organic lithium salts such as n-butyllithium, tertiary butyllithium, etc.; alkali metal alkoxides such as sodium methoxide, sodium ethoxide, potassium tertiary butoxide, etc.; alkali metal hydrides such as sodium hydride, potassium hydride, etc.; tertiary amines such as triethylamine, diazabicycloundecene, etc.; quaternary ammonium hydroxides such as tetramethylammonium hydroxide, tetrabutylammonium hydroxide, etc. One alone or two or more types of these may be used either singly or as combined.

Of those, preferred are alkali metal alkoxides capable of having sufficient basicity in the present reaction, and more preferred are sodium methoxide and sodium ethoxide that are industrially inexpensive. The alkali metal alkoxide to be used here may be powdery, or may be a liquid one such as an alcohol solution thereof. An alkali metal and an alcohol may be reacted to prepare the alkoxide.

The upper limit of the amount of the base to be used is not specifically defined relative to the starting fluorene (I); however, when the amount is too large, then the stirring load and the purification load after reaction would increase, and therefore, the upper limit is generally 10 times by mol or less the fluorene (I), preferably 5 times by mol or less, more preferably 1 time by mol or less. On the other hand, when the amount of the base used is too small, then the reaction speed would be low, and therefore, the lower limit of the amount is generally 0.01 times by mol or more the starting fluorene (I), preferably 0.1 times by mol or more, more preferably 0.2 times by mol or more.

<12-4-2-3. Solvent>

Preferably, a solvent is used in the step (ia). Specific examples of the usable solvent include alkylnitrile solvents such as acetonitrile, propionitrile, etc.; ether solvents such as diethyl ether, tetrahydrofuran, 1,4-dioxane, methylcyclopentyl ether, tertiary butyl methyl ether, etc.; halogen-containing solvents such as 1,2-dichloroethane, dichloromethane, chloroform, 1,1,2,2-tetrachloroethane, etc.; halogenoaromatic hydrocarbons such as chlorobenzene, 1,2-dichlorobenzene, etc.; amide solvents such as N,N-dimethylformamide, N,N-dimethylacetamide, N-methylpyrrolidone, etc.; sulfoxide solvents such as dimethyl sulfoxide, sulfolane, etc.; as cycloaliphatic hydrocarbons, monocyclic aliphatic hydrocarbons such as cyclopentane, cyclohexane, cycloheptane, cyclooctane, etc., and their derivatives such as methylcyclopentane, ethylcyclopentane, methylcyclohexane, ethylcyclohexane, 1,2-trimethylcyclohexane, 1,3-trimethylcyclohexane, 1,4-dimethylcyclohexane, isopropylcyclohexane, n-propylcyclohexane, tert-butylcyclohexane, n-butylcyclohexane, isobutylcyclohexane, 1,2,4-trimethylcyclohexane, 1,3,5-trimethylcyclohexane, etc.; polycyclic aliphatic hydrocarbons such as decalin, etc.; acyclic aliphatic hydrocarbons such as n-pentane, n-hexane, n-heptane, n-octane, isooctane, n-nonane, n-decane, n-dodecane, n-tetradecane, etc.; aromatic hydrocarbons such as toluene, p-xylene, o-xylene, m-xylene, etc.; alcohol solvents such as methanol, ethanol, isopropanol, n-butanol, tertiary butanol, hexanol, octanol, cyclohexanol, etc.

Above all, preferred are polar solvents of amide solvents, or sulfoxide solvents, as having a high solubility for anions derived from fluorenes (I) and capable of well promoting the reaction. Of those, more preferred is N,N-dimethylformamide in producing oligofluorene compounds (IIa) where n=1 or 2. This is because the solubility of oligofluorene with n=1 or 2 in N,N-dimethylformamide is low, and therefore the product can rapidly precipitate out after formation and the reaction can be prevented from going on any more with the result that the product selectivity could be increased.

One alone or two or more types of these solvents may be used here either singly or as combined.

It is known that, when the value n in the oligofluorene compound (IIa) produced in the step (ia) is larger, then the solubility of the compound in solvent lowers, and therefore it is considered that the formed product can rapidly precipitate out to thereby prevent the subsequent reaction from further going on. Consequently, the amount of the solvent to be used is preferably controlled suitably depending on the value n. In particular, in a case where an oligofluorene compound (IIa) where n=1 or 2 is produced, it is better not to use any excessive amount of solvent in order to increase the product selectivity. For example, the upper limit of the solvent amount in a case of using the most preferred solvent, N,N-dimethylformamide is generally 10 times by volume the starting fluorene (I), preferably 7 times by volume, more preferably 4 times by volume. On the other hand, when the amount of the solvent used is too small, then the stirring would be difficult and the reaction speed would be low. Consequently, the lower limit of the amount is generally 1 time by volume the starting fluorene (I), preferably 2 times by volume, more preferably 3 times by volume.

<12-4-2-4. Reaction Mode>

For the step (ia), the reaction mode may be any of a batch-mode reaction or a flow-through reaction, or a combination thereof. Any reaction mode is employable here with no limitation.

<12-4-2-5. Reaction Condition>

The step (ia) may be suitably controlled in accordance with the oligofluorene compound (IIa) having an intended value n. For preventing the reaction from going on any more than the intended value n, it is desirable that the reaction is carried out at a temperature as low as possible. On the other hand, when the temperature is too low, there is a possibility that a sufficient reaction speed could not be attained.

Consequently, in a case where the optimum solvent N,N-dimethylformamide and the optimum base sodium ethoxide are used, the concrete reaction temperature for n=1 or 2 is, as the upper limit thereof, generally 30° C., preferably 20° C., more preferably 10° C. On the other hand, the lower limit is generally −50° C., preferably −20° C., more preferably 0° C.

An ordinary reaction time for the step (ia) is, as the lower limit thereof, generally 30 minutes, preferably 60 minutes, more preferably 2 hours, and the upper limit thereof is not specifically defined but is generally 20 hours, preferably 10 hours, more preferably 5 hours.

<12-4-2-6. Separation/Purification of Product>

After the reaction, the intended product oligofluorene compound (IIa) may be isolated by putting the reaction liquid into acidic water such as diluted hydrochloric acid or the like, or by adding acidic water such as diluted hydrochloric acid or the like to the reaction liquid so as to precipitate the product.

After the reaction, a solvent capable of dissolving the intended product oligofluorene compound (IIa) and water may be added to the reaction liquid for product extraction. The intended product thus extracted with the solvent may be then isolated according to a method of concentrating the solvent or a method of adding a poor solvent to the system. However, the solubility of the oligofluorene compound (IIa) in solvent would be often extremely low at room temperature, and therefore, in general, preferred is a method of bringing the reaction liquid into contact with acidic water for product precipitation.

The resultant oligofluorene compound (IIa) may be used as the starting material in the step (ii) directly as it is, but may also be used in the step (ii) after purified. As the purification method, employable is any ordinary purification method of, for example, recrystallization, reprecipitation, extraction purification, column chromatography or the like with no specific limitation thereon.

<12-4-3. Step (ib): Production Method for Difluorene Compound (IIIb) where $R^3$ is any Other than Direct Bond and n=1>

A difluorene compound represented by the following general formula (IIb) can be produced starting from the fluorene (I) and reacting it with an alkylating agent (VIII) in the presence of a base according to the following step (ib):

[Chem. 79]

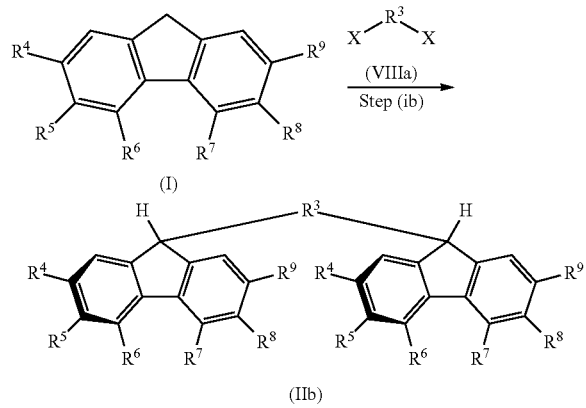

The difluorene compound of the above formula is represented by the structural formula (IIb). (In the formula, $R^3$ represents an optionally-substituted alkylene group having from 1 to 10 carbon atoms, an optionally-substituted arylene group having from 4 to 10 carbon atoms, or an optionally-substituted aralkylene group having from 6 to 10 carbon atoms, and $R^4$ to $R^9$ and n have the same meanings as those of $R^4$ to $R^9$ and n in the formula (1). X represents a leaving group. Examples of the leaving group include a halogen atom (except fluorine), a mesyl group, a tolyl group, etc.)

As the production method for the difluorene compound (IIb), widely known is a method of using n-butyllithium as a base, generating an anion of the fluorene (I) and coupling it with an alkylating agent (VIIIa), and there is known a production method for the case where $R^3$ is an ethylene group or $R^3$ is a propylene group (Organometallics, 2008, 27, 3924; J, Molec. Cat. A: Chem., 2004, 214, 187). Except the alkylene group, there is known a report of crosslinking with a xylylene group (J. Am. Chem. Soc., 2007, 129, 8458). However, industrial-scale production according to the method of using n-butyllithium is often extremely difficult from the viewpoint of safety and production cost. As the production method for the difluorene compound (IIb), there is also known a method of dehydrating condensation of fluorene and ethylene glycol in the presence of a base at a high temperature (H. Org. Chem., 1965, 30, 2540).

The alkylating agent to be used in the step (ib) includes linear alkyl dihalides (except those with fluorine) such as diiodomethane, 1,2-diiodoethane, 1,3-diiodopropane, 1,4-diiodobutane, 1,5-diiodopentane, 1,6-diiodohexane, dibromomethane, 1,2-dibromoethane, 1,3-dibromopropane, 1,4-dibromobutane, 1,5-dibromopentane, 1,6-dibromohexane, dichloromethane, 1,2-dichloroethane, 1,3-dichloropropane, 1,4-dichlorobutane, 1,5-dichloropentane, 1,6-dichlorohexane, 1-bromo-3-chloropropane, etc.; branched chain-containing alkyl dihalides (except those with fluorine) such as 2,2-dimethyl-1,3-dichloropropane, etc.; aralkyl dihalides (except those with fluorine) such as 1,4-bis(bromomethyl)benzene, 1,3-bis(bromomethyl)benzene, etc.; glycol disulfonates such as ethylene glycol dimesylate, ethylene glycol ditosylate, propylene glycol dimesylate, tetramethylene glycol dimesylate, etc.

<12-4-4. Step (ic): Production Method for Oligofluorene Compound (IIc) where $R^3$ is any Other than Direct Bond and n=2 or More>

An oligofluorene compound represented by the following general formula (IId) can be produced starting from the oligofluorene compound (IIc) and reacting it with an alkylating agent (VIIIa) in the presence of a base according to the following step (ic):

[Chem. 80]

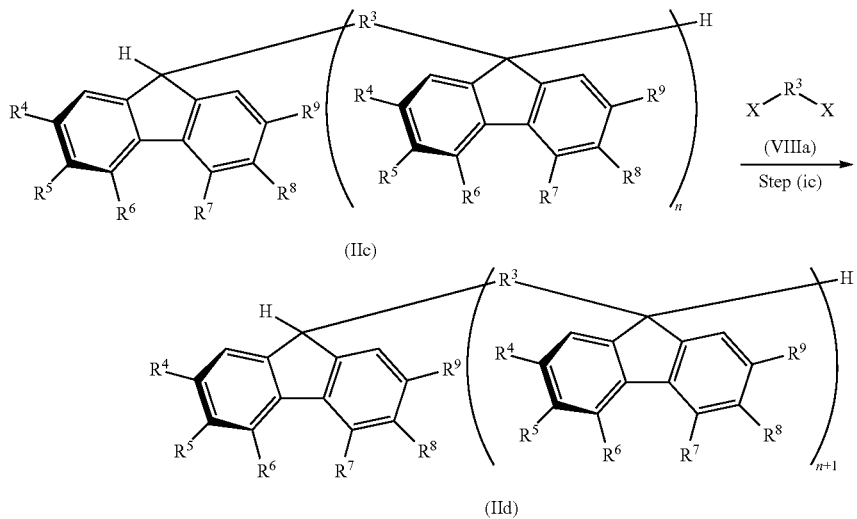

The oligofluorene compound of the above formula is represented by the structural formula (IId). (In the formula, $R^3$ represents an optionally-substituted alkylene group having from 1 to 10 carbon atoms, an optionally-substituted arylene group having from 4 to 10 carbon atoms, or an optionally-substituted aralkylene group having from 6 to 10 carbon atoms, and $R^4$ to $R^9$ and n have the same meanings as those of $R^4$ to $R^9$ and n in the formula (1). X represents a leaving group. Examples of the leaving group include a halogen atom (except fluorine), a mesyl group, a tolyl group, etc.)

<12-5. Production Method for Oligofluorene Monomer (20)>

The Production Method for the oligofluorene monomer (20) in the step (ii) shown by the following formula is described below, as divided into individual cases depending on $A^3$ and $A^4$.

[Chem. 81]

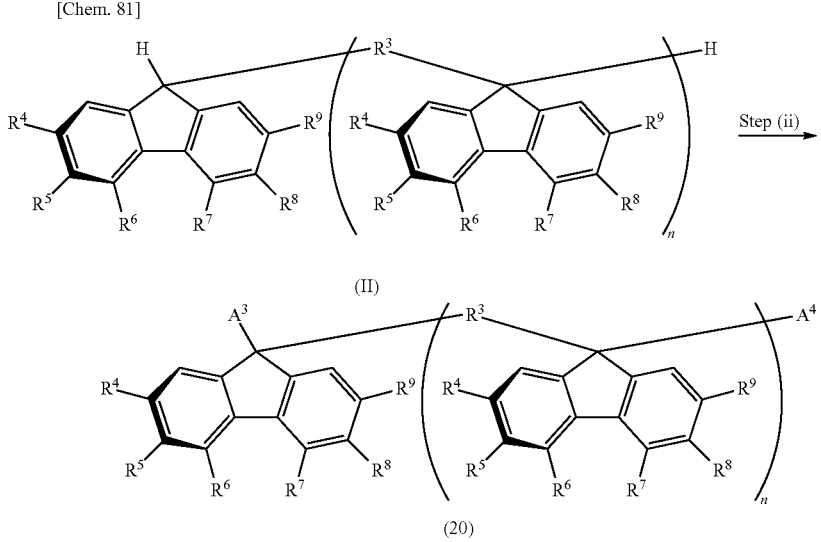

(In the formula, $R^3$ to $R^9$ and n have the same meanings as those of $R^3$ to $R^9$ and n in the formula (1). $A^3$ and $A^4$ each independently represent a polymerization-reactive group.)

<12-5-1. Step (iia): Production Method for Compound of General Formula (20) where $A^3$ and $A^4$ are Hydroxymethyl Groups>

An oligofluorene-diol (19) where $A^3$ and $A^4$ are hydroxymethyl groups can be produced from an oligofluorene compound (II) and a formaldehyde substance in the presence of a base through the reaction of the following step (iia).

[Chem. 82]

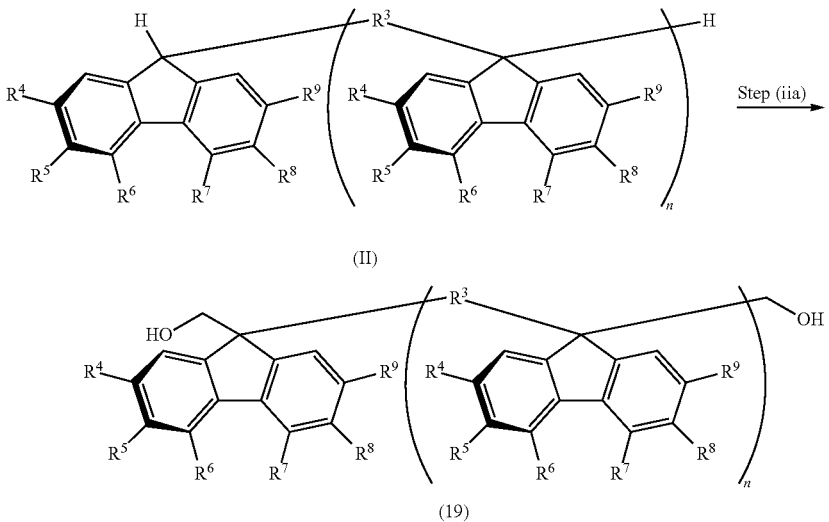

(In the formulae, $R^3$ to $R^9$ and n have the same meanings as those of $R^3$ to $R^9$ and n in the formula (1).)

<12-5-1-1. Formaldehyde Substance>

Not specifically defined, the formaldehyde substance to be used in the step (iia) may be any substance capable of donating formaldehyde to the reaction system, and includes gaseous formaldehyde, aqueous formaldehyde solution, paraformaldehyde formed through polymerization of formaldehyde, trioxane, etc. Of those, especially preferred is use of paraformaldehyde since the substance is industrially inexpensive and powdery and since the substance is easy to handle and can be accurately weighed.

The amount of the formaldehyde substance to be used is not specifically defined in point of the upper limit relative to the starting material, oligofluorene compound (II); however, when the amount is too large, then the purification load after the reaction would increase. Therefore, the amount is generally 20 times by mol or less the oligofluorene compound (II), preferably 10 times by mol or less, more preferably 5 times by mol or less. The lower limit is, as the theoretical amount thereof, 2 times by mol the starting material, and is generally 2 times by mol or more. For promoting the reaction and for preventing the starting material and the intermediate from remaining in the reaction system, the formaldehyde substance may be used somewhat excessively relative to the starting oligofluorene compound (II) with no problem. In the case, a preferred amount of the formaldehyde substance to be used may be 2.1 times by mol or more the starting oligofluorene compound (II), preferably 2.2 times by mol or more.

<12-5-1-2. Base>

As the base, usable are alkali metal hydroxides such as lithium hydroxide, sodium hydroxide, potassium hydroxide, etc.; alkaline earth metal hydroxides such as calcium hydroxide, barium hydroxide, etc.; alkali metal carbonates such as sodium carbonate, sodium hydrogencarbonate, potassium carbonate, etc.; alkaline earth metal carbonates such as magnesium carbonate, calcium carbonate, etc.; alkali metal phosphates such as sodium phosphate, sodium hydrogenphosphate, potassium phosphate, etc.; organic lithium salts such as n-butyllithium, tertiary butyllithium, etc.; alkali metal alkoxides such as sodium methoxide, sodium ethoxide, potassium tertiary butoxide, etc.; alkali metal hydrides such as sodium hydride, potassium hydride, etc.; tertiary amines such as triethylamine, diazabicycloundecene, etc.; quaternary ammonium hydroxides such as tetramethylammonium hydroxide, tetrabutylammonium hydroxide, etc. One alone or two or more types of these may be used either singly or as combined.

Of those, preferred are alkali metal alkoxides capable of having sufficient basicity in the present reaction, and more preferred are sodium methoxide and sodium ethoxide that are industrially inexpensive. The alkali metal alkoxide to be used here may be powdery, or may be a liquid one such as an alcohol solution thereof. An alkali metal and an alcohol may be reacted to prepare the alkoxide.

Regarding the amount of the base to be used, it is known that when an excessive amount of the base is used relative to the starting oligofluorene compound (II), then the decomposition of the oligofluorene-diol (19) would be promoted. Consequently, the amount is preferably 1 time by mol or less the oligofluorene compound (II), more preferably 0.5 times by mol or less, even more preferably 0.2 times by mol or less. On the other hand, when the amount of the base used is too small, then the reaction speed would be low, and therefore, the lower limit of the amount is generally 0.01 times by mol or more the starting oligofluorene compound (II), preferably 0.05 times by mol or more.

<12-5-1-3. Solvent>

Preferably, a solvent is used in the step (iia).

Specific examples of the usable solvent include alkylnitrile solvents such as acetonitrile, propionitrile, etc.; ketone solvents such as acetone, methyl ethyl ketone, methyl isobutyl ketone, etc.; as ester solvents, linear esters such as methyl acetate, ethyl acetate, propyl acetate, phenyl acetate, methyl propionate, ethyl propionate, propyl propionate, phenyl propionate, methyl 3-methoxypropionate, methyl 3-ethoxypropionate, methyl lactate, ethyl lactate, etc.; cyclic esters such as γ-butyrolactone, caprolactone, etc.; ether esters such as ethylene glycol monomethyl ether acetate, ethylene glycol monoethyl ether acetate, ethylene glycol monobutyl ether acetate, propylene glycol 1-monomethyl ether acetate, propylene glycol 1-monoethyl ether acetate, etc.; ether solvents such as diethyl ether, tetrahydrofuran, 1,4-dioxane, methylcyclopentyl ether, tertiary butyl methyl ether, etc.; halogen-containing solvents such as 1,2-dichloroethane, dichloromethane, chloroform, 1,1,2,2-tetrachloroethane, etc.; halogenoaromatic hydrocarbons such as chlorobenzene, 1,2-dichlorobenzene, etc.; amide solvents such as N,N-dimethylformamide, N,N-dimethylacetamide, N-methylpyrrolidone, etc.; sulfoxide solvents such as dimethyl sulfoxide, sulfolane, etc.; as cycloaliphatic hydrocarbons, monocyclic aliphatic hydrocarbons such as cyclopentane, cyclohexane, cycloheptane, cyclooctane, etc., and their derivatives such as methylcyclopentane, ethylcyclopentane, methylcyclohexane, ethylcyclohexane, 1,2-dimethylcyclohexane, 1,3-dimethylcyclohexane, 1,4-dimethylcyclohexane, isopropylcyclohexane, n-propylcyclohexane, tert-butylcyclohexane, n-butylcyclohexane, isobutylcyclohexane, 1,2,4-trimethylcyclohexane, 1,3,5-trimethylcyclohexane, etc.; polycyclic aliphatic hydrocarbons such as decalin, etc.; acyclic aliphatic hydrocarbons such as n-pentane, n-hexane, n-heptane, n-octane, isooctane, n-nonane, n-decane, n-dodecane, n-tetradecane, etc.; aromatic hydrocarbons such as toluene, p-xylene, o-xylene, m-xylene, etc.; alcohol solvents such as methanol, ethanol, isopropanol, n-butanol, tertiary butanol, hexanol, octanol, cyclohexanol, etc.

Above all, preferred are polar solvents of amide solvents, or sulfoxide solvents, as having a high solubility for anions derived from oligofluorenes (II) and capable of well promoting the reaction. Of those, more preferred is N,N-dimethylformamide.

One alone or two or more types of these solvents may be used here either singly or as combined. The upper limit of the amount of the solvent to be used is not specifically defined. In consideration of the production efficiency of the product per reactor, in general, the solvent is used in an amount of generally 10 times by volume the starting oligofluorene compound (II), preferably 7 times by volume, more preferably 4 times by volume. On the other hand, when the amount of the solvent used is too small, then the stirring would be difficult and the reaction speed would be low. Consequently, the lower limit of the amount is generally 1 time by volume the starting oligofluorene compound (II), preferably 2 times by volume, more preferably 3 times by volume.

<12-5-1-4. Reaction Mode>

For the step (iia), the reaction mode may be any of a batch-mode reaction or a flow-through reaction, or a combination thereof. Any reaction mode is employable here with no limitation.

Regarding the method of putting reaction reagents into the reactor in a batch mode, it is known that when a base is added all at a time at the start of the reaction, then the decomposition reaction may readily go on. Accordingly, it is desirable that the base is added little by little after the starting oligofluorene compound (II), a formaldehyde substance and a solvent have been added to the reactor.

<12-5-1-5. Reaction Condition>

It is known that, when the temperature is too low in the step (iia), then a sufficient reaction speed could not be obtained, but on the contrary, when too high, then the decomposition reaction may go on. Therefore, the temperature control is extremely important. In a case where the optimum solvent N,N-dimethylformamide and the optimum base sodium ethoxide are used, the lower limit of the temperature is generally −50° C., and the upper limit thereof is generally 30° C. Concretely, in a case where $R^3$ is a methylene group and n=1, the upper limit of the reaction temperature is preferably 20° C., more preferably 10° C. On the other hand, the lower limit is preferably −20° C., more preferably 0° C. or higher. In a case where $R^3$ is an ethylene group and n=1, the upper limit of the reaction temperature is preferably 25° C., more preferably 20° C. On the other hand, the lower limit is preferably 0° C., more preferably 10° C. or higher. In a case where $R^3$ is a methylene group and n=2, the upper limit of the reaction temperature is preferably 25° C., more preferably 20° C. On the other hand, the lower limit is preferably 0° C., more preferably 10° C. or higher.

<12-5-1-6. Separation/Purification of Product>

After the reaction, the intended product oligofluorene-diol (19) may be isolated by putting the reaction liquid into acidic water such as diluted hydrochloric acid or the like, or by adding acidic water such as diluted hydrochloric acid or the like to the reaction liquid so as to precipitate the product.

After the reaction, a solvent capable of dissolving the intended product oligofluorene-diol (19) and water may be added to the reaction liquid for product extraction. The intended product thus extracted with the solvent may be then isolated according to a method of concentrating the solvent or a method of adding a poor solvent to the system.

The resultant oligofluorene-diol (19) may be used for polymerization as the starting material for polymer directly as it is, but may also be used for polymerization after purified. As the purification method, employable is any ordinary purification method of, for example, recrystallization, reprecipitation, extraction purification, column chromatography or the like with no specific limitation thereon.

Presence of a metal component is often problematic in polymerization reaction, and the content ratio of Group-1 and Group-2 metals of the Long Periodic Table in the monomer may be 500 ppm by mass or less, preferably 200 ppm by mass or less, more preferably 50 ppm by mass or less, even more preferably 10 ppm by mass or less. For removing the metal component, in general, liquid-liquid separation is extremely effective. However, the intended product oligofluorene-diol (19) can dissolve only in a high-polar solvent such as N,N-dimethylformamide, tetrahydrofuran or the like, and therefore two-layer liquid-liquid separation for the product is extremely difficult. On the other hand, even when the product separated through precipitation after the reaction is purified according to an ordinary method of washing with water or thermal suspension washing with a solvent, it is still difficult to fully remove the contaminating metal component, and even after the washing, there may still remain a metal component on an order of a few hundred ppm by mass in the precipitate. As a favorable purification method for metal component removal, there may be mentioned a simple and effective inorganic salt removal method that comprises dissolving the impurities-containing reaction precipitate in a solvent having a relatively high solubility such as N,N-dimethylformamide and tetrahydrofuran, then pouring it into water for precipitation therein.

<12-5-2. Step (iib): Production Method for Compound of General Formula (20) where $A^3$ and $A^4$ are group having hydroxyl group, ester group, carboxyl group or amino group (Production Method by Michael Addition)>

An oligofluorene derivative represented by the following general formula (VII) can be produced from an oligofluorene compound (II) and an electron-withdrawing group-substituted olefin (VI) in the presence of a base through the reaction of the following step (iib).

[Chem. 83]

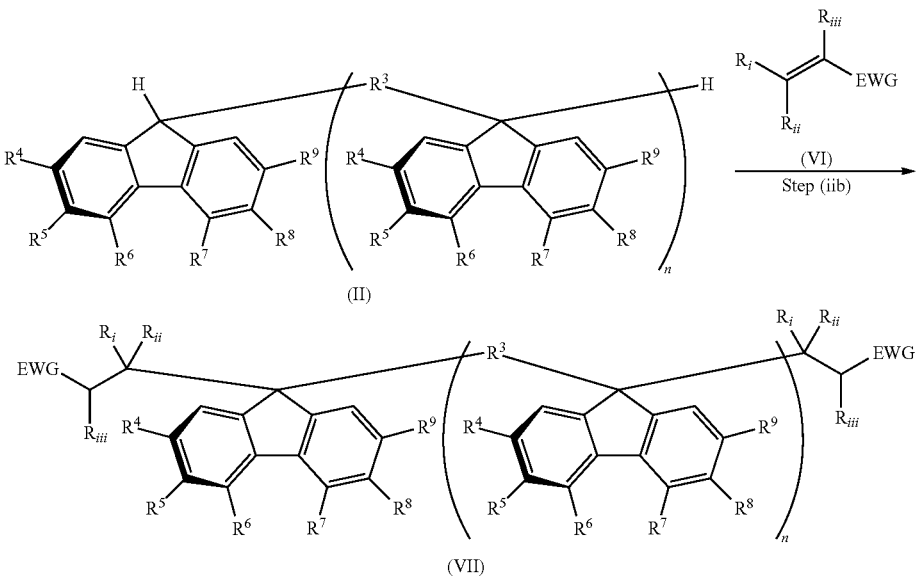

(In the formulae, $R^3$ to $R^9$ and n have the same meanings as those of $R^3$ to $R^9$ and n in the formula (1). $R_i$, $R_{ii}$ and $R_{iii}$ each represent a hydrogen atom, an optionally-substituted alkyl group having from 1 to 10 carbon atoms, an optionally-substituted aryl group having from 4 to 10 carbon atoms, or an optionally-substituted aralkyl group having from 6 to 10 carbon atoms. EWG represents an electron withdrawing group.)

<12-5-2-1. Electron-Withdrawing Group-Substituted Olefin>

The electron-withdrawing group-substituted olefin as a reaction reagent is one represented by the general formula (VI) in the step (iib). In the general formula (VI), $R_i$, $R_{ii}$ and $R_{iii}$ each independently represent a hydrogen atom, an optionally-substituted alkyl group having from 1 to 10 carbon atoms, an optionally-substituted aryl group having from 4 to 10 carbon atoms, or an optionally-substituted aralkyl group having from 6 to 10 carbon atoms. Concretely, there are mentioned an alkyl group (which may be either linear or branched), such as a methyl group, an ethyl group, an n-propyl group, an isopropyl group, a cyclohexyl group, etc.; an aryl group such as a phenyl group, a 1-naphthyl group, a 2-naphthyl group, a 2-thienyl group, etc.; an aralkyl group such as a benzyl group, a 2-phenylethyl group, a p-methoxybenzyl group, etc. In the general formula (VI), EWG of the electron-withdrawing group-substituted olefin represents an electron withdrawing group. Concretely, there are mentioned a nitro group, a cyano group, a formyl group, a carboxyl group, or a ketone group or an ester group having an organic substituent with from 1 to 10 carbon atoms. The organic substituent that the ketone group or the ester group has includes, concretely, a linear alkyl group (which may be straight or branched), such as a methyl group, an ethyl group, an n-propyl group, an isopropyl group, an n-butyl group, etc.; a cyclic alkyl group such as a cyclohexyl group, etc.; a hydroxyalkyl group such as a hydroxyethyl group, a hydroxypropyl group, etc.; an aryl group such as a phenyl group, a 1-naphthyl group, a 2-naphthyl group, a 2-thienyl group, etc.; an aralkyl group such as a benzyl group, a 2-phenylethyl group, a p-methoxybenzyl group, etc. The group may be substituted with any of these substituents within a range not detracting from the reaction in the step (iib).

The electron-withdrawing group-substituted olefin (VI) includes acrylates such as methyl acrylate, ethyl acrylate, phenyl acrylate, allyl acrylate, glycidyl acrylate, 2-hydroxyethyl acrylate, 4-hydroxybutyl acrylate, 1,4-cyclohexanedimethanol monoacrylate, etc.; methacrylates such as methyl methacrylate, ethyl methacrylate, phenyl methacrylate, allyl methacrylate, glycidyl methacrylate, 2-hydroxyethyl methacrylate, etc.; α-substituted unsaturated esters such as methyl 2-ethylacrylate, methyl 2-phenylacrylate, etc.; β-substituted unsaturated waters such as methyl cinnamate, ethyl cinnamate, methyl crotonate, ethyl crotonate, etc.; conjugated nitroolefins such as β-nitrostyrene, etc.; α,β-unsaturated nitriles such as acrylonitrile, etc.; α,β-unsaturated aldehydes such as acrolein, methacrolein, crotonaldehyde, etc. Of those, as capable of directly introducing a polymerization-reactive group, preferred are unsaturated carboxylates represented by the following general formula (VI-I):

[Chem. 84]

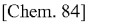

(VI-1)

(In the formula, $R^{17}$ represents an organic substituent having from 1 to 10 carbon atoms, $R_{iii}$ represents a hydrogen atom, an optionally-substituted alkyl group having from 1 to 10 carbon atoms, an optionally-substituted aryl group having from 4 to 10 carbon atoms, or an optionally-substituted aralkyl group having from 6 to 10 carbon atoms.) Of those, more preferred are acrylates, methacrylates or α-substituted unsaturated esters; and from the viewpoint of the reaction speed and the reaction selectivity, more preferred are acrylates or methacrylate where $R_{iii}$ represents a methyl group. Preferably, $R^{17}$ is a smaller substituent, since the compounds of the type are industrially inexpensive and can be readily processed for distillation purification, and have high reactivity. Accordingly, especially preferred are methyl acrylate, methyl methacrylate, ethyl acrylate, ethyl methacrylate, phenyl acrylate and phenyl methacrylate.

On the other hand, regarding the organic substituent of the ester group, especially preferred are hydroxyalkyl group-having esters such as 2-hydroxyethyl acrylate, 4-hydroxybutyl acrylate, 1,4-cyclohexanedimethanol monoacrylate, etc., since the starting materials of polyester carbonates and polyesters can be produced in one-stage reaction.

Two or more different types of electron-withdrawing group-substituted olefins (VI) may be used here; however, in view of simple purification, preferred is use of one type of electron-withdrawing group-substituted olefin (VI).

Here, when esters are used as the electron-withdrawing group-substituted olefin (VI), then the oligofluorene derivatives (VII) are to be oligofluorene diesters (20b) mentioned below. In particular, when the esters used here are esters having a hydroxyalkyl group, then the oligofluorene derivatives (VII) are to be oligofluorene-dihydroxy ester (20d) mentioned below.

[Chem. 85]

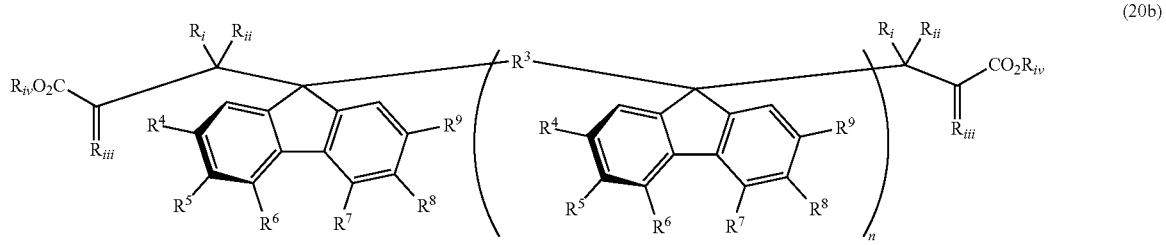

(20b)

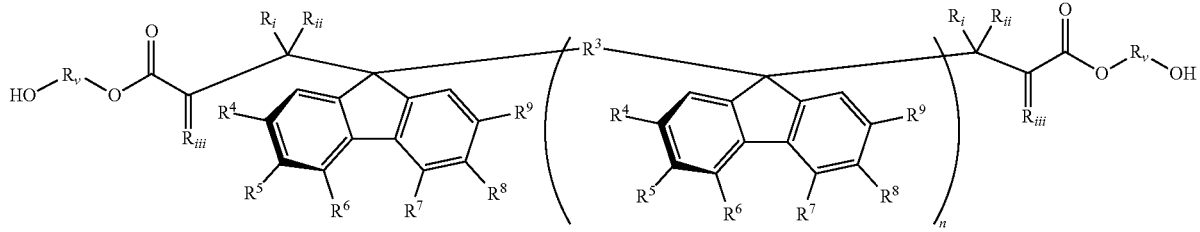

(20d)

(In the formulae, $R^3$ to $R^9$ and n have the same meanings as those of $R^3$ to $R^9$ and n in the formula (1). $R_i$, $R_{ii}$ and $R_{iii}$ each represent a hydrogen atom, an optionally-substituted alkyl group having from 1 to 10 carbon atoms, an optionally-substituted aryl group having from 4 to 10 carbon atoms, or an optionally-substituted aralkyl group having from 6 to 10 carbon atoms. $R_{iv}$ and $R_v$ each represent an organic substituent having from 1 to 10 carbon atoms.)

The electron-withdrawing group-substituted olefin (VI) has high polymerization activity, and therefore, existing at a high concentration, the olefin tends to readily polymerize when exposed to external stimuli such as light, heat, acid, base, etc. In the case, the system generates great heat and may be often extremely dangerous. Consequently, regarding the amount of the electron-withdrawing group-substituted olefin (VI) to be used, it is desirable that the olefin is not used too excessively, from the viewpoint of safety. In general, the amount of the olefin is 10 times by mol or less the starting material oligofluorene (II), preferably 5 times by mol or less, more preferably 3 times by mol or less. The lower limit is, as the theoretical amount, 2 times by mol the starting material, and is generally 2 times by mol or less. For promoting the reaction and for preventing the starting material and the intermediate from remaining in the system, the amount of the electron-withdrawing group-substituted olefin (VI) to be used is 2.2 times by mol or more the starting oligofluorene (II), more preferably 2.5 times by mol or more.

<12-5-2-2. Base>

As the base, usable are alkali metal hydroxides such as lithium hydroxide, sodium hydroxide, potassium hydroxide, etc.; alkaline earth metal hydroxides such as calcium hydroxide, barium hydroxide, etc.; alkali metal carbonates such as sodium carbonate, sodium hydrogencarbonate, potassium carbonate, etc.; alkaline earth metal carbonates such as magnesium carbonate, calcium carbonate, etc.; alkali metal phosphates such as sodium phosphate, sodium hydrogenphosphate, potassium phosphate, etc.; organic lithium salts such as n-butyllithium, tertiary butyllithium, etc.; alkali metal alkoxides such as sodium methoxide, sodium ethoxide, potassium tertiary butoxide, etc.; alkali metal hydrides such as sodium hydride, potassium hydride, etc.; tertiary amines such as triethylamine, diazabicycloundecene, etc.; quaternary ammonium hydroxides such as tetramethylammonium hydroxide, tetrabutylammonium hydroxide, benzyltrimethylammonium hydroxide, etc. One alone or two or more types of these may be used either singly or as combined.

There is a great difference in the reactivity between the oligofluorene (II) where $R^3$ is a methylene group and that where $R^3$ is any other substituent. Consequently, the case where $R^3$ is a methylene group and the case where $R^3$ is any other group are separately described below.

The oligofluorene (II) where $R^3$ is a methylene group readily decomposes in a solvent in the presence of a base. Accordingly, when the reaction is carried out in a two-layer system of an organic layer and an aqueous layer, the side reaction such as decomposition and the like can be prevented, and therefore in the case, preferred is use of a water-soluble inorganic base. Above all, from the viewpoint of the cost and the reactivity thereof, preferred is an alkali metal hydroxide, and more preferred is sodium hydroxide or potassium hydroxide.

Regarding the concentration of the aqueous solution, in a case of an aqueous solution of sodium hydroxide that is especially preferred is used, when the concentration thereof is low, then the reaction speed may greatly lower, and therefore preferred is use of an aqueous solution having a concentration of generally 5 wt/vol % or more, preferably 10 wt/vol % or more, more preferably 25 wt/vol % or more.

The oligofluorene where $R^3$ is any other substituent than a methylene group can react even in a two-layer system of an organic layer and an aqueous layer; however, in the case, when the reaction is carried out using an organic base capable of dissolving in an organic layer, the reaction may be promoted more, and therefore, use of an organic base in the case is preferred. Of those, more preferred are alkali metal alkoxides having sufficient basicity in the present reaction, and more preferred are sodium methoxide and sodium ethoxide that are industrially inexpensive. The alkali metal alkoxide to be used here may be powdery, or may be a liquid one such as an alcohol solution thereof. An alkali metal and an alcohol may be reacted to prepare the alkoxide.

In the case where $R^3$ is a methylene group, the upper limit of the amount of the base to be used is not specifically defined relative to the starting material oligofluorene (II); however, when the amount thereof used is too large, then the stirring load and the purification load after reaction would increase. Consequently, in a case where an aqueous solution of sodium hydroxide having a concentration of 25 wt/vol % or more that is a preferred base is used, the amount thereof is generally 20 times by volume or less the oligofluorene (II), preferably 10 times by volume or less, more preferably 5 times by volume or less. When the base amount is too small, then the reaction speed would greatly lower, and therefore, the base amount is generally 0.2 times by volume or more the starting material oligofluorene (II). Preferably, the base amount is 0.5 times by volume or more, more preferably 1 time by volume or more.

In the case where $R^3$ is any other substituent than a methylene group, the upper limit of the amount of the base to be used is not specifically defined relative to the starting material oligofluorene (II); however, when the amount thereof used is too large, then the stirring load and the purification load after reaction would increase. Consequently, in a case where sodium methoxide or sodium ethoxide that is a preferred base is used, the amount thereof is generally 5 times by mol or less the oligofluorene (II), preferably 2 times by mol or less, more preferably 1 time by mol or less, even more preferably 0.5 times by mol or less. When the base amount is too small, then the reaction speed would greatly lower, and therefore, the base amount is generally 0.005 times by mol or more the starting material oligofluorene (II), preferably 0.01 times by mol or more, more preferably 0.05 times by mol or more, even more preferably 0.1 times by mole or more.

<12-5-2-3. Phase-Transfer Catalyst>

In the step (iib) where the reaction is carried out in a two-layer system of an organic layer and an aqueous layer, preferably used is a phase-transfer catalyst for increasing the reaction speed.

The phase-transfer catalyst includes quaternary ammonium halides (except those with fluorine) such as tetramethylammonium chloride, tetrabutylammonium bromide, methyltrioctylammonium chloride, methyltridecylammonium chloride, benzyltrimethylammonium chloride, trioctylmethylammonium chloride, tetrabutylammonium iodide, acetyltrimethylammonium bromide, benzyltrimethylammonium chloride, etc.; quaternary pyrrolidinium halides (except those with fluorine) such as N,N-dimethylpyrrolidinium chloride, N-ethyl-N-methylpyrrolidinium iodide, N-butyl-N-methylpyrrolidinium bromide, N-benzyl-N-methylpyrrolidinium chloride, N-ethyl-N-methylpyrrolidinium bromide, etc.; quaternary morpholinium halides (except those with fluorine) such as N-butyl-N-methylmorpholinium bromide, N-butyl-N-methylmorpholinium iodide, N-allyl-N-methylmorpholinium bromide, etc.; quaternary piperidinium halides (except those with fluorine) such as N-methyl-N-benzylpiperidinium chloride, N-methyl-N-benzylpiperidinium bromide, N,N-dimethylpiperidinium iodide, N-methyl-N-ethylpiperidinium acetate, N-methyl-N-ethylpiperidinium iodide, etc.; crown ethers, etc. Preferred are quaternary ammonium salts, and more preferred are benzyltrimethylammonium chloride and benzyltrimethylammonium chloride.

One alone or two or more types of these may be used here either singly or as combined.

When the amount of the phase-transfer catalyst used is too large relative to the starting material oligofluorene (II), then promotion of side reactions such as ester hydrolysis, successive Michael reaction would be significant, and from the viewpoint of the production cost, the amount is generally 5 times by mol or less the oligofluorene (II), preferably 2 times by mol or less, more preferably 1 time by mol or less. When the amount of the phase-transfer catalyst used is too small, then the reaction speed would greatly lower, and therefore, the amount of the phase-transfer catalyst to be used is generally 0.01 times by mol or more the starting material oligofluorene (II), preferably 0.01 times by mol or more, more preferably 0.1 times by mol or more, even more preferably 0.5 times by mol or more.

<12-5-2-4. Solvent>

Preferably, a solvent is used in the step (iib).

Specific examples of the usable solvent include alkylnitrile solvents such as acetonitrile, propionitrile, etc.; ketone solvents such as acetone, methyl ethyl ketone, methyl isobutyl ketone, etc.; as ester solvents, linear esters such as methyl acetate, ethyl acetate, propyl acetate, phenyl acetate, methyl propionate, ethyl propionate, propyl propionate, phenyl propionate, methyl 3-methoxypropionate, methyl 3-ethoxypropionate, methyl lactate, ethyl lactate, etc.; cyclic esters such as γ-butyrolactone, caprolactone, etc.; ether esters such as ethylene glycol monomethyl ether acetate, ethylene glycol monoethyl ether acetate, ethylene glycol monobutyl ether acetate, propylene glycol 1-monomethyl ether acetate, propylene glycol 1-monoethyl ether acetate, etc.; ether solvents such as diethyl ether, tetrahydrofuran, 1,4-dioxane, methyl cyclopentyl ether, tertiary butyl methyl ether, etc.; halogen-containing solvents such as 1,2-dichloroethane, dichloromethane, chloroform, 1,1,2,2-tetrachloroethane, etc.; halogenoaromatic hydrocarbons such as chlorobenzene, 1,2-dichlorobenzene, etc.; amide solvents such as N,N-dimethylformamide, N,N-dimethylacetamide, etc.; sulfoxide solvents such as dimethyl sulfoxide, sulfolane, etc.; as cycloaliphatic hydrocarbons, monocyclic aliphatic hydrocarbons such as cyclopentane, cyclohexane, cycloheptane, cyclooctane, etc., and their derivatives such as methylcyclopentane, ethylcyclopentane, methylcyclohexane, ethylcyclohexane, 1,2-dimethylcyclohexane, 1,3-dimethylcyclohexane, 1,4-dimethylcyclohexane, isopropylcyclohexane, n-propylcyclohexane, tert-butylcyclohexane, n-butylcyclohexane, isobutylcyclohexane, 1,2,4-trimethylcyclohexane, 1,3,5-trimethylcyclohexane, etc.; polycyclic aliphatic hydrocarbons such as decalin, etc.; acyclic aliphatic hydrocarbons such as n-pentane, n-hexane, n-heptane, n-octane, isooctane, n-nonane, n-decane, n-dodecane, n-tetradecane, etc.; aromatic hydrocarbons such as toluene, p-xylene, o-xylene, m-xylene, etc.; aromatic heterocyclic rings such as pyridine, etc.; alcohol solvents such as methanol, ethanol, isopropanol, n-butanol, tertiary butanol, hexanol, octanol, cyclohexanol, etc.

It is known that, when $R^3$ is a methylene group, use of a solvent capable of providing phase separation from water tends to prevent side reactions such as decomposition of oligofluorene (II). Further, when a solvent well dissolving the starting material oligofluorene (II) is used, then the reaction may well go on, and therefore, it is desirable to use a solvent of which the solubility for the starting material oligofluorene (II) is 0.5% by mass or more, more preferably 1.0% by mass or more, even more preferably 1.5% by mass or more. Concretely, preferred are halogen-containing aliphatic hydrocarbons, halogen-containing aromatic hydrocarbons, aromatic hydrocarbons, or ether solvents; and more preferred are dichloromethane, chlorobenzene, chloroform, 1,2-dichlorobenzene, tetrahydrofuran, 1,4-dioxane, and methyl cyclopentyl ether.

One alone or two or more types of these solvents may be used here either singly or as combined.

The upper limit of the amount of the solvent to be used is not specifically defined. In consideration of the production efficiency of the product per reactor, in general, the solvent is used in an amount of generally 20 times by volume the starting oligofluorene compound (II), preferably 15 times by volume, more preferably 10 times by volume. On the other hand, when the amount of the solvent used is too small, then the reagent solubility would worsen and the reaction would go on slowly. Consequently, the lower limit of the amount is generally 1 time by volume the starting oligofluorene compound (II), preferably 2 times by volume, more preferably 4 times by volume.

It is known that, when $R^3$ is any other substituent than a methylene group, the solubility of the organic base and the oligofluorene (II) would have a great influence on the reaction speed, and for securing the solubility, it is desirable to use a solvent having a dielectric constant on a predetermined level or more. As the solvent capable of well dissolving an organic base and the oligofluorene (II), preferred are aromatic heterocyclic compounds, alkylnitrile solvents, amide solvents and sulfoxide solvents; and more preferred are pyridine, acetonitrile, N,N-dimethylformamide, N,N-dimethylacetamide, dimethyl sulfoxide and sulfolane.

One alone or two or more types of these solvents may be used here either singly or as combined.

The upper limit of the amount of the solvent to be used is not specifically defined. In consideration of the production efficiency of the product per reactor, in general, the solvent is used in an amount of generally 20 times by volume the starting oligofluorene compound (II), preferably 15 times by volume, more preferably 10 times by volume. On the other hand, when the amount of the solvent used is too small, then the reagent solubility would worsen and the stirring would be difficult, and additionally the reaction would go on slowly. Consequently, the lower limit of the amount is generally 1 time by volume the starting oligofluorene compound (II), preferably 2 times by volume, more preferably 4 times by volume.

<12-5-2-5. Reaction Mode>

For the step (iib), the reaction mode may be any of a batch-mode reaction or a flow-through reaction, or a combination thereof. Any reaction mode is employable here with no limitation.

Regarding the method of putting reaction reagents into the reactor in a batch mode, it is known that when an electron-withdrawing group-substituted olefin (VI) is added all at a time at the start of the reaction, then the side reaction of polymerization may readily go on since the electron-withdrawing group-substituted olefin (VI) exists in the system at a high concentration. Accordingly, it is desirable that the starting material oligofluorene (II), a phase-transfer catalyst, a solvent and a base are first added and then an electron-withdrawing group-substituted olefin (VI) is added thereto little by little.

<12-5-2-6. Reaction Condition>

It is known that, when the temperature is too low in the step (iib), then a sufficient reaction speed could not be obtained, but on the contrary, when too high, then the polymerization reaction of the electron-withdrawing group-substituted olefin (VI) tends to go on rapidly. Therefore, the temperature control is extremely important. Concretely, the lower limit of the reaction temperature is generally 0° C., preferably 10° C., more preferably 15° C. On the other hand, the upper limit is generally 40° C., preferably 30° C., more preferably 20° C.

Regarding the reaction time in the step (iib), in general, the lower limit is 2 hours, preferably 4 hours, more preferably 6 hours. The upper limit is not specifically defined but is generally 30 hours, preferably 20 hours, more preferably 10 hours.

<12-5-2-7. Separation/Purification of Product>

After the reaction, the intended product oligofluorene derivative (VII) may be isolated according to a method where the side product of metal halide and the remaining inorganic base are removed from the reaction liquid through filtration, and then the solvent is concentrated or according to a method where a poor solvent for the product is added to the system, whereby the intended product, oligofluorene derivative (VII) is precipitated out.

After the reaction, acidic water and a solvent capable of dissolving the product, oligofluorene derivative (VII) may be added to the reaction liquid for product extraction. The product thus extracted with the solvent may be isolated according to a method of concentrating the solvent or a method of adding a poor solvent to the system.

The solvent usable in extraction is not specifically defined and may be any one capable of dissolving the product, oligofluorene derivative (VII). Preferred are one or more of aromatic hydrocarbon compounds such as toluene, xylene, etc.; and halogen-containing solvents such as dichloromethane, chloroform, etc.

Of the oligofluorene derivatives (VII) to be obtained here, those in which EWG is an ester group having an organic substituent with from 1 to 10 carbon atoms may be used as starting monomers for polyesters or polyester carbonates or as precursors of starting monomers for polycarbonates, directly as they are; however, the derivatives may be used after purified. As the purification method, employable is any ordinary purification method of, for example, recrystallization, reprecipitation, extraction purification, column chromatography or the like with no specific limitation thereon. It is also possible to dissolve the oligofluorene diester (20b) in a suitable solvent and then treated with active carbon. The solvent usable in the case is the same as that for use in extraction.

Of the oligofluorene derivatives (VII) to be obtained here, those in which EWG is a carboxyl group may be used as starting monomers for polyesters or polyester carbonates or as precursors of starting monomers for polycarbonates, directly as they are. Through esterification, the derivatives may be converted into oligofluorene diesters (20b) where $A^3$ and $A^4$ each are an ester group.

Of the oligofluorene derivatives (VII) to be obtained here, those in which EWG is a nitro group or a cyano group may produce oligofluorene monomers (20) where $A^3$ and $A^4$ each a group having an amino group, through hydrogenation according to a method using palladium-carbon or the like in a hydrogen atmosphere or through hydride reduction with a reducing agent such as aluminiumlithium hydride, etc. Those in which EWG is a cyano group can be converted into oligofluorene diesters (20b) according to the method described in PTL 7 and 8, etc.

Of the oligofluorene derivatives (VII) to be obtained here, those in which EWG is an aldehyde group may produce oligofluorene-diols (20c) where $A^3$ and $A^4$ each a group having a hydroxyl group, through hydrogenation according to a method using palladium-carbon or the like in a hydrogen atmosphere or through hydride reduction with a reducing agent such as aluminiumlithium hydride, etc.

Of the oligofluorene derivatives (VII) to be obtained here, those in which EWG is a ketone group having an organic substituent with from 1 to 10 carbon atoms may produce oligofluorene monomers (20) where $A^3$ and $A^4$ each a group having a hydroxyl group, through hydrogenation according to a method using palladium-carbon or the like in a hydrogen atmosphere or through hydride reduction with a reducing agent such as aluminiumlithium hydride, etc.

<12-5-3. Step (iic): Production Method for Compound of General Formula (20) where $A^3$ and $A^4$ are Group Having Hydroxyl Group, (Production Method for Oligofluorene-diol (20c) Through Reduction of Oligofluorene Diester (20b))>

An oligofluorene-diol represented by the following general formula (20c) can be produced from an oligofluorene diester (20b) in the presence of a reducing agent, according to the following step (iic).

[Chem. 86]

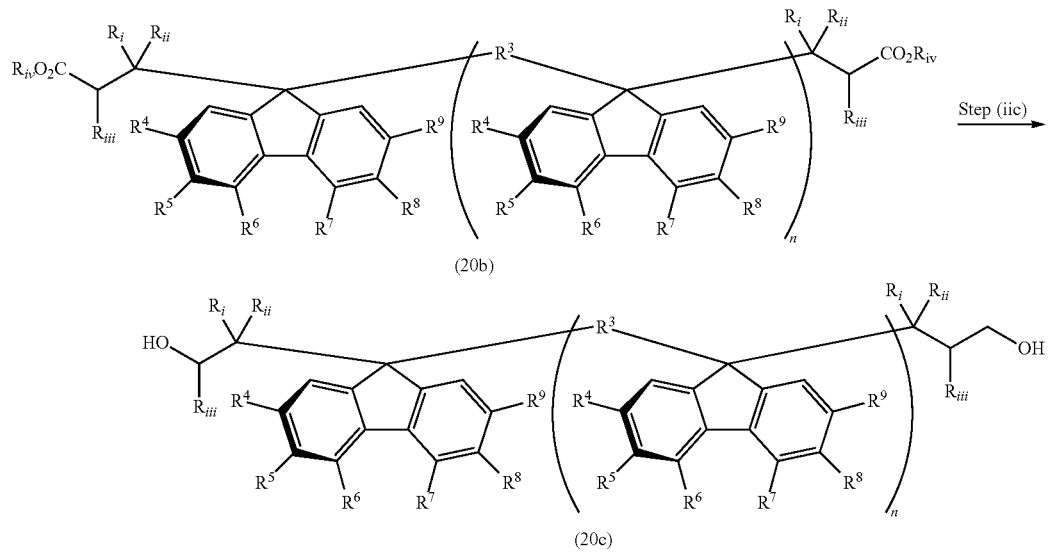

(In the formulae, $R^3$ to $R^9$ and n have the same meanings as those of $R^3$ to $R^9$ and n in the formula (1). $R_i$, $R_{ii}$ and $R_{iii}$ each represent a hydrogen atom, an optionally-substituted alkyl group having from 1 to 10 carbon atoms, an optionally-substituted aryl group having from 4 to 10 carbon atoms, or an optionally-substituted aralkyl group having from 6 to 10 carbon atoms. $R_{iv}$ represents an organic substituent having from 1 to 10 carbon atoms.)

A production method for production of diol through reduction of ester is well known. In US Patent Application Publication No. 2012/0170118, such a diol is produced through reduction using a reducing agent, aluminiumlithium hydride. As any other method of using a metal hydride, there are mentioned diisobutylaluminium hydride, bis(2-methoxyethoxy)aluminium sodium hydride, etc. In addition, a method of reduction of ester through catalytic hydrogenation using ruthenium, rhodium, palladium or platinum as a catalyst is widely known.

<12-5-4. Step (iid): Production Method for Compound of General Formula (20) where $A^3$ and $A^4$ are Group Having Hydroxylester Group (Production Method for Oligofluorene Dihydroxyester (20d) Through Interesterification of Oligofluorene Diester (20b))>

An oligofluorene dihydroxyester represented by the following general formula (20d) can be produced from an oligofluorene diester (20b) and a diol (VIII) in the presence of a reducing agent, according to the following step (iid).

[Chem. 87]

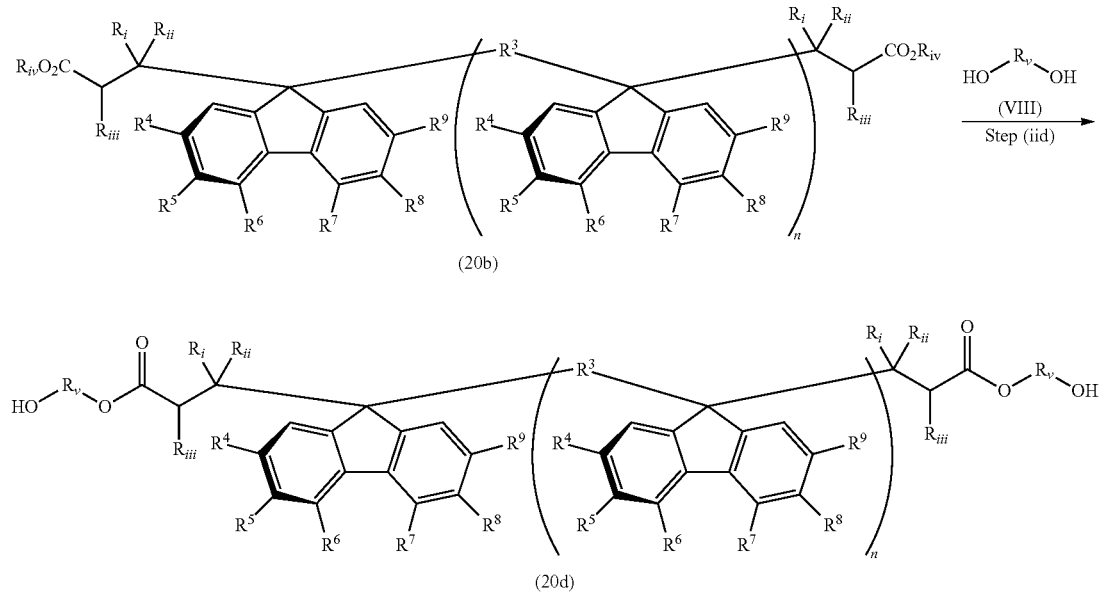

(In the formulae, $R^3$ to $R^9$ and n have the same meanings as those of $R^3$ to $R^9$ and n in the formula (1). $R_i$, $R_{ii}$ and $R_{iii}$ each represent a hydrogen atom, an optionally-substituted alkyl group having from 1 to 10 carbon atoms, an optionally-substituted aryl group having from 4 to 10 carbon atoms, or an optionally-substituted aralkyl group having from 6 to 10 carbon atoms. $R_{iv}$ represents an organic substituent having from 1 to 10 carbon atoms. $R_v$ represents an organic substituent having from 1 to 10 carbon atoms.)

even though the product of the type is contained in the oligofluorene dihydroxyester (20d), it may cause little problem as a starting material for polycarbonates and as a starting material for polyesters and polycarbonates. However, from the viewpoint of the quality of polycarbonates, polyesters and polyester carbonates, the content of the self-interesterified product (IX) is generally 0.1 times by mol or less the product, oligofluorene dihydroxyester (20d), preferably 0.05 times by mol or less, more preferably 0.03 times by mol or less.

[Chem. 88]

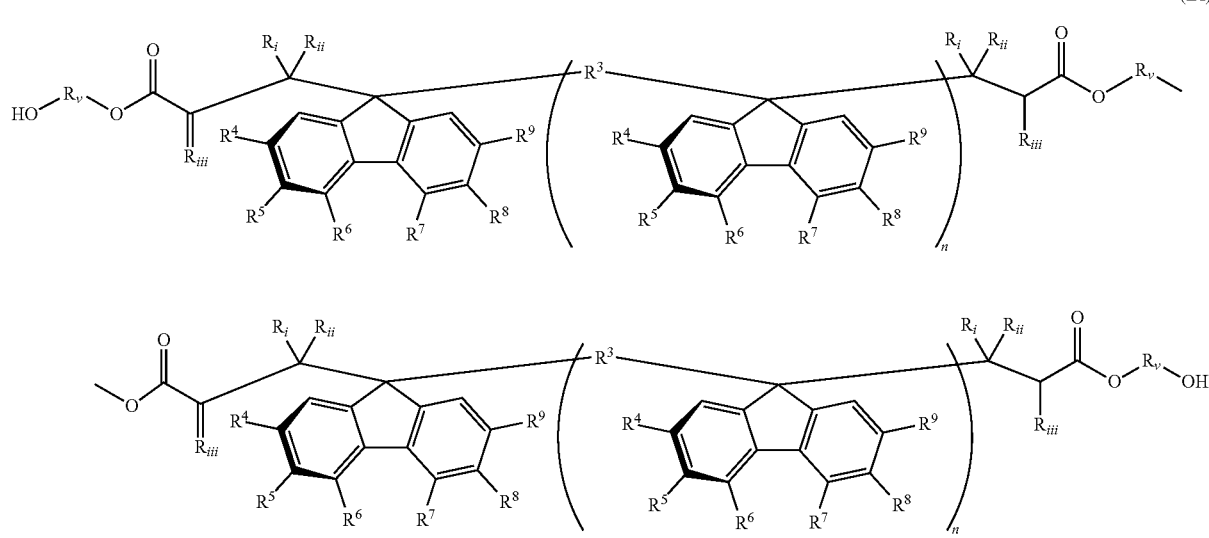

(IX)

<12-5-4-1. Diol>

The diol (VIII) for use in the step (iid) is a diol having from 1 to 10 carbon atoms. Concretely, there are mentioned linear alkylene diols (which may be straight or branched ones) such as ethylene glycol, neopentyl glycol, 1,4-butanediol, 1,6-hexanediol, etc.; cyclic alkylene diols such as cyclohexanedimethanol, etc.; oligoethylene glycols such as diethylene glycol, triethylene glycol, tetraethylene glycol, etc.; secondary diols such as isosorbide, etc.; aromatic diols such as resorcinol, etc. These diols may be substituted with any substituent within a range not detracting from the present reaction.

Above all, preferred is alkylene glycol or oligoethylene glycol from the viewpoint of the reaction speed and the production cost, and more preferred is ethylene glycol.

In the step (iid), different two or more types of diols (VIII) may be used; however, from the viewpoint of simple purification, in general, one type of diol (VIII) is used.

The amount of the diol (VIII) to be used is described. The alcohol derived from the organic substituent of the ester group in the starting material oligofluorene diester (20b) tends to take competitive reaction with the diol (VIII) added to the reaction system, and therefore, when the amount of the diol (VIII) is larger, then the reaction may go on more rapidly. In addition, when the amount of the diol (VIII) is large, it is possible to prevent the formation of a side product of oligofluorene crosslinked with diol, as represented by the following general formula (IX). The self-interesterified product (IX) acts by itself, as a starting material for polycarbonates including polyester carbonates or as a starting material for polyesters, and therefore it is considered that (In the formulae, $R^3$ to $R^9$ and n have the same meanings as those of $R^3$ to $R^9$ and n in the formula (1). $R_i$, $R_{ii}$ and $R_{iii}$ each represent a hydrogen atom, an optionally-substituted alkyl group having from 1 to 10 carbon atoms, an optionally-substituted aryl group having from 4 to 10 carbon atoms, or an optionally-substituted aralkyl group having from 6 to 10 carbon atoms. $R_v$ represents an organic substituent having from 1 to 10 carbon atoms.)

Consequently, the amount of the diol (VIII) to be used is generally 3 times by mol or more the oligofluorene diester (20b), preferably 10 times by mol or more, more preferably 50 times by mol or more.

The diol (VIII) may be put into the reactor all at a time, or may be added in portions as divided in accordance with the reaction procedure. The self-interesterified product represented by the general formula (IX) can be converted into the oligofluorene dihydroxyester (20d) through addition of the diol (VIII) thereto.

<12-5-4-2. Base>

As the base for use in the step (iid), there are mentioned alkali metal hydroxides such as lithium hydroxide, sodium hydroxide, potassium hydroxide, etc.; alkaline earth metal hydroxides such as calcium hydroxide, barium hydroxide, etc.; alkali metal carbonates such as sodium carbonate, sodium hydrogencarbonate, potassium carbonate, etc.; alkaline earth metal carbonates such as magnesium carbonate, calcium carbonate, etc.; alkali metal phosphates such as sodium phosphate, sodium hydrogenphosphate, potassium phosphate, etc.; organic lithium salts such as n-butyllithium, tertiary butyllithium, etc.; alkali metal alkoxides such as sodium methoxide, sodium ethoxide, potassium tertiary butoxide, etc.; alkali metal hydrides such as sodium hydride, potassium hydride, etc.; quaternary ammonium hydroxides such as tetramethylammonium hydroxide, tetrabutylammonium hydroxide, etc.

One alone or two or more types of these may be used either singly or as combined.

Of those, from the viewpoint of reactivity, preferred are alkali metal alkoxides, and more preferred are sodium methoxide and sodium ethoxide.

Regarding the amount of the base to be used, the upper limit thereof relative to the starting material oligofluorene diester (20b) is not specifically defined. However, when the amount used is too large, then the stirring load and the purification load after reaction would increase, and therefore the amount is generally 10 times by mol or less of fluorene, preferably 5 times by mol or less, more preferably 1 time by mol or less.

On the other hand, when the amount of the base used is too small, then the reaction speed would be low, and therefore, the lower limit of the amount is generally 0.01 times by mol or more the starting material fluorene, preferably 0.05 times by mol or more, more preferably 0.1 times by mol or more.

<12-5-4-3. Solvent>

The step (iid) may be carried out in the absence of solvent, but when the solubility of the starting material oligofluorene diester (20b) in the reaction reagent diol (VIII) is low and the reactivity is therefore low, then a solvent may be used in the step.

Concretely, the usable solvent includes alkylnitrile solvents such as acetonitrile, propionitrile, etc.; ether solvents such as diethyl ether, tetrahydrofuran, 1,4-dioxane, methylcyclopentyl ether, tertiary butyl methyl ether, diethylene glycol dimethyl ether, triethylene glycol dimethyl ether, etc.; halogen-containing solvents such as 1,2-dichloroethane, dichloromethane, chloroform, 1,1,2,2-tetrachloroethane, etc.; halogenoaromatic hydrocarbons such as chlorobenzene, 1,2-dichlorobenzene, etc.; amide solvents such as N,N-dimethylformamide, N,N-dimethylacetamide, etc.; sulfoxide solvents such as dimethyl sulfoxide, sulfolane, etc.; as cycloaliphatic hydrocarbons, monocyclic aliphatic hydrocarbons such as cyclopentane, cyclohexane, cycloheptane, cyclooctane, etc., and their derivatives such as methylcyclopentane, ethylcyclopentane, methylcyclohexane, ethylcyclohexane, 1,2-dimethylcyclohexane, 1,3-dimethylcyclohexane, 1,4-dimethylcyclohexane, isopropylcyclohexane, n-propylcyclohexane, tert-butylcyclohexane, n-butylcyclohexane, isobutylcyclohexane, 1,2,4-trimethylcyclohexane, 1,3,5-trimethylcyclohexane, etc.; polycyclic aliphatic hydrocarbons such as decalin, etc.; acyclic aliphatic hydrocarbons such as n-pentane, n-hexane, n-heptane, n-octane, isooctane, n-nonane, n-decane, n-dodecane, n-tetradecane, etc.; aromatic hydrocarbons such as toluene, p-xylene, o-xylene, m-xylene, etc.

Above all, when a solvent having high solubility both for the starting material oligofluorene diester (20b) and the diol (VIII) is used, then the reaction may well go on, and therefore preferred here are ether solvents. As enabling high-temperature reaction, more preferred are diethylene glycol dimethyl ether and triethylene glycol dimethyl ether.

One alone or two or more types of these solvents may be used here either singly or as combined.

The upper limit of the amount of the solvent to be used is not specifically defined. In consideration of the production efficiency of the product per reactor, in general, the solvent is used in an amount of generally 20 times by volume the starting oligofluorene diester (20b), preferably 15 times by volume, more preferably 10 times by volume. On the other hand, when the amount of the solvent used is too small, then the reagent solubility would be poor and the stirring would be difficult and, in addition, the reaction speed would be low. Consequently, the lower limit of the amount is generally 1 time by volume the starting oligofluorene diester (20b), preferably 2 times by volume, more preferably 4 times by volume.

<12-5-4-4. Reaction Mode>

For the step (iid), the reaction mode may be any of a batch-mode reaction or a flow-through reaction, or a combination thereof. Any reaction mode is employable here with no limitation.

<12-5-4-5. Reaction Condition>

When the solvent or the reaction reagent diol (VIII) contains water, ester hydrolysis may occur to give side products of a dicarboxylic acid (X) and a hydroxycarboxylic acid (XI) shown below in accordance with the water content.

[Chem. 89]

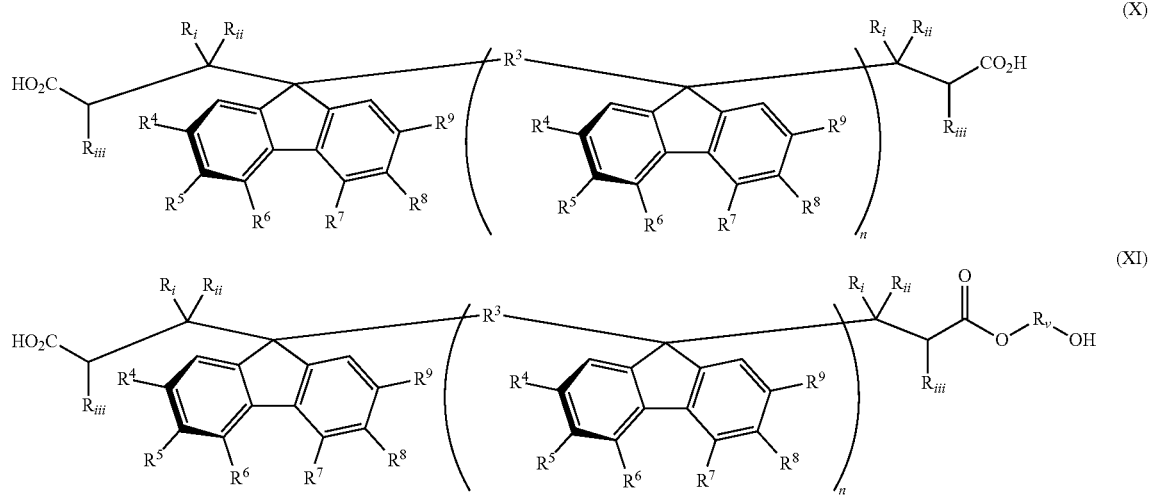

(In the formulae, $R^3$ to $R^9$ and n have the same meanings as those of $R^3$ to $R^9$ and n in the formula (1). $R_i$, $R_{ii}$ and $R_{iii}$ each represent a hydrogen atom, an optionally-substituted alkyl group having from 1 to 10 carbon atoms, an optionally-substituted aryl group having from 4 to 10 carbon atoms, or an optionally-substituted aralkyl group having from 6 to 10 carbon atoms. $R_v$ represents an organic substituent having from 1 to 10 carbon atoms.)

Consequently, it is desirable that the solvent and the reaction reagent diol (VIII) to be used are anhydrous ones, or before the reaction, these are processed for azeotropic dehydration with a solvent not participating in the reaction but capable of undergoing azeotrope with water, such as toluene, xylene or the like.

The dicarboxylic acid (X) and the hydroxycarboxylic acid (XI) can be used as starting materials for polycarbonates including polyester carbonates or as starting materials for polyesters.

In the step (iid), when the temperature is too low, then a sufficient reaction speed could not be obtained. Therefore, concretely, the lower limit of the reaction temperature is generally 20° C., preferably 50° C., more preferably 80° C. On the other hand, the upper limit is generally 150° C., preferably 120° C., more preferably 100° C.

Regarding the ordinary reaction time in the step (iid), the lower limit is generally 2 hours, preferably 4 hours, more preferably 6 hours, and the upper limit is not specifically defined but is generally 30 hours, preferably 20 hours, more preferably 10 hours.

<12-5-4-6. Separation/Purification of Product>

After the reaction, the intended product oligofluorene dihydroxyester (20d) may be isolated according to a method where insoluble substances such as the side product of metal halide and the remaining inorganic base are removed from the reaction liquid through filtration, and then the solvent is concentrated or according to a method where a poor solvent for the product is added to the system, whereby the intended product, oligofluorene dihydroxyester (20d) is precipitated out.

After the reaction, acidic water and a solvent capable of dissolving the product, oligofluorene dihydroxyester (20d) may be added to the reaction liquid for product extraction. The product thus extracted with the solvent may be isolated according to a method of concentrating the solvent or a method of adding a poor solvent to the system.

The product extracted with the solvent may be washed with an aqueous solution of sodium carbonate, potassium carbonate or the like to remove the side product, carboxylic acid.

The solvent usable in extraction is not specifically defined and may be any one capable of dissolving the product, oligofluorene dihydroxyester (20d). Preferred are one or more of ester solvents such as ethyl acetate, etc.; aromatic hydrocarbon compounds such as toluene, xylene, etc.; and halogen-containing solvents such as dichloromethane, chloroform, etc.

Oligofluorene dihydroxyesters (20d) may be used as starting monomers for polycarbonates including polyester carbonates or as starting materials for polyesters, directly as they are, but they may be purified before being used in the next step. As the purification method, employable is any ordinary purification method of, for example, recrystallization, reprecipitation, extraction purification or the like with no specific limitation thereon. It is also possible to dissolve the oligofluorene dihydroxyester (20d) in a suitable solvent and then treated with active carbon. The solvent usable in the case is the same as that for use in extraction.

<12-5-5. Production Method for Compound of General Formula (20) where $A^3$ and $A^4$ are Group Having Hydroxyl Group (Production Method for Oligofluorene-diol (10a) Through Alkylation of Oligofluorene Compound (II) Followed by Hydrolysis)>

An oligofluorene-diol (10a) can be produced according to a method that comprises a step of producing ab oligofluorene (IX) having a leaving group through alkylation of an oligofluorene compound (II) and alkylating agents (VIIIb) and (VIIIc) (step (iie)) followed by hydrolysis (step (ill)), or according to a method that comprises a step of producing an oligofluorene (XI) having a protective group through alkylation of an oligofluorene compound (II) and alkylating agents (Xa) and (Xb) (step (iig)) followed by hydrolysis (step (iih)), etc.

[Chem. 90]
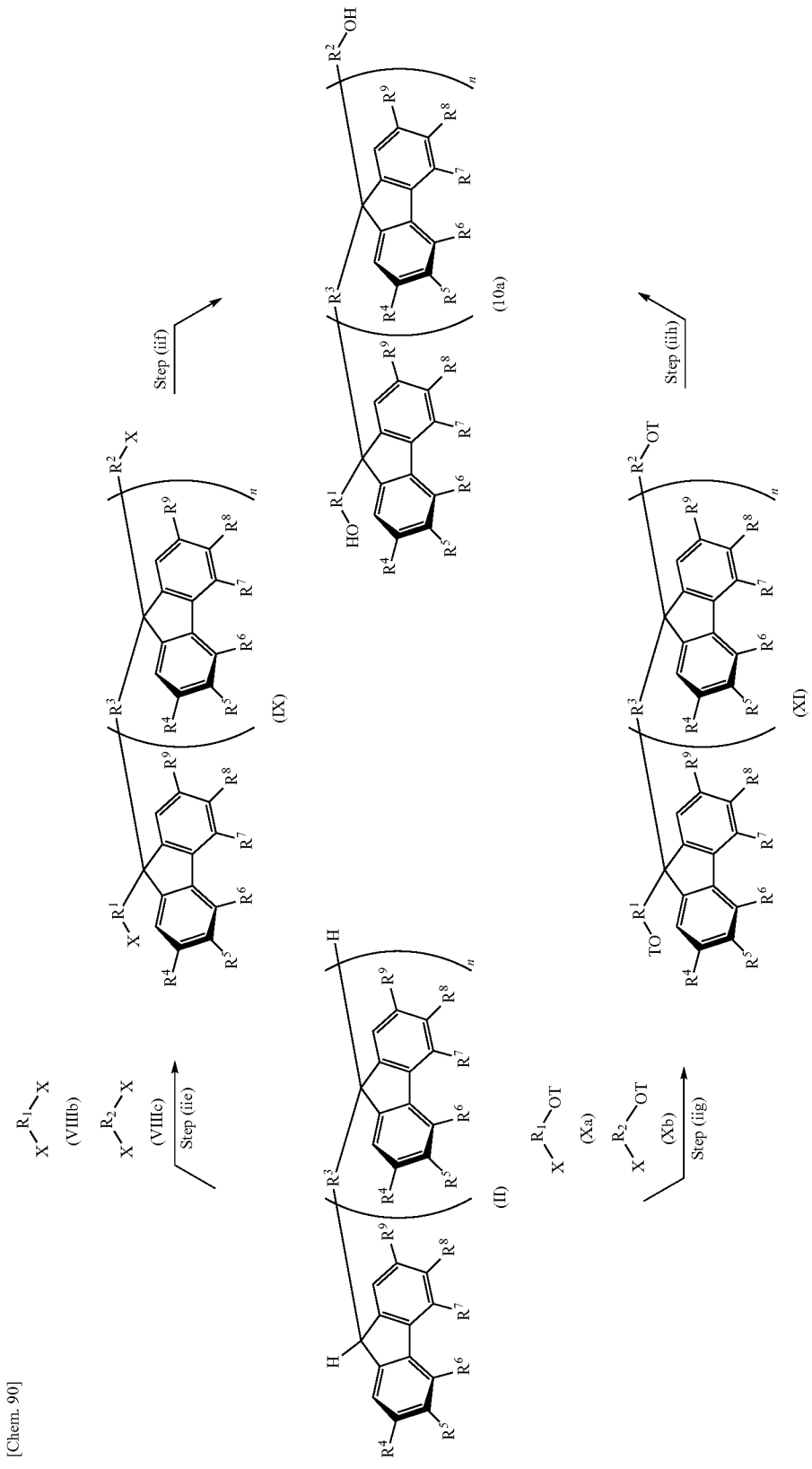

(In the formulae, $R^1$ to $R^9$ and n have the same meanings as those of $R^1$ to $R^9$ and n in the formula (1). X represents a leaving group. Examples of the leaving group include a halogen atom (except fluorine), a mesyl group, a tolyl group, etc. T represents a protective group. Examples of the protective group include a methoxymethyl group, a 2-methoxyethoxymethyl group, a tetrahydropyranyl group, a tertiary butoxycarbonyl group, a benzyloxycarbonyl group, a trimethylsilyl group, a tertiary butyldimethylsilyl group, etc.)

Alkylation of fluorenes is widely known, and, for example, there are reported 9,9-bis(haloalkyl)fluorenes such as 9,9-bis(bromohexyl)fluorene, 9,9-bis(iodohexyl)fluorene, etc. (J. Org. Chem., 2010, 75, 2714) From the knowledge, it is possible to produce leaving group-having oligofluorenes starting from oligofluorenes (II). Regarding halogen hydrolysis, there are also known many reports (Bull. Korean Chem. Soc., 2008, 29, 2491). Through the route, oligofluorene-diols (10a) can be produced.

The alkylating agent for use in the step (iie) includes linear alkyl dihalides (except those with fluorine) such as diiodomethane, 1,2-diiodoethane, 1,3-diiodopropane, 1,4-diiodobutane, 1,5-diiodopentane, 1,6-diiodohexane, dibromomethane, 1,2-dibromoethane, 1,3-dibromopropane, 1,4-dibromobutane, 1,5-dibromopentane, 1,6-dibromohexane, dichloromethane, 1,2-dichloroethane, 1,3-dichloropropane, 1,4-dichlorobutane, 1,5-dichloropentane, 1,6-dichlorohexane, 1-bromo-3-chloropropane, etc.; branched chain-containing alkyl dihalides (except those with fluorine) such as 2,2-dimethyl-1,3-dichloropropane, etc.; aralkyl dihalides (except those with fluorine) such as 1,4-bis(bromomethyl)benzene, 1,3-bis(bromomethyl)benzene, etc.; glycol disulfonates such as ethylene glycol dimesylate, ethylene glycol ditosylate, propylene glycol dimesylate, tetramethylene glycol dimesylate, etc.

The alkylating agent for use in the step (iig) includes protected forms of haloalkyl alcohols such as 3-bromopropanol, 2-bromopropanol, 3-chloro-2,2-dimethyl-1-propanol, etc.

<12-5-6. Production Method for Oligofluorene Diaryl Ester of General Formula (10d) (Production Method for Oligofluorene Diaryl Ester Compound (10d) Through Production of Oligofluorene Diester Compound (10b) Followed by Interesterification)>

An oligofluorene diaryl ester compound (10d) can be produced according to a method that comprises a step of producing an oligofluorene diester compound (10b) (step (iij), step (iik), or step (iil) followed by interesterification with a diaryl carbonate (11a) (step (iim)).

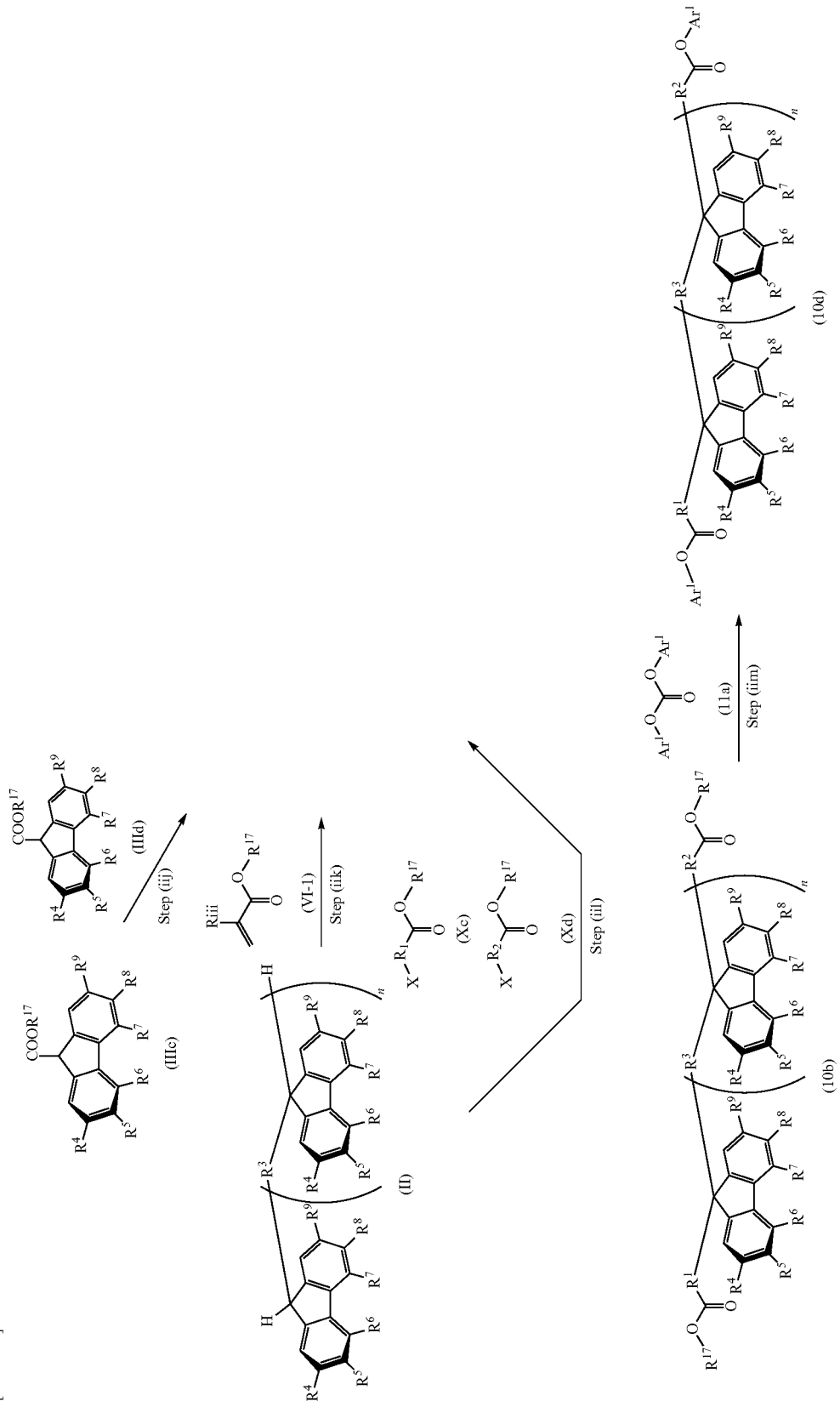

(In the formulae, $R^1$ to $R^9$ and n have the same meanings as those of $R^1$ to $R^9$ and n in the formula (1). X represents a leaving group.)

Examples of the leaving group include a halogen atom (except fluorine), a mesyl group, a tolyl group, etc. $R_{iii}$ represents a hydrogen atom, an optionally-substituted alkyl group having from 1 to 10 carbon atoms, an optionally-substituted aryl group having from 4 to 10 carbon atoms, or an optionally-substituted aralkyl group having from 6 to 10 carbon atoms, $R^{17}$ represents an organic substituent having from 1 to 10 carbon atoms, and $Ar^1$ represents an optionally-substituted aryl group having from 4 to 10 carbon atoms.)

<12-5-6-1-1. Step (iij): Production Method for Compound of General Formula (10b) where $R^1$ and $R^2$ are Direct Bonds>

An oligofluorene diester (10b) where $R^1$ and $R^2$ are direct bonds can be produced from 9-mono-substituted olefins (IIIc) and (IIId) according to the method described in the section of <12-1. Production Method A>.

<12-5-6-1-2. Step (iik): Production Method for Compound of General Formula (10b) where $R^1$ and $R^2$ Each are Optionally-Substituted Ethylene Group>

An oligofluorene diester (10b) where $R^1$ and $R^2$ each are an optionally-substituted ethylene group can be produced from an oligofluorene compound (II) and an unsaturated carboxylate (VI-1) in the presence of a base according to the method described in the section of <12-5-2: Step (iib)>.

<12-5-6-1-3. Step (iil): Production Method for Compound of General Formula (10b) where $R^1$ and $R^2$ Each are any Other than Direct Bond>

An oligofluorene diester (10b) where $R^1$ and $R^2$ each are any other substituent than a direct bond can be produced through alkylation of an oligofluorene (II) with alkylating agents (Xc) and (Xd) in the presence of a base, according to the same method as that described as the step (iie) or (iig) in the section of <12-5-5>.

[Chem. 92]

The alkylating agents for use in the step (ill) alkyl haloalkanoates such as methyl chloroacetate, ethyl chloroacetate, propyl chloroacetate, n-butyl chloroacetate, tert-butyl chloroacetate, methyl bromoacetate, ethyl bromoacetate, tert-butyl bromoacetate, methyl iodoacetate, ethyl iodoacetate, tert-butyl iodoacetate, methyl chloropropionate, ethyl chloropropionate, tert-butyl chloropropionate, methyl bromopropionate, ethyl bromopropionate, tert-butyl bromopropionate, methyl iodopropionate, ethyl iodopropionate, tert-butyl iodopropionate, etc.; alkyl haloalkylbenzoates such as methyl 4-chloromethylbenzoate, methyl 4-bromomethylbenzoate, ethyl 4-chloromethylbenzoate, ethyl 4-bromomethylbenzoate, methyl 3-chloromethylbenzoate, methyl 3-bromomethylbenzoate, etc.

<12-5-6-2. Production Method for Oligofluorene Diaryl Ester of General Formula (10d) (Production Method for Oligofluorene Diaryl Ester Compound (10d) Through Interesterification)>

An oligofluorene diaryl ester compound (10d) where $Ar^1$ is an optionally-substituted aryl group having from 4 to 10 carbon atoms can be produced from an oligofluorene diester compound (10b) and a diaryl carbonate (11a) according to the step (iim) in the presence of an interesterification catalyst.

<12-5-6-2-1. Diaryl Carbonate>

The diaryl carbonate as the reaction reagent includes diphenyl carbonate, ditolyl carbonate, bis(chlorophenyl) carbonate, m-cresyl carbonate, dinaphthyl carbonate, bis(biphenyl) carbonate, etc. Above all, preferred is inexpensive and industrially-available diphenyl carbonate.

One alone or two or more types of such diaryl carbonates may be used either singly or as combined.

Regarding the amount of the diaryl carbonate to be used, the upper limit thereof is not specifically defined relative to the starting material, oligofluorene diester (10b); however, when the amount is too large, then the purification load after reaction would increase and, therefore, the upper limit is generally 20 times by mol or less the oligofluorene diester, preferably 10 times by mol or less, more preferably 5 times by mol or less.

On the other hand, when the amount of the diaryl carbonate used is too small, then the oligofluorene diester (10b) and, as an intermediate, an oligofluorene monoaryl ester (10e) mentioned below would remain in the reaction system. Accordingly, the lower limit is generally 1 time by mol or more the starting material, oligofluorene diester (10b), preferably 1.5 times by mol or more, more preferably 2 times by mol or more.

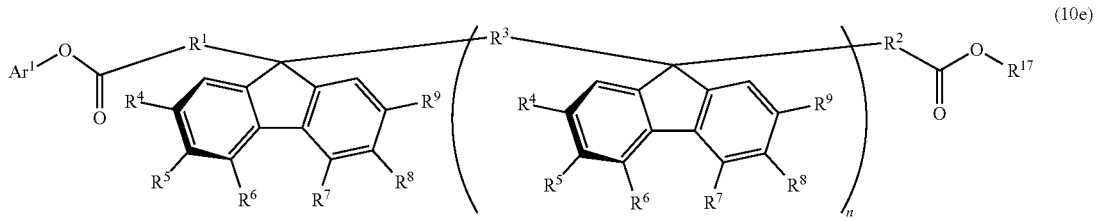

(10e)

(In the formula, $R^1$ to $R^9$ and n have the same meanings as those of $R^1$ to $R^9$ and n in the formula (1). $R^{17}$ represents an organic substituent having from 1 to 10 carbon atoms, and $Ar^1$ represents an optionally-substituted aryl group having from 4 to 10 carbon atoms.)

<12-5-6-2-2. Interesterification Catalyst>

The interesterification catalyst includes titanium compounds such as tetrabutoxytitanium, tetraisobutoxytitanium, tetramethoxytitanium, tetraisopropoxytitanium, tetramethoxytitanium, tetrakis(2-ethylhexyloxy)titanium, tetrastearyloxytitanium, tetraphenoxytitanium, titanium(IV) acetylacetonate, titanium(IV) diisopropoxide bis(acetylacetonate), etc.; alkali metal compounds such as lithium carbonate, dibutylaminolithium, lithium acetylacetonate, sodium phenoxide, potassium phenoxide, etc.; cadmium compounds such as cadmium acetylacetonate, cadmium carbonate, etc.; zirconium compounds such as zirconium acetylacetonate, zirconocene, etc.; lead compounds such as lead sulfide, lead hydroxide, plumbates, zincates, lead carbonate, lead acetate, tetrabutyllead, tetraphenyllead, triphenyllead, dimethoxylead, diphenoxylead, etc.; copper compounds such as copper acetate, copper bisacetylacetonate, copper oleate, butylcopper, dimethoxycopper, copper chloride, etc.; iron compounds such as iron hydroxide, iron carbonate, triacetoxyiron, trimethoxyiron, triphenoxyiron, etc.; zinc compounds such as zinc bisacetylacetonate, diacetoxyzinc, dimethoxyzinc, diethoxyzinc, diphenoxyzinc, etc.; organic tin compounds such as di-n-butyltin oxide, diphenyltin oxide, di-n-octyltin oxide, di-n-butyltin dimethoxide, di-n-butyltin diacrylate, di-n-butyltin dimethacrylate, di-n-butyltin dilaurate, tetramethoxytin, tetraphenoxytin, tetrabutyl-1,3-diacetoxydistannoxane, etc.; aluminium compounds such as aluminium acetate, aluminium methoxide, aluminium ethoxide, aluminium phenoxide, etc.; vanadium compounds such as vanadium dichloride, vanadium trichloride, vanadium tetrachloride, vanadium sulfate, etc.; phosphonium salts such as tetraphenylphosphonium phenoxide, etc. One alone or two or more types of these may be used here either singly or as combined.

Of those, preferred is use of phosphonium salts, lithium compounds, zirconium compounds, organic tin compounds, titanium compounds or the like, since they are industrially inexpensive and have superiority in reaction operation. Especially preferred are organic tin compounds or titanium compounds.

Regarding the amount of the interesterification catalyst to be used, the upper limit thereof is not specifically defined relative to the starting material, oligofluorene diester (20b). However, when the amount used is too large, then the purification load after reaction would increase, and therefore, in general, the upper limit is 20 mol % or less of fluorene, preferably 10 mol % or less, more preferably 5 mol % or less.

On the other hand, when the amount of the interesterification catalyst used is too small, then the reaction time would be too long. Therefore, the lower limit is generally 0.1 mol % or more of the starting material oligofluorene diester, preferably 0.5 mol % or more, more preferably 1 mol % or more.

<12-5-6-2-3. Solvent>

In the step (iim), a reaction solvent may be used, but it is desirable that the starting materials oligofluorene diester (10b) and diaryl carbonate and the interesterification catalyst alone are used for the reaction, not using a reaction solvent. However, when the starting materials oligofluorene diester (10b) and diaryl carbonate are solid at room temperature and are difficult to stir, a reaction solvent may be used. The reaction solvent, when used, may be any one capable of favorably dissolving and/or dispersing the above-mentioned starting materials, oligofluorene diester (10b) and diaryl carbonate, and the interesterification catalyst.

Concretely, the usable solvent includes alkylnitrile solvents such as acetonitrile, propionitrile, etc.; ketone solvents such as acetone, methyl ethyl ketone, methyl isobutyl ketone, etc.; ether solvents such as diethyl ether, tetrahydrofuran, 1,4-dioxane, methylcyclopentyl ether, tertiary butyl methyl ether, etc.; halogen-containing solvents such as 1,2-dichloroethane, dichloromethane, chloroform, 1,1,2,2-tetrachloroethane, etc.; halogenoaromatic hydrocarbons such as chlorobenzene, 1,2-dichlorobenzene, etc.; amide solvents such as N,N-dimethylformamide, N,N-dimethylacetamide, etc.; sulfoxide solvents such as dimethyl sulfoxide, sulfolane, etc.; as cycloaliphatic hydrocarbons, monocyclic aliphatic hydrocarbons such as cyclopentane, cyclohexane, cycloheptane, cyclooctane, etc., and their derivatives such as methylcyclopentane, ethylcyclopentane, methylcyclohexane, ethylcyclohexane, 1,2-dimethylcyclohexane, 1,3-dimethylcyclohexane, 1,4-dimethylcyclohexane, isopropylcyclohexane, n-propylcyclohexane, tert-butylcyclohexane, n-butylcyclohexane, isobutylcyclohexane, 1,2,4-trimethylcyclohexane, 1,3,5-trimethylcyclohexane, etc.; polycyclic aliphatic hydrocarbons such as decalin, etc.; acyclic aliphatic hydrocarbons such as n-pentane, n-hexane, n-heptane, n-octane, isooctane, n-nonane, n-decane, n-dodecane, n-tetradecane, etc.; aromatic hydrocarbons such as toluene, p-xylene, o-xylene, m-xylene, 1,3,5-trimethylbenzene, 1,2,4-trimethylbenzene, 1,2,3,4-tetrahydronaphthalene, etc.; aromatic heterocyclic compounds such as pyridine, etc.

The present reaction is preferably carried out at a high temperature of 100° C. or higher, and therefore, of the above-mentioned solvents, preferred are those having a boiling point of 100° C. or higher, such as chlorobenzene, 1,2-dichlorobenzene, trichlorobenzene, toluene, p-xylene, o-xylene, m-xylene, 1,3,5-trimethylbenzene, 1,2,4-trimethylbenzene, 1,2,3,4-tetrahydronaphthalene, decahydronaphthalene, N,N-dimethylformamide, N,N-dimethylacetamide, dimethyl sulfoxide or sulfolane. More preferred are those having a boiling point of 130° C. or higher, as capable of favorably dissolving the starting material, oligofluorene diester (10b) and enabling reaction at a higher temperature, such as 1,2-dichlorobenzene, xylene, 1,3,5-trimethylbenzene, 1,2,4-trimethylbenzene, 1,2,3,4-tetrahydronaphthalene, and decahydronaphthalene.

One alone or two or more types of these solvents may be used here either singly or as combined.

The upper limit of the amount of the solvent to be used is not specifically defined. In consideration of the production efficiency of the product per reactor, in general, the solvent is used in an amount of generally 15 times by volume the starting oligofluorene diester (10b), preferably 10 times by volume, more preferably 5 times by volume. On the other hand, when the amount of the solvent used is too small, then the reagent solubility would be poor and the stirring would be difficult and, in addition, the reaction speed would be low. Consequently, the lower limit of the amount is generally 1 time by volume the starting oligofluorene diester (10b), preferably 2 times by volume, more preferably 4 times by volume.

<12-5-6-2-4. Reaction Mode>

For the step (iim), the reaction mode may be any of a batch-mode reaction or a flow-through reaction, or a combination thereof. Any reaction mode is employable here with no limitation.

<12-5-6-2-5. Reaction Condition>

In the step (iim), when the temperature is too low, then a sufficient reaction speed could not be obtained. Therefore, concretely, the lower limit of the reaction temperature is generally 50° C., preferably 70° C., more preferably 100° C. On the other hand, the upper limit is generally 250° C., preferably 200° C., more preferably 180° C.

Regarding the ordinary reaction time in the step (iim), the lower limit is generally 1 hour, preferably 2 hours, more preferably 3 hours, and the upper limit is not specifically defined but is generally 30 hours, preferably 20 hours, more preferably 10 hours.

In the step (iim), in order that the equilibrium is shifted to the product side, the reaction may be carried out while the side products are removed through distillation under reduced pressure. The reduced pressure is generally 20 kPa or less, preferably 10 kPa or less, more preferably 5 kPa or less. On the other hand, however, when the degree of pressure reduction is too high, then the reagent, diaryl carbonate would also sublime, and therefore, the reaction is carried out generally under 0.1 kPa or more, preferably 0.5 kPa or more, more preferably 1.0 kPa or more.

<10-5-6-2-6. Separation/Purification of Product>

After the reaction, the intended product oligofluorene diaryl ester (10d) may be isolated through precipitation to be attained by addition of a poor solvent to the reaction liquid.

After the reaction, a solvent capable of dissolving the product, oligofluorene diaryl ester (10d) and water may be added to the reaction liquid for product extraction. The product thus extracted with the solvent may be isolated according to a method of concentrating the solvent or a method of adding a poor solvent to the system.

The resultant oligofluorene diaryl esters (10d) may be used as starting monomers for polycarbonates including polyester carbonates or as starting materials for polyesters, directly as they are. As a purification method, employable is any ordinary purification method of, for example, recrystallization, reprecipitation, extraction purification, column chromatography or the like with no specific limitation thereon.

EXAMPLES

The present invention is described in more detail with reference to the following Examples and Comparative Examples; however, not overstepping the scope and the spirit thereof, the present invention is not limited by the following examples. The quality evaluation of the oligofluorene monomers in the present invention, and the characteristics evaluation of the resin compositions and the transparent films of the present invention were carried out according to the methods mentioned below. The characteristics evaluation methods are not limited to the methods described below, and those skilled in the art can suitably select the methods.

Abbreviations of the compounds used in the following Production Examples and Examples are shown below.
ISB: isosorbide (Roquette Freres' trade name: POLYSORB)
DPC: diphenyl carbonate (by Mitsubishi Chemical)
CHDM: 1,4-cyclohexanedimethanol (cis, trans mixture, by SK Chemical)
BHEPF: 9,9-bis[4-(2-hydroxyethoxy)phenyl]-fluorenone (by Osaka Gas Chemical)
BCF: 9,9-bis[4-hydroxy-3-methylphenyl]-fluorene (by Osaka Gas Chemical)
DEF: fluorene-9,9-diethanol (produced according to the method described in JP-A 2010-261008)
CHDA: 1,4-cyclohexanedicarboxylic acid (cis, trans mixture, by Eastman Chemical)
SPG: spiroglycol (by Mitsubishi Chemical)
BPA: 2,2-bis[4-hydroxyphenyl]propane (by Mitsubishi Chemical)
TCDDM: tricyclodecanedimethanol (by Oxea)
PEG#1000: polyethylene glycol, number-average molecular weight: 1000 (by Sanyo Chemical)
THF: tetrahydrofuran (with no stabilizer, by WAKO)
(1) Aluminium and Sodium Content in Oligofluorene Monomer The aluminium and sodium content in the oligofluorene monomer was measured as follows: The analysis sample was wet-pulverized and then analyzed through ICP-AES (HORIBA Jobin Yvon's ULTIMA 2C). For sodium content measurement, a method of analyzing the analysis sample through atomic absorption VARIAN's SpectrAA-220P was also employed.

(2) Chlorine Content in Oligofluorene Monomer

The chlorine content in the oligofluorene monomer was measured as follows: Using a combustion device (Mitsubishi Chemical's AQF-2100M), the analysis sample was analyzed through burning, absorption and ion chromatography (Nippon Dionex's DX-500).

(3) Thermal Decomposition Temperature of Oligofluorene Monomer (TG/DTA)

The glass transition temperature of the oligofluorene monomer was measured using a differential thermogravimetric analyzer (SII Nanotechnology's TG-DTA6300). About 4 mg of the analysis sample was put into the SII's aluminium pan and sealed up, and then heated from room temperature (20 to 30° C.) up to 600° C. in a nitrogen stream atmosphere of 200 mL/min at a heating rate of 10° C./min. From the resultant TG data (thermogravimetric data), the temperature at which the sample weight reduced by 5 wt % was read as the 5 wt % weight loss temperature. Solvent-containing samples were analyzed as follows: The sample weight was estimated from $^1$H-NMR. After the solvent weight reduced, the weight of the sample with no more weight change was referred to as an initial weight thereof. The temperature at which the initial weight reduced by 5 wt % was referred to as the 5 wt % weight loss temperature of the sample. From the resultant TG data (thermogravimetric data), the temperature at which no sample loss was recognized and at which a steep endothermic peak was observed was read, and the peak top was referred to as the melting point of the sample.

(4) Absorption Maximum Wavelength in UV-Visible Region (UV-Vis) of Oligofluorene Monomer The absorption maximum wavelength in the UV-visible region (UV-Vis: 280 to 800 nm) of the oligofluorene monomer was measured using a UV-visible light absorption spectrophotometer (Shimadzu's UV-1650PC). Tetrahydrofuran was used as a solvent. Using a 1 cm-square quartz cell, the sample was analyzed at a temperature of 23±5° C. The concentration was accurately controlled in order that the concentration as the fluorene ring could be 10 μM. (For example, the compound 1 was controlled to have a concentration of 5.0 μM, and the compound 6B was to have a concentration of 0.33 μM.)

The absorption spectrum was measured in a range of from 280 to 800 nm, and the maximum value of absorption was referred to as the absorption maximum wavelength (λmax).

(5) Reduced Viscosity of Resin Composition

The reduced viscosity of the resin composition was measured as follows: Using an Ubbelohde viscometer by Moritomo Rika Kogyo, and using methylene chloride as a solvent, the sample was analyzed at a temperature of 20.0° C.±0.1° C. The concentration was accurately controlled to be 0.6 g/dL.

From the solvent transit time $t_0$ and the solution transit time t, the relative viscosity $\eta_{rel}$ was calculated according to a formula $\eta_{rel}=t/t_0$, and a specific viscosity $\eta_{sp}$ was calculated according to a formula $\eta_{sp}=(\eta-\eta_0)/\eta_0=\eta_{rel}-1$. The specific viscosity $\eta_{sp}$ was divided by the concentration c (g/dL), and the reduced viscosity $\eta_{red}$ was calculated according to $\eta_{red}=\eta_{sp}/c$. Samples having a higher value of the reduced viscosity have a larger molecular weight.

(6) Glass Transition Temperature (Tg) of Resin Composition

The glass transition temperature of the resin composition was measured using a differential scanning calorimeter (SII Nanotechnology's DSC6220). About 10 mg of the resin composition sample was put into the SII's aluminium pan and sealed up, and then heated from 30° C. up to 250° C. in a nitrogen stream atmosphere of 50 mL/min at a heating rate of 20° C./min. After the sample was kept at the temperature for 3 minutes, and then cooled down to 30° C. at a rate of 20° C./min. After this was kept at 30° C. for 3 minutes, and then again heated up to 200° C. at a rate of 20° C./min. From the DSC data on the 2nd-time heating, the base line on the lower temperature side was extended toward the higher temperature side to draw a straight line. A tangent line was drawn to run through the point at which the inclination of the curve in the part where the glass transition stepwise changes could be the largest. The temperature of the intersection point between the straight line and the tangent line was read to be the extrapolation glass transition starting temperature, and this is the glass transition temperature of the resin composition.

(7) Melt Viscosity of Resin Composition

Before measurement, the resin composition sample was dried in vacuum at 80° C. for 5 hours or more. Using Toyo Precision Instruments' Capillograph, and using a die having 1 mm diameter×10 mm length, the melt viscosity of the sample was measured at a temperature of 240° C. and at a shear rate of 91.2 $sec^{-1}$.

(8) Na, K, Cs and Fe Content Ratio in Resin Composition

About 0.5 f of the resin composition sample was accurately metered in a Perkin Elmer's microwave decomposition vessel, 2 mL of 97% sulfuric acid (Tama Chemical's ultra-high-purity sulfuric acid) was added thereto, and while kept sealed up, this was heated with microwaves at 230° C. for 10 minutes. This was cooled to room temperature (30° C. or lower), and then 1.5 mL of 68% nitric acid (Tama Chemical's ultra-high-purity nitric acid) was added thereto, and while kept sealed up, this was heated with microwaves at 150° C. for 10 minutes. Again this was cooled to room temperature (30° C. or lower), 2.5 mL of 68% nitric acid was again added thereto, and while again kept sealed up, this was heated with microwave at 230° C. for 10 minutes, whereby the content was completely decomposed. The temperature of the microwave heater was controlled by controlling the power of the heater to fall within a range from 300 W to 1000 W using Perkin Elmer's Multiwave 3000. After cooled to room temperature (30° C. or lower), the resultant liquid was diluted with pure water, and quantitatively analyzed with Thermoquest's ICP-MS.

(9) Remaining Monohydroxy Compound in Resin Composition

About 1 g of the resin composition sample was accurately metered, dissolved in 5 mL of methylene chloride, and then acetone was added thereto to give a total amount of 25 mL. The solution was filtered through a 0.2-μm disc filter, and processed through liquid chromatography for phenol quantification, and thereafter the content ratio was calculated.

(10) Photoelastic Coefficient of Resin Composition

About 4 g of the resin composition sample that had been dried in vacuum at 80° C. for 5 hours was thermally pressed at a thermal pressing temperature of from 200 to 250° C. for a preheating time of from 1 to 3 minutes and under a pressure of 20 mPa for 1 minutes, using a spacer having a width of 8 cm, a length of 8 cm and a thickness of 0.5 mm. This was taken out along with the spacer, and cooled for 3 minutes under a pressure of 20 MPa with a water-tube cooling press to form a sheet. A sample having a width of 5 mm and a length of 20 mm was cut out of the film.

This was analyzed using a combined apparatus of a birefringence meter equipped with an He—Ne laser, a polarizer, a compensator, an analyzer and a light detector, as combined with an oscillation viscoelastometer (Rheology's "DVE-3"). (For the details, referred to is the Journal of Nippon Rheology Society, Vol. 19, pp. 93-97 (1991)).

The cutout sample was fixed on the viscoelastometer, and the storage elastic modulus E' thereof at temperature of 25° C. was measured at a frequency of 96 Hz. Simultaneously, the outgoing laser light was led to pass through the polarizer, the sample, the compensator and the analyzer in that order and picked up in the light detector (photodiode), and via a lock-in amplifier, the wave form thereof at an angular frequency of $\omega$ or $2\omega$ was analyzed for the retardation relative to the amplitude and the strain thereof, and the strain optical coefficient O' was thus obtained. In this, the direction of the polarizer and the direction of the analyzer were orthogonal to each other, and the two were so controlled that each could be at an angle of $\pi/4$ relative to the stretching direction of the sample. The photoelastic coefficient C was calculated according to the following formula using the storage elastic modulus E' and the strain optical coefficient O'.

$$C=O'/E'$$

(11) Refractive Index Anisotropy and Wavelength Dispersion Characteristics of Retardation of Resin Composition A film having a thickness of from 100 to 200 μm was formed according to the above-mentioned thermal pressing method, and a sample having a width of 6 cm and a length of 6 cm was cut out of the film. Using a batch-type biaxial stretcher (Island Industry's biaxial stretcher BIX-277-AL), the sample was stretched at a stretching temperature of (glass transition temperature of the resin composition sample+15° C.), at a drawing rate of 1000%/min and at a draw ratio in stretching of 2 times, in a mode of free end monoaxial stretching to give a stretched film. A sample having a width of 4 cm and a length of 4 cm was cut out of the resultant stretched film, and using a retardation measuring device (Oji Scientific Instruments' KOBRA-WPR), the retardation of the sample at a measurement wavelength of 450 nm (Re) and the retardation thereof at 550 nm (Re550) were measured. The ratio of the two measured values (Re450/Re550) was referred to as an index of the wavelength dispersion characteristics of retardation of the sample. In measuring the retardation values, when the measured value of the retardation in the stretching direction is a positive value, then the refractive index anisotropy of the resin is positive.

(12) Toughness of Film (Folding Test)

A film having a thickness of from 100 to 200 μm was formed according to the above-mentioned thermal pressing method, and a sample having a length of 40 mm and a width of 10 mm was cut out of the film. The distance between the right and left joint surface of a vise was kept at 40 mm, both sides of the test sample were fixed to the joint surfaces. Next, the distance between the right and left joint surfaces was narrowed at a rate of 2 mm/sec and, while the film was kept not overstepping out of the bonding surfaces, the entire film having been dogleg-like folded was compressed on the joint surfaces. Samples that had been broken into two pieces (or three or more pieces) on the folding part until the joint surfaces were completely sealed up were considered as "broken", while those that had not been broken but had been folded even after the joint surfaces were completely sealed up were considered as "not broken". One and the same film was tested five times in total in the folding test, and the samples that had been "broken" four times or more were evaluated as "x (no good): brittle fracture occurred", while those that had been "broken" three times or less were evaluated as "○ (good): no brittle fracture occurred".

(13) Measurement of Refractive Index and Abbe's Number

A rectangular test piece having a length of 40 mm and a width of 80 mm was cut out of the film produced according to the above-mentioned thermal pressing method to be a test sample. Using a multiwavelength Abbe's refractiometer (Atago's DR-M4/1550) and using an interference filter at a wavelength 656 nm (C ray), 589 nm (D ray) and 486 nm (F ray), the refractive indices, nC, nD and nF at each wavelength were measured. Monobromonaphthalene was used as an interfacial liquid, and the sample was tested at 20° C. for the measurement.

The Abbe's number νd was calculated according to the following formula.

$$\nu d = (1-nD)/(nC-nF)$$

Samples having a larger Abbe's number have smaller wavelength dependence for refractivity.

(14) Polarization ATR Analysis

A stretched film formed of the resin composition of the present invention was heated up to a temperature not lower than the glass transition temperature (Tg) thereof on a heat stage, then the stretched film was further stretched by 2 times or so in the stretching direction, then cooled, and analyzed for polarization ATR (once reflection method, Ge crystal) measurement.

(Measurement Method)

A measurement apparatus of Nicolet's (current Thermofisher Scientific's) Magna 550 equipped with an ATR accessory "Foundation Thunderdome" was used here. A polarizing plate formed of KRS-5 was set at the inlet port on the light-incoming side of the Thunderdome so that linear polarizability was given to the infrared light. The polarization direction was fixed in the direction parallel to the film surface. By rotating the sample, the spectrum in the state in which the polarization direction is parallel to the film stretching direction was evaluated as a parallel polarization spectrum, while the spectrum in the vertical state was evaluated as a vertical polarization spectrum. Regarding the measurement condition, the resolution power was 4 cm$^{-1}$, and the scanning frequency was 64 times.

For carbonyl orientation, the C=O stretching vibration observed at about 1750 cm$^{-1}$ and the C—O stretching vibration observed at about 1250 cm$^{-1}$ were measured; and for fluorene ring orientation, the benzene ring CH out-of-plane displacement vibration observed at about 740 cm$^{-1}$ was measured.

(Evaluation Method)

The evaluation method is described. First, the difference between the parallel polarization spectrum and the vertical polarization spectrum with absorbance expression is referred to as a differential spectrum. It is confirmed that the absorption at 1750 cm$^{-1}$ in the differential spectrum has a clear peak in the minus direction and that the absorption at 1250 cm$^{-1}$ has a clear peak in the plus direction, and it is confirmed that the carbonyl group is oriented vertically to the stretching direction, or that is, the main chain is oriented in the stretching direction. The sample of that type was evaluated as "○" (good) with respect to carbonyl. Subsequently, the fluorene ring orientation is checked as follows: In the differential spectrum, when the absorption at 740 cm$^{-1}$ clearly appears in the plus direction, or that is, when the fluorene ring is oriented nearly vertically to the main chain, the sample of the time was evaluated as "○" (good) with respect to fluorene, while the sample with no clear orientation expression was evaluated as "×" (no good) with respect to fluorene.

Monomer Synthesis Examples

Synthesis Example 1

Synthesis of 9,9'-di(hydroxymethyl)-9,9'-bifluorenyl (compound 1)

[Chem. 93]

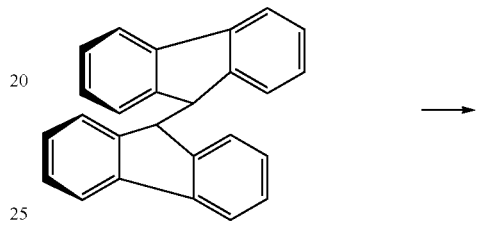

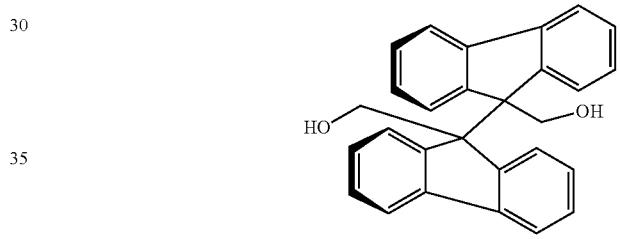

Compound 1

9,9'-Bifluorenyl (0.5 g, 1.51 mmol), paraformaldehyde (42.8 mg, 1.43 mmol) and N,N-dimethylformamide (2.5 ml) were put into a 50-ml eggplant flask, purged with nitrogen, and then sodium ethoxide (4.6 g, 0.068 mmol) was added thereto and stirred. After 1 hour, paraformaldehyde (42.8 mg, 1.43 mmol) was added and stirred for 3 hours. Further, paraformaldehyde (120 mg, 4.0 mmol) was added and stirred for 2 hours. 1 N hydrochloric acid (3 ml) was dropwise added to the reaction liquid to stop the reaction. The resultant suspension was filtered through suction, and washed with a spray of desalted water (10 ml). The resultant crude product was dispersed in toluene (4 ml), and heated under reflux for 1 hour. This was restored to room temperature (20° C.), then filtered through suction, and dried under reduced pressure at 100° C. to have a constant weight, thereby giving 313 mg (yield: 53.1%, HPLC purity: 98.8%) of a white solid of 9,9'-di(hydroxymethyl)-9,9'-bifluorenyl (compound 1).

$^1$H-NMR (400 MHz, DMSO-d$_6$) δ 7.59 (d, J=7.3 Hz, 4H), 7.21 (t, J=7.3 Hz, 4H), 7.03 (t, J=7.1 Hz, 4H), 6.85 (br, 4H), 5.81 (t, J=4.8 Hz, 2H), 4.07 (br, 4H).

UV-Vis (THF): λmax=269, 290, 302 nm.

5 wt % weight loss temperature (in nitrogen atmosphere): 241° C.

Synthesis Example 2

[Chem. 94]

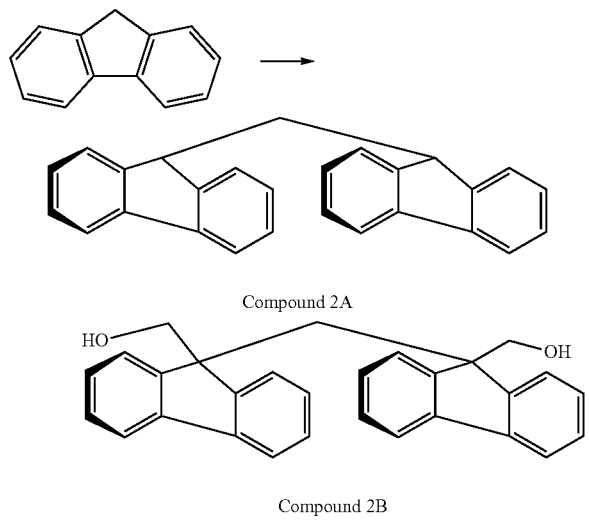

Compound 2A

Compound 2B

Synthesis Example 2A

Synthesis of bis(fluoren-9-yl)methane (compound 2A)

Fluorene (120 g, 722 mmol) and N,N-dimethylformamide (480 ml) were put into a one-liter four-neck flask, purged with nitrogen, and cooled to 5° C. or lower. Sodium ethoxide (24.6 g, 361 mmol) was added thereto, and paraformaldehyde (8.7 g, 289 mmol) was added little by little so as not to be over 10° C., and stirred. After 2 hours, 1 N hydrochloric acid (440 ml) was dropwise added to stop the reaction. The resultant suspension was filtered through suction, and washed with a spray of desalted water (240 ml). Subsequently, the resultant crude product was dispersed in desalted water (240 ml) and stirred for 1 hour. The suspension was filtered through suction, and washed with a spray of desalted water (120 ml). The resultant crude product was dispersed in toluene (480 ml) and then, using a Dean Stark apparatus, this was dewatered by heating under reflux. This was restored to room temperature (20° C.), then filtered through suction, and dried under reduced pressure at 80° C. to have a constant weight, thereby giving 80.4 mg (yield: 84.5%, HPLC purity: 94.0%) of a white solid of bis(fluoren-9-yl)methane (compound 2A).

$^1$H-NMR (400 MHz, CDCl$_3$) δ 7.83 (d, J=7.6 Hz, 4H), 7.56 (dd, J1=7.6 Hz, J2=0.8 Hz, 4H), 7.41 (t, J=7.3 Hz, 4H), 7.29 (dt, J1=7.3 Hz, J2=1.3 Hz, 4H), 4.42 (t, J=7.6 Hz, 2H), 2.24 (d, J=7.6 Hz, 2H).

Synthesis Example 2B

Synthesis of bis(9-hydroxymethylfluoren-9-yl)methane (compound 2B)

Bis(fluoren-9-yl)methane (100 g, 290 mmol) obtained in Synthesis Example 2A, and N,N-dimethylformamide (400 ml) were put into a 500-ml four-neck flask, purged with nitrogen, and paraformaldehyde (18.3 g, 610 mmol) was added thereto. After this was cooled to 5° C. or lower, sodium ethoxide (0.698 g 13 mmol) was added thereto and stirred so as not to be over 10° C. After 1.5 hours, 1 N hydrochloric acid (32 ml) was added so as not to be over 25° C. to stop the reaction. Further, water (300 ml) was added and stirred, and the resultant suspension was filtered through suction, and washed with a spray of desalted water (100 ml). The resultant crude product was dispersed in tetrahydrofuran (400 ml), and heated under reflux for 1 hour. This was restored to room temperature (20° C.), filtered through suction and dried under reduced pressure at 80° C. to have a constant weight, thereby 108 g (yield: 91%, HPLC purity: 99.1%) of a white solid was obtained. The sodium content in the resultant white solid was 620 ppm. Subsequently, the white solid was dispersed in a mixed solution of toluene (800 ml) and water (200 ml), heated under reflux for 1 hour, filtered and dried, and the sodium content in the resultant solid was measured and was 390 ppm. Further, the resultant white solid was dispersed in N,N-dimethylformamide (500 ml) and heated to be a uniform solution, then cooled to 40° C. or lower, and gradually and dropwise added to 0.03 N hydrochloric acid (1500 ml). The resultant suspension was filtered through suction, dispersed in desalted water (200 ml) and stirred for 1 hour. The suspension was filtered through suction, and washed with a spray of desalted water (100 ml). The resultant product was dispersed in toluene (800 ml) and processed for azeotropic dewatering with heating under reflux. This was restored to room temperature (20° C.), filtered through suction, and dried under reduced pressure at 100° C. to have a constant weight, thereby giving 104 g (yield: 87%, HPLC purity: 99.8%) of a white solid of bis(9-hydroxymethylfluoren-9-yl)methane (compound 2B). The sodium and chlorine content in the solid was less than 10 ppm each.

$^1$H-NMR (400 MHz, DMSO-d$_6$) δ 7.12 (d, J=7.3 Hz, 4H), 7.01-6.93 (m, 8H), 6.77 (dt, J1=7.3 Hz, J2=1.0 Hz, 4H), 4.97 (t, J=4.6 Hz, 2H), 3.31 (s, 2H), 3.23 (d, J=4.3 Hz, 4H).

UV-Vis (THF): λmax=263, 292, 304 nm.

5 wt % weight loss temperature (in nitrogen atmosphere): 289° C.

m.p.: 226° C.

Synthesis Example 3

[Chem. 95]

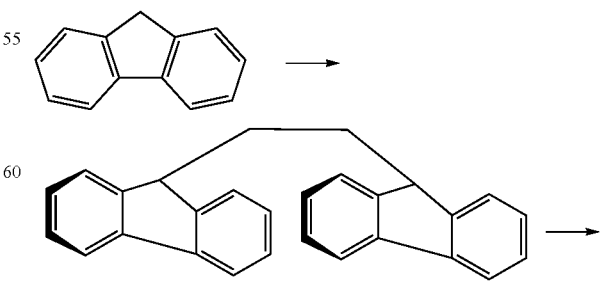

Compound 3A

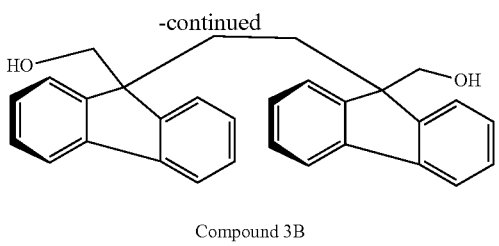

Compound 3B

Synthesis Example 3A

Synthesis of 1,2-bis(fluoren-9-yl)ethane (compound 3A)

Fluorene (2.0 g, 12 mmol) and tetrahydrofuran (35 ml) were put into a 100-ml four-neck flask, purged with nitrogen, and cooled to −50° C. or lower in an ethanol-dry ice bath. 1.6 mol/L n-butyllithium (7.8 ml, 12.5 mmol) was added thereto little by little so as not to be over −40° C., and stirred. Subsequently, this was heated up to 10° C., stirred for 1 hour, and 1,2-dibromoethane (0.55 ml, 6.4 ml) was added thereto and stirred for further 2 hours. Subsequently, 1 N hydrochloric acid (0.5 ml) was dropwise added, and the resultant suspension was filtered through suction, washed with water and dried under reduced pressure at 80° C. to have a constant weight, thereby giving 0.63 g (yield: 29.2%, HPLC purity: 98.0%) of a white solid, 1,2-bis(fluoren-9-yl) ethane (compound 3A). The solvent was evaporated away from the filtrate under reduced pressure, ethanol (25 ml) was added to the residue and stirred for 30 minutes. The suspension was filtered through suction and dried under reduced pressure at 80° C. to have a constant weight, thereby giving 0.44 g (yield: 20.5%, HPLC purity: 84.0%) of a white solid, 1,2-bis(fluoren-9-yl)ethane (compound 3A). The resultant white solids were combined to be 1.07 g (yield: 49.7%).

$^1$H-NMR (400 MHz, CDCl$_3$) δ 7.75 (d, J=7.6 Hz, 4H), 7.37 (dt, J1=7.6 Hz, J2=0.5 Hz, 4H), 7.27-7.34 (m, 8H), 3.85 (s, 2H), 1.74 (t, J=2.3 Hz, 4H).

Synthesis Example 3B

Synthesis of 1,2-bis(9-hydroxymethylfluoren-9-yl)ethane (compound 3B)

1,2-Bis(fluoren-9-yl)ethane (compound 3A, 100 g, 278.9 mmol) obtained in Synthesis Example 3A, paraformaldehyde (17.6 g, 585.8 mmol) and N,N-dimethylformamide (400 ml) were put into a one-liter four-neck flask, purged with nitrogen, and cooled to 10° C. or lower. Sodium ethoxide (1.80 g 27.9 mmol) was added thereto, heated up to room temperature (20° C.) and stirred for 1 hour. After disappearance of the starting material was confirmed through HPLC, the reaction liquid was dropwise put into 0.1 N hydrochloric acid (440 ml) to stop the reaction. The resultant suspension was filtered through suction, and washed with a spray of desalted water (100 ml). The resultant crude product was dispersed in N,N-dimethylformamide (300 ml), and stirred for 1 hour. The suspension was dropwise put into 0.005 N hydrochloric acid (1000 ml), stirred for 30 minutes and filtered through suction. The resultant crude product was dispersed in desalted water (500 ml) and stirred for 1 hour. The suspension was filtered through suction, and washed with a spray of desalted water (200 ml). The resultant crude product was dispersed in toluene (500 ml), and dewatered with heating under reflux, using a Dean Stark apparatus. This was restored to room temperature (20° C.), filtered through suction, and dried under reduced pressure at 100° C. to have a constant weight, thereby giving 112.4 g (yield: 96.3%, HPLC purity: 99.1%) of a white solid, 1,2-bis(9-hydroxymethylfluoren-9-yl)ethane (compound 3B). The sodium content in the solid was less than 1 ppm.

$^1$H-NMR (400 MHz, DMSO-d$_6$) δ 7.91 (d, J=7.3 Hz, 4H), 7.44 (dt, J1=7.6 Hz, J2=1.0 Hz, 4H), 7.35 (dt, J1=7.6 Hz, J2=1.0 Hz, 4H), 7.18 (d, J=7.3 Hz, 4H), 4.79 (t, J=5.3 Hz, 2H), 3.18 (d, J=5.3 Hz, 2H), 1.40 (s, 4H).

UV-Vis (THF): λmax=264, 291, 302 nm.

5 wt % weight loss temperature (in nitrogen atmosphere): 301° C.

m.p.: 278° C.

Synthesis Example 4

Chem. 96

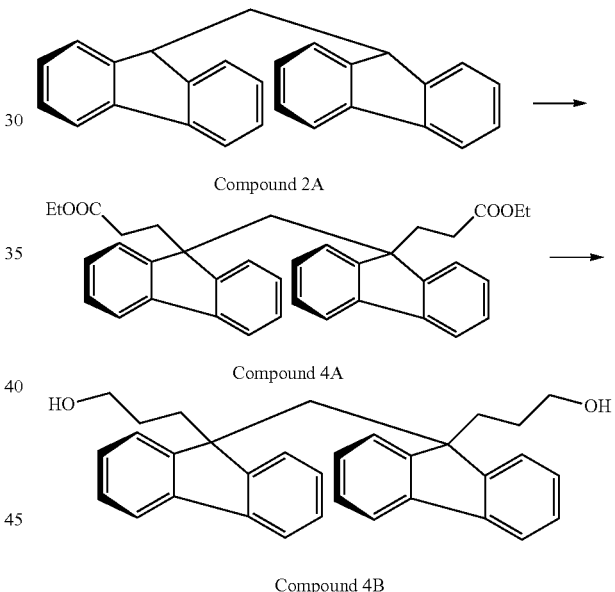

Synthesis Example 4A

Synthesis of bis[9-(2-ethoxycarbonylethyl)fluoren-9-yl]methane (compound 4A)

Bis(fluoren-9-yl)methane (compound 2A, 80 g, 232.3 mmol) obtained in Synthesis Example 2A, N-benzyl-N,N,N-trimethylammonium chloride (10.6 g, 46.5 mmol) and methylene chloride (400 ml) were put into a one-liter three-neck flask, purged with hydrogen, controlled to be at from 15° C. to 20° C. in a water bath, and 50% sodium hydroxide aqueous solution (64 ml) was added thereto, whereupon the solution changed to pale red. Subsequently, ethyl acrylate (50.5 ml, 465 mmol) was dropwise added thereto, taking 5 minutes, and after 1 hour, ethyl acrylate (25.3 ml, 232 mmol) was further added, and while the reaction procedure was kept traced through HPLC, this was stirred for 9 hours. After HPLC confirmed the content of the mono-addition form of 5% or less, this was cooled in an ice bath, then 3 N hydrochloric acid (293 ml) was dropwise added thereto under temperature control for quenching. The organic layer was washed with water until it became neutral, then dried with anhydrous magnesium sulfate, filtered and the solvent was evaporated away under reduced pressure. The resultant crude product was dispersed in methanol (400 ml), and heated under reflux for 30 minutes for washing in thermal suspension. Subsequently, this was restored to room temperature (20° C.), filtered through suction and dried under reduced pressure at 80° C. to have a constant weight, thereby giving 96.1 g (yield: 75.9%, HPLC purity: 96.0%) of a white solid, bis[9-(2-ethoxycarbonylethyl)fluoren-9-yl]methane (compound 4A).

$^1$H-NMR (400 MHz, CDCl$_3$) δ 7.03 (d, J=7.6 Hz, 4H), 6.97 (dt, J1=7.6 Hz, J2=1.5 Hz, 4H), 6.82 (dt, J1=7.6 Hz, J2=1.3 Hz, 4H), 6.77 (d, J=7.6 Hz, 4H), 3.88 (q, J=7.1 Hz, 4H), 3.12 (s, 2H), 2.23 (m, 4H), 1.13 (m, 4H), 1.02 (t, J=7.1 Hz, 6H).

5 wt % weight loss temperature (in nitrogen atmosphere): 295° C.

m.p.: 141° C.

Synthesis Example 4B

Synthesis of bis[9-(3-hydroxypropyl)fluoren-9-yl]methane (compound 4B)

Bis[9-(2-ethoxycarbonylethyl)fluoren-9-yl]methane (compound 4A, 50 g, 91.8 mmol) obtained in Synthesis Example 4A, and toluene (250 ml) were put into a 500-ml four-neck flask, purged with nitrogen, cooled to 5° C. or lower in an ice bath, and while kept at 10° C. or lower, 65 wt % toluene solution of bis(2-methoxyethoxy)aluminium sodium hydride (82.7 ml, 275 mmol) was dropwise added thereto and stirred for 1 hour. After the disappearance of the starting material was confirmed through HPLC, ethyl acetate (9.9 ml) was dropwise added and stirred for 30 minutes, and further 3.1 N sodium hydroxide aqueous solution was dropwise added and stirred for 2 hours. The resultant suspension was filtered under suction, and washed with a spray of desalted water (100 ml). Subsequently, the resultant crude product was dispersed in desalted water (150 ml), and stirred for 30 minutes. After filtration through suction, the liquid was washed by spraying until it became neutral, and washed with a spray of toluene (50 ml). The resultant crude product was dispersed in tetrahydrofuran (150 ml) and dissolved therein by heating. The tetrahydrofuran solution was restored to room temperature (20° C.), led to pass through a silica gel short path (50 g), washed with tetrahydrofuran (350 ml), and the resultant solution was evaporated with an evaporator to remove solvent under reduced pressure. The resultant crude product was dispersed in toluene (250 ml), and heated under reflux for 30 minutes for washing in thermal suspension. This was restored to room temperature (20° C.), then filtered through suction and dried under reduced pressure at 80° C. to have a constant weight, thereby giving 35.5 g (yield: 83.9%, HPLC purity: 99.8%) of a white solid, bis[9-(3-hydroxypropyl)fluoren-9-yl]methane (compound 4B). The sodium content and the aluminium content in the solid were less than 1 ppm each.

$^1$H-NMR (400 MHz, CDCl$_3$) δ 7.05 (d, J=7.6 Hz, 4H), 6.97 (dt, J1=7.6 Hz, J2=1.5 Hz, 4H), 6.81 (dt, J1=7.6 Hz, J2=1.3 Hz, 4H), 6.77 (d, J=7.6 Hz, 4H), 3.19 (q, J=6.3 Hz, 4H), 3.08 (s, 2H), 1.94 (m, 4H), 0.77 (t, J=5.8 Hz, 2H), 0.47 (m, 4H).

5 wt % weight loss temperature (in nitrogen atmosphere): 301° C.

m.p.: 214° C.

Synthesis Example 5

Synthesis of bis{9-[2-(2-hydroxyethoxyl)carbonylethyl]fluoren-9-yl}methane (compound 5)

[Chem. 97]

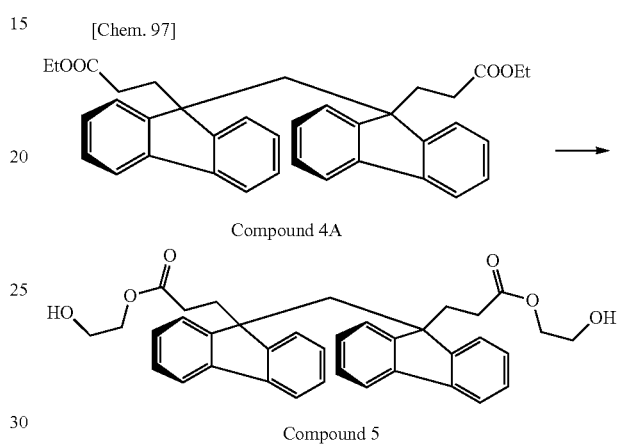

Compound 4A

Compound 5

Bis[9-(2-ethoxycarbonylethyl)fluoren-9-yl]methane (compound 4A, 50 g, 91.8 mmol), ethylene glycol (400 ml) and diethylene glycol dimethyl ether (400 ml) were put into a one-liter four-neck flask, and dissolved under heat in nitrogen to give a uniform solution. Further, a solid of sodium ethoxide (0.94 g, 13.8 mmol) was added, and while the evaporating ethanol was removed under a reduced pressure of from 100 to 150 mmHg, this was stirred at an internal temperature of from 90 to 95° C. for 10 hours. After the disappearance of the starting material was confirmed through HPLC, the reaction liquid was cooled to room temperature (20° C.), 1 N hydrochloric acid (14 ml) was added for neutralization, then the system was transferred to a different vessel, and 1.2 L of water was gradually added thereto. The precipitated solid was collected through filtration, washed with a spray of water, the resultant solid was dissolved in ethyl acetate, and washed with 5% potassium carbonate aqueous solution. Further, the organic layer was washed with water until it became neutral, then dried with anhydrous magnesium sulfate, filtered, and the solvent was evaporated away under reduced pressure. The resultant crude product was purified through recrystallization from toluene (125 ml) and dried under reduced pressure at 80° C. to have a constant weight, thereby giving 46.5 g (yield 86.2%, HPLC purity 98.1%) of a white solid, bis {9-[2-(2-hydroxyethoxyl)carbonylethyl]fluoren-9-yl}methane (compound 5).

$^1$H-NMR (400 MHz, CDCl$_3$) δ 7.05-7.02 (m, 4H), 6.97 (dt, J1=7.2 Hz, J2=1.2 Hz, 4H), 6.81 (dt, J1=7.3 Hz, J2=1.3 Hz, 4H), 6.77-6.75 (m, 4H), 3.89-3.85 (m, 4H), 3.57-3.51 (m, 4H), 3.12 (s, 2H), 2.28-2.21 (m, 4H), 1.71-1.78 (m, 2H), 1.21-1.14 (m, 4H).

5 wt % weight loss temperature (in nitrogen atmosphere): 306° C.

m.p.: 143° C.

Synthesis Example 6

[Chem. 98]

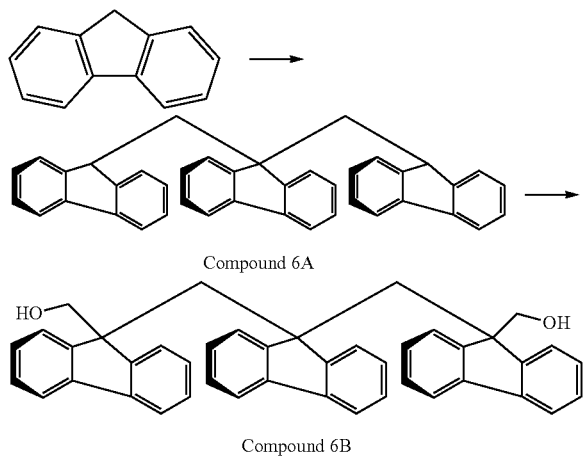

Compound 6A

Compound 6B

Synthesis Example 6A

Synthesis of 9,9-bis[(fluoren-9-yl)-methyl]fluorene (compound 6A)

Fluorene (100 g, 602 mmol) and N,N-dimethylformamide (400 ml) were put into a one-liter four-neck flask, purged with nitrogen, and cooled to 5° C. or lower. Sodium ethoxide (20.5 g, 301 mmol) was added thereto, and paraformaldehyde (11.4 g, 379 mmol) was added little by little so as not to be over 10° C., and stirred. After 1.5 hours, 1 N hydrochloric acid (330 ml) was dropwise added to stop the reaction. The resultant suspension was filtered through suction, and washed with a spray of desalted water (200 ml). Subsequently, the resultant crude product was dispersed in desalted water (300 ml), and stirred for 1 hour. The suspension was filtered through suction, and washed with a spray of desalted water (120 ml). The resultant crude product was dispersed in toluene (400 ml), and dewatered under heat with reflux, using a Dean Stark apparatus. After restored to room temperature (20° C.), this was filtered through suction and dried under reduced pressure at 80° C. to have a constant weight, thereby giving 71.6 g (yield: 73.2%, HPLC purity: 98%) of a white solid, 9,9-bis[(fluoren-9-yl)-methyl]fluorene (compound 6A).

$^1$H-NMR (400 MHz, CDCl$_3$) δ 7.87 (dd, J1=5.6 Hz, J2=1.8 Hz, 2H), 7.73 (dd, J1=6.3 Hz, J2=1.8 Hz, 2H), 7.56 (d, J=7.6 Hz, 4H), 7.47-7.54 (m, 4H), 7.20 (t, J=7.3 Hz, 4H), 7.04 (dt, J1=7.6 Hz, J2=1.0, 4H), 6.63 (dd, J1=7.6 Hz, J2=0.8, 4H), 3.24 (t, J=4.9 Hz, 2H), 2.80 (d, J=4.9 Hz, 4H).

Synthesis Example 6B

Synthesis of 9,9-bis[(9-hydroxymethylfluoren-9-yl)-methyl]fluorene (compound 6B)

9,9-Bis[(fluoren-9-yl)-methyl]fluorene (compound 6A, 54 g, 104 mmol) obtained in Synthesis Example 6A and N,N-dimethylformamide (370 ml) were put into a 500-ml four-neck flask, purged with nitrogen, and paraformaldehyde (7.8 g, 260 mmol) was added thereto. At room temperature (20° C.), sodium methoxide (0.698 g, 13 mmol) was added, and stirred so as not to be over 20° C. After 2.5 hours, the reaction liquid was dropwise put into a mixture of water (750 ml) and 1 N hydrochloric acid (25 ml) kept stirred, to thereby stop the reaction. The resultant suspension was filtered through suction, and washed with a spray of desalted water (200 ml). Subsequently, the resultant crude product was dispersed in desalted water (500 ml), and stirred for 1 hour. The suspension was filtered through suction, and washed with a spray of desalted water (100 ml). The resultant crude product was dispersed in toluene (400 ml) and dewatered with heating under reflux, using a Dean Stark apparatus. After restored to room temperature (20° C.), this was filtered through suction. The crude product was dispersed in ethanol (200 ml), heated under reflux for 30 minutes and filtered through suction to give 49.5 g (yield: 82%, LC purity: 83%) of a white solid. THF (150 ml) was added and heated under reflux, and then water (100 ml) and ethanol (50 ml) were added for crystallization. This was filtered through suction and dried under reduced pressure at 80° C. to have a constant weight, thereby giving 36 g (yield: 59%, HPLC purity: 92%) of a white solid. This was further dispersed in ethanol (200 ml), heated under reflux and filtered repeatedly, thereby giving a white solid having HPL purity of 99%, 9,9-bis[(9-hydroxymethylfluoren-9-yl)-methyl]fluorene (compound 6B). The sodium content in the solid was less than 1 ppm.

$^1$H-NMR (400 MHz, CDCl$_3$) δ 7.02 (dt, J1=7.6 Hz, J2=0.8 Hz, 4H), 6.95 (td, J1=7.6 Hz, J2=0.8 Hz, 4H), 6.74 (td, J1=7.2 Hz, J2=0.8 Hz, 4H), 6.64-6.67 (m, 6H), 6.42 (dt, J1=8.0 Hz, J2=0.8, 2H), 6.33-6.38 (m, 4H), 3.36 (d, J=6.8 Hz, 4H), 3.06 (s, 4H).

UV-Vis (THF): λmax=266, 305 nm.

5 wt % weight loss temperature TG: 304° C.

m.p.: 259° C.

Synthesis Example 7

[Chem. 99]

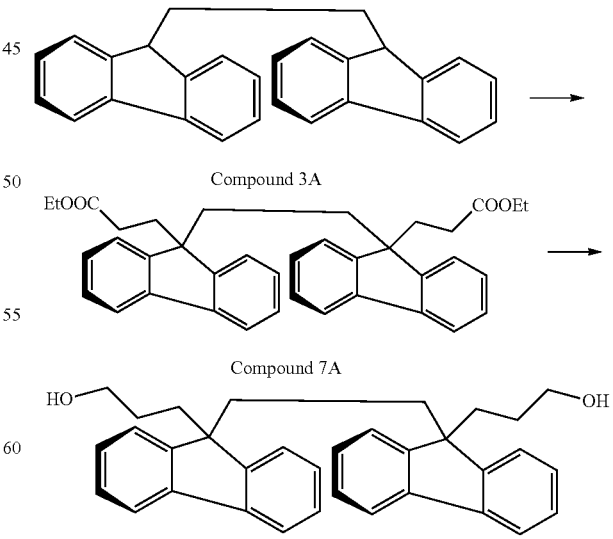

Compound 3A

Compound 7A

Compound 7B

Synthesis Example 7A

Synthesis of 1,2-bis[9-(2-ethoxycarbonylethyl)fluoren-9-yl]ethane (compound 7A)

1,2-Bis(fluoren-9-yl)ethane) compound 3A, 85 g, 237 mmol) obtained in Synthesis Example 3A, tetrahydrofuran (725 ml) and N,N-dimethylformamide (85 ml) were put into a one-liter four-neck flask, purged with nitrogen, and sodium ethoxide (3.23 g, 47.5 mmol) was added, heated up to room temperature (20° C.) and stirred for 30 minutes. Ethyl acrylate (59.3 ml, 545 mmol) was dropwise added thereto, taking 2.5 hours, and after the disappearance of the starting material was confirmed through HPLC, 0.1 N hydrochloric acid (55 ml) was dropwise added to the reaction liquid to stop the reaction. Tetrahydrofuran was evaporated away under reduced pressure, toluene (425 ml) was added to the system, the organic layer was washed with pure water until it became neutral, and then dried with anhydrous magnesium sulfate, filtered, and the solvent was evaporated away under reduced pressure. The resultant crude product was dispersed in methanol (400 ml), and heated under reflux for 1 hour for washing in thermal suspension. Subsequently, this was restored to room temperature (20° C.), filtered through suction, and dried under reduced pressure at 80° C. to have a constant weight, thereby giving 101 g (yield: 76.1%, HPLC purity: 98.6%) of a white solid, 1,2-bis[9-(2-ethoxycarbonylethyl)fluoren-9-yl]ethane (compound 7A).

$^1$H-NMR (400 MHz, CDCl$_3$) δ 7.72 (d, J=7.6 Hz, 4H), 7.36 (t, J=7.6 Hz, 4H), 7.27 (t, J=7.3 Hz, 4H), 6.97 (d, J=7.3 Hz, 4H), 3.80 (q, J=7.1 Hz, 4H), 1.93 (t, J=8.6 Hz, 4H), 1.33 (t, J=8.6 Hz, 4H), 1.23 (s, 4H), 1.01 (t, J=7.1 Hz, 6H).

5 wt % weight loss temperature (in nitrogen atmosphere): 306° C.

m.p.: 150° C.

Synthesis Example 7B

Synthesis of 1,2-bis[9-(3-hydroxypropyl)fluoren-9-yl]ethane (compound 7B)

1,2-Bis[9-(2-ethoxycarbonylethyl)fluoren-9-yl]ethane (compound 7A, 100 g, 179 mmol) obtained in Synthesis Example 7A and tetrahydrofuran (500 ml) were put into a 1000-ml four-neck flask, purged with nitrogen, cooled to 5° C. or lower in an ice bath, and while kept at 15° C. or lower, 65 wt % toluene solution of bis(2-methoxyethoxy)aluminium sodium hydride (161 ml, 537 mmol) was dropwise added thereto and stirred for 1 hour. After the disappearance of the starting material was confirmed through HPLC, ethyl acetate (32 ml) was added and stirred for 45 minutes, and then 3.1 N sodium hydroxide aqueous solution (257 ml) was dropwise added and stirred for 1 hour. Tetrahydrofuran was evaporated away under reduced pressure, and the resultant suspension was filtered through suction, and washed with a spray of desalted water (100 ml). Subsequently, the resultant crude product was dissolved in ethyl acetate (700 ml), and washed three times each with desalted water (100 ml). The organic layer was dried with magnesium sulfate, led to pass through a silica gel short path (50 g), washed with tetrahydrofuran (800 ml), and the resultant solution as evaporated with an evaporator to remove the solvent. The resultant crude product was dispersed in toluene (400 ml), and heated under reflux for 30 minutes for washing in thermal suspension. After restored to room temperature (20° C.), this was filtered through suction, and dried under reduced pressure at 100° C. to have a constant weight, thereby giving 75.6 g (yield: 89.0%, HPLC purity: 98.7%) of a white solid, 1,2-bis[9-(3-hydroxypropyl)fluoren-9-yl]ethane (compound 7B). The sodium content in the solid was 2 ppm, and the aluminium content therein was less than 2 ppm.

$^1$H-NMR (400 MHz, DMSO-d$_6$) δ 7.81 (d, J=7.3 Hz, 4H), 7.35 (t, J=7.3 Hz, 4H), 7.29 (t, J=7.3 Hz, 4H), 7.02 (d, J=7.3 Hz, 4H), 4.02 (t, J=5.0 Hz, 2H), 2.93 (m, 4H), 1.59 (m, 4H), 1.19 (s, 4H), 0.45 (m, 4H).

5 wt % weight loss temperature (in nitrogen atmosphere): 312° C.

m.p.: 253° C.

Synthesis Example 8

Synthesis of α,α'-bis-(9-hydroxymethylfluoren-9-yl)-1,4-xylene (compound 8)

[Chem. 100]

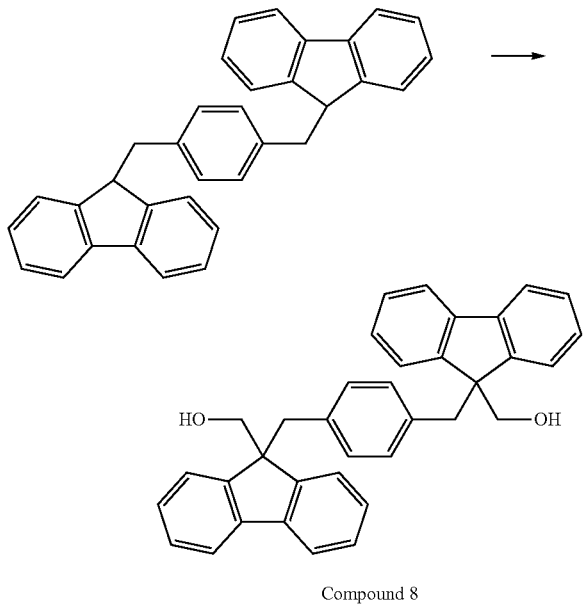

Compound 8

α,α'-bis-(fluoren-9-yl)-1,4-xylene (130 g, 0.3 mol), paraformaldehyde (18.9 g, 0.63 mol) and N,N-dimethylformamide (520 ml) were put into a one-liter four-neck flask, purged with nitrogen, and sodium ethoxide (2.04 g, 0.03 mol) was added and stirred at room temperature (20° C.) for 1 hour. Desalted water (520 ml) and 1 N hydrochloric acid (45 ml) were put into one-L beaker and kept stirred, and the reaction liquid was put thereinto to quench the reaction. The resultant crystal was collected through suction filtration, and washed with a spray of desalted water (100 ml). The resultant crude product was dispersed in desalted water (500 ml), filtered through suction, and washed with a spray of desalted water (100 ml). The resultant crude product was dispersed in toluene (500 ml) and dewatered by heating under reflux, using a Dean Stark apparatus. After restored to room temperature (20° C.), this was filtered through suction, and dried under reduced pressure at 70° C. to have a constant weight, thereby giving 130 g (yield: 87%, HPLC purity: 97.6%) of a white solid (compound 8).

$^1$H-NMR (400 MHz, CDCl$_3$) δ 7.62 (d, J=7.6 Hz, 4H), 7.33 (t, J=8.0 Hz, 4H), 7.25 (t, J=6.0 Hz, 4H), 7.19 (br, 4H), 6.45 (s, 4H), 3.80 (d, J=6.4 Hz, 4H), 3.12 (s, 4H), 1.42 (t, J=6.4 Hz, 2H).

5 wt % weight loss temperature (in nitrogen atmosphere): 327° C.

m.p.: 198° C.

Synthesis Example 9

[Chem. 101]

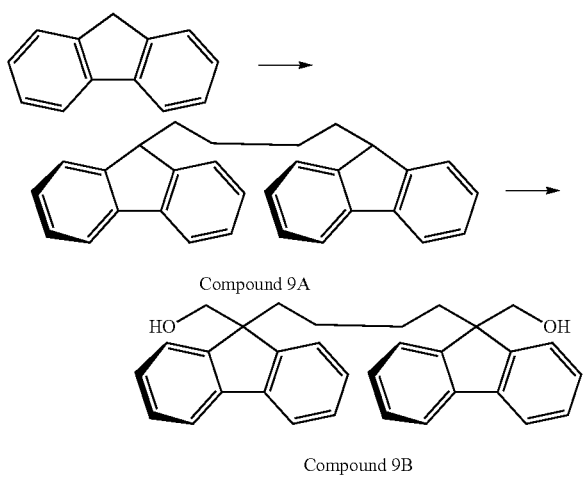

Compound 9A

Compound 9B

Synthesis Example 9A

Synthesis of 1,2-bis(fluoren-9-yl)butane (compound 9A)

Fluorene (3.5 g, 21 mmol), 1,4-butanediol (4.9 g, 54 mmol), 85% KOH (1.52 g, 23 mmol) and tetraethylene glycol dimethyl ether (4.9 g) were put into a SUS316-made autoclave having a volume of 70 ml, and reacted in a nitrogen atmosphere at 250° C. for 8 hours.

After cooled, the content was dispersed in tetrahydrofuran and water, and neutralized with diluted hydrochloric acid. A precipitated powder was collected from the resultant suspension through filtration and washed with water to give 1.7 g (yield: 41.95, HPLC purity: 97.4%) of a white solid, 1,4-bis(fluoren-9-yl)butane (compound 9A).

$^1$H-NMR (400 MHz, CDCl$_3$) δ 7.72 (d, J=7.6 Hz, 4H), 7.42 (m, 4H), 7.25-7.36 (m, 8H), 3.89 (t, J=5.8 Hz, 2H), 1.96-1.86 (m, 4H), 1.15-1.05 (m, 4H).

Synthesis Example 9B

Synthesis of 1,2-bis(9-hydroxymethylfluoren-9-yl)butane (compound 9B)

1,2-Bis(fluoren-9-yl)butane (compound 9A, 37.0 g, 95.7 mmol) obtained in Synthesis Example 9A, paraformaldehyde (6.03 g, 201 mmol) and N,N-dimethylformamide (148 ml) were put into a 500-ml four-neck flask, purged with nitrogen and cooled to 10° C. or lower. Sodium ethoxide (0.65 g, 9.6 mmol) was added, heated up to room temperature (20° C.) and stirred for 1 hour. After the disappearance of the starting material was confirmed through HPLC, the reaction liquid was dropwise put into 0.1 N hydrochloric acid (162 ml) to stop the reaction. The resultant suspension was filtered through suction, and washed with a spray of desalted water (37 ml). The resultant crude product was dispersed in toluene (185 ml), and dewatered by heating under reflux, using a Dean Stark apparatus. After restored to room temperature (20° C.), this was filtered through suction, and dried under reduced pressure at 80° C. to have a constant weight, thereby giving 39.8 g (yield: 93.1%, HPLC purity: 99.1%) of a white solid, 1,2-bis(9-hydroxymethylfluoren-9-yl)butane (compound 9B).

$^1$H-NMR (400 MHz, DMSO-d$_6$) δ 7.71-7.66 (m, 4H), 7.38-7.24 (m, 4H), 3.71 (d, J=6.3 Hz, 4H), 1.89-1.81 (m, 4H), 1.22 (t, J=6.3 Hz, 2H), 0.51-0.44 (m, 4H).

UV-Vis (THF): λmax=291, 302 nm.

5 wt % weight loss temperature (in nitrogen atmosphere): 314° C.

m.p.: 212° C.

Synthesis Example 10

Synthesis Example 10A

Synthesis of 1,1-bis(fluoren-9-yl)ethane (compound 10A)

[Chem. 102]

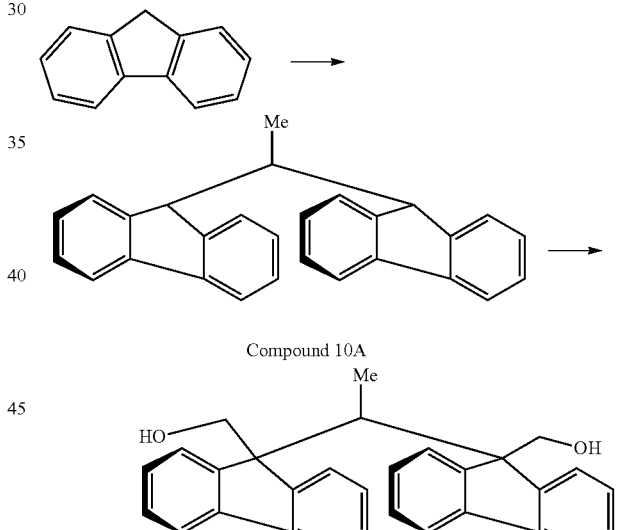

Compound 10A

Compound 10B

Fluorene (100 g, 0.6 mol) and N,N-dimethylformamide (150 ml) were put into a 500-ml four-neck flask, purged with nitrogen, and cooled to an internal temperature of 5° C. or lower. Triton B (5.3 ml, 0.012 mol) was added, and then N,N-dimethylformamide (40 ml) solution of acetaldehyde (15.6 g, 0.319 mol) was dropwise added thereto, taking 1 hour. After the disappearance of the starting material was confirmed through HPLC, 1 N hydrochloric acid (18.1 ml) was dropwise added to stop the reaction. Further, methanol (300 ml) was added, and the resultant suspension was filtered through suction, and washed with a spray of methanol (100 ml). The resultant crude product was dispersed in methanol (300 ml), and heated under reflux for 30 minutes. After restored to room temperature (20° C.), the resultant suspension was filtered through suction, and washed with a spray of methanol (80 ml). This was dried under reduced pressure at 50° C. to have a constant weight, thereby giving 95 g (yield: 88%, HPLC purity: 95%) of a white solid, 1,1-bis(fluoren-9-yl)ethane (compound 10A).

$^1$H-NMR (400 MHz, CDCl$_3$) δ 7.75 (dd, J1=16.4 Hz, J2=7.4 Hz, 4H), 7.55 (d, J=7.6 Hz, 2H), 7.40 (t, J=7.6 Hz, 2H), 7.31 (q, J=7.6 Hz, 4H), 7.17 (t, J=7.6 Hz, 2H), 6.98 (d, J=7.6 Hz, 2H) 3.98 (d, J=4.4 Hz, 2H), 3.0-3.1 (m, 1H), 0.83 (d, J=6.8 Hz, 3H).

Synthesis Example 10B

Synthesis of 1-bis(9-hydroxymethylfluoren-9-yl)ethane (compound 10B)

1,1-Bis(fluoren-9-yl)ethane (compound 10A, 100 g, 0.28 mol) obtained in Synthesis Example 10A, paraformaldehyde (45 g, 1.4 mol) and N,N-dimethylformamide (400 ml) were put into a one-liter four-neck flask, purged with nitrogen, and cooled to 10° C. or lower. Sodium ethoxide (4 g, 0.056 mmol) was added, then gradually heated up to room temperature (20° C.), and stirred for 1 hour. After the disappearance of the starting material was confirmed through HPLC, methanol (50 ml) and 1 N hydrochloric acid (112 ml) were dropwise added to stop the reaction. Toluene (400 ml) was added for liquid-liquid separation, and the aqueous layer was extracted with toluene (200 ml). The toluene layers were combined, and toluene were evaporated away with an evaporator to give 226 mg of a reaction mixture. Methanol (160 ml), 1 N hydrochloric acid (120 ml) and toluene (400 ml) were added, heated under reflux for 1 hour, then cooled to room temperature (20° C.), and the resultant suspension was filtered through suction, and washed with a spray of desalted water (100 ml) and toluene (150 ml). The resultant crude product was dispersed in toluene (380 ml), and then dewatered by heating under reflux, using a Dean Stark apparatus. After restored to room temperature (20° C.), this was filtered through suction, and dried under reduced pressure at 60° C. to be a white solid having a constant weight, thereby giving 69 g (yield: 59%, HPLC purity: 99%) of a white solid, bis(9-hydroxymethylfluoren-9-yl)ethane (compound 10B). The sodium and chlorine content in the solid was less than 10 ppm each.

$^1$H-NMR (400 MHz, CHCl3-d$_3$) δ 7.37 (dd, J1=15.0 Hz, J2=8.0 Hz, 4H), 7.18-7.23 (m, 4H), 7.13 (dt, J1=8.0 Hz, J2=1.2 Hz, 2H), 7.02 (dt, J1=7.3 Hz, J2=1.2 Hz, 2H), 6.87-6.96 (m, 4H), 3.85 (dd, J1=12 Hz, J2=6.4 Hz, 2H), 3.69 (q, J=7.2 Hz, 1H), 3.18 (dd, J1=11.2 Hz, J2=6.4 Hz, 2H), 1.49 (d, J=7.2 Hz, 2H), 1.06 (t, J=6.8 Hz, 2H).

5 wt % weight loss temperature (in nitrogen atmosphere): 283° C.

m.p.: 180° C.

Synthesis Example 11

Synthesis of 1,2-bis[9-(2-methoxycarbonylpropyl) fluoren-9-yl]ethane (compound 11)

[Chem. 103]

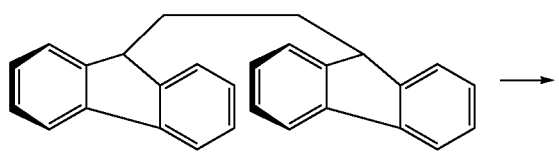

Compound 3A

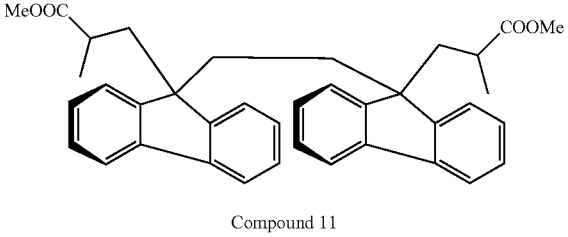

Compound 11

1,2-Bis(fluoren-9-yl)ethane (compound 3A, 45 g, 0.126 mol) obtained according to the method of Synthesis Example 3A, and N,N-dimethylformamide (360 ml) were put into a one-liter four-neck flask, purged with nitrogen, cooled with icy water, and benzyltrimethylammonium hydroxide (40% methanol solution) (2.86 ml, 6.3 mmol) was added, and with cooling with icy water, methyl methacrylate (28.1 ml, 0.264 mol) was dropwise added, taking 40 minutes, and then gradually heated up to room temperature (20° C.). After the disappearance of the starting material was confirmed through HPLC, 1 N hydrochloric acid (13.5 ml) and water (225 ml) were dropwise added to the reaction liquid to stop the reaction. The precipitated crystal was collected through filtration, the resultant crude product was dispersed in methanol (350 ml) and heated under reflux for 1 hour for washing in thermal suspension. Subsequently, this was restored to room temperature (20° C.), filtered through suction, and dried under reduced pressure at 80° C. to have a constant weight, thereby giving 65 g (yield: 93%, HPLC purity: 98%) of a white solid, 1,2-bis[9-(2-methoxycarbonylpropyl)fluoren-9-yl]ethane (compound 11).

$^1$H-NMR (400 MHz, CDCl$_3$) δ 7.72 (dd, J1=10 Hz, J2=8 Hz, 4H), 7.37 (t, J=7.2 Hz, 2H), 7.33 (t, J=6 Hz, 2H), 7.21-7.30 (m, 4H), 6.95 (t, J=9.2 Hz, 2H), 6.91 (t, J=7 Hz, 2H), 3.04 (s, 6H), 2.23 (dd, J1=12 Hz, J2=9 Hz, 2H), 1.56 (d, J=14 Hz, 2H), 1.36-1.46 (m, 2H), 1.05-1.16 (m, 4H), 0.58 (d, J=6.8 Hz, 6H).

5 wt % weight loss temperature (in nitrogen atmosphere): 292° C.

m.p.: 147° C.

Synthesis Example 12

[Chem. 104]

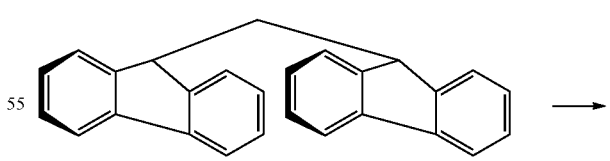

Compound 2A

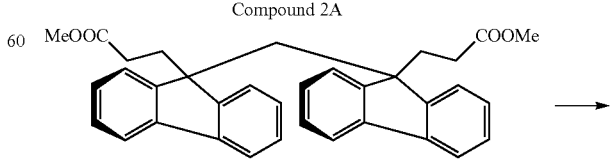

Compound 12A

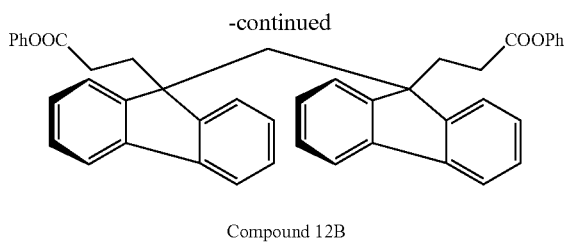

Compound 12B

Synthesis Example 12A

Synthesis of bis[9-(2-methoxycarbonylethyl)fluoren-9-yl]methane (compound 12)

Bis(fluoren-9-yl)methane (compound 2A, 10 g, 29.0 mmol) obtained in Synthesis Example 2A, N-benzyl-N,N,N-triethylammonium chloride (1.32 g, 5.8 mmol) and tetrahydrofuran (50 ml) were put into a 300-ml three-neck flask, purged with nitrogen, controlled at 15° C. to 20° C. in a water bath, and 50% sodium hydroxide aqueous solution (8 ml) was added thereto, whereupon the solution changed to pale red. Subsequently, methyl acrylate (7.8 ml, 87.1 mmol) was dropwise added, taking 3 hours. While the reaction procedure was kept traced through HPLC, this was stirred for 3 hours. After HPLC confirmed the content of the mono-addition form of 10% or less, this was cooled in an ice bath, then 3 N hydrochloric acid (21 ml) was dropwise added thereto under temperature control for quenching. The aqueous layer was removed, then toluene (20 ml) was added to the residue, and the organic layer was washed with desalted water. The solvent was evaporated away under reduced pressure, and at the time when the solid began to precipitate, the reduced pressure was released, methanol (40 ml) was added and stirred for 30 minutes. Subsequently, this was filtered through suction and dried under reduced pressure at 100° C. to have a constant weight, thereby giving 7.05 g (yield: 47%, HPLC purity: 80%) of a white solid, bis[9-(2-methoxycarbonylethyl)fluoren-9-yl]methane (compound 12A).

$^1$H-NMR (400 MHz, CDCl$_3$) δ 7.03 (d, J=7.3 Hz, 4H), 6.97 (dt, J1=6.8, J2=1.3 Hz, 4H), 6.75-6.83 (m, 8H), 3.38 (s, 6H), 3.12 (s, 2H), 2.24 (t, J=8.1 Hz, 4H), 1.14 (t, J=8.1 Hz, 4H).

Synthesis Example 12B-1

Synthesis of bis[9-(2-phenoxycarbonylethyl)fluoren-9-yl]methane (compound 12B)

Bis[9-(2-methoxycarbonylethyl)fluoren-9-yl]methane (compound 12A, 6.0 g, 11.61 mmol)) obtained according to the method of Synthesis Example 12A, diphenyl carbonate (12.1 g, 56.6 mmol), and tetraisopropyl orthotitanate (0.49 mL, 1.66 mmol) were put into a 300-ml four-neck flask, heated up to 145° C., and stirred for 3 hours. The end of the reaction was confirmed through HPLC, then toluene (15 ml) was added, and heated under reflux for 1 hour. This was cooled to 50° C., and methanol (18 ml) was added. After cooled to room temperature (20° C.), this was filtered through suction. The resultant white solid was dispersed in toluene (12 ml), and heated under reflux for 1 hour. This was cooled to 50° C., and methanol (18 ml) was added. After cooled to room temperature (20° C.), this was filtered through suction. This was dried under reduced pressure at 100° C. to have a constant weight, thereby giving 5.29 g (yield: 64%, HPLC purity: 98.1%) of a white solid, bis[9-(2-phenoxycarbonylethyl)fluoren-9-yl]methane (compound 12B).

$^1$H-NMR (400 MHz, CDCl$_3$) δ 7.23-7.28 (m, 4H), 7.07-7.16 (m, 6H), 7.03 (dt, J1=6.9 Hz, J2=2.0, 4H), 6.78-6.90 (m, 12H), 3.20 (s, 2H), 2.37 (t, J=8.3 Hz, 4H), 1.40 (t, J=8.3 Hz, 4H).

5 wt % weight loss temperature (in nitrogen atmosphere): 336° C.

m.p.: 176° C.

Synthesis Example 12B-2

Synthesis of bis[9-(2-phenoxycarbonylethyl)fluoren-9-yl]methane (compound 12B)

[Chem. 105]

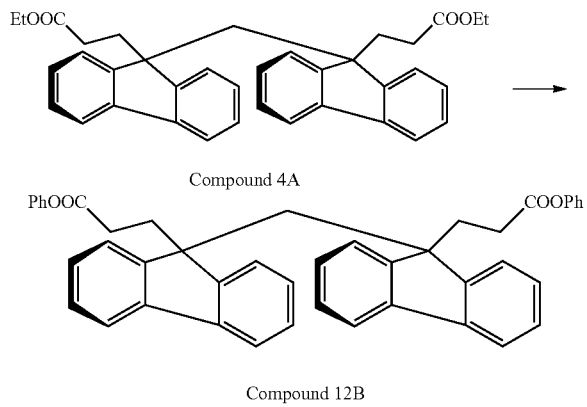

Compound 4A

Compound 12B

Bis[9-(2-ethoxycarbonylethyl)fluoren-9-yl]methane (compound 4A, 50.0 g, 91.80 mmol), diphenyl carbonate (98.3 g, 459 mmol), and tetraisopropyl orthotitanate (1.3 mL, 4.59 mmol) were put into a one-liter four-neck flask, the degree of reduced pressure therein was controlled to be 3 kPa, and while the side product was evaporated away at a temperature falling within a range of from 145° C. to 150° C., this was stirred for 6 hours. After cooled to 90° C., the end of the reaction was confirmed through HPLC, then toluene (100 ml) was added and cooled to 50° C. Methanol (250 ml) was added thereto, cooled to 5° C., and filtered through suction. The resultant white solid was dispersed in toluene (100 ml), and heated under reflux for 30 minutes. This was cooled to 50° C. and methanol (200 ml) was added. After cooled to room temperature (20° C.), this was filtered through suction, and dried under reduced pressure at 100° C. thereby giving 50 g (yield: 85%, HPLC purity: 98.1%) of bis[9-(2-phenoxycarbonylethyl)fluoren-9-yl]methane (compound 12B).

$^1$H-NMR (400 MHz, CDCl$_3$) δ 7.23-7.28 (m, 4H), 7.07-7.16 (m, 6H), 7.03 (dt, J1=6.9 Hz, J2=2.0, 4H), 6.78-6.90 (m, 12H), 3.20 (s, 2H), 2.37 (t, J=8.3 Hz, 4H), 1.40 (t, J=8.3 Hz, 4H).

5 wt % weight loss temperature (in nitrogen atmosphere): 336° C.

m.p.: 176° C.

Synthesis Example 13

Synthesis of 1,2-bis[9-(2-phenoxycarbonylethyl)fluoren-9-yl]ethane (compound 13)

[Chem. 106]

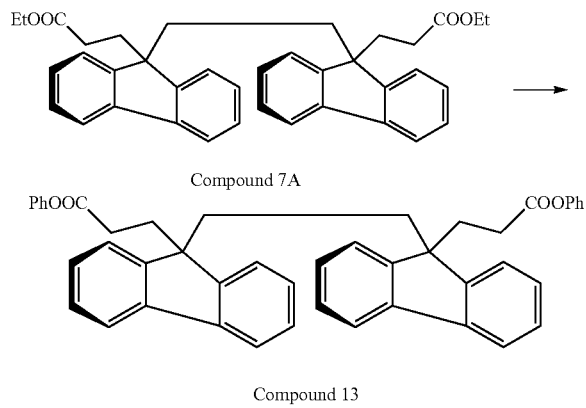

1,2-Bis[9-(2-ethoxycarbonylethyl)fluoren-9-yl]ethane (compound 7A, 100.0 g, 179 mmol) obtained according to the method of Synthesis Example 7A, diphenyl carbonate (115 g, 537 mmol) and tetraisopropyl orthotitanate (2.62 ml, 8.95 mmol) were put into a one-liter four-neck flask, purged with nitrogen, then heated up to 135° C., and stirred for 24 hours. In the middle of the step, diphenyl carbonate (38.3 g, 179 mmol) was added to the system at the time after 12 hours and at the time after 20 hours. The end of the reaction was confirmed through HPLC, then toluene (400 ml) was added, and heated under reflux for 1 hour. After cooled to room temperature (20° C.), this was filtered through suction. The resultant white solid was dispersed in toluene (300 ml), and heated under reflux for 1 hour. This was cooled to room temperature (20° C.), filtered through suction, and dried under reduced pressure at 80° C. to have a constant weight, thereby giving 82 g (yield: 70.0%, HPLC purity: 98.0%) of 1,2-bis[9-(2-phenoxycarbonylethyl)fluoren-9-yl]ethane (compound 13).

$^1$H-NMR (400 MHz, CDCl$_3$) δ 7.76 (d, J=7.6, 4H), 7.41 (dt, J1=7.3, J2=1.0, 4H), 7.32 (dt, J1=7.3, J2=1.0, 4H), 7.22 (t, J=8.3, 4H), 7.11 (t, J=7.6, 2H), 7.03 (d, J=7.6, 4H), 6.78 (d, J=8.6, 4H), 2.06 (t, J=8.1, 4H), 1.60 (t, J=8.1, 4H), 1.29 (s, 4H)

5 wt % weight loss temperature (in nitrogen atmosphere): 337° C.

m.p.: 232° C.

Synthesis Example 14

[Chem. 107]

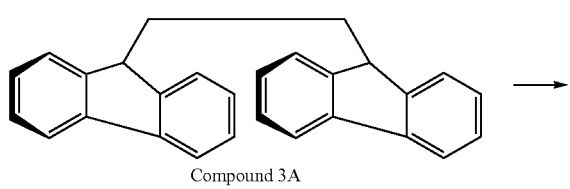

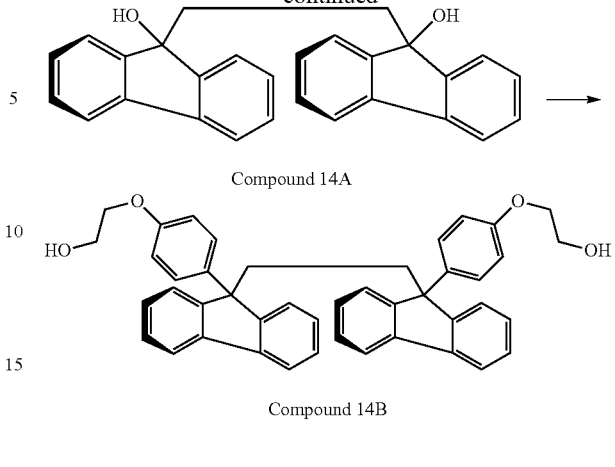

Synthesis Example 14A

Synthesis of 1,2-bis(9-hydroxyfluoren-9-yl)ethane (compound 14A)

1,2-Bis(fluoren-9-yl)ethane (compound 3A, 20 g, 59 mmol) obtained according to the method of Synthesis Example 3A, and N,N-dimethylformamide (200 ml) were put into a one-liter four-neck flask, tributyl phosphite (37.9 ml, 140 mmol) was added, purged with nitrogen, then benzyltrimethylammonium hydroxide (40% methanol solution) (25 ml) was added, and a mixed gas of air (100 ml/min) and nitrogen (300 ml/min) was led to run through the reaction system. After this was stirred for 3 hours, benzyltrimethylammonium hydroxide (40% methanol solution) (10 ml) was added, and stirred for 5 hours. Further, benzyltrimethylammonium hydroxide (40% MeOH solution) (10 ml) was added and further stirred for 1 hour. 1 N hydrochloric acid (200 ml) was added to stop the reaction, and ethyl acetate (400 ml) was added for liquid-liquid separation. Further, the organic layer was washed three times with saturated saline water (100 ml). The organic layer was dried with magnesium sulfate, then filtered, and the organic solvent was evaporated away under reduced pressure. Toluene (100 ml) and hexane (200 ml) were added to the resultant suspension, stirred for 30 minutes, then filtered through suction, and dried under reduced pressure at 80° C. to have a constant weight, thereby giving 13.9 g (yield: 63.85, HPLC purity: 92.5%) of a white solid, 1,2-bis(9-hydroxyfluoren-9-yl)ethane (compound 14A).

$^1$H-NMR (400 MHz, CDCl$_3$) δ 7.73 (d, J=7.3 Hz, 4H), 7.35 (dt, J1=7.6 Hz, J2=1.0, 6H), 7.26 (dt, J1=7.6 Hz, J2=1.0, 4H), 7.11 (d, J=7.3 Hz, 4H), 5.35 (s, 2H), 1.40 (s, 4H).

Synthesis Example 14B

Synthesis of bis {[4-(2-hydroxyethoxyl)phenyl]fluoren-9-yl}ethane 1,2-Bis(fluoren-9-yl)ethane (compound 14A, 17 g, 45 mmol) obtained according to the method of Synthesis Example 14A, and phenoxyethanol (37 g, 267 mmol) were put into a 300-ml four-neck flask, purged with nitrogen, and cooled to 10° C. or lower. Boron trifluoride-diethyl ether complex (5.6 ml, 45 mmol) was added, stirred at room temperature (20° C.) for 3 hours, and boron trifluoride-diethyl ether complex (5.6 ml, 45 mmol) and chloroform (35 ml) were further added, and stirred at 40° C. for 4 hours and at 60° C. for 2 hours. Further, boron trifluoride-diethyl ether complex (5.6 ml, 45 mmol) was added, and heated under reflux for 2 hours. After cooled to room temperature (20° C.), this was neutralized with saturated sodium hydrogencarbonate aqueous solution, and then filtered through suction to remove the insolubles. Ethyl acetate (120 ml) was added, the organic layer was washed twice with saturated saline water and once with desalted water, dried with magnesium sulfate, filtered and the organic solvent was evaporated away under reduced pressure. Again, this was dissolved in ethyl acetate (150 ml), active carbon (Norit Japan's SXPLUS, pH=7, 2.5 g) was added, stirred for 1 hours, filtered through celite, and the organic solvent was evaporated away under reduced pressure. Methanol (100 ml) was added, stirred for 1 hour, filtered through suction, and dried under reduced pressure at 80° C. to have a constant weight, thereby giving 15.8 g (yield: 56.1%, HPLC purity: 86%) of a white powder, bis{[4-(2-hydroxyethoxy)phenyl]fluoren-9-yl}ethane (compound 14B).

$^1$H-NMR (400 MHz, CDCl$_3$) δ 7.77 (d, J=7.3 Hz, 4H), 7.36 (dt, J1=7.6 Hz, J2=1.0, 4H), 7.22 (dt, J1=Hz, J2=1.0, 4H), 6.92 (d, J=7.6 Hz, 4H), 6.73 (d, J=9.1 Hz, 4H), 6.59 (d, J=9.1 Hz, 4H), 3.91-3.93 (m, 4H), 3.83-3.87 (m, 4H), 1.92 (t, J=6.3 Hz, 2H) 1.82 (s, 4H).

Polymer Synthesis Examples

Experimental Example 1

59.43 parts by mass (0.407 mol) of ISB, 28.40 parts by mass (0.062 mol) of bis[9-(3-hydroxypropyl)-fluoren-9-yl]methane (compound 4B), 101.32 parts by mass (0.473 mol) of DPC, and as a catalyst, 8.25×10$^{-4}$ parts by mass (4.68×10$^{-6}$ mol) of calcium acetate monohydrate were put into a reactor, and the materials were dissolved in a nitrogen atmosphere with optionally stirring while the heating tank temperature was controlled at 150° C. (about 10 minutes). After the dissolution, this was heated up to 220° C. in the first-stage step, taking 30 minutes, and reacted under normal pressure for 60 minutes. Next, the pressure was reduced from normal pressure down to 13.3 kPa, taking 90 minutes, and the phenol having formed while kept at 13.3 kPa for 30 minutes was discharged out of the reactor.

Next, in the second-stage step, the heating tank was heated up to 240° C., taking 15 minutes, and the pressure was lowered down to 0.10 kPa, taking 15 minutes, whereupon the phenol having formed was discharged out of the reactor. After the system reached a predetermined torque, the reaction was finished, and the formed polymer was extruded out into water to provide polycarbonate pellets.

The measurement results of the glass transition temperature of the resultant resin composition, the refractive index anisotropy and the retardation ratio (Re450/Re550) of the stretched film formed of the resin composition, and the toughness of the film are shown in Table 1.

Experimental Example 2

This is the same as Experimental Example 1, except that 46.69 parts by mass (0.320 mol) of ISB, 42.60 parts by mass (0.092 mol) of bis[9-(3-hydroxypropyl)-fluoren-9-yl]methane (compound 4B), 89.14 parts by mass (0.416 mol) of DPC, and as a catalyst, 7.26×10$^{-4}$ parts by mass (4.12×10$^{-6}$ mol) of calcium acetate monohydrate were used.

The measurement results of the glass transition temperature of the resultant resin composition, the refractive index anisotropy and the retardation ratio (Re450/Re550) of the stretched film formed of the resin composition, and the toughness of the film are shown in Table 1.

Experimental Example 3

This is the same as Experimental Example 1, except that 38.20 parts by mass (0.261 mol) of ISB, 37.86 parts by mass (0.082 mol) of bis[9-(3-hydroxypropyl)-fluoren-9-yl]methane (compound 4B), 12.71 parts by mass (0.088 mol) of CHDM, 93.14 parts by mass (0.463 mol) of DPC, and as a catalyst, 7.61×10$^{-4}$ parts by mass (4.32×10$^{-6}$ mol) of calcium acetate monohydrate were used.

The measurement results of the glass transition temperature of the resultant resin composition, the refractive index anisotropy and the retardation ratio (Re450/Re550) of the stretched film formed of the resin composition, and the toughness of the film are shown in Table 1.

Experimental Example 4

This is the same as Experimental Example 1, except that 50.94 parts by mass (0.349 mol) of ISB, 18.79 parts by mass (0.046 mol) of bis(9-hydroxymethylfluoren-9-yl)methane (compound 2B), 16.95 parts by mass (0.118 mol) of CHDM, 110.89 parts by mass (0.436 mol) of DPC, and as a catalyst, 7.61×10$^{-4}$ parts by mass (9.03×10$^{-6}$ mol) of calcium acetate monohydrate were used.

The measurement results of the glass transition temperature of the resultant resin composition, the refractive index anisotropy and the retardation ratio (Re450/Re550) of the stretched film formed of the resin composition, and the toughness of the film are shown in Table 1.

Experimental Example 5

This is the same as Experimental Example 1, except that 42.45 parts by mass (0.290 mol) of ISB, 28.72 parts by mass (0.049 mol) of 9,9-bis[(9-hydroxymethylfluoren-9-yl)-methyl]fluorene (compound 6B), 16.95 parts by mass (0.118 mol) of CHDM, 98.93 parts by mass (0.462 mol) of DPC, and as a catalyst, 8.06×10$^{-4}$ parts by mass (4.57×10$^{-6}$ mol) of calcium acetate monohydrate were used.

The measurement results of the glass transition temperature of the resultant resin composition, the refractive index anisotropy and the retardation ratio (Re450/Re550) of the stretched film formed of the resin composition, and the toughness of the film are shown in Table 1.

Experimental Example 6

This is the same as Experimental Example 1, except that 48.39 parts by mass (0.331 mol) of ISB, 16.95 parts by mass (0.040 mol) of 1,2-bis(9-hydroxymethylfluoren-9-yl)ethane (compound 3B), 21.18 parts by mass (0.147 mol) of CHDM, 112.18 parts by mass (0.524 mol) of DPC, and as a catalyst, 9.14×10$^{-4}$ parts by mass (5.19×10$^{-6}$ mol) of calcium acetate monohydrate were used.

The measurement results of the glass transition temperature of the resultant resin composition, the refractive index anisotropy and the retardation ratio (Re450/Re550) of the stretched film formed of the resin composition, and the toughness of the film are shown in Table 1.

Experimental Example 7

This is the same as Experimental Example 1, except that 29.71 parts by mass (0.203 mol) of ISB, 26.55 parts by mass (0.056 mol) of 1,2-bis[9-(3-hydroxypropyl)-fluoren-9-yl]ethane (compound 7B), 5.93 parts by mass (0.041 mol) of CHDM, 64.99 parts by mass (0.303 mol) of DPC, and as a catalyst, $2.65 \times 10^{-3}$ parts by mass ($1.50 \times 10^{-5}$ mol) of calcium acetate monohydrate were used.

The measurement results of the glass transition temperature of the resultant resin composition, the refractive index anisotropy and the retardation ratio (Re450/Re550) of the stretched film formed of the resin composition, and the toughness of the film are shown in Table 1.

Experimental Example 8

This is the same as Experimental Example 1, except that 33.18 parts by mass (0.070 mol) of 1,2-bis[9-(3-hydroxypropyl)-fluoren-9-yl]ethane (compound 7B), 23.77 parts by mass (0.163 mol) of ISB, 5.93 parts by mass (0.041 mol) of CHDM, 59.22 parts by mass (0.276 mol) of DPC, and as a catalyst, $2.41 \times 10^{-3}$ parts by mass ($1.37 \times 10^{-5}$ mol) of calcium acetate monohydrate were used.

The measurement results of the glass transition temperature of the resultant resin composition, the refractive index anisotropy and the retardation ratio (Re450/Re550) of the stretched film formed of the resin composition, and the toughness of the film are shown in Table 1.

Experimental Example 9

This is the same as Experimental Example 1, except that 22.49 parts by mass (0.050 mol) of 1,2-bis(9-hydroxymethylfluoren-9-yl)butane (compound 9B), 30.31 parts by mass (0.207 mol) of ISB, 8.90 parts by mass (0.062 mol) of CHDM, 69012 parts by mass (0.323 mol) of DPC, and as a catalyst, $2.81 \times 10^{-3}$ parts by mass ($1.60 \times 10^{-5}$ mol) of calcium acetate monohydrate were used.

The measurement results of the glass transition temperature of the resultant resin composition, the refractive index anisotropy and the retardation ratio (Re450/Re550) of the stretched film formed of the resin composition, and the toughness of the film are shown in Table 1.

Experimental Example 10

This is the same as Experimental Example 1, except that 32.95 parts by mass (0.079 mol) of 1,2-bis(9-hydroxymethylfluoren-9-yl)ethane (compound 3B), 20.80 parts by mass (0.142 mol) of ISB, 8.90 parts by mass (0.062 mol) of CHDM, 61.18 parts by mass (0.286 mol) of DPC, and as a catalyst, $4.98 \times 10^{-3}$ parts by mass ($2.83 \times 10^{-5}$ mol) of calcium acetate monohydrate were used.

The measurement results of the glass transition temperature of the resultant resin composition, the refractive index anisotropy and the retardation ratio (Re450/Re550) of the stretched film formed of the resin composition, and the toughness of the film are shown in Table 1.

Experimental Example 11

This is the same as Experimental Example 1, except that 26.60 parts by mass (0.054 mol) of α,α'-bis(9-hydroxymethylfluoren-9-yl)-1,4-xylene (compound 8), 23.77 parts by mass (0.163 mol) of ISB, 11.86 parts by mass (0.082 mol) of CHDM, 64.63 parts by mass (0.302 mol) of DPC, and as a catalyst, $5.26 \times 10^{-3}$ parts by mass ($2.99 \times 10^{-5}$ mol) of calcium acetate monohydrate were used.

The measurement results of the glass transition temperature of the resultant resin composition, the refractive index anisotropy and the retardation ratio (Re450/Re550) of the stretched film formed of the resin composition, and the toughness of the film are shown in Table 1.

Experimental Example 12

23.70 parts by mass (0.059 mol) of bis(9-hydroxymethylfluoren-9-yl)methane (compound 2B), 22.53 parts by mass (0.156 mol) of CHDM, 33.62 parts by mass (0.195 mol) of CHDA, and as a catalyst, $6.65 \times 10^{-3}$ parts by mass ($1.95 \times 10^{-5}$ mol) of tetra-n-butyl titanate were put into a reactor, and the materials were dissolved in a nitrogen atmosphere with optionally stirring while the heating tank temperature was controlled at 150° C. (about 10 minutes). After the dissolution, this was heated up to 220° C. in the first-stage step, taking 30 minutes, and reacted under normal pressure for 180 minutes. The formed water was discharged out of the reactor.

Next, in the second-stage step, the heating tank was heated up to 240° C., taking 30 minutes, and the pressure was lowered down to 13.3 kPa, taking 30 minutes. Further, the pressure was lowered down to 0.10 kPa, taking 15 minutes, and the formed phenol was discharged out of the reactor. After the system reached a predetermined torque, the reaction was finished, and the formed polymer was extruded out into water to provide polycarbonate resin pellets.

The measurement results of the glass transition temperature of the resultant resin composition, the refractive index anisotropy and the retardation ratio (Re450/Re550) of the stretched film formed of the resin composition, and the toughness of the film are shown in Table 2.

Experimental Example 13

This is the same as Experimental Example 2, except that 34.12 parts by mass (0.063 mol) of bis[9-(2-ethoxycarbonylethyl)fluoren-9-yl]methane (compound 4A), 25.81 parts by mass (0.179 mol) of CHDM, 20.03 parts by mass (0.166 mol) of CHDA, and as a catalyst, $6.09 \times 10^{-3}$ parts by mass ($1.79 \times 10^{-5}$ mol) of tetra-n-butyl titanate were used.

The measurement results of the glass transition temperature of the resultant resin composition, the refractive index anisotropy and the retardation ratio (Re450/Re550) of the stretched film formed of the resin composition, and the toughness of the film are shown in Table 2.

Experimental Example 14

26.49 parts by mass (0.049 mol) of bis[9-(2-ethoxycarbonylethyl)fluoren-9-yl]methane (compound 4A), 10.37 parts by mass (0.072 mol) of CHDM, and as a catalyst, $14.65 \times 10^{-3}$ parts by mass ($4.30 \times 10^{-5}$ mol) of tetra-n-butyl titanate were put into a reactor, and the materials were dissolved in a nitrogen atmosphere at 220° C. and under normal pressure for 120 minutes. Next, the pressure was lowered to 13.3 kPa, taking 30 minutes, and kept at 13.3 kPa for 30 minutes whereupon the formed ethanol was discharged out of the reactor. Subsequently, the reaction liquid was once cooled to room temperature (20° C.), 31.43 parts by mass (0.215 mol) of ISB and 51.66 parts by mass (0.241 mol) of DPC were put into the same reactor, and the materials were dissolved in a nitrogen atmosphere with optionally stirring while the heating tank temperature was kept at 150° C. (about 10 minutes). After the dissolution, this was heated up to 220° C. in the first-stage step, taking 30 minutes, and reacted under normal pressure for 60 minutes. Next the pressure was reduced from normal pressure to 13.3 kPa, taking 90 minutes, kept at 13.3 kPa for 30 minutes, and the formed phenol was discharged out of the reactor.

Next, in the second-stage step, the heating tank was heated up to 240° C., taking 15 minutes, and the pressure was lowered down to 0.10 kPa, taking 15 minutes, whereupon the formed phenol was discharged out of the reactor. After the system reached a predetermined torque, the reaction was finished, and the formed polymer was extruded out into water to provide polycarbonate resin pellets.

The measurement results of the glass transition temperature of the resultant resin composition, the refractive index anisotropy and the retardation ratio (Re450/Re550) of the stretched film formed of the resin composition, and the toughness of the film are shown in Table 3.

Experimental Example 15

16.76 parts by mass (0.031 mol) of bis[9-(2-ethoxycarbonylethyl)fluoren-9-yl]methane (compound 4A), 7.16 parts by mass (0.050 mol) of CHDM, and as a catalyst, 16.89×10$^{-3}$ parts by mass (4.90×10$^{-5}$ mol) of tetra-n-butyl titanate were put into a reactor, and reacted in a nitrogen atmosphere at 220° C. and under normal pressure for 120 minutes. Next, the pressure was lowered to 13.3 kPa, taking 30 minutes, and kept at 13.3 kPa for 30 minutes whereupon the formed ethanol was discharged out of the reactor. Subsequently, the reaction liquid was once cooled to room temperature (20° C.), 41.11 parts by mass (0.281 mol) of ISB and 65.01 parts by mass (0.303 mol) of DPC were put into the same reactor, and the materials were dissolved in a nitrogen atmosphere with optionally stirring while the heating tank temperature was kept at 150° C. (about 10 minutes). After the dissolution, this was heated up to 220° C. in the first-stage step, taking 30 minutes, and reacted under normal pressure for 60 minutes. Next the pressure was reduced from normal pressure to 13.3 kPa, taking 90 minutes, kept at 13.3 kPa for 30 minutes, and the formed phenol was discharged out of the reactor.

Next, in the second-stage step, the heating tank was heated up to 240° C., taking 15 minutes, and the pressure was lowered down to 0.10 kPa, taking 15 minutes, whereupon the formed phenol was discharged out of the reactor. After the system reached a predetermined torque, the reaction was finished, and the formed polymer was extruded out into water to provide polycarbonate resin pellets.

The measurement results of the glass transition temperature of the resultant resin composition, the refractive index anisotropy and the retardation ratio (Re450/Re550) of the stretched film formed of the resin composition, and the toughness of the film are shown in Table 3.

Experimental Example 16

20.90 parts by mass (0.037 mol) of bis[9-(2-ethoxycarbonylethyl)fluoren-9-yl]methane (compound 4A), 10.79 parts by mass (0.075 mol) of CHDM, and as a catalyst, 15.91×10$^{-3}$ parts by mass (4.68×10$^{-5}$ mol) of tetra-n-butyl titanate were put into a reactor, and reacted in a nitrogen atmosphere at 220° C. and under normal pressure for 120 minutes. Next, the pressure was lowered to 13.3 kPa, taking 30 minutes, and kept at 13.3 kPa for 30 minutes whereupon the formed ethanol was discharged out of the reactor. Subsequently, the reaction liquid was once cooled to room temperature (20° C.), 34.62 parts by mass (0.237 mol) of ISB and 59.44 parts by mass (0.277 mol) of DPC were put into the same reactor, and the materials were dissolved in a nitrogen atmosphere with optionally stirring while the heating tank temperature was kept at 150° C. (about 10 minutes). After the dissolution, this was heated up to 220° C. in the first-stage step, taking 30 minutes, and reacted under normal pressure for 60 minutes. Next the pressure was reduced from normal pressure to 13.3 kPa, taking 90 minutes, kept at 13.3 kPa for 30 minutes, and the formed phenol was discharged out of the reactor.

Next, in the second-stage step, the heating tank was heated up to 240° C., taking 15 minutes, and the pressure was lowered down to 0.10 kPa, taking 15 minutes, whereupon the formed phenol was discharged out of the reactor. After the system reached a predetermined torque, the reaction was finished, and the formed polymer was extruded out into water to provide polycarbonate resin pellets.

The measurement results of the glass transition temperature of the resultant resin composition, the refractive index anisotropy and the retardation ratio (Re450/Re550) of the stretched film formed of the resin composition, and the toughness of the film are shown in Table 3.

Experimental Example 17

20.31 parts by mass (0.049 mol) of bis(9-hydroxymethylfluoren-9-yl)methane (compound 10B), 22.45 parts by mass (0.156 mol) of CHDM, 34.81 parts by mass (0.202 mol) of CHDA, and as a catalyst, 51.61×10$^{-3}$ parts by mass (1.52×10$^{-4}$ mol) of tetra-n-butyl titanate were put into a reactor, and the materials were dissolved in a nitrogen atmosphere optionally with stirring while the heating tank temperature was kept at 150° C. (about 10 minutes). After the dissolution, this was heated up to 220° C. in the first-stage step, taking 30 minutes, and reacted under normal pressure for 150 minutes. Next, while the system was heated up to 240° C., taking 30 minutes, the pressure was reduced to 13.3 kPa. Further, the pressure was reduced to 0.10 kPa, taking 15 minutes, and the formed water was discharged out of the system. After the system reached a predetermined torque, the reaction was finished, and the formed polymer was extruded out into water to provide polyester resin pellets.

The measurement results of the glass transition temperature of the resultant resin composition, the refractive index anisotropy and the retardation ratio (Re450/Re550) of the stretched film formed of the resin composition, and the toughness of the film are shown in Table 2.

Experimental Example 18

22.65 parts by mass (0.042 mol) of bis[9-(2-ethoxycarbonylethyl)fluoren-9-yl]methane (compound 4A), 10.77 parts by mass (0.075 mol) of CHDM, and as a catalyst, 15.54×10$^{-3}$ parts by mass (4.57×10$^{-5}$ mol) of tetra-n-butyl titanate were put into a reactor, and reacted in a nitrogen atmosphere at 220° C. and under normal pressure for 120 minutes. Next, the pressure was lowered to 13.3 kPa, taking 30 minutes, and kept at 13.3 kPa for 30 minutes whereupon the formed ethanol was discharged out of the reactor. Subsequently, the reaction liquid was once cooled to room temperature, 33.58 parts by mass (0.230 mol) of ISB and 56.96 parts by mass (0.266 mol) of DPC were put into the same reactor, and the materials were dissolved in a nitrogen atmosphere with optionally stirring while the heating tank temperature was kept at 150° C. (about 10 minutes). After the dissolution, this was heated up to 220° C. in the first-stage step, taking 30 minutes, and reacted under normal pressure for 60 minutes. Next the pressure was reduced from normal pressure to 13.3 kPa, taking 90 minutes, kept at 13.3 kPa for 30 minutes, and the formed phenol was discharged out of the reactor.

Next, in the second-stage step, the heating tank was heated up to 240° C., taking 15 minutes, and the pressure was lowered down to 0.10 kPa, taking 15 minutes, whereupon the formed phenol was discharged out of the reactor. After the system reached a predetermined torque, the reaction was finished, and the formed polymer was extruded out into water to provide polycarbonate resin pellets.

The measurement results of the glass transition temperature of the resultant resin composition, the refractive index anisotropy and the retardation ratio (Re450/Re550) of the stretched film formed of the resin composition, and the toughness of the film are shown in Table 3.

Experimental Example 19

28.37 parts by mass (0.051 mol) of 1,2-bis[9-(2-ethoxy-carbonylethyl)fluoren-9-yl]ethane (compound 7A), 11.01 parts by mass (0.076 mol) of CHDM, and as a catalyst, $14.17 \times 10^{-3}$ parts by mass ($4.16 \times 10^{-5}$ mol) of tetra-n-butyl titanate were put into a reactor, and reacted in a nitrogen atmosphere at 220° C. and under normal pressure for 120 minutes. Next, the pressure was lowered to 13.3 kPa, taking 30 minutes, and kept at 13.3 kPa for 30 minutes whereupon the formed ethanol was discharged out of the reactor. Subsequently, the reaction liquid was once cooled to room temperature, 29.40 parts by mass (0.201 mol) of ISB and 49.17 parts by mass (0.230 mol) of DPC were put into the same reactor, and the materials were dissolved in a nitrogen atmosphere with optionally stirring while the heating tank temperature was kept at 150° C. (about 10 minutes). After the dissolution, this was heated up to 220° C. in the first-stage step, taking 30 minutes, and reacted under normal pressure for 60 minutes. Next the pressure was reduced from normal pressure to 13.3 kPa, taking 90 minutes, kept at 13.3 kPa for 30 minutes, and the formed phenol was discharged out of the reactor.

Next, in the second-stage step, the heating tank was heated up to 240° C., taking 15 minutes, and the pressure was lowered down to 0.10 kPa, taking 15 minutes, whereupon the formed phenol was discharged out of the reactor. After the system reached a predetermined torque, the reaction was finished, and the formed polymer was extruded out into water to provide polycarbonate resin pellets.

The measurement results of the glass transition temperature of the resultant resin composition, the refractive index anisotropy and the retardation ratio (Re450/Re550) of the stretched film formed of the resin composition, and the toughness of the film are shown in Table 3.

Experimental Example 20

This is the same as Experimental Example 1, except that 27.36 parts by mass (0.042 mol) of 1,2-bis[9-(2-phenoxy-carbonylethyl)fluoren-9-yl]ethane (compound 13), 12.05 parts by mass (0.084 mol) of CHDM, 31.72 parts by mass (0.217 mol) of ISB, 55.45 parts by mass (0.259 mol) of DPC and, as a catalyst, $2.65 \times 10^{-3}$ parts by mass ($1.50 \times 10^{-5}$ mol) of calcium acetate monohydrate were used.

The measurement results of the glass transition temperature of the resultant resin composition, the refractive index anisotropy and the retardation ratio (Re450/Re550) of the stretched film formed of the resin composition, and the toughness of the film are shown in Table 3.

Experimental Example 21

This is the same as Experimental Example 1, except that 33.25 parts by mass (0.051 mol) of 1,2-bis[9-(2-phenoxy-carbonylethyl)fluoren-9-yl]ethane (compound 13), 10.99 parts by mass (0.076 mol) of CHDM, 29.42 parts by mass (0.201 mol) of ISB, 48.57 parts by mass (0.227 mol) of DPC and, as a catalyst, $4.89 \times 10^{-4}$ parts by mass ($2.78 \times 10^{-6}$ mol) of calcium acetate monohydrate were used.

The measurement results of the glass transition temperature of the resultant resin composition, the refractive index anisotropy and the retardation ratio (Re450/Re550) of the stretched film formed of the resin composition, and the toughness of the film are shown in Table 3.

Experimental Example 22

This is the same as Experimental Example 1, except that 26.63 parts by mass (0.042 mol) of bis[9-(2-phenoxycarbo-nylethyl)fluoren-9-yl]methane (compound 12B), 0.78 parts by mass (0.075 mol) of CHDM, 33.58 parts by mass (0.230 mol) of ISB, 56.33 parts by mass (0.263 mol) of DPC and, as a catalyst, $5.36 \times 10^{-4}$ parts by mass ($3.04 \times 10^{-6}$ mol) of calcium acetate monohydrate were used.

The measurement results of the glass transition temperature of the resultant resin composition, the refractive index anisotropy and the retardation ratio (Re450/Re550) of the stretched film formed of the resin composition, and the toughness of the film are shown in Table 3.

Comparative Experimental Example 1

This is the same as Experimental Example 1, except that 61.79 parts by mass (0.163 mol) of 9,9-bis(4-hydroxy-3-methylphenyl)fluorene (BCF), 30.49 parts by mass (0.134 mol) of 2,2-bis(4-hydroxyphenyl)propane (BPA), 67.40 parts by mass (0.315 mol) of DPC, and as a catalyst, $2.61 \times 10^{-3}$ parts by mass ($1.48 \times 10^{-5}$ mol) of calcium acetate monohydrate were used, and that the final polymerization temperature was 280° C.

The measurement results of the glass transition temperature of the resultant resin composition, the refractive index anisotropy and the retardation ratio (Re450/Re550) of the stretched film formed of the resin composition, and the toughness of the film are shown in Table 1.

Comparative Experimental Example 2

This is the same as Experimental Example 1, except that 32.20 parts by mass (0.085 mol) of 9,9-bis(4-hydroxy-3-methylphenyl)fluorene (BCF), 60.43 parts by mass (0.199 mol) of spiroglycol (SPG), 63.18 parts by mass (0.295 mol) of DPC, and as a catalyst, $2.50 \times 10^{-3}$ parts by mass ($1.42 \times 10^{-5}$ mol) of calcium acetate monohydrate were used, and that the final polymerization temperature was 280° C.

The measurement results of the glass transition temperature of the resultant resin composition, the refractive index anisotropy and the retardation ratio (Re450/Re550) of the stretched film formed of the resin composition, and the toughness of the film are shown in Table 1.

Comparative Experimental Example 3

This is the same as Experimental Example 1, except that 34.63 parts by mass (0.091 mol) of 9,9-bis(4-hydroxy-3-methylphenyl)fluorene (BCF), 53.48 parts by mass (0.366 mol) of ISB, 100.93 parts by mass (0.471 mol) of DPC, and as a catalyst, $4.03 \times 10^{-3}$ parts by mass ($2.29 \times 10^{-5}$ mol) of calcium acetate monohydrate were used, and that the final polymerization temperature was 250° C.

The measurement results of the glass transition temperature of the resultant resin composition, the refractive index anisotropy and the retardation ratio (Re450/Re550) of the stretched film formed of the resin composition, and the toughness of the film are shown in Table 1.

Comparative Experimental Example 4

This is the same as Experimental Example 1, except that 80.49 parts by mass (0.184 mol) of 9,9-bis(4-(2-hydroxyethoxyl)phenyl)fluorene (BHEPF), 13.23 parts by mass (0.058 mol) of 2,2-bis(4-hydroxyphenyl)propane (BPA), 53.29 parts by mass (0.249 mol) of DPC, and as a catalyst, $1.28 \times 10^{-3}$ parts by mass ($7.25 \times 10^{-6}$ mol) of calcium acetate monohydrate were used, and that the final polymerization temperature was 260° C.

The measurement results of the glass transition temperature of the resultant resin composition, the refractive index anisotropy and the retardation ratio (Re450/Re550) of the stretched film formed of the resin composition, and the toughness of the film are shown in Table 1.

Comparative Experimental Example 5

This is the same as Experimental Example 1, except that 62.40 parts by mass (0.142 mol) of 9,9-bis(4-(2-hydroxyethoxyl)phenyl)fluorene (BHEPF), 28.78 parts by mass (0.197 mol) of ISB, 73.40 parts by mass (0.343 mol) of DPC, and as a catalyst, $7.28 \times 10^{-4}$ parts by mass ($3.39 \times 10^{-6}$ mol) of magnesium acetate tetrahydrate were used.

The measurement results of the glass transition temperature of the resultant resin composition, the refractive index anisotropy and the retardation ratio (Re450/Re550) of the stretched film formed of the resin composition, and the toughness of the film are shown in Table 1.

Comparative Experimental Example 6

This is the same as Experimental Example 1, except that 27.22 parts by mass (0.107 mol) of DFE, 59.43 parts by mass (0.407 mol) of ISB, 111.69 parts by mass (0.521 mol) of DPC, and as a catalyst, $4.53 \times 10^{-4}$ parts by mass ($2.57 \times 10^{-6}$ mol) of calcium acetate monohydrate were used.

The measurement results of the glass transition temperature of the resultant resin composition, the refractive index anisotropy and the retardation ratio (Re450/Re550) of the stretched film formed of the resin composition, and the toughness of the film are shown in Tables 1 to 3.

TABLE 1

| | | | Polycarbonate Resin Composition | | | | | | | |
|---|---|---|---|---|---|---|---|---|---|---|
| | | | Experimental Example 1 | Experimental Example 2 | Experimental Example 3 | Experimental Example 4 | Experimental Example 5 | Experimental Example 6 | Experimental Example 7 | Experimental Example 8 |
| Fluorene Ring-Containing Monomer | compound 2B | mol % | | | | 9.1 | | | | |
| | compound 4B | mol % | 13.2 | 22.4 | 19.0 | | | | | |
| | compound 6B | mol % | | | | | 10.8 | | | |
| | compound 3B | mol % | | | | | | 7.8 | | |
| | compound 7B | mol % | | | | | | | 18.6 | 25.5 |
| | compound 8 | mol % | | | | | | | | |
| | compound 9B | mol % | | | | | | | | |
| | compound 14B | mol % | | | | | | | | |
| | BCF | mol % | | | | | | | | |
| | BHEPF | mol % | | | | | | | | |
| Comonomer | ISB | mol % | 86.8 | 77.6 | 60.5 | 68.0 | 63.5 | 63.9 | 67.7 | 59.4 |
| | CHDM | mol % | | | 20.4 | 22.9 | 25.7 | 28.3 | 13.7 | 15.0 |
| | SPG | mol % | | | | | | | | |
| | BPA | mol % | | | | | | | | |
| Fluorene Ring-Containing Monomer | compound 2B | wt % | | | | 20.0 | | | | |
| | compound 4B | wt % | 30.0 | 45.0 | 40.0 | | | | | |
| | compound 6B | wt % | | | | | 30.0 | | | |
| | compound 3B | wt % | | | | | | 18.0 | | |
| | compound 7B | wt % | | | | | | | 40.0 | 50.0 |
| | compound 8 | wt % | | | | | | | | |
| | compound 9B | wt % | | | | | | | | |
| | compound 14B | wt % | | | | | | | | |
| | BCF | wt % | | | | | | | | |
| | BHEPF | wt % | | | | | | | | |
| Comonomer | ISB | wt % | 70.0 | 55.0 | 45.0 | 60.0 | 50.0 | 57.0 | 50.0 | 40.0 |
| | CHDM | wt % | | | 15.0 | 20.0 | 20.0 | 25.0 | 10.0 | 10.0 |
| | SPG | wt % | | | | | | | | |
| | BPA | wt % | | | | | | | | |

| | | | Polycarbonate Resin Composition | | | | | | | |
|---|---|---|---|---|---|---|---|---|---|---|
| | | | Experimental Example 9 | Experimental Example 10 | Experimental Example 11 | Comparative Experimental Example 1 | Comparative Experimental Example 2 | Comparative Experimental Example 3 | Comparative Experimental Example 4 | Comparative Experimental Example 5 |
| Fluorene Ring- | compound 2B | mol % | | | | | | | | |
| | compound 4B | mol % | | | | | | | | |

TABLE 1-continued

| | | | | | | | | | | | |
|---|---|---|---|---|---|---|---|---|---|---|---|
| Containing Monomer | compound 6B | mol % | | | | | | | | | |
| | compound 3B | mol % | | 27.8 | | | | | | | |
| | compound 7B | mol % | | | | | | | | | |
| | compound 8 | mol % | | | 18.0 | | | | | | |
| | compound 9B | mol % | 15.8 | | | | | | | | |
| | compound 14B | mol % | | | | | | | | | |
| | BCF | mol % | | | | 55.0 | 30.0 | 20.0 | | | |
| | BHEPF | mol % | | | | | | | | 76.0 | 41.9 |
| Comonomer | ISB | mol % | 64.9 | 50.3 | 54.5 | | | | 80.0 | | 58.1 |
| | CHDM | mol % | 19.3 | 21.8 | 27.5 | | | | | | |
| | SPG | mol % | | | | | | 70.0 | | | |
| | BPA | mol % | | | | 45.0 | | | | 24.0 | |
| Fluorene Ring-Containing Monomer | compound 2B | wt % | | | | | | | | | |
| | compound 4B | wt % | | | | | | | | | |
| | compound 6B | wt % | | | | | | | | | |
| | compound 3B | wt % | | 50.0 | | | | | | | |
| | compound 7B | wt % | | | | | | | | | |
| | compound 8 | wt % | | | 18.0 | | | | | | |
| | compound 9B | wt % | 34.0 | | | | | | | | |
| | compound 14B | wt % | | | | | | | | | |
| | BCF | wt % | | | | 66.0 | 34.4 | 37.0 | | | |
| | BHEPF | wt % | | | | | | | | 85.3 | 66.1 |
| Comonomer | ISB | wt % | 51.0 | 35.0 | 40.0 | | | | 63.0 | | 33.9 |
| | CHDM | wt % | 15.0 | 15.0 | 20.0 | | | | | | |
| | SPG | wt % | | | | | | 65.6 | | | |
| | BPA | wt % | | | | 34.0 | | | | 14.7 | |

| | | | Polycarbonate Resin Composition | | | | | | | |
|---|---|---|---|---|---|---|---|---|---|---|
| | | | Experimental Example 1 | Experimental Example 2 | Experimental Example 3 | Experimental Example 4 | Experimental Example 5 | Experimental Example 6 | Experimental Example 7 | Experimental Example 8 |
| Resin Composition | weight of fluorene skeleton relative to weight of resin composition | wt % | 20.3 | 30.3 | 27.0 | 15.3 | 24.3 | 13.3 | 26.6 | 33.2 |
| | glass transition temperature | ° C. | 146 | 140 | 122 | 134 | 133 | 125 | 137 | 134 |
| | reduced viscosity | dL/g | 0.310 | 0.344 | 0.401 | 0.330 | 0.315 | 0.436 | 0.398 | 0.372 |
| | melt viscosity | Pa · s | 2560 | 2490 | 2710 | 2620 | 2690 | 2710 | 2650 | 2360 |
| | photoelastic coefficient | $\times 10^{-12}$ $Pa^{-1}$ | 16 | 14 | 18 | 28 | 15 | 23 | 24 | 25 |
| | Na, K, Cs, Fe content | ppm | 0.1 | 0.2 | 0.1 | 0.1 | 0.2 | 0.1 | 0.2 | 0.2 |
| | monohydroxy compound content | ppm | 896 | 761 | 581 | 900 | 841 | 668 | 990 | 995 |
| Film | refractive index anisotropy | — | positive | positive | positive | positive | positive | positive | positive | positive |
| | Re450/Re550 | — | 0.99 | 0.80 | 0.93 | 1.04 | 1.04 | 1.04 | 0.97 | 0.54 |
| | Re630/Re550 | — | 1.00 | 1.07 | 1.02 | 0.99 | 0.99 | 0.98 | 1.01 | 1.17 |
| | film toughness | — | ○ | ○ | ○ | ○ | ○ | ○ | ○ | ○ |
| | refractive index 656 nm $n_C$ | — | 1.5391 | 1.5587 | 1.5507 | 1.5259 | 1.5466 | 1.5235 | 1.5462 | 1.5575 |
| | refractive index 589 nm $n_D$ | — | 1.5423 | 1.5694 | 1.5550 | 1.5295 | 1.5571 | 1.5272 | 1.5547 | 1.5666 |
| | refractive index 486 nm $n_F$ | — | 1.5534 | 1.5759 | 1.5667 | 1.5386 | 1.5619 | 1.5362 | 1.5616 | 1.5783 |
| | Abbe's number $v_D$ | — | 38 | 33 | 35 | 42 | 36 | 42 | 36 | 27 |

| | | | Polycarbonate Resin Composition | | | | | | | |
|---|---|---|---|---|---|---|---|---|---|---|
| | | | Experimental Example 9 | Experimental Example 10 | Experimental Example 11 | Comparative Experimental Example 1 | Comparative Experimental Example 2 | Comparative Experimental Example 3 | Comparative Experimental Example 4 | Comparative Experimental Example 5 |
| Resin Composition | weight of fluorene skeleton relative to weight of resin composition | wt % | 25.3 | 39.7 | 26.9 | 26.8 | 14.0 | 15.0 | 30.1 | 23.4 |
| | glass transition temperature | ° C. | 129 | 142 | 130 | 218 | 135 | 174 | 149 | 151 |
| | reduced viscosity | dL/g | 0.422 | 0.396 | 0.428 | 0.338 | 0.499 | 0.322 | 0.344 | 0.320 |
| | melt viscosity | Pa · s | 2750 | 2630 | 2900 | 4660 | 2940 | 2990 | 2920 | 2760 |

TABLE 1-continued

|  |  |  |  |  |  |  |  |  |  |
|---|---|---|---|---|---|---|---|---|---|
|  | photoelastic coefficient | ×10⁻¹² Pa⁻¹ | 24 | 30 | 28 | 42 | 17 | 22 | 46 | 39 |
|  | Na, K, Cs, Fe content | ppm | 0.2 | 0.2 | 0.2 | 0.2 | 0.2 | 0.1 | 0.1 | 0.1 |
|  | monohydroxy compound content | ppm | 853 | 740 | 895 | 214 | 197 | 799 | 335 | 687 |
| Film | refractive index anisotropy | — | positive | positive | positive | positive | positive | positive | positive | positive |
|  | Re450/Re550 | — | 1.02 | 1.04 | 1.04 | 0.98 | 0.92 | 1.00 | 0.88 | 0.90 |
|  | Re630/Re550 | — | 0.99 | 0.98 | 0.98 | 1.00 | 1.03 | 1.00 | 1.03 | 1.03 |
|  | film toughness | — | ○ | ○ | ○ | x | x | x | ○ | ○ |
|  | refractive index 656 nm $n_C$ | — | 1.5461 | 1.5667 | 1.5564 | — | 1.5292 | — | 1.6245 | 1.5912 |
|  | refractive index 589 nm $n_D$ | — | 1.5507 | 1.5754 | 1.5613 | — | 1.5325 | — | 1.6317 | 1.5973 |
|  | refractive index 486 nm $n_F$ | — | 1.5618 | 1.5889 | 1.5738 | — | 1.5424 | — | 1.6506 | 1.6127 |
|  | Abbe's number $\nu_D$ | — | 35 | 26 | 32 | — | 40 | — | 24 | 28 |

TABLE 2

|  |  |  | Polyester Resin Composition | | |
|---|---|---|---|---|---|
|  |  |  | Experimental Example 12 | Experimental Example 13 | Experimental Example 17 |
| Fluorene Ring-Containing Monomer | Compound 2B | mol % | 15.0 |  |  |
|  | Compound 4A | mol % |  | 17.5 |  |
|  | Compound 10B | mol % |  |  | 12.0 |
|  | BCF | mol % |  |  |  |
|  | BHEPF | mol % |  |  |  |
|  | DEF | mol % |  |  |  |
| Comonomer | ISB | mol % |  |  |  |
|  | CHDM | mol % | 35.0 | 50.0 | 38.0 |
|  | SPG | mol % |  |  |  |
|  | CHDA | mol % | 50.0 | 32.5 | 50.0 |
|  | BPA | mol % |  |  |  |
| Fluorene Ring-Containing Monomer | Compound 2B | wt % | 33.7 |  |  |
|  | Compound 4A | wt % |  | 40.7 |  |
|  | Compound 10B | wt % |  |  | 28.9 |
|  | BCF | wt % |  |  |  |
|  | BHEPF | wt % |  |  |  |
|  | DEF | wt % |  |  |  |
| Comonomer | ISB | wt % |  |  |  |
|  | CHDM | wt % | 27.8 | 36.4 | 31.2 |
|  | SPG | wt % |  |  |  |
|  | CHDA | wt % | 38.5 | 23.0 | 39.9 |
|  | BPA | wt % |  |  |  |
| Resin Composition | weight of fluorene skeleton relative to weight of resin composition | wt % | 27.7 | 24.8 | 23.0 |
|  | glass transition temperature | °C. | 99 | 94 | 100 |
|  | reduced viscosity | dL/g | 0.424 | 0.562 | 0.369 |
|  | melt viscosity | Pa·s | 1540 | 2010 | 1500 |
|  | photoelastic coefficient | ×10⁻¹² Pa⁻¹ | 39 | 28 | 41 |
|  | Na, K, Cs, Fe content | ppm | 0.1 | 0.1 | 0.2 |
|  | monohydroxy compound content | ppm | — | — | — |
| Film | refractive index anisotropy | — | positive | positive | positive |
|  | Re450/Re550 | — | 1.06 | 0.36 | 1.02 |
|  | Re630/Re550 | — | 0.99 | 1.51 | 0.99 |
|  | film toughness | — | ○ | ○ | ○ |
|  | refractive index 656 nm $n_C$ | — | 1.5514 | 1.5567 | 1.5424 |
|  | refractive index 589 nm $n_D$ | — | 1.5558 | 1.5611 | 1.5479 |
|  | refractive index 486 nm $n_F$ | — | 1.5668 | 1.5731 | 1.5570 |
|  | Abbe's number $\nu_D$ | — | 36 | 34 | 38 |

TABLE 3

| | | | Polyester Carbonate Resin Composition | | | | | | | |
|---|---|---|---|---|---|---|---|---|---|---|
| | | | Experimental Example 14 | Experimental Example 15 | Experimental Example 16 | Experimental Example 18 | Experimental Example 19 | Experimental Example 20 | Experimental Example 21 | Experimental Example 22 |
| Fluorene Ring-Containing Monomer | Compound 4A | mol % | 14.5 | 8.5 | | 12.0 | | | | |
| | Compound 7 A | mol % | | | 10.7 | | 15.5 | | | |
| | Compound 12B | mol % | | | | | | | | 12.0 |
| | Compound 13 | mol % | | | | | | 12.2 | 15.5 | |
| | BCF | mol % | | | | | | | | |
| | BHEPF | mol % | | | | | | | | |
| | DEF | mol % | | | | | | | | |
| Comonomer | ISB | mol % | 64.1 | 77.8 | 67.9 | 66.4 | 61.3 | 63.4 | 61.3 | 66.4 |
| | CHDM | mol % | 21.4 | 13.7 | 21.4 | 21.6 | 23.2 | 24.4 | 23.2 | 21.6 |
| Fluorene Ring-Containing Monomer | Compound 4A | wt % | 31.7 | 20.0 | | 27.0 | | | | |
| | Compound 7A | wt % | | | 25.0 | | 34.0 | | | |
| | Compound 12B | wt % | | | | | | | | 27.0 |
| | Compound 13 | wt % | | | | | | 28.0 | 34.0 | |
| | BCF | wt % | | | | | | | | |
| | BHEPF | wt % | | | | | | | | |
| | DEF | wt % | | | | | | | | |
| Comonomer | ISB | wt % | 52.9 | 69.2 | 58.3 | 56.5 | 49.5 | 53.3 | 49.5 | 56.5 |
| | CHDM | wt % | 15.5 | 10.8 | 16.7 | 16.5 | 16.5 | 18.7 | 16.5 | 16.5 |
| Resin Composition | weight of fluorene skeleton relative to weight of resin composition | wt % | 19.3 | 14.6 | 17.8 | 19.7 | 24.1 | 19.9 | 24.1 | 19.7 |
| | glass transition temperature | °C. | 132 | 139 | 134 | 129 | 132 | 129 | 133 | 130 |
| | reduced viscosity | dL/g | 0.403 | 0.407 | 0.382 | 0.488 | 0.465 | 0.440 | 0.500 | 0.436 |
| | melt viscosity | Pa·s | 2530 | 2610 | 2290 | 3090 | 2920 | 2560 | 3200 | 2810 |
| | photoelastic coefficient | $\times 10^{-12}$ Pa$^{-1}$ | 15 | 14 | 21 | 18 | 23 | 22 | 23 | 13 |
| | Na, K, Cs, Fe content | ppm | 0.2 | 0.2 | 0.2 | 0.2 | 0.1 | 0.1 | 0.2 | 0.2 |
| | monohydroxy compound content | ppm | 788 | 709 | 830 | 600 | 780 | 790 | 540 | 790 |
| | polymerization mode | — | two-stage | two-stage | two-stage | two-stage | two-stage | one-stage | one-stage | one-stage |
| Film | refractive index anisotropy | — | positive | positive | positive | positive | positive | positive | positive | positive |
| | Re450/Re550 | — | 0.59 | 0.99 | 0.96 | 0.90 | 0.83 | 0.94 | 0.77 | 0.83 |
| | Re630/Re550 | — | 1.15 | 1.00 | 1.01 | 1.03 | 1.05 | 1.02 | 1.08 | 1.06 |
| | film toughness | — | ○ | ○ | ○ | ○ | ○ | ○ | ○ | ○ |
| | refractive index 656 nm $n_C$ | — | 1.5446 | 1.5310 | 1.5343 | 1.5392 | 1.5466 | 1.5369 | 1.5462 | 1.5390 |
| | refractive index 589 nm $n_D$ | — | 1.5490 | 1.5349 | 1.5382 | 1.5434 | 1.5517 | 1.5415 | 1.5510 | 1.5428 |
| | refractive index 486 nm $n_F$ | — | 1.5598 | 1.5437 | 1.5478 | 1.5534 | 1.5633 | 1.5517 | 1.5622 | 1.5529 |
| | Abbe's number $\nu_D$ | — | 36 | 42 | 40 | 38 | 33 | 37 | 34 | 39 |

From Tables 1 to 3, it may be said that the resin compositions of the present invention have positive refractive index anisotropy, that the physical properties such as toughness of the films thereof are good and that the films are useful for applications such as retardation films and other optical films and lenses, etc.

Regarding the film toughness, Comparative Experimental Examples 1 to 3 were unsuitable, but all the resin compositions of the present invention shown in Experimental Examples had good toughness. In addition, all the resin compositions of the present invention shown in Experimental Examples had a good glass transition temperature falling within a range of from 90° C. to 170° C., and the results are that the resin compositions are well balanced in point of both melt processability and heat resistance.

<Discussion about Retardation Films Having Reversed Wavelength Dispersion Characteristics of Retardation>

In Table 4, the measurement results of the optical properties of the stretched films obtained in Experimental Examples 1 to 3, Experimental Examples 7 and 8 and Comparative Examples 1 to 5 are marshaled.

TABLE 4

| | | | Experimental Example 1 | Experimental Example 2 | Experimental Example 3 | Experimental Example 7 | Experimental Example 8 |
|---|---|---|---|---|---|---|---|
| Fluorene Ring-Containing | compound 4B | mol % | 13.2 | 22.4 | 19.0 | | |
| | compound 7B | mol % | | | | 18.6 | 25.5 |
| | compound 14B | mol % | | | | | |

TABLE 4-continued

| | | | | | | | |
|---|---|---|---|---|---|---|---|
| Monomer | BCF | mol % | | | | | |
| | BHEPF | mol % | | | | | |
| Comonomer | ISB | mol % | 86.8 | 77.6 | 60.5 | 67.7 | 59.4 |
| | CHDM | mol % | | | 20.4 | 13.7 | 15.0 |
| | SPG | mol % | | | | | |
| | BPA | mol % | | | | | |
| Film | refractive index anisotropy | — | positive | positive | positive | positive | positive |
| | Re450/Re550 | — | 0.99 | 0.80 | 0.93 | 0.97 | 0.54 |
| | Re630/Re550 | — | 1.00 | 1.07 | 1.02 | 1.01 | 1.17 |
| | film toughness | — | ○ | ○ | ○ | ○ | ○ |

| | | | Comparative Experimental Example 1 | Comparative Experimental Example 2 | Comparative Experimental Example 3 | Comparative Experimental Example 4 | Comparative Experimental Example 5 |
|---|---|---|---|---|---|---|---|
| Fluorene Ring-Containing Monomer | compound 4B | mol % | | | | | |
| | compound 7B | mol % | | | | | |
| | compound 14B | mol % | | | | | |
| | BCF | mol % | 55.0 | 30.0 | 20.0 | | |
| | BHEPF | mol % | | | | 76.0 | 41.9 |
| Comonomer | ISB | mol % | | | 80.0 | | 58.1 |
| | CHDM | mol % | | | | | |
| | SPG | mol % | | 70.0 | | | |
| | BPA | mol % | 45.0 | | | 24.0 | |
| Film | refractive index anisotropy | — | positive | positive | positive | positive | positive |
| | Re450/Re550 | — | 0.98 | 0.92 | 1.00 | 0.88 | 0.90 |
| | Re630/Re550 | — | 1.00 | 1.03 | 1.00 | 1.03 | 1.03 |
| | film toughness | — | x | x | x | ○ | ○ |

Experimental Example 1 and Comparative Experimental Example 3, in which the retardation ratio (Re450/Re550) is on the same level, are compared under assumption of use for retardation films having reversed wavelength dispersion characteristics of retardation. The retardation ratio (Re450/Re550) in Experimental Example 1 using the compound 4B as the fluorene-ring containing monomer is 0.99, while the retardation ratio (Re450/Re550) in Comparative Experimental Example 3 using BCF is 1.00, and the two are on the same level. However, the content of the fluorene ring-containing monomer in Experimental Example 1 is 13.2 mol % and is small, while that in Comparative Experimental Example 3 is 20.0 mol % and is large. It may be said that the film of Experimental Example 1 using the compound 4B expresses more effectively the reversed wavelength dispersion characteristics of retardation. In addition, the film of Comparative Experimental Example 3 using BCF is problematic in point of the toughness thereof.

Experimental Example 2 using the compound 4B as the fluorene ring-containing monomer is compared with Comparative Experimental Example 5 using BHEPF. Though the proportion (molar fraction) of the fluorene ring-containing monomer is smaller in Experimental Example 2, the retardation ratio (Re450/Re550) therein is 0.80; while, on the other hand, the retardation ratio (Re450/Re550) in Comparative Experimental Example 5 in which the proportion (molar fraction) of the fluorene ring-containing monomer is higher than in Experimental Example 2 is 0.90, and it may be said that the compound 4B can more strongly express reversed wavelength dispersion characteristics of retardation in small amounts.

Experimental Example 1, Experimental Example 2 and Experimental Example 3 are compared, all using the compound 4B as the fluorene ring-containing monomer but differing in the content ratio (molar fraction) thereof. The retardation ratio (Re450/Re550) in Experimental Example 3 is 0.93 while the retardation ratio (Re450/Re550) in Experimental Example 2 is 0.80, and therefore it may be said that changing the content ratio of the fluorene ring-containing monomer makes it possible to control the retardation ratio to fall within a preferred range.

Experimental Example 7 and Comparative Experimental Example 3 are compared, in which the proportion (molar fraction) of the fluorene ring-containing monomer is on the same level. In Experimental Example 7 using the compound 7B as the fluorene-containing monomer, the retardation ratio (Re450/Re550) is 0.97 and the film therefore exhibits reversed wavelength dispersion characteristics of retardation, while in Comparative Experimental Example 3 using BCF, the retardation ratio is 1.00 and the expression of reversed wavelength dispersion characteristics of retardation by the film is extremely weak. From this, it may be said that Experimental Example 7 using the compound 7B is more effective for expressing reversed wavelength dispersion characteristics of retardation. Further, Experimental Example 7 and Experimental Example 8 are compared both using the same compound 7B as the fluorene ring-containing monomer but differing in the content proportion of the compound. It may be said that, in Experimental Example 8, the retardation ratio (Re450/Re550) is 0.54 and therefore, changing the fluorene ring-containing monomer content ratio makes it possible to control the retardation ration to fall within a preferred range.

Comparative Experimental Example 1 and Comparative Experimental Example 2 are compared, both providing polycarbonate using BCF as the fluorene ring-containing monomer. In Comparative Experimental Example 1, the BCF content ratio (molar fraction) is remarkably higher than in Comparative Experimental Example 2. However, in Comparative Experimental Example 1, the retardation ratio (Re450/Re550) is 0.98 and is higher than the retardation ratio (Re450/Re550) of 0.92 in Comparative Experimental Example 2, or that is, in the former, the expression efficiency of reversed wavelength dispersion characteristics of retardation is poor. Further, as obvious from Table 1, the photoelastic coefficient in Comparative Experimental Example 1 is 42×10$^{-12}$ Pa$^{-1}$ and is remarkably larger than the value 17×10$^{-12}$ Pa$^{-1}$ in Comparative Experimental Example 2. The reason is considered because of the use of aromatic BPA as the comonomer. From this, use of a nonaromatic monomer is preferred as the comonomer, and it may be expected that the same could apply to the case of the resin composition of the present invention. Similarly, Comparative Experimental Example 4 and Comparative Experimental Example 5 both using BHEPF as the fluorene ring-containing monomer are compared. In Comparative Experimental Example 4 using aromatic BPA as the comonomer, the proportion of BHEPF must be high for expressing the same degree of retardation ratio, and the photoelastic coefficient is high.

Next in Table 5, the measurement results of the optical properties of the stretched films obtained in Experimental Examples 1, 3, 7, 8, 13 to 16 and 18 to 22 are marshaled.

both terminals is 0.36. It is known that Experimental Example 13 expresses more strongly the reversed wavelength dispersion characteristics of the retardation. From this, it is considered that the compound 4A used in Experimental Example 13 has a higher effect of expressing reversed wavelength dispersion characteristics of retardation than the compound 4B used in Experimental Example 1, and that the retardation ratio could be controlled to fall within a preferred range by reducing the content ratio of the compound 4A.

Similarly, Experimental Example 8 and Experimental Example 16 are compared, each using the compound 7A or 7B having the same structure except both terminals. Of the polycarbonate in Experimental Example 8 using the compound 7B having a hydroxypropyl group at both terminals, the retardation ratio (Re450/Re550) is 0.97, while the retardation ratio (Re450/Re550) of the polyester carbonate in Experimental Example 16 using the compound 7B having an ethoxycarbonylethyl group at both terminals is 0.96, or that is, the two are on the same level. However, it is known that the proportion (molar fraction) of the fluorene ring-containing monomer is smaller in Experimental Example 16. From this, it may be said that the compound 7A used in Experimental Example 16 is more effective for expressing reversed wavelength dispersion characteristics of retardation than the compound 7B used in Experimental Example 8. Further, in

TABLE 5

| | | | Experimental Example 1 | Experimental Example 3 | Experimental Example 7 | Experimental Example 8 | Experimental Example 13 | Experimental Example 14 | Experimental Example 15 |
|---|---|---|---|---|---|---|---|---|---|
| Fluorene Ring-Containing Monomer | compound 4B | mol % | 13.2 | 19 | | | | | |
| | compound 7B | mol % | | | 18.6 | 25.5 | | | |
| | compound 4A | mol % | | | | | 17.5 | 14.5 | 8.5 |
| | compound 7 A | mol % | | | | | | | |
| | compound 12B | mol % | | | | | | | |
| | compound 13 | mol % | | | | | | | |
| | BCF | mol % | | | | | | | |
| | BHEPF | mol % | | | | | | | |
| | DEF | mol % | | | | | | | |
| Comonomer | ISB | mol % | 86.8 | 60.5 | 67.7 | 59.4 | | 64.1 | 77.8 |
| | CHDM | mol % | | 20.4 | 13.7 | 15.0 | 50.0 | 21.4 | 13.7 |
| | CHDA | mol % | | | | | 32.5 | | |
| Film | refractive index anisotropy | — | positive | positive | positive | positive | positive | positive | positive |
| | Re450/Re550 | — | 0.99 | 0.93 | 0.97 | 0.54 | 0.36 | 0.59 | 0.99 |
| | Re630/Re550 | — | 1.00 | 1.02 | 1.01 | 1.17 | 1.51 | 1.15 | 1.01 |
| | film toughness | — | ○ | ○ | ○ | ○ | ○ | ○ | ○ |

| | | | Experimental Example 16 | Experimental Example 18 | Experimental Example 19 | Experimental Example 20 | Experimental Example 21 | Experimental Example 22 |
|---|---|---|---|---|---|---|---|---|
| Fluorene Ring-Containing Monomer | compound 4B | mol % | | | | | | |
| | compound 7B | mol % | | | | | | |
| | compound 4A | mol % | | 12.0 | | | | |
| | compound 7A | mol % | 10.7 | | 15.5 | | | |
| | compound 12B | mol % | | | | | | 12.0 |
| | compound 13 | mol % | | | | 12.2 | 15.5 | |
| | BCF | mol % | | | | | | |
| | BHEPF | mol % | | | | | | |
| | DEF | mol % | | | | | | |
| Comonomer | ISB | mol % | 67.9 | 66.4 | 61.3 | 63.4 | 61.3 | 66.4 |
| | CHDM | mol % | 21.4 | 21.6 | 23.2 | 24.4 | 23.2 | 21.6 |
| | CHDA | mol % | | | | | | |
| Film | refractive index anisotropy | — | positive | positive | positive | positive | positive | positive |
| | Re450/Re550 | — | 0.96 | 0.90 | 0.83 | 0.94 | 0.77 | 0.83 |
| | Re630/Re550 | — | 1.01 | 1.03 | 1.05 | 1.02 | 1.08 | 1.06 |
| | film toughness | — | ○ | ○ | ○ | ○ | ○ | ○ |

Experimental Example 1 and Experimental Example 13 are compared, in which the proportion (molar fraction) of the fluorene ring-containing monomer is on the same level and in which is used the compound 4A or 4B having the same structure except the terminals. Of the polycarbonate in Experimental Example 1 using the compound 4B having a hydroxypropyl group at both terminals, the retardation ratio (Re450/Re550) is 0.99, while the retardation ratio (Re450/Re550) of the polyester in Experimental Example 13 using the compound 4A having an ethoxycarbonylethyl group at Experimental Example 19 in which the content ratio of the compound 7A is increased, the retardation ratio (Re450/Re550) is 0.83 and can be controlled to fall within an especially preferred range.

The same shall apply to the polyester carbonate in Experimental Example 14 using the same compound 4A as in Experimental Example 13. When compared with the polyester carbonate in Experimental Example 3 using the compound 4B, it may be said that the polyester carbonate in Experimental Example 14 is more effective for expressing reversed wavelength dispersion characteristics of retardation. In Experimental Example 15 in which the content ratio of the compound 4A is reduced, the expression of reversed wavelength dispersion characteristics of retardation is weak. Using the compound 4A, Experimental Example 18 has the retardation ratio (Re450/Re550) falling within a more preferred range, in which the proportion (molar fraction) of the fluorene ring-containing monomer is set between Experimental Example 14 and Experimental Example 15.

The polyester carbonate of Experimental Example 19 using the compound 7A is compared with that of Experimental Example 21 using the compound 13, in which the proportion (molar fraction) of the fluorene ring-containing monomer is the same. Between the two, the terminal structure of the polyester carbonate differs, but it is considered that the resin compositions of the two are nearly the same. The retardation ratio (Re450/Re550) in Experimental Example 19 is 0.83 and is close to the value 0.77 in Experimental Example 21. However, in Experimental Example 19, the polymer is produced in two stages of esterification and polymerization, but in Example 20, the polyester carbonate can be produced in one stage. Therefore, it is considered that the case of using the diphenyl ester, compound 13 having higher reactivity can shorten the production process than the use of using the diethyl ester, compound 7A. In Experimental Example 20 in which the content ratio of the compound 13 is reduced, the expression of reversed wavelength dispersion characteristics of retardation is somewhat weak. Consequently, in a case of using the compound 13, it is considered that the fluorene ring-containing monomer proportion (molar fraction) may be set, for example, between Experimental Example 20 and Experimental Example 21 to thereby control the retardation ratio (Re450/Re550) to fall within a more preferred range.

The same shall apply to the diethyl ester, compound 4A and the diphenyl ester, compound 12B having the same structure except the terminals. Experimental Example 22 using the compound 12B has the fluorene ring-containing monomer proportion (molar fraction) falling between Experimental Example 14 and Experimental Example 15 both using the compound 4A and has the retardation ratio (Re450/Re550) also falling between the two, and accordingly, it is considered that the expression of reversed wavelength dispersion characteristics of retardation is nearly on the same level. However, in Experimental Example 14 and Experimental Example 15, the polymer is produced in two stages of esterification and polymerization, while in Example 20, the polyester carbonate can be produced in one stage. Consequently, it is considered that using the diphenyl ester compound 12B having higher reactivity can shorten more the production process than using the diethyl ester compound 4A.

The above indicates that, assuming use for retardation films having reversed wavelength dispersion characteristics of retardation, the resin composition that contains a polymer having a repeating unit of oligofluorene of the present invention attains various physical properties and positive intrinsic birefringence and retardation ratio, in a small mass and/or molar fraction of oligofluorene monomer therein.

<Discussion about Retardation Films or Broadband Zero Birefringence Materials Having Flat Wavelength Dispersion Characteristics of Retardation>

In Table 6, the measurement results of the optical properties of the stretched films obtained in Experimental Examples 4 to 6, 9 to 12 and 17 are marshaled.

TABLE 6

| | | | Experimental Example 4 | Experimental Example 5 | Experimental Example 6 | Experimental Example 9 | Experimental Example 10 | Experimental Example 11 | Experimental Example 12 | Experimental Example 17 |
|---|---|---|---|---|---|---|---|---|---|---|
| Fluorene Ring-Containing Monomer | compound 2B | mol % | 9.1 | | | | | | 15.0 | |
| | compound 6B | mol % | | 10.8 | | | | | | |
| | compound 3B | mol % | | | 7.8 | | 27.8 | | | |
| | compound 8 | mol % | | | | | | 18.0 | | |
| | compound 9B | mol % | | | | 15.8 | | | | |
| | compound 10B | mol % | | | | | | | | 12.0 |
| Comonomer | ISB | mol % | 68.0 | 63.5 | 63.9 | 64.9 | 50.3 | 54.5 | | |
| | CHDM | mol % | 22.9 | 25.7 | 28.3 | 19.3 | 21.8 | 27.5 | 35.0 | 38.0 |
| | CHDA | mol % | | | | | | | 50.0 | 50.0 |
| Film | refractive index anisotropy | — | positive | positive | positive | positive | positive | positive | positive | positive |
| | Re450/Re550 | — | 1.04 | 1.04 | 1.04 | 1.02 | 1.04 | 1.04 | 1.06 | 1.02 |
| | Re630/Re550 | — | 0.99 | 0.99 | 0.98 | 0.99 | 0.98 | 0.98 | 0.99 | 0.99 |
| | film toughness | — | ○ | ○ | ○ | ○ | ○ | ○ | ○ | ○ |
| | refractive index 656 nm $n_C$ | — | 1.5259 | 1.5466 | 1.5235 | 1.5461 | 1.5667 | 1.5564 | 1.5514 | 1.5424 |
| | refractive index 589 nm $n_D$ | — | 1.5295 | 1.5571 | 1.5272 | 1.5507 | 1.5754 | 1.5613 | 1.5558 | 1.5479 |
| | refractive index 486 nm $n_F$ | — | 1.5386 | 1.5619 | 1.5362 | 1.5618 | 1.5889 | 1.5738 | 1.5668 | 1.5570 |
| | Abbe's number $v_D$ | — | 42 | 36 | 42 | 35 | 26 | 32 | 36 | 38 |

The resin compositions of Experimental Examples 4 to 6 and Experimental Examples 9 to 12 and 17 using an oligofluorene-diol having a hydroxymethyl group in the side chain as the fluorene ring-containing monomer all have a retardation ratio (Re450/Re550) of from 1.0 to 1.06 and have flat wavelength dispersion characteristics of retardation, and are therefore useful as retardation films having flat wavelength dispersion characteristics of retardation, and as other optical films.

In general, of the resin composition using a fluorene ring-containing monomer such as those in Experimental Examples 1 to 3 using the compound 4B and those in Experimental Examples 7 and 8 using the compound 7B, the retardation ratio (Re450/Re550) tends to greatly vary depending on the proportion of the fluorene ring-containing monomer therein. As opposed to these, the polycarbonates of Experimental Example 6 and Experimental Example 10 using the compound 3B of a fluorene ring-containing monomer having a hydroxylmethyl group in the side chain along with ISB and CHDM which have a specific characteristic that the retardation ratio (Re450/Re550) thereof is 1.04 and changes little even when the proportion of the compound 3B therein varies. Not limited to Experimental Example 6 and Experimental Example 10, this characteristic is common to Experimental Example 4, Experimental Example 5, Experimental Example 9, Experimental Example 11 and Experimental Example 12 using an oligofluorene-diol having a hydroxymethyl group in the side chain. Consequently, the resin composition of the present invention using an oligofluorene-diol having a hydroxymethyl group can control the birefringence thereof while maintaining the flat wavelength dispersion characteristics of retardation, and accordingly, using the oligofluorene-diol in a suitable molar fraction therein, the resin composition of the present invention is expected to be applicable to broadband zero birefringence materials.

Between Experimental Example 4 and Experimental Example 12, and between Experimental Example 6 and Experimental Example 10 both having the same hydroxymethyl group-having oligofluorene-diol, the resin composition in which the proportion of the hydroxymethyl group-having oligofluorene-diol is higher has a higher refractive index and a lower Abbe's number. This is considered to be the characteristic common to the resin composition of the present invention using a hydroxymethyl group-having oligofluorene-diol, and for example, in a case where the proportion of the hydroxymethyl group-having oligofluorene-diol is increased, both the refractive index and the Abbe's number can be controlled each to fall within a preferred range while the broadband zero birefringence is kept as such. Consequently, the resin composition of the type is expected to be applicable to imaging optical lenses.

From the above, the resin composition of the present invention using an oligofluorene-diol having a hydroxymethyl group in the side chain can attain flat wavelength dispersion characteristics of retardation in any desired ratio, and tends to enable easy birefringence control.

<Discussion about Broadband Low-Birefringence Material>

Experimental Example 4 and Experimental Example 12, and Experimental Example 6 and Experimental Example 10 all using the same fluorene ring-containing monomer are compared. In these, the proportion (molar fraction) of the fluorene ring-containing monomer differs, but both the retardation ratio Re450/Re550 and the retardation ratio Re630/Re550 change little, or that is, the materials are considered to show flat wavelength dispersion characteristics of retardation in any desired ratio of the monomer therein. Consequently, it is presumed that, in the region in which the proportion (molar fraction) of the fluorene ring-containing monomer is high, the materials could show broadband zero birefringence. Between Experimental Example 6 and Experimental Example 10 using the compound 3B, the film in Experimental Example 10 in which the proportion of the compound 3B is higher has a higher refractive index and a lower Abbe's number.

Of all the resin compositions of Experimental Examples 4 to 6 and Experimental Examples 9 to 12 and Experimental Example 17 using an oligofluorene-diol having a hydroxymethyl group in the side chain, the retardation ratio (Re450/Re550) is from 1.0 to 1.06, or that is, all the resin compositions show flat wavelength dispersion characteristics of retardation and the films thereof have good physical properties such as high toughness, etc. Consequently, the resin compositions are useful as retardation films having flat wavelength dispersion characteristics of retardation and as any other optical films.

As shown in the above-mentioned Experimental Examples, the resin compositions using a fluorene ring-containing monomer differ depending on the structure of the fluorene ring-containing monomer therein even though the monomer content is the same molar fraction therein. For example, some would strongly exhibit reversed wavelength dispersion characteristics of retardation, or some would exhibit moderately reversed wavelength dispersion characteristics of retardation, or some would exhibit flat wavelength dispersion characteristics of retardation. Consequently, depending on the intended object, the type of the fluorene ring-containing monomer to be in the resin composition as well as the molar fraction thereof may be suitably selected.

<Fluorene Ratio>

In Table 7, the chemical structural formulae of fluorene ring-containing monomer-derived repeating units synthesized in Synthesis Examples, and the fluorene ratio therein are marshaled. The fluorene ratio was calculated according to the following formula. The molecular weight of the fluorene skeleton in the following formula is based on 13 carbon atoms (not including hydrogen atom).

Fluorene Ratio (%)=(molecular weight of fluorene skeleton)/(molecular weight of repeating unit)×100

Table 8 shows the amount of the monomer composition put in a reactor, and the analytical data of the monomer-derived repeating unit in the resin composition, in typical Synthesis Examples for the resin composition of the present invention, and in Experimental Example 6. The composition of the repeating unit in the resin composition was calculated from the $^1$H-NMR spectrum.

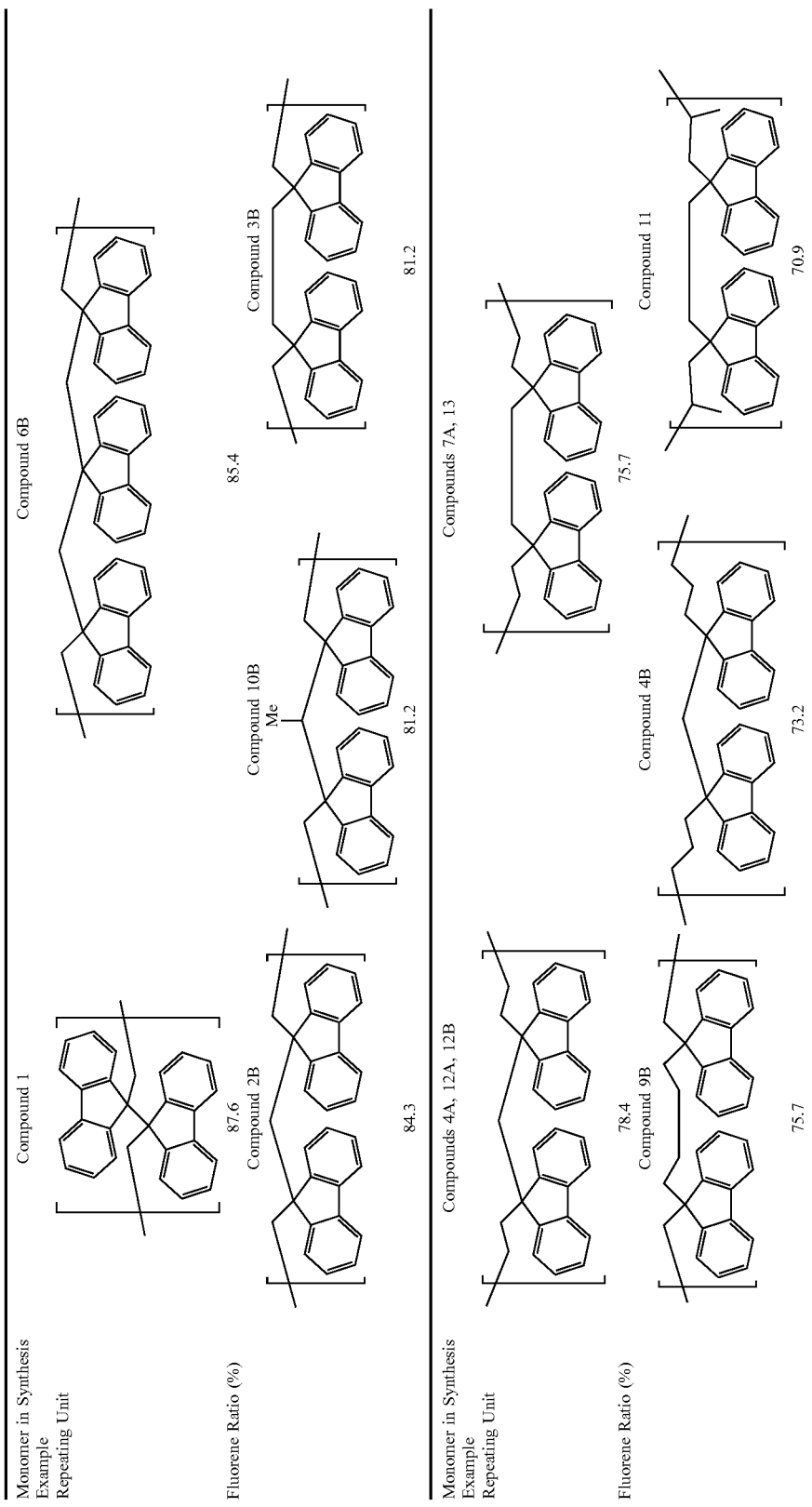

-continued

| Monomer in Synthesis Example Repeating Unit | Compound 7B | Compound 8 | Compound 8 |
|---|---|---|---|
| Fluorene Ratio (%) | 70.9 | 67.8 | 52.3 |

| Monomer in Comparative Experimental Example Repeating Unit | DEF | BCF | BHEPF |
|---|---|---|---|
| Fluorene Ratio (%) | 70.9 | 45.3 | 38.6 |

TABLE 8

| | | | Compound 4B | ISB |
|---|---|---|---|---|
| Experimental Example 1 | analytical value | [mol %] | 13.5 | 86.5 |
| | charge-in quantity | [mol %] | 13.2 | 86.8 |
| | | | Compound 7B | ISB |
| Experimental Example 7 | analytical value | [mol %] | 18.8 | 67.5 |
| | charge-in quantity | [mol %] | 18.6 | 67.7 |
| | | | Compound 4B | CHDM |
| Experimental Example 13 | analytical value | [mol %] | 17.5 | 50.1 |
| | charge-in quantity | [mol %] | 17.5 | 50.0 |
| | | | Compound 7B | ISB |
| Experimental Example 16 | analytical value | [mol %] | 11.0 | 67.6 |
| | charge-in quantity | [mol %] | 10.7 | 67.9 |
| | | | Compound 13 | ISB |
| Experimental Example 21 | analytical value | [mol %] | 15.7 | 61.1 |
| | charge-in quantity | [mol %] | 15.5 | 61.3 |
| | | | Compound 12B | ISB |
| Experimental Example 22 | analytical value | [mol %] | 12.2 | 66.2 |
| | charge-in quantity | [mol %] | 12.0 | 66.4 |
| | | | DEF | ISB |
| Comparative Experimental Example 6 | analytical value | [mol %] | 19.8 | 80.2 |
| | charge-in quantity | [mol %] | 20.8 | 79.2 |

As described above, it is considered that increasing the proportion of fluorene in the repeating unit would make it possible to efficiently express the desired optical properties; however, the fluorene proportion in the monomer produced in Synthesis Examples is 50% or more in every case, and therefore, it is considered that the resin composition of the present invention that uses the monomer is suitable for efficiently expressing the desired optical properties. As opposed to this, in Comparative Experimental Examples using any of BCF and BHEPF, the fluorene proportion in the monomer-derived repeating unit is less than 50% and is therefore not efficient for expressing the desired optical properties, and in these, it is considered that the amount of the fluorene-having monomer to be used must be increased for expressing the desired optical properties. On the other hand, in Comparative Experimental Example 6 using DEF, the fluorene proportion in the monomer-derived repeating unit is high, and it is considered that the desired optical properties could be expressed even though the amount of the monomer is small. However, as shown in Table 8, in the resin composition of the present invention, any of the molar ratio of the monomer composition put in the reactor or the composition of the repeating unit in the resin composition is 0.3% or less, while in the polycarbonate resin composition in Comparative Experimental Example 6 using DEF, the molar ratio differs between them by 1.0%. This is considered because DEF would have changed to a low-boiling-point decomposed product during polymerization, and therefore the molar ratio of the DEF-derived repeating unit in the resin composition after polymerization would have greatly changed from the molar ratio of DEF put in the reactor. Consequently, there is a drawback in that the desired optical properties are difficult to control and the reproducibility of optical properties is poor. In addition, the resin composition produced using DEF has another problem in that Tg thereof tends to be low.

<Polarization ATR Analysis, and Calculation of Conformation Energy and Angle>

For investigating the chemical structure and the optical properties of oligofluorene, the energy of the specific conformation of the repeating unit derived from an oligofluorene monomer is calculated and the angle between the fluorene ring and the main chain in the conformation is calculated, as follows.

The software is US Wavefunction's PC Spartan Pro 1.0.5 (Windows (registered trademark) 32 bit edition) for the AM1 method, and is US Gaussian's Gaussian 03 Rev-B.05 (Windows (registered trademark) 32 bit edition for the B3LYP/6-31G* method. The inputted values relating to calculation accuracy such as convergence values and others are all default values of the software.

Here, the diol monomer-derived repeating unit is calculated relative to the structure methyl-carbonated on both hydroxyl groups under assumption of a resin polymerized through carbonate bond; and the diester monomer-derived repeating unit is calculated relative to the structure methyl-esterified on both ester groups under assumption of a resin polymerized through interesterification.

First, one side chain of a structure derived from the compound 3B, the compound 7B or the compound 4B is described. As described below, the dihedral angle between the bond A between the 9-positioned carbon of fluorene and the carbon atom bonding to fluorene on the adjacent fluorene side, and the bond B between the atom on the side chain bonding to fluorene and the atom in the main chain bonding to that atom is 180° (that is, the side chain is trans conformation), 60° and −60° (that is, the side chain is in two types of gauche conformations) is referred to as the initial structure, and the equilibrium structure and the energy (heat of formation) thereof are calculated according to the AM1 method. Here, in each compound, the substituent having methyl carbonate or methyl ester and bonding to the 9-carbon atom of fluorene is referred to as the side chain. Of those three types of conformations, the energy of the most stable one is 0 (kJ/mol), and the energy difference (kJ/mol) between the individual conformations is shown in Table 10. In the case where two types of gauche conformations are symmetric, the two have the same value. In the case where the energy difference is 4 kJ/mol or more, the conformation with 0 (kJ/mol) is referred to as a stable conformation. Further, based on the initial structure according to the results of the AM1 method, the energy difference was calculated similarly according to the B3LYP/6-31G* method.

Next, the energy difference between the conformer in which both the two side chains existing in each monomer are trans conformations and the conformer in which the two side chains are two types of gauche conformations was calculated, using the AM1 method (Tables 11 to 13). Regarding the trans conformation and the gauche conformation (stable one of two gauche conformations), the angle between the main chain and the fluorene ring was calculated and shown in the Tables.

The angle between the main chain and the fluorene ring was determined as follows. First, the straight line bonding the carbon atoms of the methyl groups at both terminals is referred to as the main chain direction, and the plane passing through the 3-position, the 6-position and the 9-position of fluorene is referred to as the fluorene plane. In this, there may exist infinite straight lines on the fluorene plane crossing the main chain direction, but the straight line on the fluorene plane with which the angle to the main chain direction is the minimum is defined as one. The angle is referred to as the angle between the main chain and the fluorene ring.

[Chem. 108]

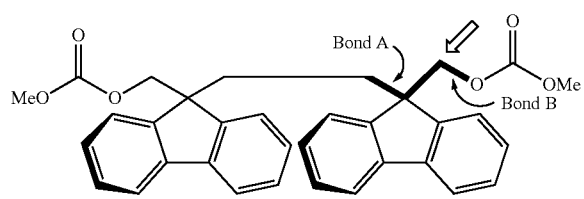

Compound 3 B methyl carbonate

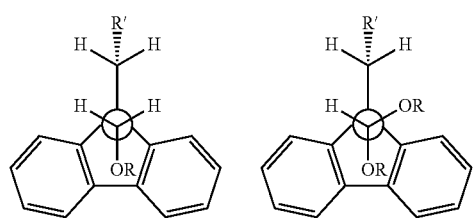

180° (trans conformation)   60° (gauche conformation)

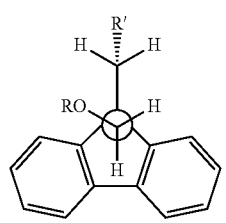

-60° (gauche conformation)

cm$^{-1}$ in Experimental Examples 8, 2, 6 and 9, and between 1080 cm$^{-1}$ and 1280 cm$^{-1}$ in Experimental Example 12), the intensity ratio (dichroic ratio) between the stretching direction and the vertical direction shows a large value (intensity in the stretching direction/intensity in the vertical direction >1.2), the case was defined as good (○), and all the films were good (○). Of those, some gave a clear differential spectrum of absorption at 740 cm$^{-1}$ derived from fluorene ring orientation, but some others did not. In other words, at the peak intensity at 740 cm$^{-1}$ (the highest peak intensity in the case where a base line was drawn as a straight line between 715 cm$^{-1}$ and 830 cm$^{-1}$ in all Experimental Examples), the intensity ratio (dichroic ratio) between the stretching direction and the vertical direction shows a large value (intensity in the stretching direction/intensity in the vertical direction >1.2), the case was defined as good (○), while the other case were defined as no good (x). Experimental Examples 8 and 2 were given "good (○)", but Experimental Examples 6, 9 and 12 were given "no good (x)". The relationship between the decision results and the reversed wavelength dispersion characteristics of retardation was investigated. As a result, those having provided a definite differential spectrum of absorption at 740 cm$^{-1}$ derived from fluorene ring orientation (that is, those given a dichroic ratio decision of good (○)) have reversed wavelength dispersion characteristics of retardation (Re450/Re550≤1.0), whole those not having provided it (that is, those given a dichroic ratio decision of no good (x)) do not have reversed wavelength dispersion characteristics of retardation (Re450/Re550>1.0).

TABLE 9

|  |  | Experimental Example 8 | Experimental Example 2 | Experimental Example 6 | Experimental Example 9 | Experimental Example 12 |
|---|---|---|---|---|---|---|
| Chemical Structure | monomer | compound 7B | compound 4B | compound 3B | compound 9B | compound 2B |
|  | R1, R2 in formula (1) | propylene group | propylene group | methylene group | methylene group | methylene group |
| Polarization ATR dichroic ratio | carbonyl | 2.01 | 1.55 | 1.43 | 1.47 | 1.76 |
|  | decision | ○ | ○ | ○ | ○ | ○ |
|  | fluorene ring | 1.53 | 1.37 | 0.93 | 1.09 | 0.99 |
|  | decision | ○ | ○ | x | x | x |
| Reversed Wavelength Dispersion Characteristics of Retardation |  | ○ | ○ | x | x | x |

First, in Table 9, shown are the results of polarization ATR analysis of films formed of a resin composition containing the compound 7B, the compound 4B, the compound 3B, the compound 9B or the compound 2B as the fluorene-containing monomer (the resin composition obtained in Experimental Examples 8, 2, 6, 9 and 12, respectively), and presence or absence of reversed wavelength dispersion characteristics of retardation of the films. It was confirmed that in all the films, the differential spectrum appeared obviously at the peak of 1245 cm$^{-1}$ derived from carbonyl orientation. In other words, in the case where, at the peak intensity at 1245 cm$^{-1}$ (the highest peak intensity in the case where a base line was drawn as a straight line between 1170 cm$^{-1}$ and 1420

Next, Table 10 shows the results of the formed energy difference of trans or gauche conformation of the repeating unit derived from the compound 7B, the compound 4B or the compound 3B, as calculated according to the AM1 method and the B3LYP/6-21*G method. As described above, in assuming the possible structure of each diol monomer in the polycarbonate resin, both terminals of the monomer are assumed to be methyl carbonate for simplifying the calculation. The difference is obtained between the case where one alone of the two terminals in each compound is a trans conformation and the case where it is a gauche conformation. Here, the case where the energy difference is 4 kJ/mol or more, the confirmation with low energy (heat of formation) is referred to as a stable conformation.

TABLE 10

| Calculation Method | Conformation | Compound 7B | Compound 4B | Compound 3B |
|---|---|---|---|---|
| AM1 | trans [kJ/mol] | 0 | 1.6 | 8.7 |
|  | gauche 1 [kJ/mol] | 0.4 | 0 | 0 |
|  | gauche 2 [kJ/mol] | 0.4 | 2.2 | 0 |
|  | stable conformation | — | — | gauche |
| B3LYP 6-31G* | trans [kJ/mol] | 0 | 0 | 6.1 |
|  | gauche 1 [kJ/mol] | 5.5 | 5.7 | 0 |
|  | gauche 2 [kJ/mol] | 5.5 | 6.6 | 0 |
|  | stable conformation | trans | trans | gauche |

As shown in Table 10, as a result of combination of the AM1 method and the B3LYP6-31* method, it is known that the stable conformation of the compound 7B and the compound 4B is trans while the stable conformation of the compound 3B is gauche.

Next, Tables 11 to 14 each show the results of the energy difference of the trans and gauche conformations of the repeating unit derived from the compound shown in the following group [X], as calculated according to the AM1 method. In this, the diol monomer was calculated for the structure in which both hydroxyl groups were methylcarbonates; and the diester monomer was calculated for the structure in which both ester groups were methyl esters. Here, for assuming the steric structure of the repeating unit in the polymer, both the two side chains in each compound were changed. In other words, in Tables 11 to 14, the trans conformation means a structure in which both the two side chains existing in each monomer are trans conformations; and the gauche conformation means a structure both the two side chains existing in each monomer are gauche conformations. The gauche conformations include two types at 60° and −60°. Here, the two types where both the two side chains are at 60° and −60° are calculated. In the case where the energy difference is 4 kJ/mol or more, the conformation having a lower energy (heat of formation) is taken as a stable conformation.

In the trans conformation and the gauche conformation (stable one of two gauche conformations), the straight line drawn by bonding the carbon atoms of the methyl groups at both terminals is defined as the main chain direction, and the angle thereof on the fluorene ring plane (minimum value of the angle between the main chain direction and the straight line crossing thereto on the plane) is described as the angle between the main chain and the fluorene ring.

In the repeating unit shown in Table 13, the phenylene group substituted at the para-position bonds to the carbon atom at the 9-position of fluorene, and the positional relationship of the side chains in these do not change even when the dihedral angle is changed, and therefore, trans conformation and gauche conformation do not exist. Consequently, the angle between the main chain and the fluorene ring of one imaginable type of structure was determined.

[Chem. 109]

[X]

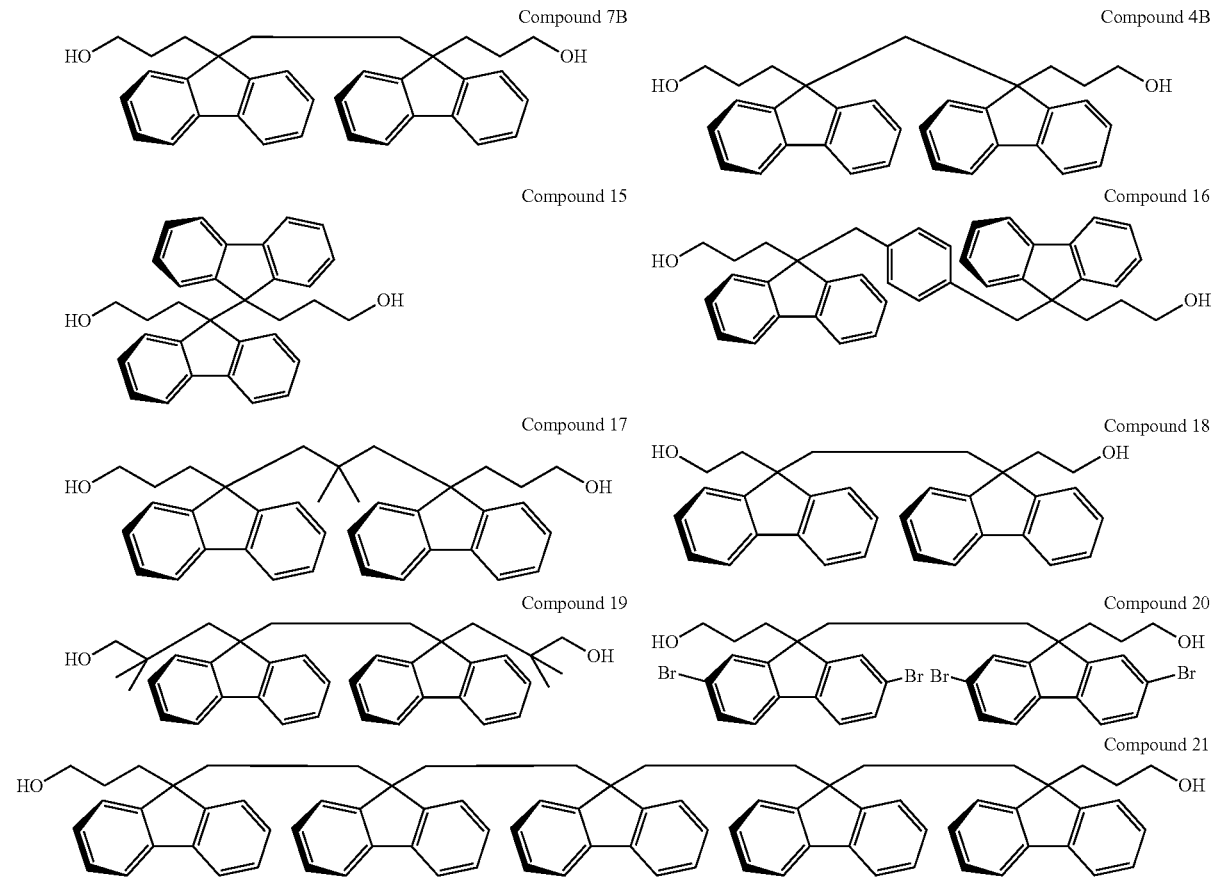

-continued
Compound 3B
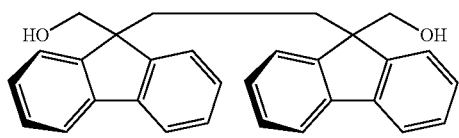
Compound 2B
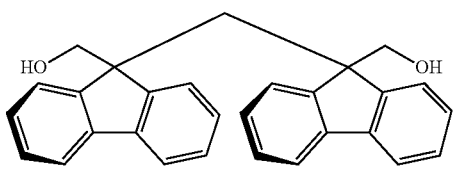
Compound 9B
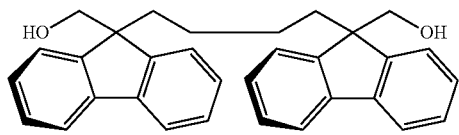
Compound 8
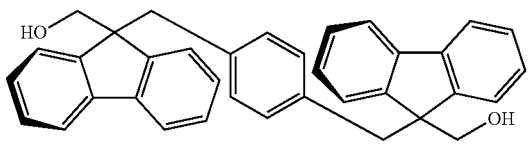
Compound 10B
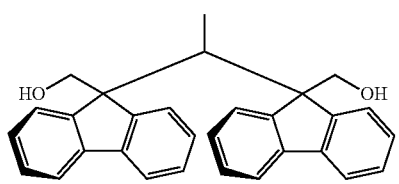
Compound 22
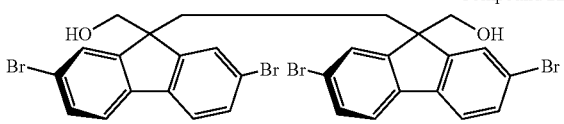
Compound 23
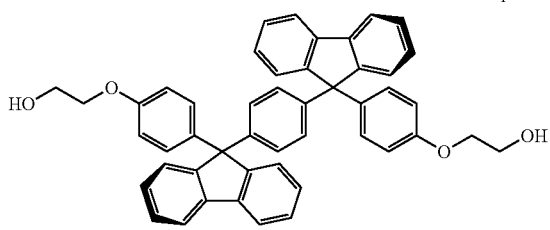
Compound 24
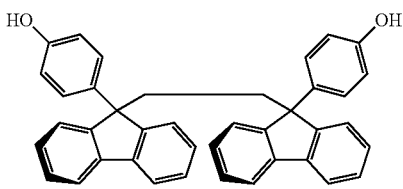
Compound 14B
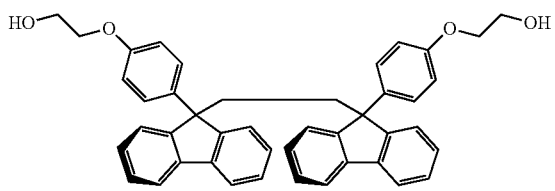
BPEF
Compound 25
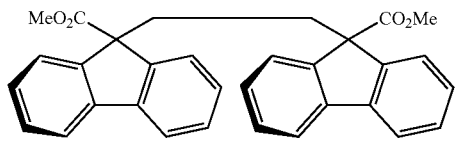
Compound 26
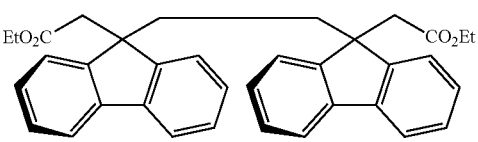
Compound 7A
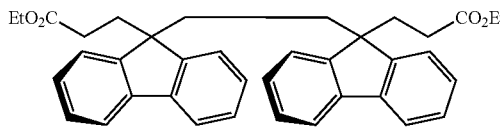
Compound 11
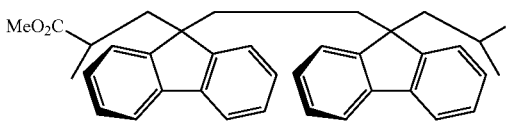
Compound 4A
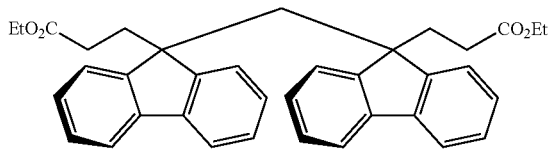

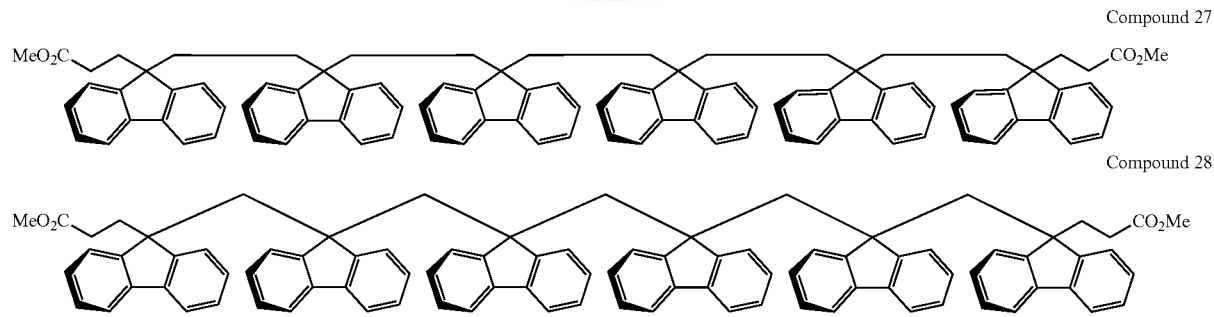

Compound 27

Compound 28

TABLE 11

| | | Chemical Structure Monomer | | | | | | | | |
|---|---|---|---|---|---|---|---|---|---|---|
| | | Compound 7B | Compound 4B | Compound 15 | Compound 16 | Compound 17 | Compound 18 | Compound 19 | Compound 20 | Compound 21 |
| | | R1, R2 in Formula (1) | | | | | | | | |
| | | propylene group | propylene group | propylene group | propylene group | propylene group | ethylene group | 2,2-dimethyl-propylene group | propylene group | propylene group |
| Conformation | trans [kJ/mol] | 0.0 | 3.3 | 0.0 | 0.0 | 1.6 | 0.0 | 0.0 | 0.0 | 0.0 |
| | gauche 1 [kJ/mol] | 0.8 | 0.0 | 26.1 | 0.0 | 0.0 | 2.4 | 12.3 | 1.3 | 0.8 |
| | gauche 2 [kJ/mol] | 0.8 | 4.4 | 26.1 | 0.0 | 2.4 | 2.4 | 12.3 | 1.3 | 0.8 |
| | stable conformation | — | — | trans | — | — | — | trans | — | — |
| Angle | trans [°] | 89.3 | 74.5 | 87.7 | 85.8 | 67.6 | 85.2 | 75.3 | 89.3 | 89.4 |
| | gauche 1 [°] | 47.8 | 66.0 | 51.5 | 51.7 | 65.4 | 54.3 | 55.5 | 47.1 | 66.4 |
| | gauche 2 [°] | 47.8 | 50.1 | 51.5 | 51.7 | 47.4 | 54.3 | 55.5 | 47.1 | 66.4 |

TABLE 12

| | | Chemical Structure Monomer | | | | | |
|---|---|---|---|---|---|---|---|
| | | Compound 3B | Compound 2B | Compound 9B | Compound 8 | Compound 10B | Compound 22 |
| | | R1, R2 in Formula (1) | | | | | |
| | | methylene group | methylene group | methylene group | methylene group | methylene group | methylene group |
| Conformation | trans [kJ/mol] | 17.3 | 26.2 | 19.0 | 21.2 | 19.8 | 15.6 |
| | gauche 1 [kJ/mol] | 0.0 | 0.0 | 0.0 | 0.0 | 0.0 | 0.0 |
| | gauche 2 [kJ/mol] | 0.0 | 0.9 | 0.0 | 0.0 | 1.2 | 0.0 |
| | stable conformation | gauche | gauche | gauche | gauche | gauche | gauche |
| Angle | trans [°] | 89.5 | 73.7 | 88.9 | 85.8 | 75.5 | 89.2 |
| | gauche 1 [°] | 49.1 | 59.9 | 55.5 | 54.4 | 53.7 | 47.8 |
| | gauche 2 [°] | 49.1 | 49.4 | 55.5 | 54.4 | 59.8 | 47.8 |

TABLE 13

| Monomer | Compound 23 | Compound 24 | Compound 14B | BPEF |
|---|---|---|---|---|
| R1, R2 in Formula (1) | * | phenylene group | * | * |
| angle [°] | 77.9 | 72.3 | 77.5 | 85.2 |

In Table 13, * means the following functional group.

[Chem. 110]

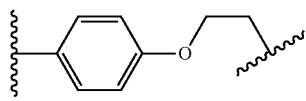

TABLE 14

| | | Chemical Structure Monomer | | | | | | |
|---|---|---|---|---|---|---|---|---|
| | | Compound 25 | Compound 26 | Compound 7A | Compound 11 | Compound 4A | Compound 27 | Compound 28 |
| | | R1, R2 in Formula (1) | | | | | | |
| | | direct bond | methylene group | ethylene group | 2-methyl-ethylene group | ethylene group | ethylene group | ethylene group |
| Confor-mation | trans [kJ/mol] | 5.4 | 16.9 | 0.0 | 0.0 | 0.0 | 0.0 | 0.0 |
| | gauche 1 [kJ/mol] | 0.0 | 0.0 | 4.7 | 6.3 | 6.3 | 4.2 | 5.4 |
| | gauche 2 [kJ/mol] | 0.0 | 3.1 | 4.7 | 8.3 | 3.4 | 4.2 | 4.4 |
| | stable conformation | gauche | gauche | trans | trans | trans | trans | trans |
| Angle | trans [°] | 86.1 | 75.5 | 85.4 | 73.3 | 74.6 | 87.5 | 60.8 |
| | gauche 1 [°] | 62.5 | 39.7 | 58.7 | 58.0 | 59.9 | 74.6 | 49.0 |
| | gauche 2 [°] | 62.5 | 58.5 | 58.7 | 38.5 | 71.1 | 74.6 | 45.2 |

As shown in the above-mentioned Experimental Examples 1 to 24, the resin composition of the present invention that contains a polymer having a divalent oligofluorene as a repeating unit therein greatly differs in the properties thereof, depending on the type of the terminal group that the oligofluorene monomer has. The phenomenon can be clarified by the results of polarization ATR analysis, and the calculation results of equilibrium structure.

In Table 9, the results of polarization ATR analysis of the resin composition produced using an oligofluorene-diol of which the terminal group is a hydroxypropyl group (compound 7B and compound 4B, in the formula (1), $R^1=R^2=$propylene group) conclude as follows. The appearance of the differential spectrum of carbonyl that is derived from the carbonate bond contained in the main chain indicates that the main chain is oriented in the stretching direction, and further, the appearance of the differential spectrum of fluorene ring confirms that the fluorene ring is oriented vertically to the main chain of the polymer.

On the other hand, in the case of the oligofluorene-diol in which the terminal group is a hydroxymethyl group (compound 3B, compound 9B, compound 2B, in the formula (1), $R^1=R^2=$methylene group), the differential spectrum of carbonyl appeared, but any clear differential spectrum did not appear relative to the fluorene ring. The appearance of the carbonyl differential spectrum indicates that the main chain is oriented in the stretching direction, while, on the other hand, the absence of the differential spectrum of fluorene ring may indicate that the fluorene ring would be nearly in an equivalent state relative to the direction vertical to the stretching direction (that is, the orientation direction of the main chain).

This result could be presumed as follows, from the calculation results of the equilibrium structure of each repeating unit.

Through the calculation in Table 10 where one terminal group has been rotated, the compound 7B and the compound 4B in which the terminal group is a hydroxypropyl group provided the result that, according to the AM1 method, the energy (heat of formation) of the trans conformation and that of the gauche conformation are nearly on the same level, and according to a more accurate calculation method, B3LYP/6-31G* method, the trans conformation is stable. For expressing high-level reversed wavelength dispersion characteristics of retardation, it is considered to be important that the fluorene ring takes a conformation orthogonal to the main chain; however, the compound 7B and the compound 4B of which the trans conformation is stable in calculation could readily take a conformation where the fluorene ring is orthogonal to the main chain, as described below, and therefore, it is considered that the polarization ATR analysis of the compounds confirmed the orientation of the fluorene ring and the compound could have high-level reversed wavelength dispersion characteristics of retardation.

On the other hand, of the compound 3B in which the terminal group is a hydroxymethyl group, the gauche conformation was stable both in the AM1 method and the B3LYP/6-31G* method. In the gauche conformation, the fluorene ring takes a position inclined relative to the main chain, and therefore it is considered that the compound could not express reversed wavelength dispersion characteristics of retardation though having a fluorene ring. The result could explain the absence of any significant differential spectrum of fluorene ring in polarization ATR analysis of the compound 3B therefore indicating that the compound could not express reversed wavelength dispersion characteristics of retardation. This could be the reason of the specific property that the wavelength dispersion characteristics of retardation of the polymer do not change even though the monomer amount is changed.

[Chem. 111]

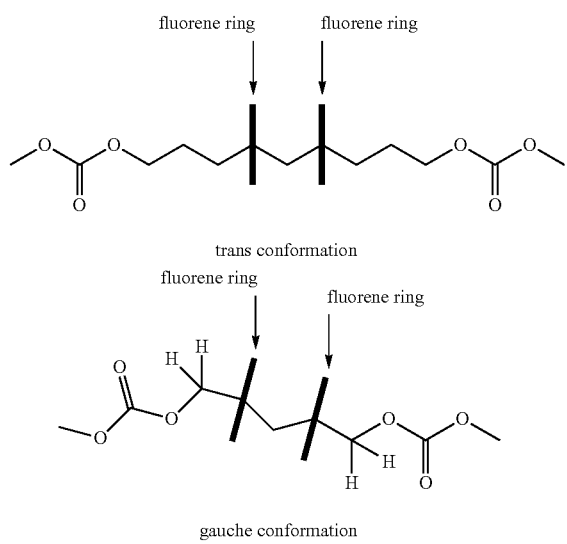

trans conformation gauche conformation

Figure 1B:
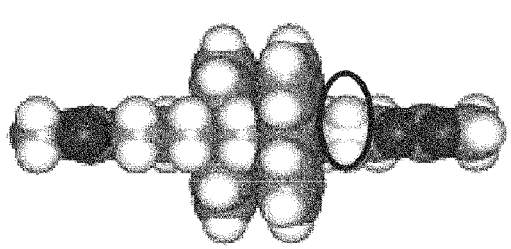
Figure 1C:
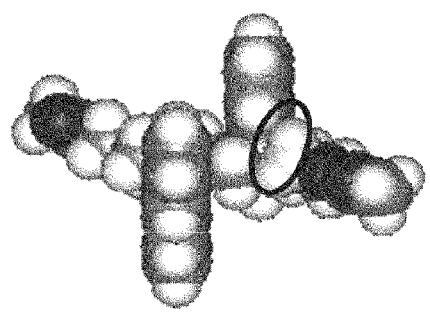

As shown in Table 11, in the case of the resin composition that contains a polycarbonate polymer having, as the repeating unit therein, an oligofluorene of the formula (1) where $R^1$ and $R^2$ each are any other group than a methylene group, the energy (heat of formation) of the trans conformation and that of the gauche conformation are nearly on the same level in the AM1 method, like those of the compound 7B and the compound 4B, or the trans conformation is a stable conformation. The structural formula of the compound 7B where the terminal group has been modified with methyl carbonate, and the space-filling model of the trans conformation and that of the gauche conformation are shown in FIGS. 1A to 1C. In the terminal group, the methylene group spaced by 2 atoms from the fluorene ring (in the structural formula, and in the space-filling models, the part surrounded by the circle) does not provide any significant steric repulsion in the trans conformation, while, on the other hand, it is known that, in the gauche conformation, there has occurred repulsion between the hydrogen atoms of the adjacent fluorene rings and those between the adjacent methylene groups, and therefore the conformation has become unstable.

As shown in Table 9, the compound 7B and the compound 4B showed orientation of carbonyl and fluorene ring in the polarization ATR analysis thereof, or that is, the compounds expressed reversed wavelength dispersion characteristics of retardation. As a result of the calculation according to the AM1 method shown in Table 11, the stability of the trans conformation and that of the gauche conformation of these compounds are on the same level, or the trans conformation thereof is a stable conformation, or that is, the gauche conformation is not a stable conformation. In other words, it is considered that in case where the gauche conformation could not be a stable conformation in the AM1 method, the contribution of the repeating structure that occupies the trans conformation where the fluorene ring is orthogonal to the main chain is great, and therefore the compound of the type could express reversed wavelength dispersion characteristics of retardation. Further, in the case of the formula (1) where $R^1$ and/or $R^2$ each are a group having 2 or more carbon atoms, more concretely, in the case where a methylene group or a group having a higher degree of steric hindrance than a methylene group exists in the terminal group, as spaced by 2 atoms from the fluorene ring, the gauche conformation would be disadvantageous owing to the steric hindrance, and therefore the gauche conformation could not be a stable conformation.

As a result of the calculation shown in Table 11, in the compound 7B, the angle between the main chain and the fluorene ring is 89.3° in the trans conformation and is 47.8° in the gauche conformation; while in the compound 4B, the angle is 74.5° in the trans conformation and is 66.0° in the gauche conformation. The differential spectrum in polarization ATR analysis does not appear at an angle of around 45°, but appears more largely when the angle comes close to 90°. From the appearance of the differential spectrum in polarization IR analysis, it is considered that the contribution of the trans conformation to the compound 7B and the compound 4B would be great.

Including the compound 7B and the compound 4B having shown the fluorene ring orientation in polarization ATR analysis and having expressed reversed wavelength dispersion characteristics, in all the compounds in Table 11, the angle between the main chain and the fluorene ring in the trans conformation is 60° or more. At an angle of around 45°, the compounds do not have a differential spectrum of fluorene ring in polarization ATR analysis and do not express reversed wavelength dispersion characteristics of retardation. On the other hand, at an angle of 50° C. or more, preferably 60° C. or more, more preferably 70° C. or more in the trans conformation, the compounds express reversed wavelength dispersion characteristics of retardation, and it is expected that the repeating structures shown in Table 11 could all express reversed wavelength dispersion characteristics of retardation.

Figure 2A:
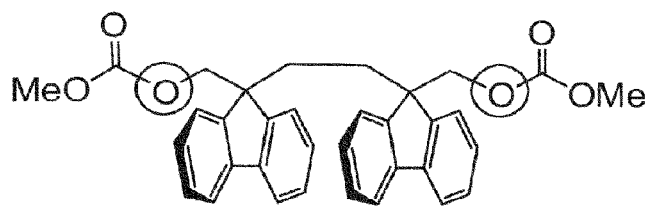
FIGS. 2A to 2C show the compound 3B modified with methyl carbonate at the terminal group thereof.
Figure 2B:
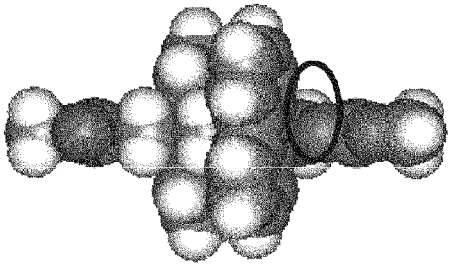
Figure 2C:
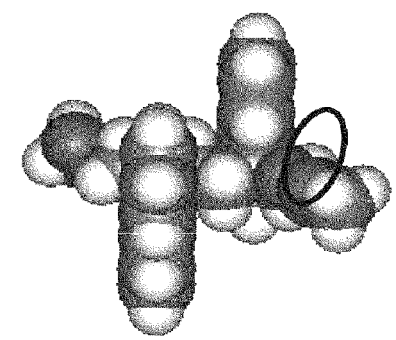

On the other hand, in the case of the resin composition that contains a polycarbonate polymer having, as the repeating unit therein, an oligofluorene of the general formula (1) shown in Table 12 where $R^1$ and $R^2$ are methylene groups, the gauche conformation is a stable conformation in the AM1 method, like in the compound 3B. The structural formula of the compound 3B where the terminal group has been modified with methyl carbonate, and the space-filling model of the trans conformation and that of the gauche conformation are shown in FIGS. 2A to 2C. In the terminal group, the oxygen atom spaced from the fluorene ring by 2 atoms (in the structural formula, and in the space-filling models, the part surrounded by the circle) does not give any repulsion like that seen in the corresponding methylene group in the compound 7B, even in the gauche conformation, and therefore, it is known that the gauche conformation is relatively stabilized.

As shown in Table 9, the compound 3B, the compound 2B and the compound 9B do not show orientation of fluorene ring in the polarization ATR analysis, or that is, the compounds did not express reversed wavelength dispersion characteristics of retardation. As a result of the calculation according to the AM1 method shown in Table 12, of all these compounds, the gauche conformation is a stable conformation. In other words, in the resin composition having a repeating structure in which the gauche conformation could be a stable conformation, the fluorene ring would incline relative to the main chain, and therefore the resin composition could not exhibit reversed wavelength dispersion characteristics of retardation. Further, in the case of the general formula (1) where $R^1$ and $R^2$ each are a group having one carbon atom, or that is, they are methylene groups, the steric hindrance of the gauche conformation could be relieved, and therefore the gauche conformation could be a stable conformation.

In Table 12, the angle between the main chain and the fluorene ring in the gauche conformation of a stable confirmation in the compound 3B, the compound 2B and the compound 9B is 49.1° in the compound 3B, 59.9° in the compound 2B and 55.5° in the compound 9B. In polarization IR analysis, the compounds do not provide a differential spectrum at an angle of around 45°. These compounds did not give a differential spectrum of fluorene ring, and therefore it is considered that the gauche conformation would be preferential in these compounds.

Including the compound 3B, the compound 2B and the compound 9B not having shown fluorene ring orientation in polarization ATR analysis and not having expressed reversed wavelength dispersion characteristics, in all the compounds in Table 12, the angle between the main chain and the fluorene ring in the gauche conformation is less than 60°. At an angle of around 45°, the compounds do not have a differential spectrum of fluorene ring in polarization ATR analysis and do not express reversed wavelength dispersion characteristics of retardation. At an angle of less than 60°, preferably 55° or less, more preferably 50° or less in the gauche conformation, the expression of reversed wavelength dispersion characteristics of retardation by these compounds may be weakened, and it is presumed that all the repeating structures shown in Table 12 would not express reversed wavelength dispersion characteristics of retardation or could express reversed wavelength dispersion characteristics of retardation only weakly.

As shown in Table 13, in the repeating unit in which the para-substituted phenylene group bonds to the 9-positioned carbon atom of fluorene, the angle is more than 70° in every case, including BPEF that is known to have reversed wavelength dispersion characteristics of retardation and the repeating unit having an oligofluorene group. From this, it may be said that these compounds have reversed wavelength dispersion characteristics of retardation.

As shown in Table 14, the same as above shall apply also to diester monomers. In the compound of the formula (1) where $R^1$ and $R^2$ are methylene groups (compound 26), the gauche conformation is more stable by 16.9 kJ/mol than the trans conformation (AM1 method), and it is considered that the compound could not have reversed wavelength dispersion characteristics of retardation. On the other hand, regarding the compound having a methylene group or having a group that has a higher degree of steric hindrance than a methylene group, at the position spaced by 2 atoms from the fluorene ring, the trans conformation of the compound of the type is a stable conformation even in the AM1 method, and it is considered that the compound of the type could express reversed wavelength dispersion characteristics of retardation.

The diol monomers in Table 11 and the diester monomers in Table 14 are compared. In the diester monomers, the trans conformation is more stable in the AM1 method. It is considered that, of all conformations, the contribution of the trans conformation is greater, and therefore the diester monomers could express higher reversed wavelength dispersion characteristics of retardation. For example, the compounds where $R^3$ is an ethylene group are compared. Of the diol monomers, in the compound where $R^1$ and $R^2$ are ethylene groups (compound 18) and in the compound where they are propylene groups (compound 7B), the trans conformation is stable at 2.4 kJ/mol and 0.8 kJ/mol, respectively; however, in the diester monomer where $R^1$ and $R^2$ are ethylene groups (compound 7A), the trans conformation is stable at 4.7 kJ/mol, or that is, the stability of the trans conformation higher in the diester monomer. Regarding the compounds where $R^3$ is a methylene group, the gauche conformation of the diol monomer where $R^1$ and $R^2$ are propylene groups (compound 4B) is stable at 3.3 kJ/mol, but the trans conformation in the diester monomer where $R^1$ and $R^2$ are ethylene groups (compound 4A) is stable at 3.4 kJ/mol.

As described above, in the case where a methylene group exists in the position spaced by 2 atoms from the fluorene ring, any significant steric repulsion appears in the trans conformation, as in the following drawings; however, on the other hand, in the gauche conformation, owing to the steric repulsion to the hydrogen atom on the fluorene ring or owing to the steric repulsion to the hydrogen atom on the carbon atom directly bonding to the 9-positioned carbon atom on the fluorene ring, the trans conformation is considered to be more stable. This effect is more remarkable in the case where the methylene group has a substituent.

[Chem. 112]

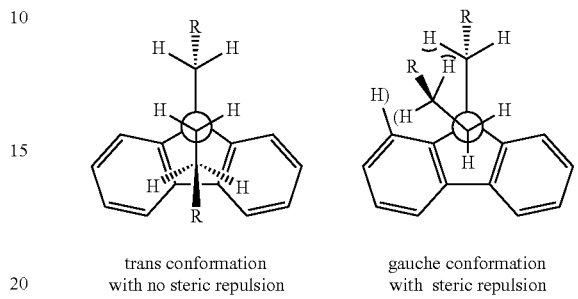

trans conformation with no steric repulsion gauche conformation with steric repulsion While the invention has been described in detail with reference to specific examples thereof, it will be apparent to one skilled in the art that various changes and modifications can be made therein without departing from the spirit and scope thereof. The present application is based on a Japanese patent application filed on Oct. 16, 2012 (Application No. 2012-228946) and a Japanese patent application filed on Jun. 21, 2013 (Application No. 2013-130882), the contents of which are incorporated herein by reference.

The invention claimed is:

1. A resin composition, comprising a polymer having a divalent oligofluorene as a repeating unit, wherein:
   the divalent oligofluorene contains at least two fluorene units optionally having a substituent;
   9-positioned carbon atoms of the fluorene units bond to each other via a direct bond, via an alkylene group optionally having a substituent, via an arylene group optionally having a substituent, or via an aralkylene group optionally having a substituent; and
   a ratio of a retardation measured at a wavelength of 450 nm (Re450) to a retardation measured at a wavelength of 550 nm (Re550) satisfies formula (2):

Re450/Re550<1.0  (2).

2. A resin composition, comprising a polymer having a divalent oligofluorene as a repeating unit, wherein:
   the divalent oligofluorene contains at least two fluorene units optionally having a substituent;
   9-positioned carbon atoms of the fluorene units bond to each other via a direct bond, via an alkylene group optionally having a substituent, via an arylene group optionally having a substituent, or via an aralkylene group optionally having a substituent;
   a molar fraction of the divalent oligofluorene to the polymer is 1% or more; and
   the resin composition has a positive refractive index anisotropy.

3. The resin composition according to claim 1, wherein the polymer is a polycarbonate.

4. A resin composition, comprising a polycarbonate polymer having a divalent oligofluorene as a repeating unit, wherein:
   the divalent oligofluorene contains at least two fluorene units optionally having a substituent; and
   9-positioned carbon atoms of the fluorene units bond to each other via a direct bond, via an alkylene group optionally having a substituent, via an arylene group optionally having a substituent, or via an aralkylene group optionally having a substituent.

5. The resin composition according to claim 2 or 4, wherein a ratio of a retardation measured at a wavelength of 450 nm (Re450) to a retardation measured at a wavelength of 550 nm (Re550) satisfies formula (2):

$$Re450/Re550 \leq 1.0 \tag{2}$$

6. The resin composition according to any one of claims 1, 2 and 4, wherein the divalent oligofluorene is represented by formula (1):

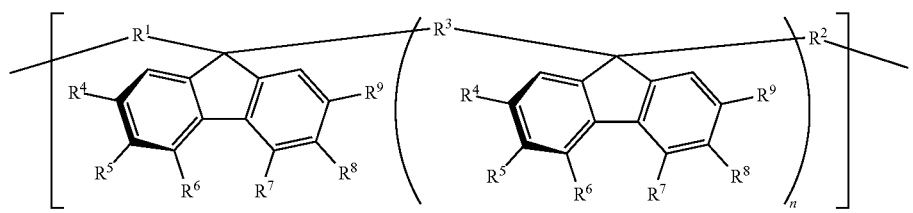

(1)

wherein:
R¹ and R² each independently represent a direct bond, an optionally-substituted alkylene group having from 1 to 10 carbon atoms, an optionally-substituted arylene group having from 4 to 10 carbon atoms, an optionally-substituted aralkylene group having from 6 to 10 carbon atoms, or a group formed by bonding at least two groups selected from the group consisting of an optionally-substituted alkylene group having from 1 to 10 carbon atoms, an optionally-substituted arylene group having from 4 to 10 carbon atoms, and an optionally-substituted aralkylene group having from 6 to 10 carbon atoms, via an oxygen atom, an optionally-substituted sulfur atom, an optionally-substituted nitrogen atom, or a carbonyl group;

R³ represents a direct bond, an optionally-substituted alkylene group having from 1 to 10 carbon atoms, an optionally-substituted arylene group having from 4 to 10 carbon atoms, or an optionally-substituted aralkylene group having from 6 to 10 carbon atoms;

R⁴ to R⁹ each independently represent a hydrogen atom, an optionally-substituted alkyl group having from 1 to 10 carbon atoms, an optionally-substituted awl group having from 4 to 10 carbon atoms, an optionally-substituted acyl group having from 1 to 10 carbon atoms, an optionally-substituted alkoxy group having from 1 to 10 carbon atoms, an optionally-substituted aryloxy group having from 1 to 10 carbon atoms, an optionally-substituted amino group, a substituent-having sulfur atom, a halogen atom, a nitro group, or a cyano group;

at least two adjacent groups of R⁴ to R⁹ may bond to each other to form a ring; and n is an integer of from 1 to 5.

7. The resin composition according to any one of claims 1, 2 and 4, wherein the polymer further contains a divalent organic group represented by formula (3) as a repeating unit:

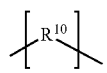

(3)

wherein R¹⁰ represents an optionally-substituted alkylene group having from 2 to 20 carbon atoms, an optionally-substituted arylene group having from 4 to 20 carbon atoms, an optionally-substituted aralkylene group having from 6 to 20 carbon atoms, an optionally-substituted alkylene-ether group having from 2 to 100 carbon atoms, an optionally-substituted organic group having an alicyclic structure of from 4 to 20 carbon atoms, or an optionally-substituted organic group having heterocyclic structure of from 4 to 20 carbon atoms.

8. The resin composition according to claim 7, wherein the divalent organic group represented by formula (3) is represented by at least one of formulae (4) to (9):

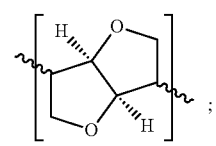

(4)

(5)

where R¹¹ represents an optionally-substituted linear alkylene group having from 0 to 18 carbon atoms;

(6)

where R¹² represents an optionally-substituted cycloalkylene group having from 4 to 20 carbon atoms;

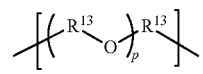

(7)

where R¹³ represents an optionally-substituted alkylene group having from 2 to 10 carbon atoms, and p indicates an integer of from 1 to 40;

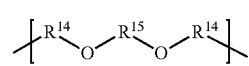

(8)

where R¹⁴ represents an optionally-substituted alkylene group having from 2 to 10 carbon atoms, and R¹⁵ represents an optionally-substituted arylene group having from 12 to 30 carbon atoms; and

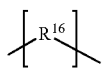

(9)

where $R^{16}$ represents an optionally-substituted group having an acetal ring of from 2 to 20 carbon atoms.

9. The resin composition according to any one of claims 1, 2 and 4, wherein a glass transition temperature of the composition is 90° C. or higher and 170° C. or lower.

10. The resin composition according to any one of claims 1, 2 and 4, wherein a melt viscosity of the composition at a measurement temperature of 240° C. and at a shear rate of 91.2 sec$^{-1}$ is 500 Pa·s or more and 5000 Pa·s or less.

11. The resin composition according to any one of claims 1, 2 and 4, wherein a photoelastic coefficient of the composition is $45 \times 10^{-12}$ Pa$^{-1}$ or less.

12. The resin composition according to any one of claims 1, 2 and 4, wherein a molar fraction of the divalent oligofluorene to the polymer is 1% or more and less than 50%.

13. The resin composition according to any one of claims 1, 2 and 4, wherein the polymer is produced through melt polycondensation of a dihydroxy compound represented by formula (10a) and a diester carbonate represented formula (11):

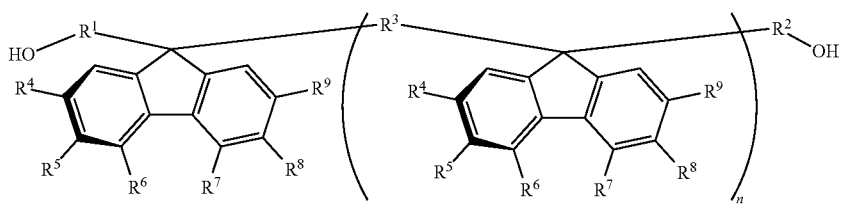

(10a)

where:
$R^1$ and $R^2$ each independently represent a direct bond, an optionally-substituted alkylene group having from 1 to 10 carbon atoms, an optionally-substituted arylene group having from 4 to 10 carbon atoms, an optionally-substituted aralkylene group having from 6 to 10 carbon atoms, or a group formed by bonding at least two groups selected from the group consisting of an optionally-substituted alkylene group having from 1 to 10 carbon atoms, an optionally-substituted arylene group having from 4 to 10 carbon atoms, and an optionally-substituted aralkylene group having from 6 to 10 carbon atoms, via an oxygen atom, an optionally-substituted sulfur atom, an optionally-substituted nitrogen atom, or a carbonyl group;

$R^3$ represents a direct bond, an optionally-substituted alkylene group having from 1 to 10 carbon atoms, an optionally-substituted arylene group having from 4 to 10 carbon atoms, or an optionally-substituted aralkylene group having from 6 to 10 carbon atoms;

$R^4$ to $R^9$ each independently represent a hydrogen atom, or a substituent selected from the group consisting of an optionally-substituted alkyl group having from 1 to 10 carbon atoms, an optionally-substituted aryl group having from 4 to 10 carbon atoms, an optionally-substituted acyl group having from 1 to 10 carbon atoms, an optionally-substituted alkoxy group having from 1 to 10 carbon atoms, an optionally-substituted aryloxy group having from 1 to 10 carbon atoms, an optionally-substituted amino group, a substituent-having sulfur atom, a halogen atom, a nitro group, and a cyano group, and at least two adjacent groups of $R^4$ to $R^9$ may bond to each other to form a ring; and n is an integer of from 1 to 5;

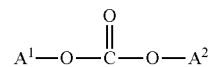

(11)

where $A^1$ and $A^2$ each represent a substituted or unsubstituted aliphatic hydrocarbon group having from 1 to 18 carbon atoms, or a substituted or unsubstituted aromatic hydrocarbon group, and $A^1$ and $A^2$ may be the same or different.

14. The resin composition according to claim 13, wherein a total content of Na, K, Cs, and Fe in the composition is 3 ppm by mass or less.

15. The resin composition according to claim 13, wherein a content of a monohydroxy compound formed from the diester carbonate represented by formula (11) in the composition is 1500 ppm by mass or less.

16. The resin composition according to claim 13, wherein each of $R^1$ and $R^2$ in formula (10a) is a methylene group.

17. A shaped article obtained by shaping the resin composition of any one of claims 1, 2 and 4.

18. An optical member comprising the resin composition of any one of claims 1, 2 and 4.

19. A film comprising the resin composition of any one of claims 1, 2 and 4.

20. A stretched film produced by stretching the film of claim 19 in at least one direction.

21. A ¼λ plate comprising the stretched film of claim 20.

22. A circularly polarizing plate comprising the ¼λ plate of claim 21.

23. An image display device comprising the circularly polarizing plate of claim 22.

24. An oligofluorene-diol represented by formula (19):

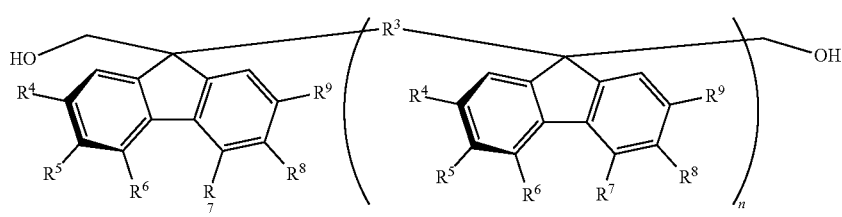

(19)

wherein:

$R^3$ represents an optionally-substituted alkylene group having from 1 to 10 carbon atoms, an optionally-substituted arylene group having from 4 to 10 carbon atoms, or an optionally-substituted aralkylene group having from 6 to 10 carbon atoms;

$R^4$ to $R^9$ each independently represent a hydrogen atom, an optionally-substituted alkyl group having from 1 to 10 carbon atoms, an optionally-substituted aryl group having from 4 to 10 carbon atoms, an optionally-substituted acyl group having from 1 to 10 carbon atoms, an optionally-substituted alkoxy group having from 1 to 10 carbon atoms, an optionally-substituted aryloxy group having from 1 to 10 carbon atoms, an optionally-substituted amino group, a substituent-having sulfur atom, a halogen atom, a nitro group, or a cyano group;

at least two adjacent groups of $R^4$ to $R^9$ may bond to each other to form a ring; and n is an integer of from 1 to 5.

25. The oligofluorene-diol according to claim 24, wherein a chlorine content of the oligofluorene-diol is 100 ppm by mass or less.

26. The oligofluorene-diol according to claim 24, wherein a content of metals of Group 1 and Group 2 of the Long Periodic Table in the oligofluorene-diol is 500 ppm by mass or less.

27. The oligofluorene-diol according to claim 24, wherein a 5% weight reduction temperature in thermogravimetry of the oligofluorene-diol is 250° C. or higher.

28. The oligofluorene-diol according to claim 24, wherein:
 $R^3$ is a methylene group, an ethylene group, an n-propylene group, an n-butylene group, or a 2,2-dimethylpropylene group;
 each of $R^4$ to $R^9$ is a hydrogen atom; and
 n is 1 or 2.

29. A method for producing an oligofluorene diester represented by the formula (VII-1), comprising:
 reacting an oligofluorene compound represented by the formula (II) with an unsaturated carboxylate ester represented by formula (VI-1) in the presence of a base:

wherein:

$R^3$ represents a direct bond, an optionally-substituted alkylene group having from 1 to 10 carbon atoms, an optionally-substituted arylene group having from 4 to 10 carbon atoms, or an optionally-substituted aralkylene group having from 6 to 10 carbon atoms;

$R^4$ to $R^9$ each independently represent a hydrogen atom, an optionally-substituted alkyl group having from 1 to 10 carbon atoms, an optionally-substituted aryl group having from 4 to 10 carbon atoms, an optionally-substituted acyl group having from 1 to 10 carbon atoms, an optionally-substituted alkoxy group having from 1 to 10 carbon atoms, an optionally-substituted aryloxy group having from 1 to 10 carbon atoms, an optionally-substituted amino group, a substituent-having sulfur atom, a halogen atom, a nitro group, or a cyano group;

at least two adjacent groups of $R^4$ to $R^9$ may bond to each other to form a ring;

$R_{iii}$ represents a hydrogen atom, an optionally-substituted alkyl group having from 1 to 10 carbon atoms, an optionally-substituted aryl group having from 4 to 10 carbon atoms, or an optionally-substituted aralkyl group having from 6 to 10 carbon atoms;

$R^{17}$ represents an organic substituent having from 1 to 10 carbon atoms; and n is an integer of from 1 to 5.

30. An oligofluorene diaryl ester represented by formula (10d):

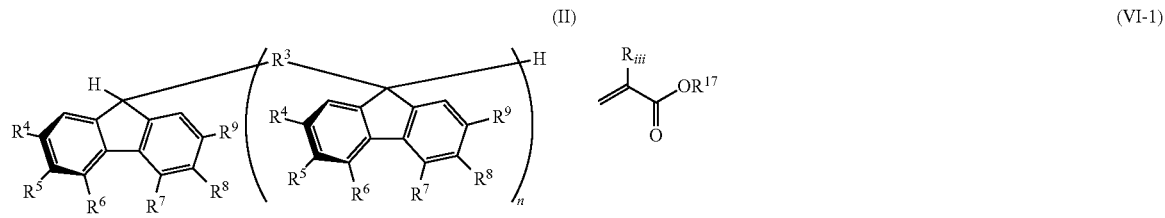

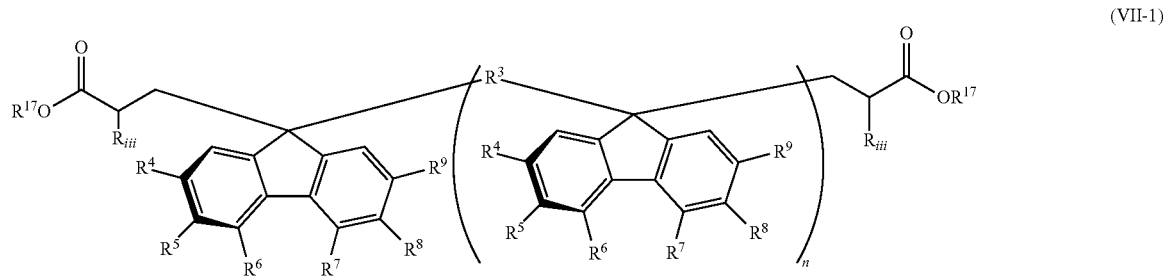

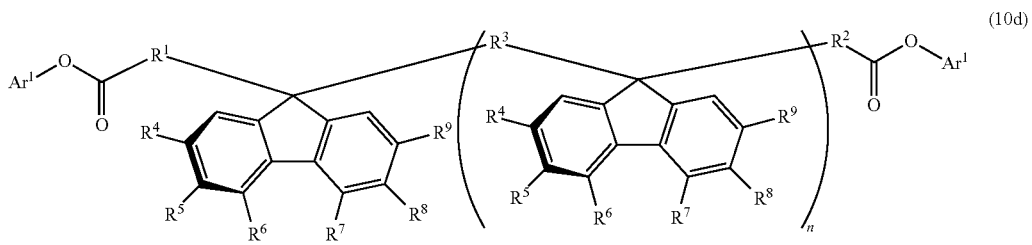

(10d)

wherein:
$R^1$ and $R^2$ each independently represent a direct bond, an optionally-substituted alkylene group having from 1 to 10 carbon atoms, an optionally-substituted arylene group having from 4 to 10 carbon atoms, an optionally-substituted aralkylene group having from 6 to 10 carbon atoms, or a group formed by bonding at least two groups selected from the group consisting of an optionally-substituted alkylene group having from 1 to 10 carbon atoms, an optionally-substituted arylene group having from 4 to 10 carbon atoms, and an optionally-substituted aralkylene group having from 6 to 10 carbon atoms, via an oxygen atom, an optionally-substituted sulfur atom, an optionally-substituted nitrogen atom, or a carbonyl group;

$R^3$ represents an optionally-substituted alkylene group having from 1 to 10 carbon atoms, an optionally-substituted arylene group having from 4 to 10 carbon atoms, or an optionally-substituted aralkylene group having from 6 to 10 carbon atoms;

$R^4$ to $R^9$ each independently represent a hydrogen atom, an optionally-substituted alkyl group having from 1 to 10 carbon atoms, an optionally-substituted aryl group having from 4 to 10 carbon atoms, an optionally-substituted acyl group having from 1 to 10 carbon atoms, an optionally-substituted alkoxy group having from 1 to 10 carbon atoms, an optionally-substituted aryloxy group having from 1 to 10 carbon atoms, an optionally-substituted amino group, a substituent-having sulfur atom, a halogen atom, a nitro group, or a cyano group;

at least two adjacent groups of $R^4$ to $R^9$ may bond to each other to form a ring;

$Ar^1$ represents an optionally-substituted aryl group having from 4 to 10 carbon atoms; and n is an integer of from 1 to 5.

31. The oligofluorene diaryl ester according to claim 30, wherein a 5% weight reduction temperature in thermogravimetry of the oligofluorene diaryl ester is 250° C. or higher.

32. The oligofluorene diaryl ester according to claim 30, wherein:
$R^3$ is a methylene group, an ethylene group, an n-propylene group, an n-butylene group or a 2,2-dimethylpropylene group;
each of $R^4$ to $R^9$ is a hydrogen atom;

$Ar^1$ is a phenyl group; and
n is 1 or 2.

33. A method for producing the oligofluorene diaryl ester of claim 30, comprising:
reacting an oligofluorene dialkyl ester represented by formula (10f) with a diaryl carbonate represented by formula (11a) in the presence of an interesterification catalyst:

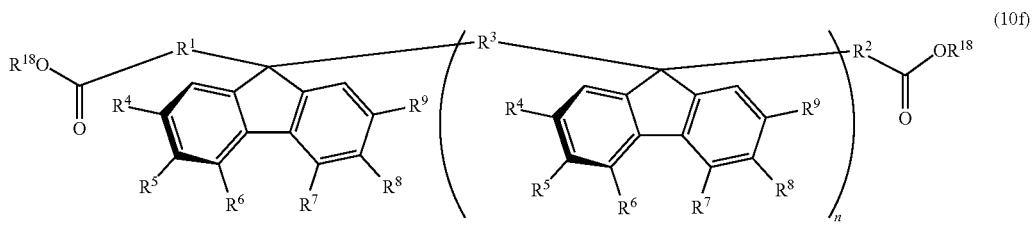

(10f)

where:
$R^1$ and $R^2$ each independently represent a direct bond, an optionally-substituted alkylene group having from 1 to 10 carbon atoms, an optionally-substituted arylene group having from 4 to 10 carbon atoms, an optionally-substituted aralkylene group having from 6 to 10 carbon atoms, or a group formed by bonding at least two groups selected from the group consisting of an optionally-substituted alkylene group having from 1 to 10 carbon atoms, an optionally-substituted arylene group having from 4 to 10 carbon atoms, and an optionally-substituted aralkylene group having from 6 to 10 carbon atoms, via an oxygen atom, an optionally-substituted sulfur atom, an optionally-substituted nitrogen atom, or a carbonyl group;

$R^3$ represents a direct bond, an optionally-substituted alkylene group having from 1 to 10 carbon atoms, an optionally-substituted arylene group having from 4 to 10 carbon atoms, or an optionally-substituted aralkylene group having from 6 to 10 carbon atoms;

$R^4$ to $R^9$ each independently represent a hydrogen atom, an optionally-substituted alkyl group having from 1 to 10 carbon atoms, an optionally-substituted aryl group having from 4 to 10 carbon atoms, an optionally-substituted acyl group having from 1 to 10 carbon atoms, an optionally-substituted alkoxy group having from 1 to 10 carbon atoms, an optionally-substituted aryloxy group having from 1 to 10 carbon atoms, an optionally-substituted amino group, a substituent-having sulfur atom, a halogen atom, a nitro group, or a cyano group;

at least two adjacent groups of $R^4$ to $R^9$ may bond to each other to form a ring;

$R^{18}$ represents a hydrogen atom or an optionally-substituted alkyl group having from 1 to 10 carbon atoms; and n is an integer of from 1 to 5; and

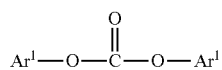
(11a)

where $Ar^1$ represents an optionally-substituted aryl group having from 4 to 10 carbon atoms.

34. The resin composition according to claim 2, wherein the polymer is a polycarbonate.

35. The resin composition according to claim 1, wherein, when the resin composition is formed into a film, the film exhibits melt processability.

36. The resin composition according to claim 2, wherein, when the resin composition is formed into a film, the film exhibits melt processability.

37. The resin composition according to claim 1, wherein the resin composition is free of thermosetting resins.

38. The resin composition according to claim 2, wherein the resin composition is free of thermosetting resins.

39. The resin composition according to claim 1, wherein the polymer is selected from the group consisting of a polyester, a polycarbonate, and a polyester carbonate.

40. The resin composition according to claim 2, wherein the polymer is selected from the group consisting of a polyester, a polycarbonate, and a polyester carbonate.

41. The resin composition according to claim 1, wherein a glass transition temperature of the resin composition is 90° C. or higher.

42. The resin composition according to claim 2, wherein a glass transition temperature of the resin composition is 90° C. or higher.

43. The oligofluorene diaryl ester according to claim 30, wherein $R^1$ and $R^2$ each independently represent an optionally-substituted alkylene group having from 1 to 10 carbon atoms, an optionally-substituted arylene group having from 4 to 10 carbon atoms, an optionally-substituted aralkylene group having from 6 to 10 carbon atoms, or a group formed by bonding at least two groups selected from the group consisting of an optionally-substituted alkylene group having from 1 to 10 carbon atoms, an optionally-substituted arylene group having from 4 to 10 carbon atoms, and an optionally-substituted aralkylene group having from 6 to 10 carbon atoms, via an oxygen atom, an optionally-substituted sulfur atom, an optionally-substituted nitrogen atom, or a carbonyl group.

* * * * *